US012780797B2

(12) United States Patent
Wu et al.

(10) Patent No.: US 12,780,797 B2
(45) Date of Patent: Nov. 3, 2026

1

(54) QUINOLINE DERIVATIVE INHIBITOR

(71) Applicant: TransThera Sciences (Nanjing), Inc., Nanjing (CN)

(72) Inventors: Frank Wu, Nanjing (CN); Zhonghui Wan, Nanjing (CN)

(73) Assignee: TransThera Sciences (Nanjing), Inc., Nanjing (CN)

( * ) Notice: Subject to any disclaimer, the term of this patent is extended or adjusted under 35 U.S.C. 154(b) by 335 days.

(21) Appl. No.: 17/268,309

(22) PCT Filed: Aug. 23, 2019

(86) PCT No.: PCT/CN2019/102230

§ 371 (c)(1),
(2) Date: Feb. 12, 2021

(87) PCT Pub. No.: WO2020/038460

PCT Pub. Date: Feb. 27, 2020

(65) Prior Publication Data

US 2022/0073496 A1 Mar. 10, 2022

(30) Foreign Application Priority Data

Aug. 24, 2018 (CN) ......................... 201810971406.2
Nov. 23, 2018 (CN) ......................... 201811403888.8
Feb. 20, 2019 (CN) ......................... 201910126817.6
Jun. 6, 2019 (CN) ......................... 201910490783.9

(51) Int. Cl.
*C07D 401/14* (2006.01)
*A61K 31/4709* (2006.01)
*A61K 45/06* (2006.01)
*A61P 35/00* (2006.01)
*C07D 491/056* (2006.01)

(52) U.S. Cl.
CPC ........ *C07D 401/14* (2013.01); *A61K 31/4709* (2013.01); *A61K 45/06* (2013.01); *A61P 35/00* (2018.01); *C07D 491/056* (2013.01)

(58) Field of Classification Search
CPC .......................... C07D 401/14; A61K 31/4709
See application file for complete search history.

(56) References Cited

U.S. PATENT DOCUMENTS 7,572,915 B2 8/2009 Barker et al.
7,858,623 B2 12/2010 Kim et al.
8,569,295 B2 10/2013 Chen et al.
8,916,591 B2 12/2014 Stokes et al.
9,029,538 B2 5/2015 Dandu et al.
9,133,183 B2 9/2015 Flynn et al.
9,221,805 B2 12/2015 Flynn
9,833,455 B2 12/2017 Flynn
2010/0022529 A1 1/2010 Li et al.
2013/0281428 A1 10/2013 Ohki et al.
2014/0228367 A1 8/2014 Flynn
2014/0315917 A1 10/2014 Flynn et al.
2016/0046619 A1 2/2016 Flynn et al.
2016/0297775 A1 10/2016 Zhang
2016/0303128 A1 10/2016 Flynn
2017/0129947 A1 5/2017 Lemke et al.
2018/0093968 A1 4/2018 Nam et al.
2018/0125848 A1 5/2018 Flynn

FOREIGN PATENT DOCUMENTS

CA 3063596 C 8/2022
CN 103958497 A 7/2014
CN 107667101 A 2/2018
JP 2008539275 A 11/2008
JP 2011510055 A 3/2011
JP 2011529054 A 12/2011
(Continued)

OTHER PUBLICATIONS

"Database Registry Accession No. 1903204-76-1", Chemical Abstracts Service, Columbus, OH; XP002806085, (May 4, 2016).
(Continued)

*Primary Examiner* — Brenda L Coleman
*Assistant Examiner* — Madeline E Braun
(74) *Attorney, Agent, or Firm* — Schwegman Lundberg & Woessner, P.A.
(74) *Attorney, Agent, or Firm* — "Database Registry Accession No. 1903258-44-5", Chemical Abstracts Service, Columbus, OH; XP002806084, (May 4, 2016).
(74) *Attorney, Agent, or Firm* — "Database Registry Accession No. 1903364-23-7", Chemical Abstracts Service, Columbus, OH; XP002806083, (May 4, 2016).
(74) *Attorney, Agent, or Firm* — "Database Registry Accession No. 1903462-51-0", Chemical Abstracts Service, Columbus, OH; XP002806082, (May 4, 2016).
(74) *Attorney, Agent, or Firm* — "Database Registry Accession No. 1903583-19-6", Chemical Abstracts Service, Columbus, OH; XP002806081, (May 4, 2016).

(57) ABSTRACT

A novel quinoline derivative inhibitor has a structure represented by the following general formula (I). The compound may selectively inhibit the TAM•family of tyrosine kinases/and CSFIR kinase, and may be used for the treatment and/or prevention of diseases mediated by the abnormal expression of TAM family kinases/and CSFIR kinase receptors and/or ligands thereof Furthermore, the compound may be used to treat and/or prevent related diseases caused by NTRK, more specifically, the compound may be used for the treatment and/or prevention of drug-resistant related diseases caused by NTRK mutations. The definitions of each group are as shown in the description.

(I)

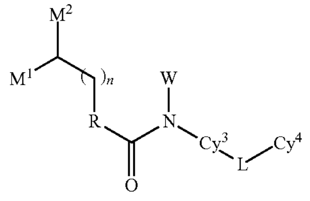

17 Claims, No Drawings

Specification includes a Sequence Listing.

(56) References Cited

FOREIGN PATENT DOCUMENTS

| | | | | |
|---|---|---|---|---|
| JP | 2013501047 | A | 1/2013 | |
| JP | 2014533287 | A | 12/2014 | |
| JP | 2017500362 | A | 1/2017 | |
| KR | 20080004617 | A | 1/2008 | |
| KR | 20120055608 | A | 5/2012 | |
| KR | 20140090678 | A | 7/2014 | |
| KR | 20160110390 | A | 9/2016 | |
| RU | 2335493 | C2 | 10/2008 | |
| WO | WO-2006116713 | A1 * | 11/2006 | ................ A61P 1/04 |
| WO | WO-2009093012 | A1 | 7/2009 | |
| WO | WO-2011017142 | A1 | 2/2011 | |
| WO | WO-2011139891 | A1 | 11/2011 | |
| WO | WO-2013022766 | A1 | 2/2013 | |
| WO | WO-2014018535 | A1 | 1/2014 | |
| WO | WO-2014145015 | A2 | 9/2014 | |
| WO | WO-2015100117 | A1 | 7/2015 | |
| WO | WO-2016104617 | A1 | 6/2016 | |
| WO | WO-2018214867 | A1 | 11/2018 | |
| WO | WO-2019080723 | A1 * | 5/2019 | ........... A61K 31/455 |
| WO | WO-2020038460 | A1 | 2/2020 | |
| WO | WO-2020047184 | A1 | 3/2020 | |
| WO | WO-2020141470 | A1 | 7/2020 | |

OTHER PUBLICATIONS

"Database Registry Accession No. 1903661-66-4", Chemical Abstracts Service, Columbus, OH; XP002806080, (May 4, 2016).
"Database Registry Accession No. 1903692-14-7", Chemical Abstracts Service, Columbus, OH; XP002806079, (May 4, 2016).
"Database Registry Accession No. 1904047-27-3", Chemical Abstracts Service, Columbus, OH, XP002806078, (May 5, 2016).
"Database Registry Accession No. 1904282-77-4", Chemical Abstracts Service, Columbus, OH; XP002806077, (May 5, 2016), 155-168.
"European Application No. 19851019.0, Extended European Search Report dated Apr. 19, 2022", (Apr. 19, 2022), 22 pgs.
Dannhardt, G., et al., "Anti-mycobacterial 4-hydroxy-3-phenylpyridin-2 (1H)-ones", European Journal of Medicinal Chemistry, vol. 26, No. 6, (Sep. 1, 1991), 599-604.
Dragovich, Peter S., et al., "Novel HCV NS5B polymerase inhibitors derived from 4-(1',1'-dioxo-1',4'-dihydro-1'?6-benzo[1',2',4']thiadiazin-3'-yl)-5-hydroxy-2H-pyridazin-3-ones. Part 5: Exploration of pyridazinones containing 6-amino-substituents", Bioorganic & Medicinal Chemistry Letters, vol. 18, No. 20, (Oct. 15, 2008), 5635-5639.
Li, Lian-Sheng, et al., "Synthesis of New Pyridazinone Derivatives: 2,6-Disubstituted 5-Hydroxy-3(2 H)-pyridazinone-4-carboxylic Acid Ethyl Esters", Synthesis, vol. 2007, No. 21, (Nov. 7, 2007), 3301-3308.
Traore, Tenin, et al., "New aminopyrimidine derivatives as inhibitors of the TAM family", European Journal of Medicinal Chemistry, vol. 70, (Oct. 22, 2013), 789-801.
Zhu, Tong, et al., "Polymer-Supported Synthesis of Pyridone-Focused Libraries as Inhibitors of Anaplastic Lymphoma Kinase", Journal of Combinatorial Chemistry, vol. 8, No. 3 [abstract only], (Apr. 12, 2006), 401-409.
"Indonesian Application Serial No. P00202102081, Office Action mailed Nov. 7, 2022", (w/ English Translation), 8 pgs.
"International Application No. PCT/CN2019/102230, International Search Report and Written Opinion mailed Dec. 3, 2019", (Dec. 3, 2019), 13 pgs.
Suarez, Rosa, et al., "Inhibitors of the TAM subfamily of tyrosine kinases: Synthesis and Biological evaluation", European Journal of Medicinal Chemistry 61 (2013), (Jun. 12, 2012), 2-25.
Traore, Tenin, et al., "New aminopyrimidine derivatives as inhibitors of the TAM family", European Journal of Medicinal Chemistry 70 (2013), (Oct. 12, 2013), 789-801.
"Korean Application No. 10-2021-7008562, Request for the Submission of an Opinion dated Aug. 13, 2024", (Aug. 13, 2024), 18 pgs.
"Japanese Application No. 2021-510026, Notice of Reasons for Refusal dated Apr. 10, 2023", (Apr. 10, 2023), 11 pgs.
Wermuth, Camille, "Molecular Variations Based on Isoteric Replacements", The Practice of Medicinal Chemistry. Academic Press, Chapter 13, (1996), 203-237.
"Russian Application Serial No. 2021107342, Office Action mailed Sep. 30, 2022", (w/ English Translation), 22 pgs.
"Chinese Application No. 201910785074.3, Chinese First Office Action mailed Apr. 28, 2022", (Apr. 28, 2022), 7 pgs.
"Chinese Application No. 201910785074.3, Chinese Search Report mailed Apr. 23, 2022", (Apr. 23, 2022), 2 pgs.
"Chinese Application No. 201910785074.3, Chinese Second Office Action mailed Sep. 9, 2022", (Sep. 9, 2022), 6 pgs.
"Research Progress of Trk Small Molecular Kinase Inhibitors", (w/ English Translation), Journal of Clinical Pharmacotherapy, vol. 15, No. 12, (Dec. 2017), 78-79 (4 Pages).
Akalu, Yemsratch, et al., "TAM receptor tyrosine kinases as emerging targets of Innate", Immunological Reviews, 276, (2017), 165-177.
Cejalvo, Juan M., et al., "Abstract 4867—AXL as a potential primary and secondary trastuzumab resistance mechanism in breast cancer cells with HER2 overexpression", ESMO 2017 Congress, (2017), 5 pgs.
Drilon, A., et al., "What hides behind the MASC: clinical response and acquired resistance to entrectinib after ETV6-NTRK3 identification in a mammary analogue secretory carcinoma (MASC)", Annals of Oncology, 27, (2016), 920-926.
Graham, Douglas K., et al., "The TAM family: phosphatidylserine-sensing receptor tyrosine kinases gone awry in cancer", Nature Reviews Cancer, vol. 14, (Dec. 2014), 769-785.
Holland, Sacha J., et al., "R428, a Selective Small Molecule Inhibitor of Axl Kinase, Blocks Tumor Spread and Prolongs Survival in Models of Metastatic Breast Cancer", Cancer Res., 70(4), (2010), 1544-1554.
Khotskaya, Yekaterina B., et al., "Targeting TRK family proteins in cancer", Pharmacology & Therapeutics, vol. 173, (May 2017), 58-68.
Lemke, Greg, et al., "Immunobiology of the TAM receptors", Nature Reviews Immunology, vol. 8, (May 2008), 327-336.
Li, Gary, et al., "Abstract A173—Potent Anti-tumor Activity of Entrectinib (RXDX-101) in Patient-derived Models Harboring Oncogenic Gene Rearrangements of NTRKs Predictive of Clinical Responses", Poster, AACR-NCI-EORTO, (2015), 1 Pg.
Lu, Ping, et al., "Progress of the relationship between Mer signaling pathway and tumor", J Chinese Pract. Diagn. Ther., vol. 30, No. 6, (Jun. 2016), 540-542.
O'Brien, Jenean, et al., "Alternatively Activated Macrophages and Collagen Remodeling Characterize the Postpartum Involuting Mammary Gland across Species", The American Journal of Pathology, vol. 176, No. 3, (Mar. 2010), 1241-1255.
Ohno, Hiroaki, et al., "A c-fms tyrosine kinase inhibitor, Ki20227, suppresses osteoclast differentiation and osteolytic bone destruction in a bone metastasis model", Mol Cancer Ther, 5(11), (2006), 2634-2643.
Pyonteck, Stephanie M., et al., "CSF-1R inhibition alters macrophage polarization and Blocks glioma progress", Nature Medicine (Advance Online Publication), (2013), 1-12.
Wu, Yan-Jun, et al., "Advances in the development of Axl inhibitors", Chinese Journal of New Drugs, (2016), 1225-1235.
"Canadian Application No. 3,109,891, Examination Search Report dated Apr. 25, 2024", (Apr. 25, 2024), 3 pgs.
"European Application No. 19851019.0, Communication pursuant to Article 94(3) EPC dated Jun. 13, 2023", (Jun. 13, 2023), 4 pgs.

* cited by examiner

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: A synthetic amino acid sequence
<221> NAME/KEY: misc_feature
<222> LOCATION: 3
<223> OTHER INFORMATION: Xaa = Ile or Leu
<221> NAME/KEY: misc_feature
<222> LOCATION: 5
<223> OTHER INFORMATION: Xaa = Ile or Leu

<400> SEQUENCE: 1

Lys Trp Xaa Ala Xaa Glu Ser
1               5
```

-continued

<210> SEQ ID NO 2
<211> LENGTH: 13
<212> TYPE: PRT
<213> ORGANISM: Artificial Sequence
<220> FEATURE:
<223> OTHER INFORMATION: A synthetic amino acid sequence

<400> SEQUENCE: 2

```
Lys Lys Ser Arg Gly Asp Tyr Met Thr Met Gln Ile Gly
1               5                   10
```

<210> SEQ ID NO 3
<211> LENGTH: 16
<212> TYPE: PRT
<213> ORGANISM: Artificial Sequence
<220> FEATURE:
<223> OTHER INFORMATION: A synthetic amino acid sequence

<400> SEQUENCE: 3

```
Gly Gly Met Glu Asp Ile Tyr Phe Glu Phe Met Gly Gly Lys Lys Lys
1               5                   10                  15
```

<210> SEQ ID NO 4
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 4

```
Lys Val Glu Lys Ile Gly Glu Gly Thr Tyr Gly Val Val Tyr Lys
1               5                   10                  15
```

<210> SEQ ID NO 5
<211> LENGTH: 14
<212> TYPE: PRT
<213> ORGANISM: Artificial Sequence
<220> FEATURE:
<223> OTHER INFORMATION: A synthetic amino acid sequence

<400> SEQUENCE: 5

```
Lys Lys Lys Ser Pro Gly Glu Tyr Val Asn Ile Glu Phe Gly
1               5                   10
```

<210> SEQ ID NO 6
<211> LENGTH: 14
<212> TYPE: PRT
<213> ORGANISM: Artificial Sequence
<220> FEATURE:
<223> OTHER INFORMATION: A synthetic amino acid sequence

<400> SEQUENCE: 6

```
Gly Glu Glu Pro Leu Tyr Trp Ser Phe Pro Ala Lys Lys Lys
1               5                   10
```

QUINOLINE DERIVATIVE INHIBITOR

PRIORITY CLAIM TO RELATED APPLICATIONS

This application is a U.S. national stage filing under 35 U.S.C. § 371 from International Application No. PCT/CN2019/102230, filed on 23 Aug. 2019, and published as WO2020/038460 on 27 Feb. 2020, which claims the benefit under 35 U.S.C. 119 to Chinese Application No. 201810971406.2, filed on 24 Aug. 2018, the benefit under 35 U.S.C. 119 to Chinese Application No. 201811403888.8, filed on 23 Nov. 2018, the benefit under 35 U.S.C. 119 to Chinese Application No. 201910126817.6, filed on 20 Feb. 2019, and the benefit under 35 U.S.C. 119 to Chinese Application No. 201910490783.9, filed on 6 Jun. 2019, the benefit of priority of each of which is claimed herein, and which applications and publication are hereby incorporated herein by reference in their entirety.

INCORPORATION BY REFERENCE OF SEQUENCE LISTING

A Sequence Listing is provided herewith as a text file, “5443005US1.txt”, created on Jul. 8, 2024 and having a size of 1,945 bytes. The contents of the text file are incorporated by reference herein in their entirety.

TECHNICAL FIELD

The present invention belongs to the medical field, particularly to a compound represented by general formula (I) (which is an inhibitor of TAM family kinases/ and CSF1R kinase), a pharmaceutically acceptable salt, an ester, a stereoisomer, and a tautomer thereof, a pharmaceutical composition comprising same, a pharmaceutical formulation and their use. The compound of the present invention may selectively inhibit the TAM family of tyrosine kinases/ and CSF1R kinase, and may be used for the treatment and/or prevention of diseases mediated by the abnormal expression of TAM family kinases/ and CSF1R kinase receptors and/or ligands thereof. Furthermore, the compound of the present invention may be used to treat and/or prevent related diseases caused by NTRK, more specifically, said compound may be used for the treatment and/or prevention of drug-resistant related diseases caused by NTRK mutations.

BACKGROUND ART

The TAM family includes three members, i.e., Axl, Mer, and Tyro-3. This family contains an extracellular domain, a transmembrane domain, and a conservative intracellular kinase domain. The extracellular domain consists of repeat units formed by linking two immunoglobulin-like domains to two fibronectin type III. The conservative amino acid sequence KW(I/L)A(I/L)ES (SEQ ID NO: 1) in its intracellular kinase domain is a unique structural feature of the TAM family. This family has one common ligand-growth arrest-specific protein 6 (GAS6), which ligand can bind to all TAM receptors with different binding strengths. Besides this, the TAM family further comprises relevant receptors such as vitamin K dependent protein S (ProS), tubby-like protein Tubby, recombinant human tubby-like protein 1 (Tulp1), and galectin-3 (WU Yan jun, Chinese Journal of New Drugs 2016; Lu Ping, Journal of Chinese Practical Diagnosis and Therapy, 2016).

Among others, Axl (also referred to as UFO, Ark, Tyro-7, JTK1), Mer (also referred to as c-Mer, Mertk, Eyk, Nyk, Tyro-12), Tyro-3 (also referred to as Sky, Byk, Rse, Dtk and the like), galectin-3, Gas6, ProS are aberrantly expressed in a wide range of solid tumors such as lung cancer, gastric cancer, and liver cancer and hematological tumors such as AML, ALL, and CML, and are significantly associated with poor prognosis in diseases, the progression of disease, the tumor metastasis, the drug resistance of tumor and the like (Douglas K, Nature reviews, 2014). In particular, Axl, as a tyrosine kinase, has been proven to be one of the reasons for the resistance to EGFR inhibitors in NSCLC, and is closely related to the metastasis of various solid tumors. The drugs developed based on this target also confirm that the inhibition of Axl may delay the resistance to EGFR inhibitors and the tumor metastasis (T. Jimbo, Annals of Oncology, 2017; Sacha J. Holland, American Association for Cancer Research, 2010). At the same time, Axl, Mei, Tryo-3 and TAM ligands also play a major role in tumor immunization. Inhibition of the TAM family and its ligands can reverse the tumor's immunosuppressive environment and enhance the ability of the immune system to kill tumor cells by promoting the polarization of macrophages to M1 macrophages, increasing the activation and function of effector T cells, and enhancing the anti-tumor activity of NK cells (Yemsratch T. Akalu, Immunological Reviews, 2017; Greg Lemke, Nature Reviews Immunology, 2008). Therefore, the development of such inhibitors can have strong inhibitory and therapeutic effects on various solid and hematological tumors induced by said family, such as lung cancer, liver cancer, breast cancer, brain glioma, melanoma, AML, ALL, and CML.

In addition to the above-mentioned tumor diseases, the TAM family receptors and its ligands can regulate several physiological functions such as vascular smooth muscle homeostasis, platelet aggregation, thrombus stabilization, erythropoiesis, oligodendrocyte survival, osteoclast function, phagocytosis of apoptotic cells, inflammation, and innate immunity. Therefore, the TAM family inhibitor may also be used for related diseases caused by the TAM family signaling pathway disorder such as adenomyosis, vascular disease/injury, psoriasis, visual defect/impairment (caused by macular degeneration, diabetes, premature birth and the like), kidney disease, rheumatoid arthritis, and osteoporosis.

Colony Stimulating Factor 1 Receptor (CSF1R), also referred to as c-FMS, FMS, FIM2, MCSF and CD115, is a single-chain transmembrane glycoprotein composed of 972 amino acid residues. Like FLT-3, PDGFR and KIT, it belongs to the III-type receptor tyrosine kinase (RTK) family. CSF1R is only expressed on the surface of monocyte lines, such as macrophages. Currently reported CSF1R ligands include colony stimulating factor 1 (CSF1, macrophage colony-stimulating factor, also referred to as M-CSF) and interleukin-34 (IL-34). CSF1 affects various cellular functions of monocyte cell lines by binding to CSF1R. IL-34 can bind to CSF1R firmly, thereby promoting the survival, proliferation and differentiation of monocyte cell lines. They constitute the CSF1/IL-34/CSF1R pathway.

In the CSF1/CSF1R pathway, CSF1 and CSF1R form a signal axis to promote the growth of macrophages in the body, and regulate the normal development and homeostasis of tissues and organs, whereas the imbalance of the body's homeostasis can cause various diseases such as inflammation, immune system diseases, and tumors. Although macrophages have the potential to kill tumor cells, tumor-associated macrophages (TAMs) mainly exert immunosuppressive effects. In particular, myeloid-derived suppressor cells (MDSCs) can prompt the macrophage to selectively neglect the presence of tumor cells by high expression of CSF1R, which further promotes tumor development and metastasis. At present, increased expression of CSF1/CSF1R has been found in a variety of tumors such as breast cancer, ovarian cancer, colorectal cancer, prostate cancer, lung cancer, and Hodgkin's lymphoma (O'Brien J, Am J Pathol, 2010). Overexpression of CSF1/CSF1R is associated with malignant invasiveness and poor prognosis of tumors. High expression of CSF1R can be detected in CSF1-induced fibroblasts and epithelial cells, and tumors are eventually formed in nude mice, suggesting that the CSF1/CSF1R axis promotes the proliferation and survival of tumor cells, and plays a vital role in the tumorigenesis and the tumor development. Furthermore, in bone metastasis, CSF1R plays a role in osteolytic bone destruction (Ono, Mol. Cancer Ther, 2006). Therefore, inhibition of the CSF1/IL-34/CSF1R signaling pathway can alleviate the immunosuppressive effect of tumors and enhance the activity of the immune system, thereby inhibiting the development and metastasis of tumors. It has also been reported that CSF1R inhibitors can significantly reduce tumors, e.g. the volume of tumors such as glioblast tumor, and reduces tumor invasiveness and proliferation (Pyonteck Stephanie M, Nature Medicine, 2013). In summary, inhibition of the CFS1R pathway has become one of the main therapeutic targets for cancer.

Both TAM and CSF1R inhibitors can improve the immunosuppressive environment of tumors and enhance the ability of the immune system to kill tumor cells. However, based on the complexity of tumor pathogenesis, if they can simultaneously target these two targets, they can exert their double immunotherapy effect on tumors. Currently, clinically used CSF1R inhibitors are generally combined with PD-1 in therapy, and there is no inhibitor concurrently targeting TAN/ and CSF1R available in the market.

The NTRK gene contains NTRK1, NTRK2 and NTRK3, which are responsible for the synthesis of the Tropomyosin-related kinase (TRK) family proteins TRKA, TRKB and TRKC, respectively. Gene expression studies indicate that the NTRK gene is mainly expressed in the nervous system and is also expressed during embryonic development and in adults. When activated by signal induction, TRK can autophosphorylate and activate downstream signaling pathways to achieve a variety of physiological functions. The downstream signaling molecules of TRK include SHC, FRS2, PLCγ, MAPK, PI3K and PKC. Most of these signaling molecules are closely related to the functions of cell energy exchange, survival and proliferation. If TRK is dysfunctional, the physiological functions of cells may be out of control, of which cells may be even transformed into cancer cells. Therefore, when chromosomal variation occurs in terms of NTRK gene fusion, the TRK fusion protein will be in a continually active state, thus triggering a permanent cascade of downstream signaling pathways that drive the spread and growth of TRK fusion tumors (Yekaterina B. Khotskaya, Pharmacology & Therapeutics, 2017).

NTRK gene fusion may occur anywhere in the body and is found in a variety of solid tumors in adults and children, including mammary analogue secretory carcinoma (MASC), colon cancer, lung cancer, pancreatic cancer, thyroid cancer, and various sarcomas. NTRK fusion occurs at a low frequency of less than 5% in common types of cancer such as colon cancer and lung cancer; however, it is found in some rare types of cancer, such as congenital renal tumor, infant sarcoma, salivary gland cancer, and secretory breast cancer, with a very high mutation rate, and the occurrence frequency of individual cancer types is greater than 90% (Clinical Medication Journal, Vol. 15, No. 12, December, 2017). Therefore, the development of NTRK inhibitors has great clinical value.

Although the first generation of NTRK inhibitors targeting NTRK gene fusion, such as Larotrectinib and Entrectinib are available now, TKI (tyrosine kinase inhibitor) therapy targeting NTRK is still facing the problem of acquired drug-resistance. Currently, it is found in some patients who had received the TRK inhibitor therapy that some TRKs generated mutations in kinase sites, such as NTRK1-LMNA-G667C and NTRK1-LMNA-V573 M, resulting in the occurrence of the secondary drug resistance of cancer cells, including colon cancer, MASC and the like (Marangela Russo, American Association for Cancer Research, 2015; A. Drilon, Annals of Oncology, 2016). These emerging mutations prevent the first-generation NTRK inhibitors, Entrectinib and Larotrectinib, from binding to the kinase, thereby rendering the drug ineffective. Therefore, acquired drug-resistance to the first-generation NTRK inhibitor therapy is a continuing challenge, and the second-generation NTRK inhibitors are urgently needed to address some drug resistance problems.

SUMMARY OF THE INVENTION

The prevent invention provides a novel inhibitor compound and a pharmaceutically acceptable salt, an ester, a stereoisomer, and a tautomer thereof (hereinafter, sometimes referred to as the compound of the present invention). The compound of the present invention has an inhibitory effect on the TAM family kinases. In addition, the compound of the present invention can also target the CSF1R kinase, and has an inhibitory effect on the CSF1R kinase. The compound of the present invention may be used for the treatment and/or prevention of diseases mediated by the abnormal expression of the TAM family kinase receptors and/or ligands thereof. In addition, the compound of the present invention may be used for the treatment and/or prevention of diseases mediated by the abnormal expression of TAM family kinases/ and CSF1R kinase receptors and/or ligands thereof. The compound of the present invention, by inhibiting the TAM family kinases/ and CSF1R kinase, reverses the immunosuppression in the tumor microenvironment, inhibits tumor growth, migration, and/or drug-resistance performance, and exerts the tumor immunity effect and the antitumor effect. In addition, the compound of the present invention may be used for the treatment and/or prevention of related diseases caused by NTRK, in particular, drug-resistant related diseases caused by NTRK mutations.

Specifically, the technical solutions according to the present invention comprise the followings:

A compound represented by general formula (I), or a pharmaceutically acceptable salt, an ester, a stereoisomer, or a tautomer thereof.

(I)

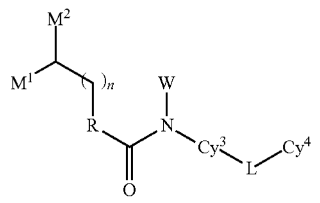

wherein W is selected from hydrogen or $C_{1-6}$alkyl;

R represents a group represented by the following general formula (a), (b) or (c).

(a)

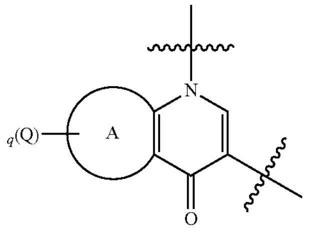

or (b)

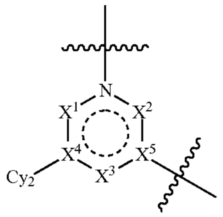

or (c)

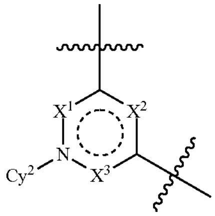

, in formula (a), ring A is selected from phenyl, 5-6-membered heteroaryl or 5-6-membered heterocyclyl;

Q is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R', 3-12-membered cycloalkyl, 3-12-membered cycloalkenyl, 3-14-membered heterocyclyl, 6-14-membered aryl, or 5-10-membered heteroaryl;

q is an integer of 0-4;

in formulae (a) and (b), the

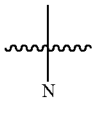

N moiety is attached via a linking group to groups $M^1$ and $M^2$;

in formula (c), the

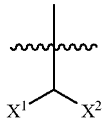

moiety is attached via a linking group to groups $M^1$ and $M^2$ $X^1$, $X^2$ and $X^3$ are each independently selected from $CR^a$, C═O, $NR^b$ or O, and at least one of $X^1$, $X^2$ and $X^3$ is C═O;

$X^4$ and $X^5$ are each independently selected from C or N;

$M^1$ and $M^2$ are each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy $C_{2-8}$alkenyl, $C_{2-8}$alkynyl, —$C_{1-6}$alkyl-R', —$C_{1-6}$alkoxy-R', —O—R', —C(O)—R', —$SO_2$—R', or —$NR^b$C(O)—R', or $M^1$ and $M^2$ together with the atoms to which they are attached may form a 3-8-membered cycloalkyl; or the

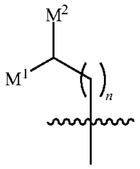

moiety may form a hydrogen atom;

$Cy^2$ is selected from 3-12-membered cycloalkyl, 3-12-membered cycloalkenyl, 3-14-membered heterocyclyl, 6-14-membered aryl, or 5-10-membered heteroaryl, all of which are optionally substituted by one or more $R^2$, $R^2$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)R', 3-12-membered cycloalkyl, 3-12-membered cycloalkenyl, 3-14-membered heterocyclyl, 6-14-membered aryl, or 5-10-membered heteroaryl;

$Cy^3$ is selected from 3-12-membered cycloalkyl, 3-14-membered heterocyclyl, or 5-10-membered heteroaryl, all of which are optionally substituted by one or more $R^3$, $R^3$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^bC(O)$—R', 3-12-membered cycloalkyl, 3-12-membered cycloalkenyl, 3-14-membered heterocyclyl, 6-14-membered aryl, or 5-10-membered heteroaryl; when $X^1$ or $X^2$ represents $NR^b$, $Cy^3$ may also be a 6-14 membered aromatic group optionally substituted by one or more $R^3$;

$Cy^4$ is selected from 3-14-membered heterocyclyl or 5-14-membered heteroaryl, both of which are optionally substituted by one or more $R^4$, $R^4$ is each independently selected from hydrogen, cyano, hydroxy, halogen, carboxyl, nitro, —$NR^bR^c$, —$C(O)R^d$, —$C(O)NR^cR^d$, —$OC(O)NR^bR^c$, —$NR^bC(O)OR^d$, —$NR^bC(O)R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$ alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$ alkyl-R', —$C_{1-6}$alkoxy-R', —O—R', —C(O)—R', —$SO_2$—R', —$NR^bC(O)$—R', 3-12-membered cycloalkyl, 3-12-membered cycloalkenyl, 3-14-membered heterocyclyl, 6-14-membered aryl, or 5-10-membered heteroaryl, or two $R^4$ together with the atoms to which they are attached may form a 5-6-membered cyclic group;

L is selected from —$NR^b$—, —O—, —S—, or —$(CR^aR^a)_m$—, m is an integer of 1-3;

$R^a$ is absent, or at each occurrence, is each independently selected from hydrogen, cyano, hydroxy, halogen, carboxyl, nitro, —$NR^eR^f$, —$C(O)R^g$, —$C(O)NR^eR^f$, —$OC(O)NR^eR^f$, —$NR^eC(O)OR^g$, —$NR^eC(O)R^g$, —$SO_2$—$NR^eR^f$, —$SO_2R^g$, —$NR^eSO_2R^g$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^eC(O)$—R', 3-12-membered cycloalkyl, 3-12-membered cycloalkenyl, 3-14-membered heterocyclyl, 6-14-membered aryl, or 5-10-membered heteroaryl;

$R^b$ and $R^c$ are absent, or at each occurrence, are each independently selected from hydrogen, hydroxy, —$C(O)R^g$, —$C(O)NR^eR^f$, —$SO_2$—$NR^eR^f$, —$SO_2R^g$, $C_{1-6}$alkyl, hydroxy$C_{1-6}$alkyl, cyano$C_{1-6}$alkyl, amino$C_{1-6}$ alkyl, $C_{1-6}$alkylamino$C_{1-6}$alkyl, halo$C_{1-6}$alkyl, $C_{1-6}$alkoxy$C_{1-6}$alkyl, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

$R^d$ is absent, or at each occurrence, is each independently selected from hydrogen, —$NR^eR^f$, —$NR^eC(O)OR^g$, —$NR^eC(O)R^g$, —$NR^eSO_2R^f$, $C_{1-6}$alkyl, hydroxy$C_{1-6}$ alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$ alkoxy, $C_{1-6}$alkoxy$C_{1-6}$alkyl, $C_{1-6}$alkoxy$C_{1-6}$alkoxy, —$C_{1-6}$alkyl-R', —$C_{1-6}$alkoxy-R', —O—R', —$NR^eC(O)$—R', 3-12-membered cycloalkyl, 3-12-membered cycloalkenyl, 3-14-membered heterocyclyl, 6-14-membered aryl, or 5-10-membered heteroaryl;

$R^e$ and $R^f$ are absent, or at each occurrence, are independently selected from hydrogen, hydroxy, carboxyl, cyano, nitro, halogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy$C_{1-6}$alkyl, 3-12-membered cycloalkyl, 3-12-membered cycloalkenyl, 3-14-membered heterocyclyl, 6-14-membered aryl, or 5-10-membered heteroaryl;

$R^g$ is absent, or at each occurrence, is independently selected from hydrogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, 3-12-membered cycloalkyl, 3-12-membered cycloalkenyl, 3-14-membered heterocyclyl, 6-14-membered aryl, or 5-10-membered heteroaryl;

R' is selected from 3-12-membered cycloalkyl, 3-12-membered cycloalkenyl, 3-14-membered heterocyclyl, 6-14-membered aryl, or 5-10-membered heteroaryl;

n is an integer of 0-4,

 in the groups represented by formula (b) and formula (c) represents a double bond moiety that is optionally present in the cyclic structure;

provided that in the groups represented by formula (a) and formula (c), the

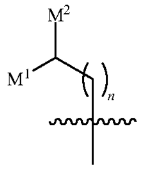

moiety will not form a hydrogen atom;

provided that in the group represented by formula (b), when $X^1$ and $X^3$ are C═O, and $X^4$ is N, $R^2$ as the substituent of $Cy^2$ does not represent a halogen atom.

In another embodiment, provided is the aforesaid compound represented by formula (I) or a pharmaceutically acceptable salt, an ester, a stereoisomer, or a tautomer thereof, (I)

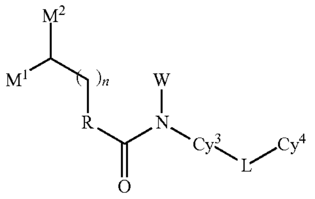

wherein W is selected from hydrogen or $C_{1-6}$alkyl;

R represent a group represented by the following formula (a), (b), (b-1), (b-2) or (c):

(a)

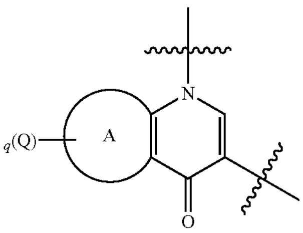

or

-continued (b)

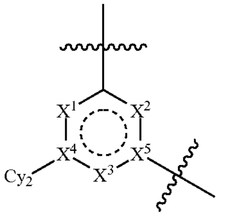

or (c)

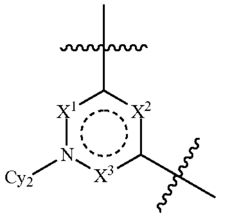

or (b-1)

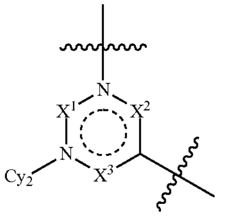

or (b-2)

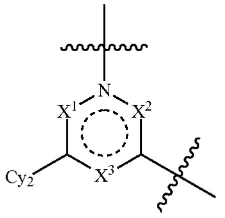

, in formula (a), ring A is selected from phenyl, 5-6-membered heteroaryl or 5-6-membered heterocyclyl;

Q is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R', 3-12-membered cycloalkyl, 3-12-membered cycloalkenyl, 3-14-membered heterocyclyl, 6-14-membered aryl, or 5-10-membered heteroaryl;

q is an integer of 0-4;

in formulae (a), (b), (b-1) and (b-2), the

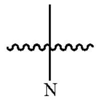 [SMILES: *N]

moiety is attached via a linking group to groups $M^1$ and $M^2$; in formula (c), the

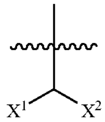

moiety is attached via a linking group to groups $M^1$ and $M^2$ $X^1$, $X^2$ and $X^3$ are each independently selected from $CR^a$, C═O, $NR^b$ or O, and at least one of $X^1$, $X^2$ and $X^3$ is C═O;

$M^1$ and $M^2$ are each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', or —$NR^b$C(O)—R'; or $M^1$ and $M^2$ together with the atoms to which they are attached may form 3-8-membered cycloalkyl; or the

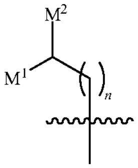

moiety may form a hydrogen atom;

$Cy^2$ is selected from 3-12-membered cycloalkyl, 3-12-membered cycloalkenyl, 3-14-membered heterocyclyl, 6-14-membered aryl, or 5-10-membered heteroaryl, all of which are optionally substituted by one or more $R^2$, $R^2$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R' —$C_{1-6}$alkoxy-R', —O—R', —C(O)—R', —$SO_2$—R', —$NR^b$C(O)—R', 3-12-membered cycloalkyl, 3-12-membered cycloalkenyl, 3-14-membered heterocyclyl, 6-14-membered aryl, or 5-10-membered heteroaryl;

$Cy^3$ is selected from 3-12-membered cycloalkyl, 3-14-membered heterocyclyl, or 5-10-membered heteroaryl, all of which are optionally substituted by one or more $R^3$, $R^3$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R', 3-12-membered cycloalkyl, 3-12-membered cycloalkenyl, 3-14-membered heterocyclyl, 6-14-membered aryl, or 5-10-membered heteroaryl; when $X^1$ or $X^2$ represents $NR^b$, $Cy^3$ may also be a 6-14 membered aromatic group optionally substituted by one or more $R^3$;

$Cy^4$ is selected from 3-14-membered heterocyclyl, or 5-14-membered heteroaryl, both of which are optionally substituted by one or more $R^4$, $R^4$ is each independently selected from hydrogen, cyano, hydroxy, halogen, carboxyl, nitro, —$NR^bR^c$, —$C(O)R^d$, —$C(O)NR^bR^c$, —$OC(O)NR^bR^c$, —$NR^bC(O)OR^d$, —$NR^bC(O)R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$ alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$ alkyl-R', —$C_{1-6}$alkoxy-R', —O—R', —C(O)—R', —$SO_2$—R', —$NR^bC(O)$—R', 3-12-membered cycloalkyl, 3-12-membered cycloalkenyl, 3-14-membered heterocyclyl, 6-14-membered aryl, or 5-10-membered heteroaryl, or two $R^4$ together with the atoms to which they are attached may form a 5-6-membered cyclic group;

L is selected from —$NR^b$—, —O—, —S—, or —$(CR^aR^a)_m$—, m is an integer of 1-3;

$R^a$ at each occurrence is each independently selected from hydrogen, cyano, hydroxy, halogen, carboxyl, nitro, —$NR^eR^f$, —$C(O)R^g$, —$C(O)NR^eR^f$, —$OC(O)NR^eR^f$, —$NR^eC(O)OR^g$, —$NR^eC(O)R^g$, —$SO_2$—$NR^eR^f$, —$SO_2R$, —$NR^eSO_2R^g$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R' —$NR^eC(O)$—R', 3-12-membered cycloalkyl, 3-12-membered cycloalkenyl, 3-14-membered heterocyclyl, 6-14-membered aryl, or 5-10-membered heteroaryl;

$R^b$ and $R^c$ at each occurrence are each independently selected from hydrogen, hydroxy, —$C(O)R^g$, —$C(O)NR^eR^f$, —$SO_2$—$NR^eR^f$, —$SO_2R^g$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy$C_{1-6}$ alkyl, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

$R^d$ at each occurrence is each independently selected from hydrogen, —$NR^eR^f$, —$NR^eC(O)OR^g$, —$NR^eC(O)R^g$, —$NR^eSO_2R^g$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, —$C_{1-6}$alkyl-R', —$C_{1-6}$alkoxy-R', —O—R', —$NR^eC(O)$—R', 3-12-membered cycloalkyl, 3-12-membered cycloalkenyl, 3-14-membered heterocyclyl, 6-14-membered aryl, or 5-10-membered heteroaryl;

$R^e$ and $R^f$ are absent, or at each occurrence, are independently selected from hydrogen, hydroxy, carboxyl, cyano, nitro, halogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy$C_{1-6}$alkyl, 3-12-membered cycloalkyl, 3-12-membered cycloalkenyl, 3-14-membered heterocyclyl, 6-14-membered aryl, or 5-10-membered heteroaryl;

$R^g$ is absent, or at each occurrence, is independently selected from hydrogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, 3-12-membered cycloalkyl, 3-12-membered cycloalkenyl, 3-14-membered heterocyclyl, 6-14-membered aryl, or 5-10-membered heteroaryl;

R' is selected from 3-12-membered cycloalkyl, 3-12-membered cycloalkenyl, 3-14-membered heterocyclyl, 6-14-membered aryl, or 5-10-membered heteroaryl;

n is an integer of 0-4,

 in the groups represented by formula (b), formula (b-1) and formula (b-2) represents a double bond moiety that is optionally present in the cyclic structure;

provided that in the groups represented by formula (a) and formula (c), the

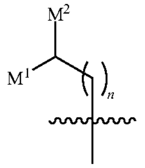

moiety will not form a hydrogen atom;

provided that in the group represented by formula (b), when $X^1$ and $X^3$ are C═O, and $X^4$ is N, $R^2$ as the substituent of $Cy^2$ does not represent a halogen atom, in the group represented by formula (b-1), when $X^1$ and $X^3$ are C═O, $R^2$ as the substituent of $Cy^2$ does not represent a halogen atom.

In another preferable embodiment, provided is the aforesaid compound represented by formula (I) or a pharmaceutically acceptable salt, an ester, a stereoisomer, or a tautomer thereof, wherein W is selected from hydrogen or $C_{1-6}$alkyl;

R represent a group represented by the following formula (a), (b-1) or (b-2):

(a)

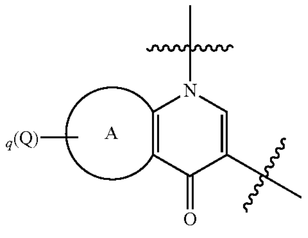

or (b-1)

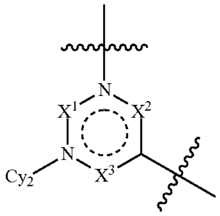

or

-continued (b-2)

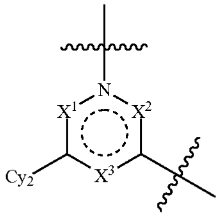

in formula (a), ring A is selected from phenyl, 5-6-membered heteroaryl or 5-6-membered heterocyclyl;

Q is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)R', 3-12-membered cycloalkyl, 3-12-membered cycloalkenyl, 3-14-membered heterocyclyl, 6-14-membered aryl, or 5-10-membered heteroaryl;

q is an integer of 0-4;

in formula (a), (b-1) or (b-2), the

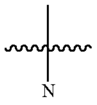 [SMILES: *N]

moiety is attached via a linking group to groups $M^1$ and $M^2$;

$X^1$, $X^2$ and $X^3$ are each independently selected from $CR^a$, C═O, $NR^b$ or O, and at least one of $X^1$, $X^2$ and $X^3$ is C═O;

$M^1$ and $M^2$ are each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^b$R', —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', or —$NR^b$C(O)—R', or $M^1$ and $M^2$ together with the atoms to which they are attached may form a 3-8-membered cycloalkyl; or the

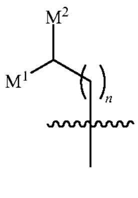

moiety may form a hydrogen atom;

$Cy^2$ is selected from 3-8-membered cycloalkyl, 3-8-membered cycloalkenyl, 3-10-membered heterocyclyl, 6-14-membered aryl, or 5-10-membered heteroaryl, all of which are optionally substituted by one or more $R^2$, $R^2$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R', 3-12-membered cycloalkyl, 3-12-membered cycloalkenyl, 3-14-membered heterocyclyl, 6-14-membered aryl, or 5-10-membered heteroaryl;

$Cy^3$ is selected from 3-8-membered cycloalkyl, 3-10-membered heterocyclyl, or 5-10-membered heteroaryl, all of which are optionally substituted by one or more $R^3$, $R^3$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R', 3-12-membered cycloalkyl, 3-12-membered cycloalkenyl, 3-14-membered heterocyclyl, 6-14-membered aryl, or 5-10-membered heteroaryl; when $X^1$ or $X^2$ represents $NR^b$, $Cy^3$ may also be a 6-14 membered aromatic group optionally substituted by one or more $R^3$;

$Cy^4$ is selected from 3-10-membered heterocyclyl, or 5-10-membered heteroaryl, both of which are optionally substituted by one or more $R^4$, $R^4$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)O$R^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$ alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$ alkyl-R', —$C_{1-6}$alkoxy-R', —O—R', —C(O)—R', —$SO_2$—R', —$NR^b$C(O)—R', 3-12-membered cycloalkyl, 3-12-membered cycloalkenyl, 3-14-membered heterocyclyl, 6-14-membered aryl, or 5-10-membered heteroaryl, or two $R^4$ together with the atoms to which they are attached may form a 5-6-membered cyclic group;

L is selected from —$NR^b$—, —O—, or —S—;

$R^a$ is absent, or at each occurrence, is each independently selected from hydrogen, cyano, hydroxy, halogen, carboxyl, nitro, —$NR^eR^f$, —C(O)$R^e$, —C(O)$NR^eR^f$, —OC(O)$NR^eR^f$, —$NR^e$C(O)O$R^f$, —$NR^e$C(O)$R^f$, —$SO_2$—$NR^eR^f$, —$SO_2R^g$, —$NR^eSO_2R^g$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^e$C(O)—R', 3-8-membered cycloalkyl, 3-10-membered cycloalkenyl, 3-14-membered heterocyclyl, 6-14-membered aryl, or 5-10-membered heteroaryl;

$R^b$ and $R^c$ are absent, or at each occurrence, are each independently selected from hydrogen, hydroxy, —C(O)$R^g$, —C(O)$NR^eR^f$, —$SO_2$—$NR^eR^f$, —$SO_2R^g$, $C_{1-6}$alkyl, hydroxy$C_{1-6}$alkyl, cyano$C_{1-6}$alkyl, amino$C_{1-6}$ alkyl, $C_{1-6}$alkylamino$C_{1-6}$alkyl, halo$C_{1-6}$alkyl, $C_{1-6}$alkoxy$C_{1-6}$alkyl, —$C_{1-6}$alkyl-R', —C(O)—R', —$SO_2$—R', 3-10-membered cycloalkyl, 3-10-membered cycloalkenyl, 3-14-membered heterocyclyl, 6-14-membered aryl, or 5-10-membered heteroaryl;

$R^d$ is absent, or at each occurrence, is each independently selected from hydrogen, —$NR^eR^f$, —$NR^eC(O)OR^g$, —$NR^eC(O)R^g$, —$NR^eSO_2R^g$, $C_{1-6}$alkyl, hydroxy$C_{1-6}$ alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$ alkoxy, $C_{1-6}$alkoxy$C_{1-6}$alkyl, $C_{1-6}$alkoxy$C_{1-6}$alkoxy, —$C_{1-6}$alkyl-R', —$C_{1-6}$alkoxy-R', —O—R', —$NR^e$C(O)—R', 3-12-membered cycloalkyl, 3-12-membered cycloalkenyl, 3-14-membered heterocyclyl, 6-14-membered aryl, or 5-10-membered heteroaryl;

$R^e$ and $R^f$ are absent, or at each occurrence, are independently selected from hydrogen, hydroxy, carboxyl, cyano, nitro, halogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy$C_{1-6}$alkyl, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

$R^g$ is absent, or at each occurrence, is independently selected from hydrogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

R' is 3-8-membered cycloalkyl, 3-10-membered cycloalkenyl, 3-14-membered heterocyclyl, 6-14-membered aryl, or 5-10-membered heteroaryl;

n is an integer of 0-4,

 in the groups represented by formula (b-1) and formula (b-2) represents a double bond moiety that is optionally present in the cyclic structure;

provided that in the group represented by formula (b-1), when $X^1$ and $X^3$ are C═O, $R^2$ as the substituent of $Cy^2$ does not represent a halogen atom; provided that in the groups represented by formula (a), the

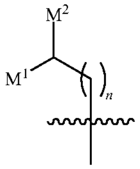

moiety will not form a hydrogen atom.

In another preferable embodiment, the aforesaid compound represented by formula (I), or a pharmaceutically acceptable salt, an ester, a stereoisomer, or a tautomer thereof, has a structure represented by general formula (II), (II)

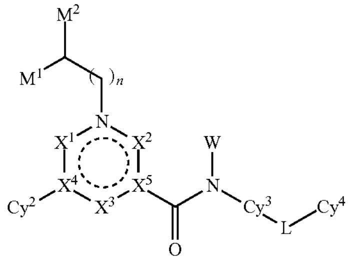

wherein W is selected from hydrogen or $C_{1-6}$alkyl;

is $X^1$, $X^2$ and $X^3$ are each independently selected from $CR^a$, C═O, or $NR^b$, and at least one of $X^1$, $X^2$ and $X^3$ is C═O;

$X^4$ and $X^5$ are each independently selected from C or N;

$M^1$ and $M^2$ are each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)$OR^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, or halo$C_{1-6}$alkoxy, or $M^1$ and $M^2$ together with the atoms to which they are attached may form a 3-8-membered cycloalkyl; or the

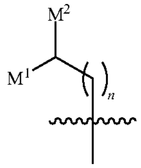

moiety may form a hydrogen atom;

$Cy^2$ is selected from 6-14-membered aryl, or 5-10-membered heteroaryl, both of which are optionally substituted by one or more $R^2$, $R^2$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)$OR^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R', 3-8-membered cycloalkyl, 3-8-membered cycloalkenyl, 3-14-membered heterocyclyl, 6-14-membered aryl, or 5-10-membered heteroaryl;

$Cy^3$ is selected from 3-8-membered cycloalkyl, or 5-10-membered heteroaryl, both of which are optionally substituted by one or more $R^3$, $R^3$ is each independently selected from hydrogen, cyano, hydroxy, halogen, carboxyl, nitro, —$NR^bR^c$, —C(O)$R^d$, —C(O)$NR^bR^c$, —OC(O)$NR^bR^c$, —$NR^b$C(O)$OR^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R', 3-8-membered cycloalkyl, 3-8-membered cycloalkenyl, 3-14-membered heterocyclyl, 6-14-membered aryl, or 5-10-membered heteroaryl; when $X^1$ or $X^2$ represents $NR^b$, $Cy^3$ may also be a 6-14 membered aromatic group optionally substituted by one or more $R^3$;

$Cy^4$ is 9-10-membered heteroaryl optionally substituted by one or more $R^4$, $R^4$ is each independently selected from hydrogen, cyano, hydroxy, halogen, carboxyl, nitro, —$NR^bR^c$, —$C(O)R^d$, —C(O))$NR^bR^c$, —OC(O)$NR^bR^c$, —$NR^bC(O)OR^d$, —$NR^bC(O)R^d$, —$SO_2$—$NR^bR^c$, —$SO_2R^d$, —$NR^cSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^bC(O)$—R', 3-8-membered cycloalkyl, 3-8-membered cycloalkenyl, 3-14-membered heterocyclyl, 6-14-membered aryl, or 5-10-membered heteroaryl, or two $R^4$ together with the atoms to which they are attached may form a 5-6-membered cyclic group;

L is selected from —$NR^b$—, —O—, or —S—;

$R^a$ is absent, or at each occurrence, is each independently selected from hydrogen, cyano, hydroxy, halogen, carboxyl, nitro, —$NR^eR^f$, —$C(O)R^g$, —$C(O)NR^eR^f$, —$OC(O)NR^eR^f$, —$NR^eC(O)OR^g$, —$NR^eC(O)R^g$, —$SO_2$—$NR^eR^f$, —$SO_2R^g$, —$NR^eSO_2R^g$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$-alkyl-R', —$C_{1-6}$alkoxy-R', —O—R', —C(O)—R', —$SO_2$—R', —$NR^eC(O)$—R', 3-8-membered cycloalkyl, 3-8-membered cycloalkenyl, 3-14-membered heterocyclyl, 6-14-membered aryl, or 5-10-membered heteroaryl;

$R^b$ and $R^c$ are absent, or at each occurrence, are each independently selected from hydrogen, hydroxy, —C(O)R—, —$C(O)NR^eR^f$, —$SO_2$—$NR^eR^f$, —$SO_2R^f$, $C_{1-6}$alkyl, hydroxy$C_{1-6}$alkyl, cyano$C_{1-6}$alkyl, amino$C_{1-6}$ alkyl, $C_{1-6}$alkylamino$C_{1-6}$alkyl, halo$C_{1-6}$alkyl, $C_{1-6}$alkoxy$C_{1-6}$alkyl, —$C_{1-6}$alkyl-R', —C(O)—R', —$SO_2$—R', 3-8-membered cycloalkyl, 3-8-membered cycloalkenyl, 3-14-membered heterocyclyl, 6-14-membered aryl, or 5-10-membered heteroaryl;

$R^d$ is absent, or at each occurrence, is each independently selected from hydrogen, —$NR^eR^f$, —$NR^eC(O)OR^f$, —$NR^eC(O)R^g$, —$NR^eSO_2R^f$, $C_{1-6}$alkyl, hydroxy$C_{1-6}$ alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$ alkoxy, $C_{1-6}$alkoxy$C_{1-6}$alkyl, $C_{1-6}$alkoxy$C_{1-6}$alkoxy, —$C_{1-6}$alkyl-R', —$C_{1-6}$alkoxy-R', —O—R', —$NR^eC(O)R^g$, 3-8-membered cycloalkyl, 3-8-membered cycloalkenyl, 3-14-membered heterocyclyl, 6-14-membered aryl, or 5-10-membered heteroaryl;

$R^e$ and $R^f$ are absent, or at each occurrence, are independently selected from hydrogen, hydroxy, carboxyl, cyano, nitro, halogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy$C_{1-6}$alkyl, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

$R^g$ is absent, or at each occurrence, is independently selected from hydrogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

R' is selected from 3-8-membered cycloalkyl, 3-8-membered cycloalkenyl, 3-14-membered heterocyclyl, 6-14-membered aryl, or 5-10-membered heteroaryl;

n is an integer of 0-3;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is C═O, $X^2$ is $CR^a$, and $X^3$ is C═O;

preferably, $X^1$ is $CR^a$, $X^2$ is C═O, and $X^3$ is C═O;

preferably, $X^1$ is $CR^a$, $X^2$ is $CR^a$, and $X^3$ is C═O;

preferably, $X^1$ is C═O, $X^2$ is $CR^a$, and $X^3$ is $CR^a$;

preferably, $X^1$ is $CR^a$, $X^2$ is C═O, and $X^3$ is $CR^a$,

 represents a double bond moiety that is optionally present in the cyclic structure;

provided that when $X^1$ and $X^3$ are C═O, and $X^4$ is N, $R^2$ as the substituent of $Cy^2$ does not represent a halogen atom.

In another preferable embodiment, the aforesaid compound represented by formula (I) or the aforesaid compound represented by general formula (II), or a pharmaceutically acceptable salt, an ester, a stereoisomer, or a tautomer thereof, has a structure represented by general formula (II), (II)

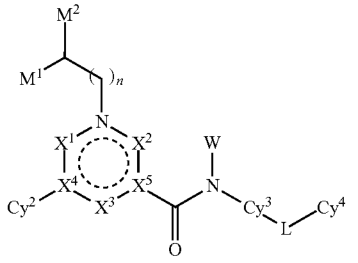

wherein W is selected from hydrogen or $C_{1-6}$alkyl;

$X^1$, $X^2$ and $X^3$ are each independently selected from $CR^a$, C═O, or $NR^b$, and at least one of $X^1$, $X^2$ and $X^3$ is C═O;

$M^1$ and $M^2$ are each independently selected from hydrogen, cyano, hydroxy, halogen, carboxyl, nitro, —$NR^bR^c$, —$C(O)R^d$, —$C(O)NR^bR^c$, —$OC(O)NR^bR^c$, —$NR^bC(O)OR^d$, —$NR^bC(O)R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, or halo$C_{1-6}$alkoxy, or $M^1$ and $M^2$ together with the atoms to which they are attached may form a 3-8-membered cycloalkyl; or the

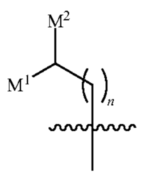

moiety may form a hydrogen atom:

$Cy^2$ is selected from 6-14-membered aryl, or 5-10-membered heteroaryl, both of which are optionally substituted by one or more $R^2$, $R^2$ is each independently selected from hydrogen, cyano, hydroxy, halogen, carboxyl, nitro, —$NR^bR^c$, —$C(O)R^d$, —$C(O)NR^bR^c$, —$OC(O)NR^bR^c$, —$NR^bC(O)OR^d$, —$NR^bC(O)R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^bC(O)$—R', 3-8-membered cycloalkyl, 3-8-membered cycloalkenyl, 3-14-membered heterocyclyl, 6-14-membered aryl, or 5-10-membered heteroaryl;

$Cy^3$ is selected from 3-8-membered cycloalkyl, or 5-10-membered heteroaryl, both of which are optionally substituted by one or more $R^3$, $R^3$ is each independently selected from hydrogen, cyano, hydroxy, halogen carboxyl, nitro, —$NR^bR^c$, —$C(O)R^d$, —$C(O)NR^bR^c$, —$OC(O)NR^bR^c$, —$NR^bC(O)OR^d$, —$NR^bC(O)R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^bC(O)$—R', 3-8-membered cycloalkyl, 3-8-membered cycloalkenyl, 3-14-membered heterocyclyl, 6-14-membered aryl, or 5-10-membered heteroaryl; when $X^1$ or $X^2$ represents $NR^b$, $Cy^3$ may also be a 6-14 membered aromatic group optionally substituted by one or more $R^3$;

$Cy^4$ is 9-10-membered heteroaryl optionally substituted by one or more $R^4$, $R^4$ is each independently selected from hydrogen, cyano, hydroxy, halogen, carboxyl, nitro, —$NR^bR^c$, —$C(O)R^d$, —$C(O)NR^bR^c$, —$OC(O)NR^cR^d$, —$NR^bC(O)OR^d$, —$NR^bC(O)R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^bC(O)$—R', 3-8-membered cycloalkyl, 3-8-membered cycloalkenyl, 3-14-membered heterocyclyl, 6-14-membered aryl, or 5-10-membered heteroaryl, or two $R^4$ together with the atoms to which they are attached may form a 5-6-membered cyclic group;

L is selected from —$NR^b$—, —O—, or —S—;

$R^a$ at each occurrence is each independently selected from hydrogen, cyano, hydroxy, halogen, carboxyl, nitro, —$NR^eR^f$, —$C(O)R^g$, —$C(O)NR^eR^f$, —$OC(O)NR^eR^f$, —$NR^eC(O)OR^g$, —$NR^eC(O)R^g$, —$SO_2$—$NR^eR^f$, —$SO_2R^g$, —$NR^eSO_2R^g$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^eC(O)$—R', 3-8-membered cycloalkyl, 3-8-membered cycloalkenyl, 3-14-membered heterocyclyl, 6-14-membered aryl, or 5-10-membered heteroaryl;

$R^b$ and $R^c$ at each occurrence are each independently selected from hydrogen, hydroxy, —$C(O)R^g$, —$C(O)NR^eR^f$, —$SO_2$—$NR^eR^f$, —$SO_2R^g$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy$C_{1-6}$ alkyl, —$C_{1-6}$alkyl-R', —C(O)—R', —$SO_2$—R, 3-8-membered cycloalkyl, 3-8-membered cycloalkenyl, 3-14-membered heterocyclyl, 6-14-membered aryl, or 5-10-membered heteroaryl;

$R^d$ at each occurrence is each independently selected from hydrogen, —$NR^eR^f$, —$NR^eC(O)OR^g$, —$NR^eC(O)R^g$, —$NR^eSO_2R^g$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, —$C_{1-6}$alkyl-R', —$C_{1-6}$alkoxy-R', —O—R', —$NR^eC(O)$—R', 3-8-membered cycloalkyl, 3-8-membered cycloalkenyl, 3-14-membered heterocyclyl, 6-14-membered aryl, or 5-10-membered heteroaryl;

$R^e$ and $R^f$ are absent, or at each occurrence, are independently selected from hydrogen, hydroxy, carboxyl, cyano, nitro, halogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy$C_{1-6}$alkyl, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

$R^g$ is absent, or at each occurrence, is independently selected from hydrogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

n is an integer of 0-3;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is C═O, $X^2$ is $CR^a$, and $X^3$ is C═O;

preferably, $X^1$ is $CR^a$, $X^2$ is C═O, and $X^3$ is C═O;

preferably, $X^1$ is $CR^a$, $X^2$ is $CR^a$, and $X^3$ is C═O;

preferably, $X^1$ is C═O, $X^2$ is $CR^a$, and $X^3$ is $CR^a$;

preferably, $X^1$ is $CR^a$, $X^2$ is C═O, and $X^3$ is $CR^a$,

 represents a double bond moiety that is optionally present in the cyclic structure;

provided that when $X^1$ and $X^3$ are C═O, and $X^4$ is N, $R^2$ as the substituent of $Cy^2$ does not represent a halogen atom.

In another preferable embodiment, provided is the aforesaid compound represented by formula (I) or (II), or a pharmaceutically acceptable salt, an ester, a stereoisomer, or a tautomer thereof, wherein $X^1$, $X^2$ and $X^3$ are each independently selected from $CR^a$, C═O, or $NR^b$, and at least one of $X^1$, $X^2$ and $X^3$ is C═O;

$X^4$ is selected from C or N, $X^5$ is C;

$M^1$ and $M^2$ are each independently selected from hydrogen, hydroxy, halogen, carboxyl, nitro, —$NR^bR^c$, —$C(O)R^d$, —$C(O)NR^bR^c$, —$NR^bC(O)R^d$, and $C_{1-6}$alkyl, or $M^1$ and $M^2$ together with the atoms to which they are attached may form a 3-8-membered cycloalkyl; or the

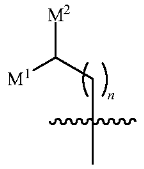

moiety may form a hydrogen atom;

$Cy^2$ is selected from phenyl, or 5-6-membered heteroaryl, both of which are optionally substituted by one or more $R^2$, $R^2$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$Cy^3$ is selected from 5-6-membered heteroaryl, or 3-6-membered cycloalkyl, both of which are optionally substituted by one or more $R^3$, $R^3$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$Cy^4$ is 9-10-membered heteroaryl optionally substituted by one or more $R^4$, $R^4$ is each independently selected from hydrogen, hydroxy, halogen, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is C═O, $X^2$ is $CR^a$, and $X^3$ is C═O;

preferably, $X^1$ is $CR^a$, $X^2$ is $CR^a$, and $X^3$ is C═O;

preferably, $X^1$ is C═O, $X^2$ is $CR^a$, and $X^3$ is $CR^a$;

preferably, $X^1$ is $CR^a$, $X^2$ is C═O, and $X^3$ is $CR^a$;

preferably, $Cy^3$ is

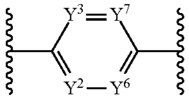, $Y^2$, $Y^3$, $Y^6$, and $Y^7$ are each independently selected from CH or N, and at least one of $Y^2$, $Y^3$, $Y^6$, and $Y^7$ is N.

In another preferable embodiment, provided is the aforesaid compound represented by formula (I) or formula (II), or a pharmaceutically acceptable salt, an ester, a stereoisomer, or a tautomer thereof, wherein $X^1$, $X^2$ and $X^3$ are each independently selected from $CR^a$, C═O, or $NR^b$, and at least one of $X^1$, $X^2$ and $X^3$ is C═O;

$X^4$ is selected from C or N, $X^5$ is C;

$Cy^2$ is selected from phenyl, or 5-6-membered heteroaryl, both of which are optionally substituted by one or more $R^2$ $Cy^3$ represents

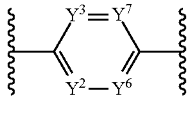

optionally substituted by one or more $R^3$;

$Y^2$, $Y^3$, $Y^6$ and $Y^7$ are each independently selected from CH or N, and at least one of $Y^2$, $Y^3$, $Y^6$ and $Y^7$ is N;

$Cy^4$ is

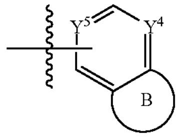

optionally substituted by one or more $R^4$, $Y^4$ and $Y^5$ are independently selected from CH or N, and at least one of $Y^4$ and $Y^5$ is N, ring B is phenyl or 5-6-membered heteroaryl;

$M^1$ and $M^2$ are each independently selected from hydrogen, hydroxy, halogen, carboxyl, nitro, —$NR^bR^c$, —C(O)$R^d$, —C(O)$NR^bR^c$, —$NR^b$C(O)$R^d$, or $C_{1-6}$alkyl, or $M^1$ and $M^2$ together with the atoms to which they are attached may form a 3-6-membered cycloalkyl; or the

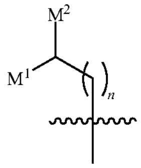

moiety may form a hydrogen atom;

$R^2$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^3$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is C═O, $X^2$ is $CR^a$, and $X^3$ is C═O;

preferably, $X^1$ is $CR^a$, $X^2$ is $CR^a$, and $X^3$ is C═O;

preferably, $X^1$ is C═O, $X^2$ is $CR^a$, and $X^3$ is $CR^a$;

preferably, $X^1$ is $CR^a$, $X^2$ is C═O, and $X^3$ is $CR^a$.

In another preferable embodiment, the aforesaid compound represented by formula (I) or formula (II), or a pharmaceutically acceptable salt, an ester, a stereoisomer, or a tautomer thereof, has a structure represented by general formula (III), (III)

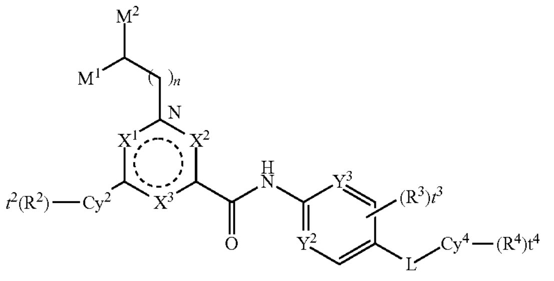

wherein $X^1$, $X^2$ and $X^3$ are each independently selected from $CR^a$, C═O, or $NR^b$, and at least one of $X^1$, $X^2$ and $X^3$ is C═O;

$Cy^2$ is selected from phenyl, or 5-6-membered heteroaryl;

$Y^2$ and $Y^3$ are independently selected from CH or N, and at least one of $Y^2$ and $Y^3$ is N;

$Cy^4$ is

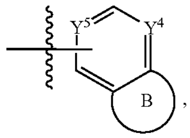, $Y^4$ and $Y^5$ are independently selected from CH or N, and at least one of $Y^4$ and $Y^5$ is N, ring B is phenyl or 5-6-membered heteroaryl;

$M^1$ and $M^2$ are each independently selected from hydrogen, hydroxy, halogen, carboxyl, nitro, —$NR^bR^c$, —C(O)$R^d$, —C(O)$NR^bR^c$, —$NR^b$C(O)$R^d$, or $C_{1-6}$alkyl, or $M^1$ and $M^2$ together with the atoms to which they are attached may form a 3-6-membered cycloalkyl; or the

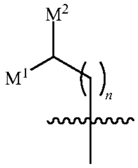

moiety may form a hydrogen atom;

$R^2$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^3$ is each independently selected from hydrogen, hydroxy, halogen, carboxyl, nitro, —$NR^bR^c$, —C(O)$R^d$, —C(O)$NR^bR^c$, —$NR^b$C(O)$R^c$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$ alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2;

$t^2$, $t^3$ and $t^4$ are each independently selected from an integer of 1-5;

 represents a double bond moiety that is optionally present in the cyclic structure;

provided that when $X^1$ and $X^3$ are C═O, $R^2$ as the substituent of $Cy^2$ does not represent a halogen atom;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is C═O, $X^2$ is $CR^a$, and $X^3$ is C═O;

preferably, $X^1$ is $CR^a$, $X^2$ is $CR^a$, and $X^3$ is C═O;

preferably, $X^1$ is C═O, $X^2$ is $CR^a$, and $X^3$ is $CR^a$;

preferably, $X^1$ is $CR^a$, $X^2$ is C═O, and $X^3$ is $CR^a$.

In another preferable embodiment, the aforesaid compound represented by formula (I) or formula (II), or a pharmaceutically acceptable salt, an ester, a stereoisomer, or a tautomer thereof, has a structure represented by general formula (IV), (IV)

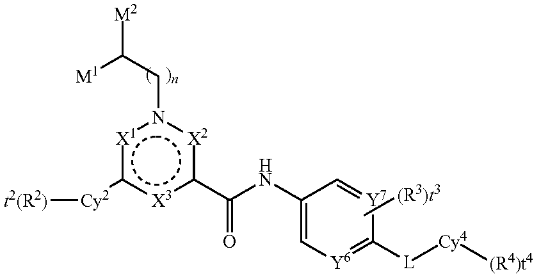

wherein $X^1$, $X^2$ and $X^3$ are each independently selected from $CR^a$, C═O, or $NR^b$, and at least one of $X^1$, $X^2$ and $X^3$ is C═O;

$Cy^2$ is selected from phenyl, or 5-6-membered heteroaryl;

$Y^6$ and $Y^7$ are each independently selected from CH or N, and at least one of $Y^6$ and $Y^7$ is N;

$Cy^4$ is

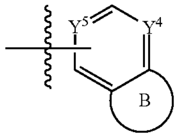, $Y^4$ and $Y^5$ are independently selected from CH or N, and at least one of $Y^4$ and $Y^5$ is N, ring B is phenyl or 5-6-membered heteroaryl;

$M^1$ and $M^2$ are each independently selected from hydrogen, hydroxy, halogen, carboxyl, nitro, —$NR^bR^c$, —$C(O)R^d$, —$C(O)NR^bR^c$, —$NR^bC(O)R^d$, or $C_{1-6}$alkyl, or $M^1$ and $M^2$ together with the atoms to which they are attached may form a 3-6-membered cycloalkyl; or the

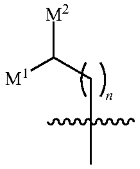

moiety may form a hydrogen atom;

$R^2$ is each independently selected from hydrogen, hydroxy, halogen, carboxyl, nitro, —$NR^bR^c$, —$C(O)R^d$, —$C(O)NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^3$ is each independently selected from hydrogen, hydroxy, halogen, carboxyl, nitro, —$NR^bR^c$, —$C(O)R^d$, —$C(O)NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, nitro, —$NR^bR^c$, —$C(O)R^d$, —$C(O)NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

is L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2;

$t^2$, $t^3$ and $t^4$ are each independently selected from an integer of 1-5;

 represents a double bond moiety that is optionally present in the cyclic structure;

provided that when $X^1$ and $X^3$ are C═O, $R^2$ as the substituent of $Cy^2$ does not represent a halogen atom;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is C═O, $X^2$ is $CR^a$, and $X^3$ is C═O;

preferably, $X^1$ is $CR^a$, $X^2$ is $CR^a$, and $X^3$ is C═O;

preferably, $X^1$ is C═O, $X^2$ is $CR^a$, and $X^3$ is $CR^a$;

preferably, $X^1$ is $CR^a$, $X^2$ is C═O, and $X^3$ is $CR^a$.

In another preferable embodiment, provided is the aforesaid compound represented by formula (I) or formula (II), or a pharmaceutically acceptable salt, an ester, a stereoisomer, or a tautomer thereof, wherein R represents the following group, (b-1)

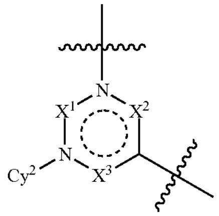

$X^1$, $X^2$ and $X^3$ are each independently selected from $CR^a$, C═O, or $NR^b$, and at least one of $X^1$, $X^2$ and $X^3$ is C═O;

$Cy^2$ is selected from phenyl, or 5-6-membered heteroaryl, both of which are optionally substituted by one or more $R^2$;

$Cy^3$ represents

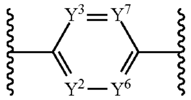

optionally substituted by one or more $R^3$;

$Y^2$, $Y^3$, $Y^6$ and $Y^7$ are each independently selected from CH or N, and at least one of $Y^2$, $Y^3$, $Y^6$ and $Y^7$ is N;

$Cy^4$ is

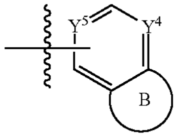

optionally substituted by one or more $R^4$, $Y^4$ and $Y^5$ are independently selected from CH or N, and at least one of $Y^4$ and $Y^5$ is N, ring B is phenyl or 5-6-membered heteroaryl;

$M^1$ and $M^2$ are each independently selected from hydrogen, hydroxy, halogen, carboxyl, nitro, —$NR^bR^c$, —$C(O)R^d$, —$C(O)NR^bR^c$, —$NR^bC(O)R^d$, or $C_{1-6}$alkyl, or $M^1$ and $M^2$ together with the atoms to which they are attached may form a 3-6-membered cycloalkyl; or the

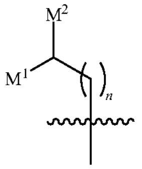

moiety may form a hydrogen atom;

$R^2$ is each independently selected from hydrogen, hydroxy, halogen, carboxyl, nitro, —$NR^bR^c$, —$C(O)R^d$, —$C(O)NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^3$ is each independently selected from hydrogen, hydroxy, halogen, carboxyl, nitro, —$NR^bR^c$, —$C(O)R^d$, —$C(O)NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, nitro, —$NR^bR^c$, —$C(O)R^d$, —C(O)$NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$ alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

is L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2;

$t^2$, $t^3$ and $t^4$ are each independently selected from an integer of 1-5;

 represents a double bond moiety that is optionally present in the cyclic structure;

provided that when $X^1$ and $X^3$ are C═O, $R^2$ as the substituent of $Cy^2$ does not represent a halogen atom;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is C═O, $X^2$ is $CR^a$, and $X^3$ is C═O;

preferably, $X^1$ is $CR^a$, $X^2$ is $CR^a$, and $X^3$ is C═O;

preferably, $X^1$ is C═O, $X^2$ is $CR^a$, and $X^3$ is $CR^a$;

preferably, $X^1$ is $CR^a$, $X^2$ is C═O, and $X^3$ is $CR^a$.

In another preferable embodiment, provided is a compound represented by formula (I) or (II) or (III) or (IV), or a pharmaceutically acceptable salt, an ester, a stereoisomer, or a tautomer thereof, wherein $X^1$ and $X^2$ are each independently selected from $CR^a$ or $NR^b$, $X^3$ is C═O;

$Cy^2$ is phenyl optionally substituted by one or more $R^2$;

$Cy^3$ represents

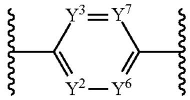

optionally substituted by one or more $R^3$;

$Y^2$ and $Y^3$ are independently selected from CH or N, and at least one of $Y^2$ and $Y^3$ is N, $Y^6$ and $Y^7$ are each independently selected from CH or N;

$Cy^4$ is selected from

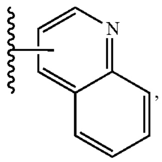, 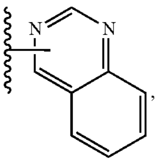, 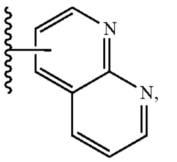

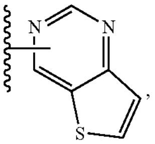, 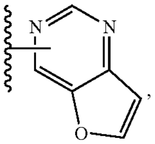, or 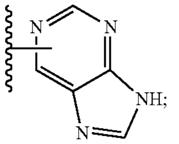

all of which are optionally substituted by one or more $R^4$;

$M^1$ and $M^2$ are each independently selected from hydrogen, hydroxy, halogen, carboxyl, nitro, —$NR^bR^c$, or $C_{1-6}$alkyl, or $M^1$ and $M^2$ together with the atoms to which they are attached may form a 3-6-membered cycloalkyl; or the

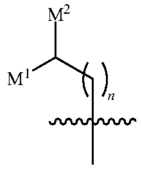

moiety may form a hydrogen atom;

$R^2$ is each independently selected from hydrogen, hydroxy, halogen, carboxyl, nitro, —$NR^bR^c$, —C(O)$R^d$, —C(O)$NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^3$ is each independently selected from hydrogen, hydroxy, halogen, carboxyl, nitro, —$NR^bR^c$, —C(O)$R^d$, —C(O)$NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, nitro, —$NR^bR^c$, —$C(O)R^d$, —C(O)$NR^bR^c$, —$NR^bC(O)R^d$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$ alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is selected from —NR—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-1;

$t^2$, $t^3$ and $t^4$ are each independently selected from an integer of 1-3;

preferably, $X^1$ is N, $X^2$ is $CR^3$, and $X^3$ is C═O;

preferably, $X^1$ is $CR^8$, $X^2$ is N, and $X^3$ is C═O;

preferably, $X^1$ is $CR^8$, $X^2$ is $CR^a$, and $X^3$ is C═O.

In another preferable embodiment, provided is a compound represented by formula (I) or (II) or (III) or (IV), or a pharmaceutically acceptable salt, an ester, a stereoisomer, or a tautomer thereof, wherein $M^1$ and $M^2$ are each independently selected from hydrogen, hydroxy, halogen, carboxyl, nitro, —$NR^bR^c$, —C(O)$R^d$, —C(O)$NR^bR^c$, —$NR^bC(O)R^d$, or $C_{1-6}$alkyl, or $M^1$ and $M^2$ together with the atoms to which they are attached may form a 3-6-membered cycloalkyl; or the

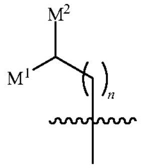

moiety may form a hydrogen atom;

$Cy^2$ is selected from phenyl, or pyridinyl, both of which are optionally substituted by one or more $R^2$, $R^2$ is each independently selected from hydrogen, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$Cy^3$ is selected from 5-6-membered nitrogen-containing heteroaryl optionally substituted by one or more $R^3$, $R^3$ is each independently selected from hydrogen, hydroxy, halogen, $C_{1-6}$alkyl, hydroxy$C_{1-6}$-alkyl, amino$C_{1-6}$alkyl, halo$C_{1-6}$alkyl, $C_{1-6}$alkoxy, or halo$C_{1-6}$ alkoxy;

$Cy^4$ is

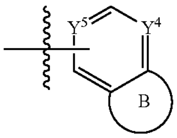

optionally substituted by one or more $R^4$, $Y^4$ and $Y^5$ are independently selected from CH or N, and at least one of $Y^4$ and $Y^5$ is N, ring B is phenyl or 5-6-membered heteroaryl;

$R^4$ is each independently selected from hydrogen, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$ alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is —O—;

$R^b$ is absent, or at each occurrence, is each independently selected from hydrogen, or $C_{1-6}$alkyl;

$R^d$ is absent, or at each occurrence, is each independently selected from hydrogen, or $C_{1-6}$alkyl;

n is an integer of 0-2;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is C═O, $X^2$ is $CR^a$, and $X^3$ is C═O;

preferably, $X^1$ is $CR^a$, $X^2$ is $CR^a$, and $X^3$ is C═O;

preferably, $X^1$ is C═O, $X^2$ is $CR^a$, and $X^3$ is $CR^a$;

preferably, $X^1$ is $CR^a$, $X^2$ is C═O, and $X^3$ is $CR^a$.

In another preferable embodiment, provided is a compound represented by formula (I) or (II) or (III) or (IV), or a pharmaceutically acceptable salt, an ester, a stereoisomer, or a tautomer thereof, wherein W is hydrogen;

$X^1$ and $X^2$ are each independently selected from $CR^a$ or $NR^b$, $X^3$ is C═O;

$X^4$ is selected from C or N;

$M^1$ and $M^2$ are each independently selected from hydrogen, hydroxy, halogen, nitro, or $C_{1-4}$alkyl, or $M^1$ and $M^2$ together with the atoms to which they are attached may form a 3-6-membered cycloalkyl; or the

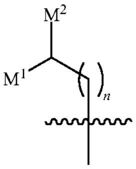

moiety may form a hydrogen atom;

$Cy^2$ is

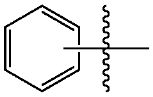

and

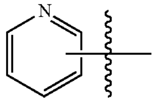

, both of which are optionally substituted by one or more $R^2$, $R^2$ is each independently selected from hydrogen, hydroxy, fluoro, chloro, bromo, or $C_{1-4}$alkyl;

$Cy^3$ is selected from

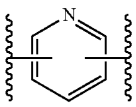

,

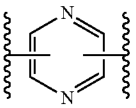

,

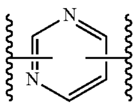

,

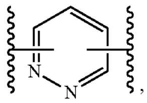

, or

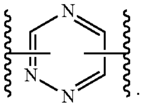

.

all of which are optionally substituted by one or more $R^3$, $R^3$ is each independently selected from hydrogen, hydroxy, fluoro, chloro, bromo, or $C_{1-4}$alkyl;

$Cy^4$ is selected from

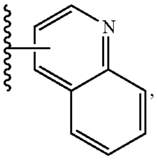

,

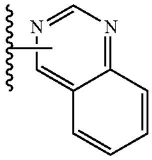

,

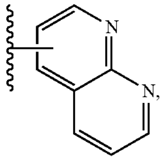

,

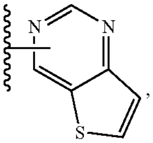

,

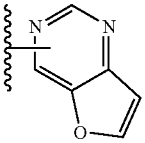

, or

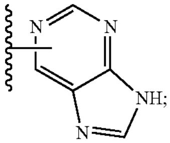

all of which are optionally substituted by one or more $R^4$;

$R^4$ is each independently selected from hydrogen, hydroxy, halogen, $C_{1-4}$alkyl, halo$C_{1-4}$alkyl, $C_{1-4}$alkoxy, halo$C_{1-4}$alkoxy, or 3-14-membered heterocyclyl, or two $R^4$ together with the atoms to which they are attached may form a 5-6-membered oxygen-containing cyclic group;

L is —O—;

$R^a$ is absent, or at each occurrence, is each independently selected from hydrogen, $C_{1-6}$alkyl, or halo$C_{1-6}$alkyl;

$R^b$ is absent, or at each occurrence, is each independently selected from hydrogen, or $C_{1-6}$alkyl;

n is an integer of 0-1;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is $CR^a$, $X^2$ is $CR^a$, and $X^3$ is C═O.

In another preferable embodiment, provided is a compound represented by formula (I) or (II) or (III) or (IV), or a pharmaceutically acceptable salt, an ester, a stereoisomer, or a tautomer thereof, wherein W is hydrogen;

$X^1$ and $X^2$ are selected from $CR^a$ or $NR^b$, $X^3$ is C═O;

$X^4$ is C;

$M^1$ and $M^2$ are each independently selected from hydrogen, hydroxy, or $C_{1-4}$alkyl, or $M^1$ and $M^2$ together with the atoms to which they are attached may form a 3-6-membered cycloalkyl; or the

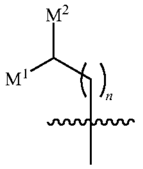

moiety may form a hydrogen atom;

$Cy^2$ is

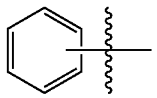

optionally substituted by one or more $R^2$, $R^2$ is each independently selected from hydrogen, fluoro, chloro, or $C_{1-4}$alkyl;

$Cy^3$ is selected from

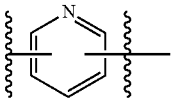,
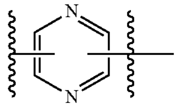,
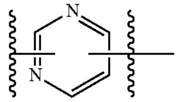,
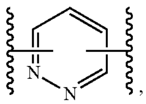, or
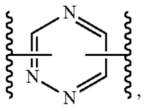, all of which are optionally substituted by one or more $R^3$, $R^3$ is each independently selected from hydrogen, fluoro, chloro, or $C_{1-4}$alkyl;

$Cy^4$ is

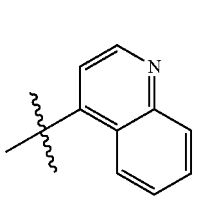 [SMILES: *c1ccnc2ccccc12]

optionally substituted by one or more $R^4$, $R^4$ is each independently selected from hydrogen, halogen, $C_{1-4}$alkyl, or $C_{1-4}$alkoxy, or two $R^4$ together with the atoms to which they are attached may form a 5-6-membered oxygen-containing cyclic group;

L is —O—;

$R^a$ is absent, or at each occurrence, is each independently selected from hydrogen, $C_{1-4}$alkyl, or halo$C_{1-6}$alkyl;

$R^b$ is absent, or at each occurrence, is each independently selected from hydrogen, or $C_{1-4}$alkyl;

n is an integer of 0-1;

preferably, $X^1$ is N, $X^2$ is $CR^a$, and $X^3$ is C═O;

preferably, $X^1$ is $CR^a$, $X^2$ is N, and $X^3$ is C═O;

preferably, $X^1$ is $CR^a$, $X^2$ is $CR^a$, and $X^3$ is C═O.

In another preferable embodiment, provided is a compound represented by formula (I) or (II) or (III) or (IV), or a pharmaceutically acceptable salt, an ester, a stereoisomer, or a tautomer thereof, $X^1$ and $X^3$ are each independently selected from $CR^a$, C═O, or $NR^b$, and $X^1$ and $X^3$ are not both C═O simultaneously; $X^2$ is $CR^a$ or $NR^b$.

In another preferable embodiment, provided is a compound represented by formula (I) or (II) or (III) or (IV), or a pharmaceutically acceptable salt, an ester, a stereoisomer, or a tautomer thereof, $Cy^3$ is 5-6-membered heteroaryl optionally substituted by one or more $R^3$.

More specifically, the present invention provides the following technical solutions.

SOLUTION 1. A compound represented by general formula (I), or a pharmaceutically acceptable salt, an ester, a stereoisomer, or a tautomer thereof:

(I)

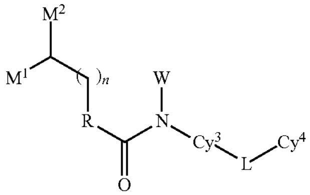

wherein W is hydrogen or $C_{1-6}$alkyl optionally substituted by a substituent;

R represents a group represented by the following general formula (a'), (b') or (c'):

(a')

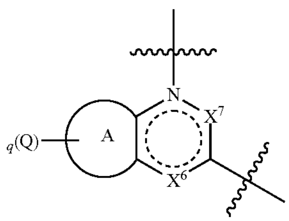, (b')

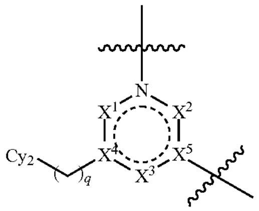, or

-continued (c')

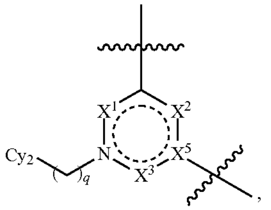

in formula (a'), ring A represents 6-10-membered aromatic ring, 5-6-membered heteroaromatic ring having 1-3 heteroatoms selected from $NR^b$, O and S, or 5-6-membered heterocyclic ring having 1-4 heteroatoms selected from $NR^b$, O and S; preferably, ring A represents benzene ring, naphthalene ring, furan ring, thiophene ring, pyrrole ring, oxazole ring, isoxazole ring, thiazole ring, isothiazole ring, pyrazole ring, thiazole ring, imidazole ring, pyridine ring, pyridazine ring, pyrimidine ring, pyrazine ring, pyran ring, thiopyran ring, pyrrolidine ring, pyrroline ring, tetrahydrofuran ring, tetrahydrothiophene ring, piperidine ring, or tetrahydropyran ring;

Q is each independently selected from H, cyano, hydroxy, mercapto, halogen, carboxyl, nitro, $—NR^bR^c$, $—C(O)R^d$, $—C(O)NR^bR^c$, $—OC(O)NR^bR^c$, $—NR^bC(O)R^d$, $—SO_2—NR^bR^c$, $—SO_2R^d$, $—NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, $—C_{1-6}$alkyl-R' optionally substituted by a substituent, $—C_{1-6}$alkoxy-R' optionally substituted by a substituent, —O—R', —C(O)—R', $—SO_2—R'$, $—NR^bC(O)—R'$, 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

in formula (a'), the moiety

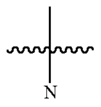 [SMILES: *N]

is attached via a linking group to the moiety

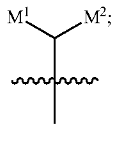

in formula (a'), $X^6$ and $X^7$ are each independently selected from $CR^aR^a$, C═O and $NR^b$, and at least one of $X^6$ and $X^7$ is C═O;

in formula (b'), the moiety

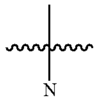

is attached via a linking group to the moiety

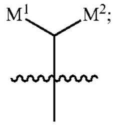

in formula (c'), the moiety

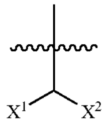

is attached via a linking group to the moiety

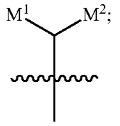

$X^1$, $X^2$ and $X^3$ are each independently selected from $CR^aR^a$, C═O and $NR^b$, and at least one of $X^1$, $X^2$, and $X^3$ is C═O;

$X^4$ and $X^5$ are each independently selected from $CR^a$ or N;

$M^1$ and $M^2$ are each independently selected from H, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, $—C_{1-6}$alkyl-R' optionally substituted by a substituent, or $—C_{1-6}$alkoxy-R' optionally substituted by a substituent, or $M^1$ and $M^2$ together with the atoms to which they are attached may form 3-8-membered cycloalkyl optionally substituted by a substituent, or the

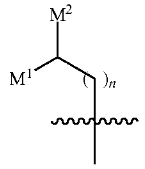

moiety may form a hydrogen atom;

$Cy^2$ is selected from 3-12-membered cycloalkyl optionally substituted by one or more $R^2$, 3-12-membered cycloalkenyl optionally substituted by one or more $R_2$, 3-14-membered heterocyclyl optionally substituted by one or more $R^2$, 6-14-membered aryl optionally substituted by one or more $R^2$, or 5-10-membered heteroaryl optionally substituted by one or more $R^2$, $R^2$ is each independently selected from H, cyano, hydroxy, mercapto, halogen, carboxyl, nitro, —$NR^bR^c$, —C(O)$R^d$, —C(O)$NR^bR^c$, —OC(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R', —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

$Cy^3$ is selected from 3-12-membered cycloalkyl optionally substituted by one or more $R^3$, 3-14-membered heterocyclyl optionally substituted by one or more $R^3$, or 5-10-membered heteroaryl optionally substituted by one or more $R^3$, $R^3$ is each independently selected from H, cyano, hydroxy, mercapto, halogen, carboxyl, nitro, —$NR^bR^c$, —C(O)$R^d$, —C(O)$NR^bR^c$, —OC(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R, —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent; when $X^1$ or $X^2$ represents $NR^b$, $Cy^3$ may also be a 6-14 membered aromatic group optionally substituted by one or more $R^3$;

$Cy^4$ is selected from 3-12-membered cycloalkyl optionally substituted by one or more $R^4$, 3-14-membered heterocyclyl optionally substituted by one or more $R^4$, 5-14-membered heteroaryl optionally substituted by one or more $R^4$, and 6-14-membered aryl optionally substituted by one or more $R^4$, $R^4$ is each independently selected from H, cyano, hydroxy, mercapto, halogen, carboxyl, nitro, —$NR^bR^c$, —C(O)$R^d$, —C(O)$NR^bR^c$, —OC(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R', —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent, or two $R^4$ together with the atoms to which they are attached may form a 5-14-membered cyclic group;

L is selected from —$NR^b$—, —O—, —S— and —$(CR^aR^a)_m$—, m is an integer of 1-3;

$R^a$ is absent, or at each occurrence, is each independently selected from H, cyano, hydroxy, mercapto, halogen, carboxyl, nitro, —$NR^bR^c$, —C(O)$R^d$, —C(O)$NR^bR^c$, —OC(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R', —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

$R^b$ and $R^c$ are each absent, or at each occurrence, are each independently selected from H, hydroxy, $C_{1-6}$alkyl optionally substituted by a substituent, —$C_{1-6}$alkyl-R' optionally substituted by a substituent, —C(O)—R', —$SO_2$—W, 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

$R^d$ is absent, or at each occurrence, is each independently selected from hydroxy, halogen, amino, -amino($C_{1-6}$ alkyl optionally substituted by a substituent)$_{1-2}$, $C_{1-6}$alkyl optionally substituted by a substituent, $C_{1-6}$alkoxy optionally substituted by a substituent, —$C_{1-6}$alkyl-R' optionally substituted by a substituent, —$C_{1-6}$alkoxy-R' optionally substituted by a substituent, —O—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

R' is each independently selected from 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

q is an integer of 0-4;

n is an integer of 0-4.

The substituent in said "optionally substituted by a substituent" is each independently selected from hydroxy, mercapto, amino, carboxyl, cyano, nitro, halogen, $C_{1-6}$alkyl, $C_{1-6}$alkoxy$C_{1-6}$alkyl, $C_{1-6}$alkoxy, $C_{1-6}$alkyl$C_{1-6}$alkoxy, $C_{1-6}$alkoxy$C_{1-6}$alkoxy, $C_{1-6}$alkylamino, $(C_{1-6}alkyl)_2$amino, $C_{1-6}$alkylaminocarbonyl, $(C_{1-6}alkyl)_2$aminocarbonyl, $C_{1-6}$alkylcarbonyl, $C_{1-6}$alkylcarbonyloxy, $C_{1-6}$alkylcarbonylamino, $C_{1-6}$alkylsulfonamido, halo$C_{1-6}$alkyl, halo$C_{1-6}$ alkoxy, $C_{1-6}$alkylsulfonyl, $C_{1-6}$alkylthio, 3-12-membered cycloalkyl, 6-14-membered aryl, 3-12-membered heterocyclyl, 5-10-membered heteroaryl and oxo;

 in the groups represented by formula (a'), formula (b') and formula (c') represents a double bond moiety that is optionally present in the cyclic structure; provided that in the groups represented by formula (a') and formula (c'), the

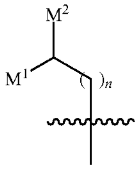

moiety will not form a hydrogen atom;

provided that in the group represented by formula (b), when $X^1$ and $X^3$ are C═O, and $X^4$ is N, $R^2$ as the substituent of $Cy^2$ does not represent a halogen atom.

SOLUTION 2. The compound according to SOLUTION 1, or a pharmaceutically acceptable salt, an ester, a stereoisomer, or a tautomer thereof, wherein $M^1$ and $M^2$ are each independently selected from H, $C_{1-6}$alkyl optionally substituted by a substituent, and $C_{2-8}$alkenyl optionally substituted by a substituent, or $M^1$ and $M^2$ together with the atoms to which they are attached may form 3-8-membered cycloalkyl optionally substituted by a substituent, or the

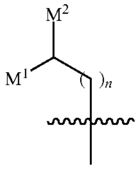

moiety may form a hydrogen atom; preferably, $M^1$ and $M^2$ are each independently $C_{1-6}$alkyl optionally substituted by a substituent, or $M^1$ and $M^2$ together with the atoms to which they are attached may form 3-8-membered cycloalkyl optionally substituted by a substituent, or the

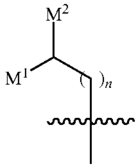

moiety may form a hydrogen atom; preferably, $M^1$ and $M^2$ are each independently $C_{1-6}$alkyl, or $M^1$ and $M^2$ together with the atoms to which they are attached may form cyclopropyl, cyclobutyl, cyclopentyl, or cyclohexyl, in formula (a'), ring A represents 6-10-membered aromatic ring; preferably, ring A represents benzene ring, or naphthalene ring;

Q is each independently selected from H, hydroxy, halogen, carboxyl, nitro, —$NR^bR^c$, $C_{1-6}$alkyl optionally substituted by a substituent, and $C_{1-6}$alkoxy optionally substituted by a substituent;

$Cy^2$ is selected from 6-14-membered aryl optionally substituted by one or more $R^2$, or 5-10-membered heteroaryl optionally substituted by one or more $R^2$, preferably, $Cy^2$ is selected from phenyl or naphthalenyl, both of which is optionally substituted by one or more $R^2$;

$R^2$ is each independently selected from H, hydroxy, halogen, carboxyl, nitro, —$NR^bR^c$, —C(O)$R^d$, —C(O)$NR^bR^c$, —$NR^b$C(O)$OR^d$, $C_{1-6}$alkyl optionally substituted by a substituent, or $C_{1-6}$alkoxy optionally substituted by a substituent; preferably, $R^2$ is each independently selected from H, hydroxy, halogen, $C_{1-6}$alkyl, hydroxy$C_{1-6}$alkyl, amino$C_{1-6}$alkyl, halo$C_{1-6}$ alkyl, $C_{1-6}$alkoxy, or halo$C_{1-6}$alkoxy; preferably, $R^2$ is each independently selected from H, hydroxy, fluoro, chloro, bromo, or $C_{1-4}$alkyl;

$Cy^3$ is selected from 3-8-membered cycloalkyl optionally substituted by one or more $R^3$, or 5-10-membered heteroaryl optionally substituted by one or more $R^3$, when $X^1$ or $X^2$ represents $NR^b$, $Cy^3$ may also be 6-10-membered aromatic group optionally substituted by one or more $R^3$; preferably, $Cy^3$ is selected from 3-6-membered cycloalkyl optionally substituted by one or more $R^3$, or 5-6-membered heteroaryl optionally substituted by one or more $R^3$, when $X^1$ or $X^2$ represents $NR^b$, $Cy^3$ may also be selected from phenyl or naphthalenyl, both of which are optionally substituted by one or more $R^3$; preferably, $Cy^3$ is selected from pyrrolyl optionally substituted by one or more $R^3$, pyridinyl optionally substituted by one or more R, pyrimidinyl optionally substituted by one or more $R^3$, pyridazinyl optionally substituted by one or more $R^3$, or pyrazinyl optionally substituted by one or more $R^3$;

$R^3$ is each independently selected from H, hydroxy, halogen, carboxyl, nitro, —$NR^bR^c$, —C(O)$R^d$, —C(O)$NR^bR^c$, —$NR^b$C(O)$R^d$, $C_{1-6}$alkyl optionally substituted by a substituent, and $C_{1-6}$alkoxy optionally substituted by a substituent; preferably, $R^3$ is each independently selected from H, hydroxy, halogen, $C_{1-6}$alkyl, hydroxy$C_{1-6}$alkyl, amino$C_{1-6}$alkyl, halo$C_{1-6}$ alkyl, $C_{1-6}$alkoxy, or halo$C_{1-6}$alkoxy; preferably, $R^3$ is each independently selected from H, hydroxy, fluoro, chloro, bromo, or $C_{1-4}$alkyl;

$Cy^4$ is selected from 5-10-membered heterocyclyl optionally substituted by one or more $R^4$, 5-10-membered heteroaryl optionally substituted by one or more $R^4$, and 6-10-membered aryl optionally substituted by one or more $R^4$; preferably, $Cy^4$ is selected from 9-10-membered heteroaryl optionally substituted by one or more $R^4$ and phenyl or naphthalenyl, both of which are optionally substituted by one or more $R^4$;

$R^4$ is each independently selected from H, hydroxy, halogen, carboxyl, nitro, —$NR^bR^c$, —C(O)$R^d$, —C(O)$NR^bR^c$, —$NR^b$C(O)$R^d$, $C_{1-6}$alkyl optionally substituted by a substituent, and $C_{1-6}$alkoxy optionally substituted by a substituent, or two $R^4$ together with the atoms to which they are attached may form a 5-6-membered cyclic group; preferably, $R^4$ is each independently selected from H, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkyl$C_{1-6}$alkoxy, and $C_{1-6}$alkoxy$C_{1-6}$alkoxy, or two $R^4$ together with the atoms to which they are attached may form a 5-6-membered oxygen-containing cyclic group; preferably, $R^4$ is selected from H, hydroxy, mercapto, halogen, $C_{1-6}$alkyl, halo$C_{1-6}$alkyl, $C_{1-4}$alkoxy, $C_{1-4}$alkoxy$C_{1-6}$alkyl, $C_{1-4}$alkyl$C_{1-4}$alkoxy, $C_{1-4}$alkoxy$C_{1-4}$alkoxy, and halo$C_{1-4}$alkoxy, or two $R^4$ together with the atoms to which they are attached may form a 5-6-membered oxygen-containing cyclic group;

L is selected from —$NR^b$—, —O— or —S—;

$R^a$ is absent, or at each occurrence, is each independently selected from H, halogen, hydroxy, carboxyl, nitro, —$NR^bR^c$, —C(O)$R^d$, —C(O)$NR^bR^c$, —$NR^b$C(O)$R^d$, $C_{1-6}$alkyl optionally substituted by a substituent, and $C_{1-6}$alkoxy optionally substituted by a substituent; preferably, $R^4$ is absent, or at each occurrence, is each independently selected from H, hydroxy, halogen, carboxyl, nitro, $C_{1-6}$alkyl, $C_{1-6}$alkoxy, or halo$C_{1-6}$alkyl, preferably, $R^a$ is absent, or at each occurrence, is each independently selected from H, $C_{1-6}$alkyl, and $C_{1-6}$alkoxy;

$R^b$ and $R^c$ are each absent, or at each occurrence, are each independently selected from H, or $C_{1-6}$alkyl optionally substituted by a substituent; preferably, $R^b$ and $R^c$ are each absent, or at each occurrence, are each independently selected from H, $C_{1-6}$alkyl, or halo$C_{1-6}$alkyl; preferably, $R^b$ and $R^c$ are each absent, or at each occurrence, are each independently selected from H or $C_{1-6}$alkyl;

$R^d$ is absent, or at each occurrence, is each independently selected from hydroxy, halogen, amino, -amino($C_{1-6}$alkyl optionally substituted by a substituent)$_{1-2}$, $C_{1-6}$alkyl optionally substituted by a substituent, and $C_{1-6}$alkoxy optionally substituted by a substituent; preferably, $R^d$ is absent, or at each occurrence, is each independently selected from hydroxy, amino, -amino ($C_{1-6}$alkyl)$_{1-2}$, $C_{1-6}$alkyl, halo$C_{1-6}$alkyl, $C_{1-6}$alkoxy, or halo$C_{1-6}$alkoxy; preferably, $R^d$ is absent, or at each occurrence, is each independently selected from hydroxy, amino, $C_{1-6}$alkyl, halo$C_{1-4}$alkyl, $C_{1-4}$alkoxy, and halo$C_{1-6}$alkoxy;

R' is selected from 3-8-membered cycloalkyl optionally substituted by a substituent, 3-8-membered cycloalkenyl optionally substituted by a substituent, 3-10-membered heterocyclyl optionally substituted by a substituent, 6-10-membered aryl optionally substituted by a substituent, or 5-6-membered heteroaryl optionally substituted by a substituent; preferably, R' is selected from 3-6-membered cycloalkyl optionally substituted by a substituent, 4-7-membered heterocyclyl optionally substituted by a substituent, 6-10-membered aryl optionally substituted by a substituent, or 5-6-membered heteroaryl optionally substituted by a substituent; preferably, R' is selected from cyclopropyl, cyclobutyl, cyclopentyl, cyclohexyl, phenyl, naphthalenyl, oxacyclopropyl, oxacyclobutyl, oxacyclopentyl, oxacyclohexyl, oxacycloheptyl, pyrrolyl, furanyl, thiophenyl, oxazolyl, isoxazolyl, pyrazolyl, thiazolyl, pyridinyl, pyrimidinyl, and pyridazinyl;

the substituent in said "optionally substituted by a substituent" is each independently selected from hydroxy, mercapto, amino, carboxyl, cyano, nitro, halogen, $C_{1-6}$alkyl, $C_{1-6}$alkoxy$C_{1-6}$alkyl, $C_{1-6}$alkoxy, $C_{1-6}$alkyl$C_{1-6}$alkoxy, $C_{1-6}$alkoxy$C_{1-6}$alkoxy, $C_{1-6}$alkylamino, ($C_{1-6}$alkyl)$_2$amino, $C_{1-6}$alkylaminocarbonyl, ($C_{1-6}$alkyl)$_2$aminocarbonyl, $C_{1-6}$alkylcarbonyl, $C_{1-6}$alkylcarbonyloxy, $C_{1-6}$alkylcarbonylamino, $C_{1-6}$alkylsulfonamido, halo$C_{1-6}$alkyl, halo$C_{1-6}$alkoxy, $C_{1-6}$alkylsulfonyl, $C_{1-6}$alkylthio, 3-8-membered cycloalkyl, 6-10-membered aryl, 3-8-membered heterocyclyl, 5-6-membered heteroaryl and oxo; preferably, the substituent in said "optionally substituted by a substituent" is each independently selected from hydroxy, mercapto, amino, carboxyl, cyano, nitro, halogen, $C_{1-4}$alkyl, $C_{1-4}$alkoxy$C_{1-4}$alkyl, $C_{1-4}$alkoxy, $C_{1-4}$alkyl$C_{1-4}$alkoxy, $C_{1-4}$alkoxy$C_{1-4}$alkoxy, $C_{1-4}$alkylamino, ($C_{1-4}$alkyl)$_2$amino, $C_{1-4}$alkylaminocarbonyl, ($C_{1-4}$alkyl)$_2$aminocarbonyl, $C_{1-4}$alkylcarbonyl, $C_{1-4}$alkylcarbonyloxy, $C_{1-4}$alkylcarbonylamino, $C_{1-4}$alkylsulfonamido, halo$C_{1-4}$alkyl, halo$C_{1-4}$alkoxy, $C_{1-4}$alkylsulfonyl, $C_{1-4}$alkylthio, cyclopropyl, cyclobutyl, cyclopentyl, cyclohexyl, cycloheptyl, phenyl, naphthalenyl, oxacyclopropyl, oxacyclobutyl, oxacyclopentyl, oxacyclohexyl, oxacycloheptyl, pyrrolyl, furanyl, thiophenyl, oxazolyl, isoxazolyl, pyrazolyl, thiazolyl, pyridinyl, pyrimidinyl, pyridazinyl, and oxo, n is 0, 1, 2, 3 or 4, q is 0, 1, 2, 3 or 4.

SOLUTION 3. The compound according to SOLUTION 1 or 2, or a pharmaceutically acceptable salt, an ester, a stereoisomer, or a tautomer thereof wherein $X^1$ is $NR^b$, $X^2$ is $CR^aR^a$, $X^3$ is C═O; or $X^1$ is $CR^aR^a$, $X^2$ is $NR^b$, $X^3$ is C═O; or $X^1$ is C═O, $X^2$ is $CR^aR^a$, $X^3$ is C═O; or $X^1$ is $CR^aR^a$, $X^2$ is C═O, $X^3$ is C═O; or $X^1$ is $CR^aR^a$, $X^2$ is $CR^aR^a$, $X^3$ is C═O, or $X^1$ is C═O, $X^2$ is $CR^a$W, $X^3$ is $CR^aR^a$; or $X^1$ is $CR^aR^a$, $X^2$ is C═O, $X^3$ is $CR^aR^a$.

SOLUTION 4. The compound according to any of SOLUTIONs 1-3, or a pharmaceutically acceptable salt, an ester, a stereoisomer, or a tautomer thereof wherein $X^4$ is N, $X^5$ is $CR^a$; or $X^4$ is $CR^a$, $X^5$ is $CR^a$; or $X^4$ is N, $X^5$ is N; or $X^4$ is $CR^a$, $X^5$ is N.

SOLUTION 5. The compound according to any of SOLUTIONs 1-4, or a pharmaceutically acceptable salt, an ester, a stereoisomer, or a tautomer thereof, wherein $X^6$ is C═O, $X^7$ is $CR^aR^a$; or $X^6$ is $CR^aR^a$, $X^7$ is C═O; or $X^6$ is C═O, $X^7$ is $NR^b$; or $X^6$ is $NR^b$, $X^7$ is C═O.

SOLUTION 6. The compound according to any of SOLUTIONs 1-5, or a pharmaceutically acceptable salt, an ester, a stereoisomer, or a tautomer thereof, wherein on the rings of formula (a'), formula (b') and formula (c'), only one C═O group is present.

SOLUTION 7. The compound according to any of SOLUTIONs 1-6, or a pharmaceutically acceptable salt, an ester, a stereoisomer, or a tautomer thereof, wherein $Cy^3$ represents a group represented by

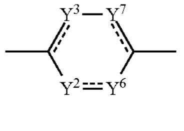

optionally substituted by one or more $R^3$, wherein ═ represents a single bond or a double bond, $Y^2$, $Y^3$, $Y^6$ and $Y^7$ are each independently selected from $CR^aR^a$ and $NR^b$, and at least one of $Y^2$, $Y^3$, $Y^6$ and $Y^7$ is $NR^b$, preferably, $Cy^3$ represents a group represented by

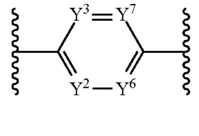

optionally substituted by one or more $R^3$, $Y^2$, $Y^3$, $Y^6$, and $Y^7$ are each independently selected from CH or N, and at least one of $Y^2$, $Y^3$, $Y^6$, and $Y^7$ is N;

$R^3$ is each independently selected from H, hydroxy, halogen, carboxyl, nitro, —$NR^bR^c$, —$C(O)R^d$, —C(O)$NR^bR^c$, —$NR^bC(O)R^d$, $C_{1-6}$alkyl optionally substituted by a substituent, and $C_{1-6}$alkoxy optionally substituted by a substituent; preferably, $R^3$ is each independently selected from H, hydroxy, halogen, $C_{1-6}$alkyl, hydroxy$C_{1-6}$alkyl, amino$C_{1-6}$alkyl, halo$C_{1-6}$ alkyl, $C_{1-6}$alkoxy, or halo$C_{1-6}$alkoxy; preferably, $R^3$ is each independently selected from H, hydroxy, fluoro, chloro, bromo, or $C_{1-4}$alkyl;

$Cy^4$ represents a group represented by

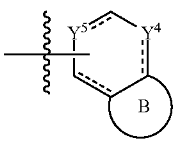

optionally substituted by one or more $R^4$, wherein ═ represents a single bond or a double bond, $Y^4$ and $Y^5$ are each independently selected from $CR^aR^a$ and $NR^b$, and at least one of $Y^4$ and $Y^5$ is $NR^b$, ring B is benzene ring, naphthalene ring or 5-6-membered heteroaromatic ring preferably, $Cy^4$ represents a group represented by

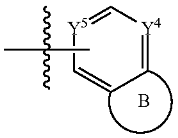

optionally substituted by one or more $R^4$, $Y^4$ and $Y^5$ are each independently selected from CH or N, and at least one of $Y^4$ and $Y^5$ is N, preferably, ring B is benzene ring or 5-6-membered heteroaromatic ring containing 1-3 heteroatoms selected from $NR^b$, O, and S;

$R^4$ is each independently selected from H, hydroxy, halogen, carboxyl, nitro, —$NR^bR^b$, —$C(O)R^d$, —C(O)$NR^bR^c$, —$NR^bC(O)R^d$, $C_{1-6}$alkyl optionally substituted by a substituent, and $C_{1-6}$alkoxy optionally substituted by a substituent, or two $R^4$ together with the atoms to which they are attached may form a 5-6-membered cyclic group; preferably, $R^4$ is each independently selected from H, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkyl$C_{1-6}$alkoxy, and $C_{1-6}$alkoxy$C_{1-6}$alkoxy, or two $R^4$ together with the atoms to which they are attached may form a 5-6-membered oxygen-containing cyclic group; preferably, $R^4$ is selected from H, hydroxy, mercapto, halogen, $C_{1-4}$alkyl, halo$C_{1-4}$alkyl, $C_{1-4}$alkoxy, $C_{1-4}$alkoxy$C_{1-4}$alkyl, $C_{1-4}$alkyl$C_{1-4}$alkoxy, $C_{1-4}$alkoxy$C_{1-4}$alkoxy, and halo$C_{1-4}$alkoxy, or two $R^4$ together with the atoms to which they are attached may form a 5-6-membered oxygen-containing cyclic group;

L is selected from —NR— and —O—.

SOLUTION 8. The compound according to any of SOLUTIONs 1-7, or a pharmaceutically acceptable salt, an ester, a stereoisomer, or a tautomer thereof, wherein R represents the group represented by formula (b'), the six-membered ring in the group represented by formula (b') is represented by any of the following, wherein ═ represents a single bond or a double bond,

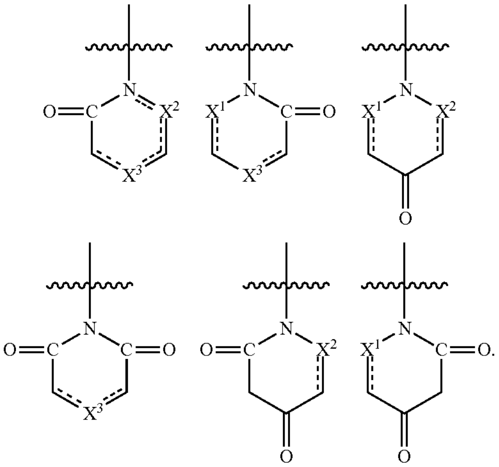

$X^1$ and $X^2$ are as defined in SOLUTIONs 1-7.

SOLUTION 9. The compound according to any of SOLUTIONs 1-8, or a pharmaceutically acceptable salt, an ester, a stereoisomer, or a tautomer thereof, wherein $Cy^3$ is selected from the following groups optionally substituted by one or more $R^3$:

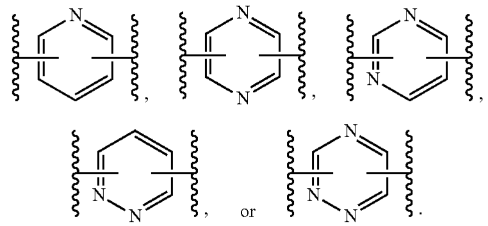

or preferably, $Cy^3$ is selected from the following groups optionally substituted by one or more $R^3$:

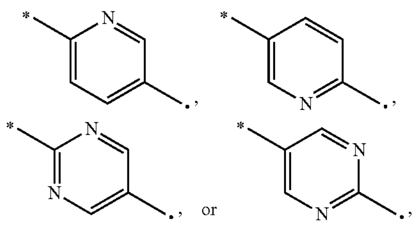

or the * end is attached to N, and the • end is attached to L, $R^3$ is each independently selected from H, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy; preferably, $R^3$ is each independently selected from H, hydroxy, fluoro, chloro, bromo, or $C_{1-4}$alkyl;

$Cy^4$ is selected from the following groups optionally substituted by one or more $R^4$:

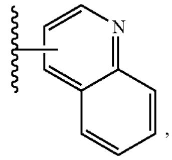, 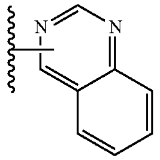, 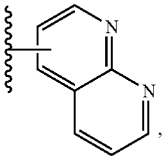, 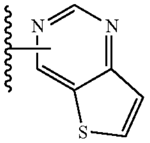, 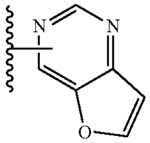, or 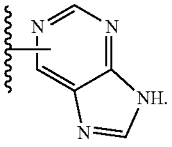

preferably, $Cy^4$ is the following group optionally substituted by one or more $R^4$:

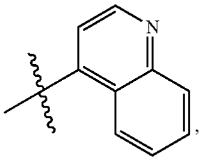 [SMILES: *c1ccnc2ccccc12], $R^4$ is each independently selected from H, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkyl$C_{1-6}$alkoxy, and $C_{1-6}$alkoxy$C_{1-6}$alkoxy, or two $R^4$ together with the atoms to which they are attached may form a 5-6-membered oxygen-containing cyclic group; preferably, $R^4$ is selected from H, hydroxy, mercapto, halogen, $C_{1-4}$alkyl, halo$C_{1-4}$alkyl, $C_{1-4}$alkoxy, $C_{1-4}$alkoxy$C_{1-4}$ alkyl, $C_{1-4}$alkyl$C_{1-4}$alkoxy, $C_{1-4}$alkoxy$C_{1-4}$alkoxy, and halo$C_{1-4}$alkoxy, or two $R^4$ together with the atoms to which they are attached may form a 5-6-membered oxygen-containing cyclic group.

SOLUTION 10. The compound according to any of SOLUTIONS 1-9, or a pharmaceutically acceptable salt, an ester, a stereoisomer, or a tautomer thereof, having a structure represented by general formula (II), (II)

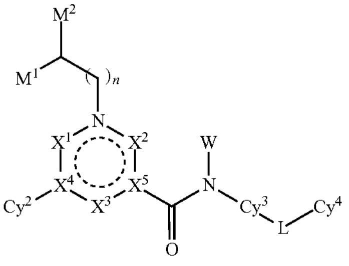

wherein each of variables is as defined in SOLUTIONs 1-9.

SOLUTION 11. The compound according to any of SOLUTIONs 1-9, or a pharmaceutically acceptable salt, an ester, a stereoisomer, or a tautomer thereof, having a structure represented by general formula (III), (III)

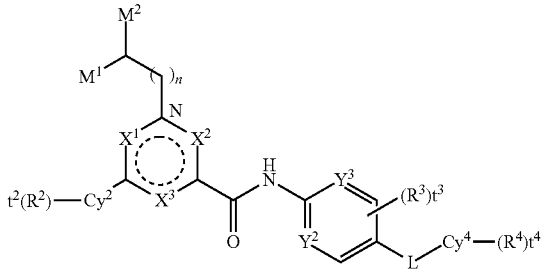

wherein $M^1$ and $M^2$ are each independently $C_{1-6}$alkyl, or $M^1$ and $M^2$ together with the atoms to which they are attached may form a 3-6-membered cycloalkyl; preferably, $M^1$ and $M^2$ together with the atoms to which they are attached may form cyclopropyl;

$X^1$, $X^2$, and $X^3$ are each independently selected from $CR^aR^a$, C═O, or $NR^b$, and at least one of $X^1$, $X^2$, and $X^3$ is C═O; preferably, $X^1$ and $X^2$ are each independently selected from $CR^aR^a$ and $NR^b$, $X^3$ represents C═O, $Y^2$ and $Y^3$ are each independently selected from CH or N, and at least one of $Y^2$ and $Y^3$ is N;

L is selected from —$NR^b$— and —O—;

$t^2$, $t^3$, and $t^4$ are each independently selected from an integer of 1-5, other variables are as defined in SOLUTIONs 1-9.

SOLUTION 12. The compound according to any of SOLUTIONs 1-9, or a pharmaceutically acceptable salt, an ester, a stereoisomer, or a tautomer thereof, having a structure represented by general formula (IV), (III)

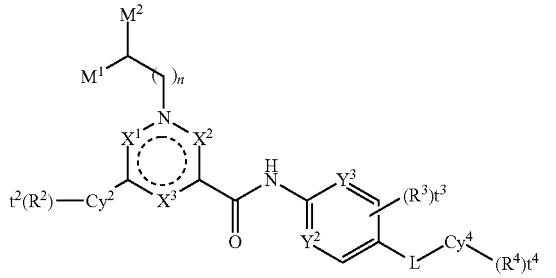

wherein $M^1$ and $M^2$ are each independently $C_{1-6}$alkyl, or $M^1$ and $M^2$ together with the atoms to which they are attached may form a 3-6-membered cycloalkyl; preferably, $M^1$ and $M^2$ together with the atoms to which they are attached may form cyclopropyl;

$X^1$, $X^2$, and $X^3$ are each independently selected from $CR^aR^a$, C═O, or $NR^b$, and at least one of $X^1$, $X^2$, and $X^3$ is C═O; preferably, $X^1$ and $X^2$ are each independently selected from $CR^aR^a$ and $NR^b$, $X^3$ represents C═O, $Y^6$ and $Y^7$ are each independently selected from CH or N, and at least one of $Y^6$ and $Y^7$ is N, L is selected from —$NR^b$— and —O—;
$t^2$, $t^3$, and $t^4$ are each independently selected from an integer of 1-5,
Other variables are as defined in SOLUTIONs 1-9.
In an embodiment of the present invention, provided is the compound represented by formula (I), or a pharmaceutically acceptable salt, an ester, a stereoisomer, or a tautomer thereof, said compound is:
| No. | Structure |
| --- | --- |
| 1 | 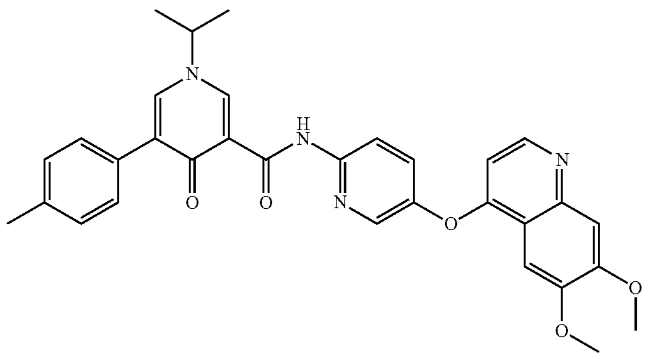 |
| 2 | 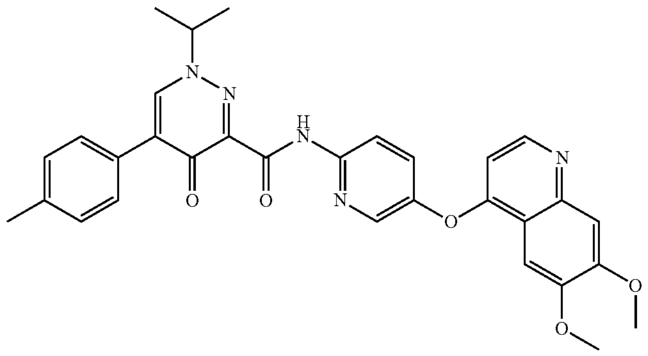 |
| 3 | 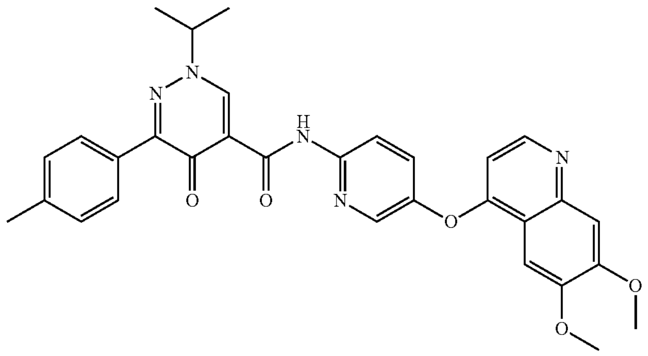 |
| 4 | 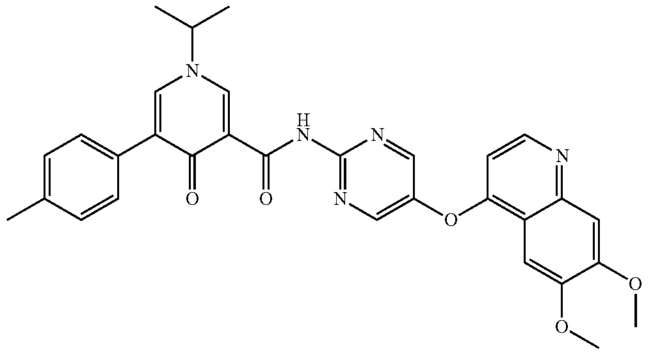 |

-continued
| No. | Structure |
|---|---|
| 5 | 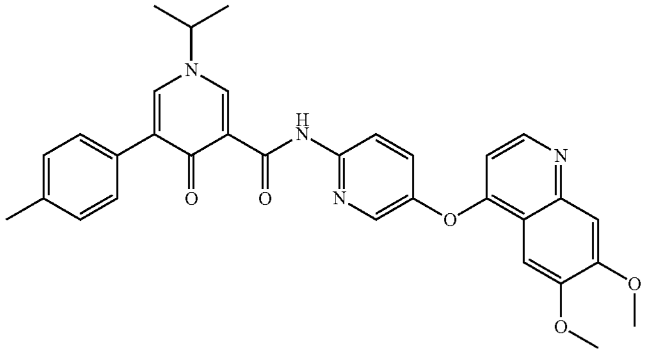 |
| 6 | 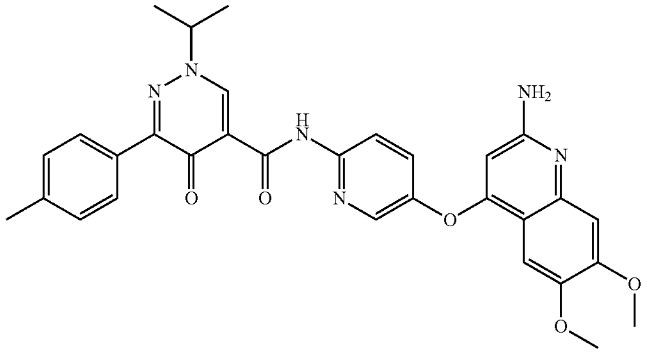 |
| 7 | 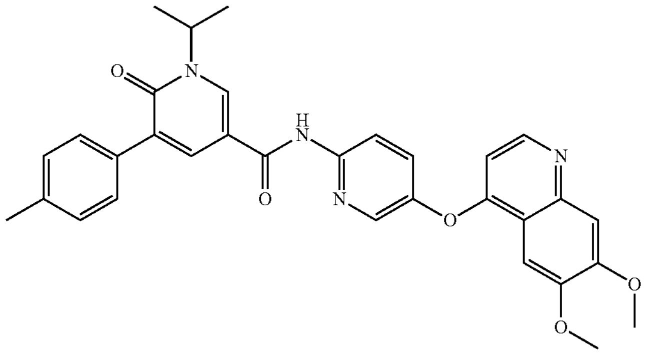 |
| 8 | 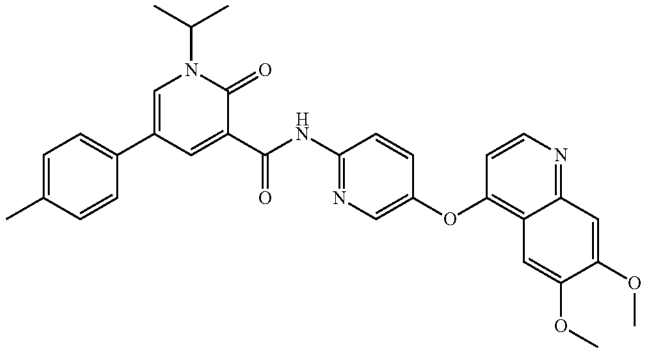 |

-continued
| No. | Structure |
|---|---|
| 9 | 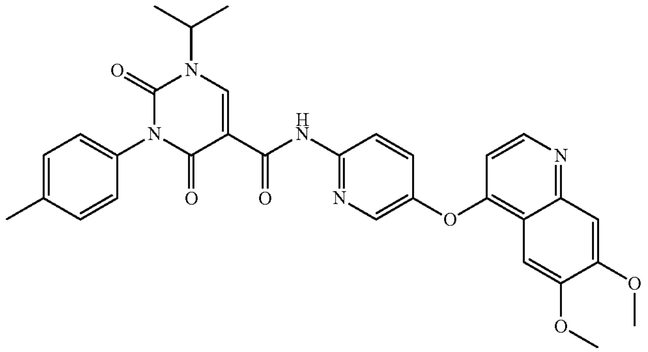 |
| 10 | 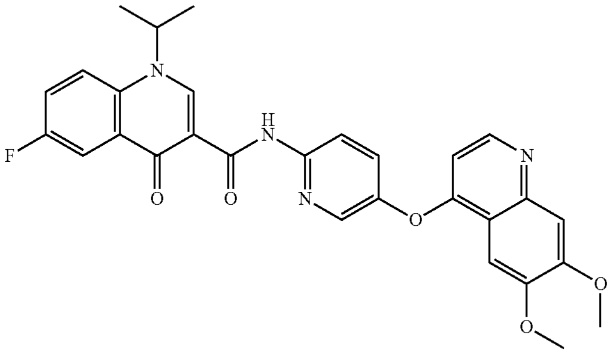 [SMILES: COc1cc2nccc(Oc3ccc(NC(=O)c4cn(C(C)C)c5ccc(F)cc5c4=O)nc3)c2cc1OC] |
| 11 | 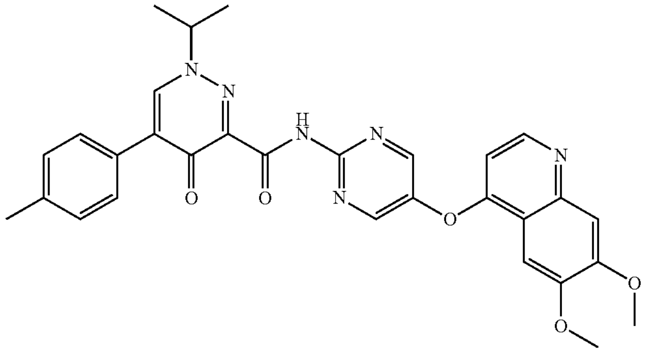 |
| 12 | 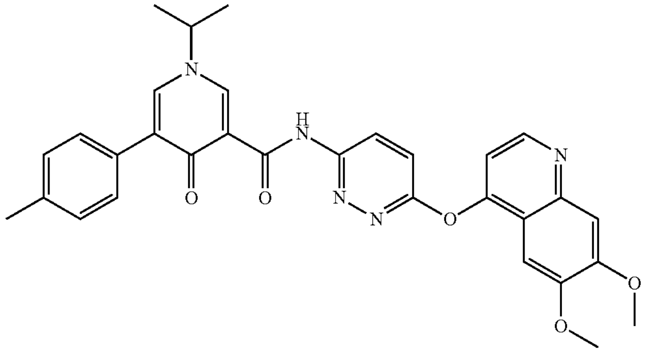 |

-continued
| No. | Structure |
| --- | --- |
| 13 | 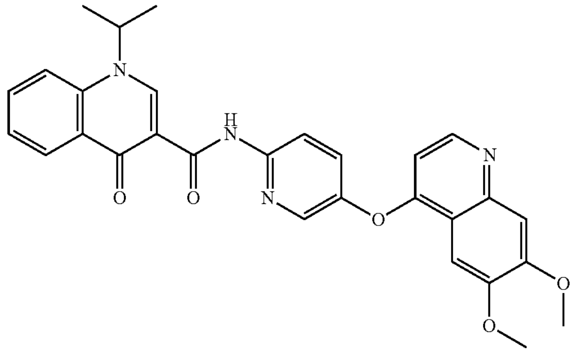 [SMILES: COc1cc2nccc(Oc3ccc(NC(=O)c4cn(C(C)C)c5ccccc5c4=O)nc3)c2cc1OC] |
| 14 | 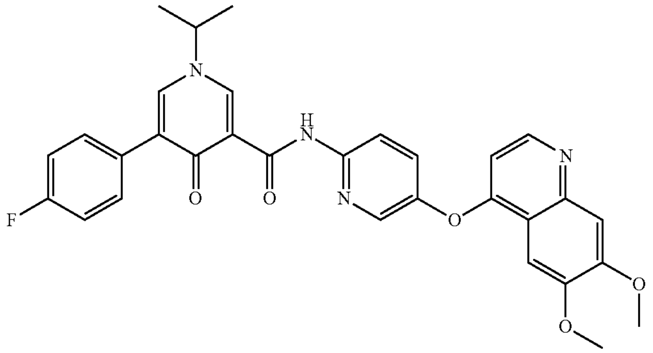 |
| 15 | 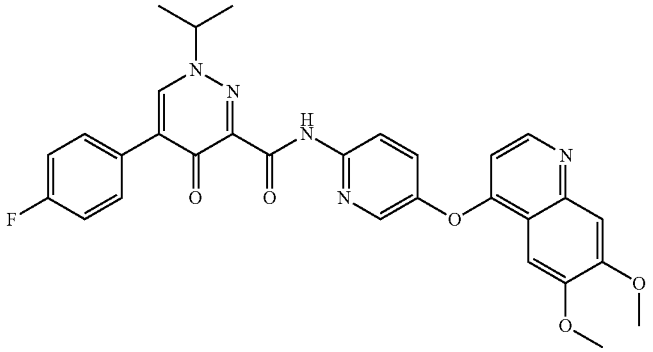 [SMILES: COc1cc2nccc(Oc3ccc(NC(=O)c4nn(C(C)C)cc(-c5ccc(F)cc5)c4=O)nc3)c2cc1OC] |
| 16 | 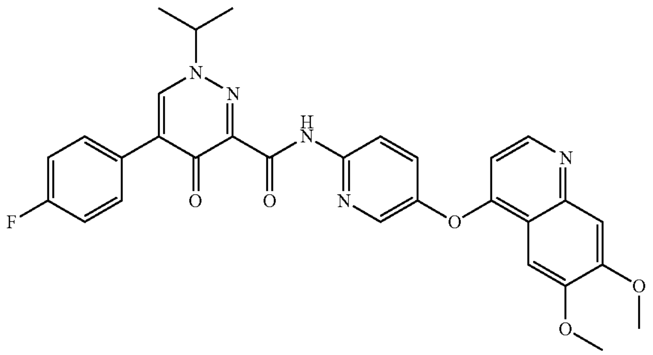 |

-continued
| No. | Structure |
| --- | --- |
| 17 | 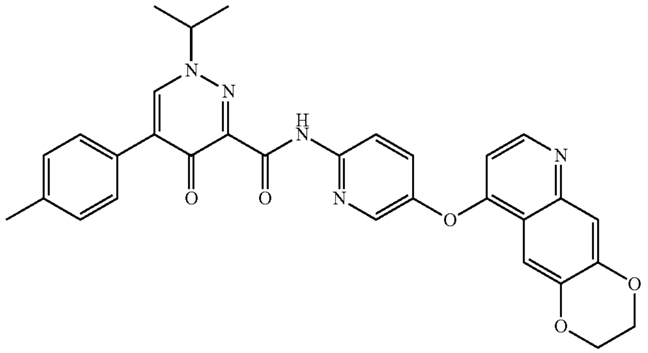 [SMILES: Cc1ccc(-c2cn(C(C)C)nc(C(=O)Nc3ccc(Oc4ccnc5cc6c(cc45)OCCO6)cn3)c2=O)cc1] |
| 18 | 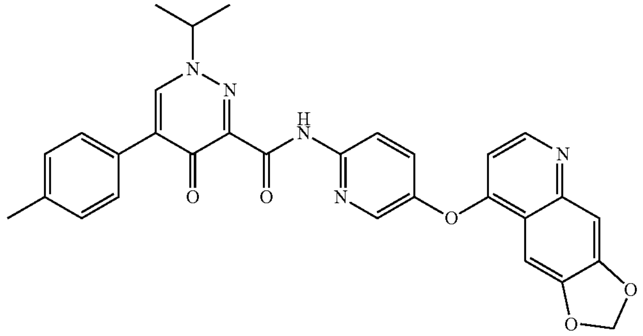 [SMILES: Cc1ccc(-c2cn(C(C)C)nc(C(=O)Nc3ccc(Oc4ccnc5cc6c(cc45)OCO6)cn3)c2=O)cc1] |
| 19 | 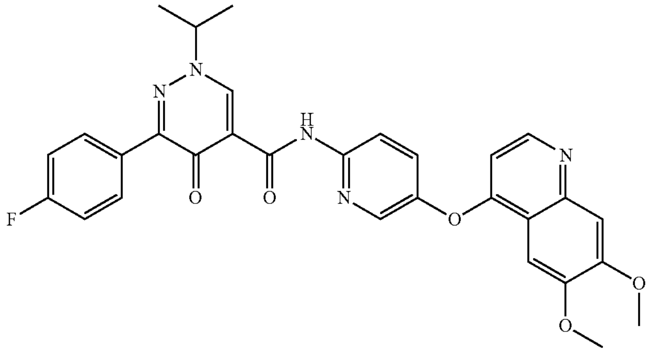 [SMILES: COc1cc2nccc(Oc3ccc(NC(=O)c4cn(C(C)C)nc(-c5ccc(F)cc5)c4=O)nc3)c2cc1OC] |
| 20 | 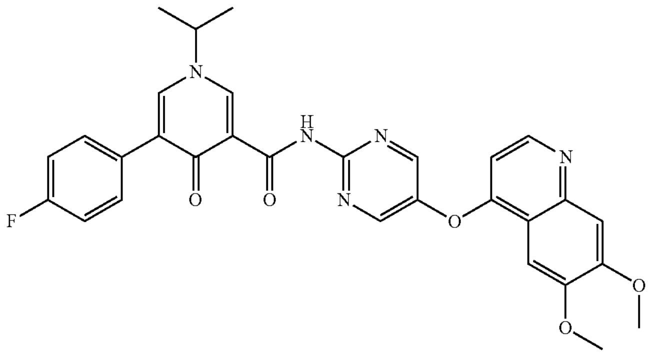 [SMILES: COc1cc2nccc(Oc3cnc(NC(=O)c4cn(C(C)C)cc(-c5ccc(F)cc5)c4=O)nc3)c2cc1OC] |

-continued
| No. | Structure |
|---|---|
| 21 | 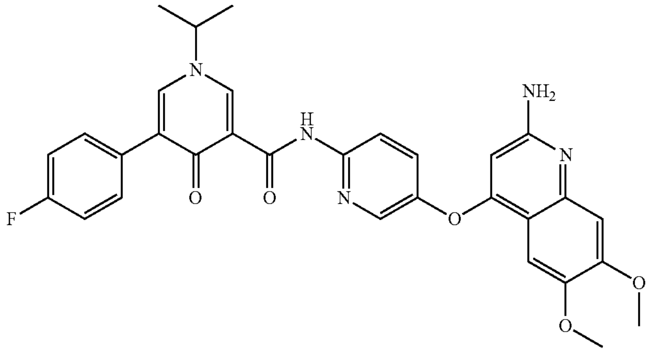 [SMILES: COc1cc2nc(N)cc(Oc3ccc(NC(=O)c4cn(C(C)C)cc(-c5ccc(F)cc5)c4=O)nc3)c2cc1OC] |
| 22 | 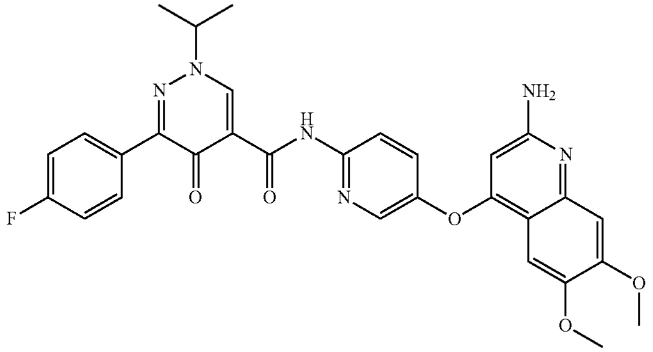 [SMILES: COc1cc2nc(N)cc(Oc3ccc(NC(=O)c4cn(C(C)C)nc(-c5ccc(F)cc5)c4=O)nc3)c2cc1OC] |
| 23 | 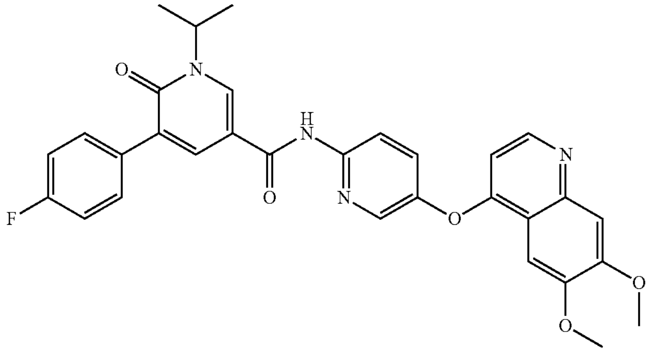 [SMILES: COc1cc2nccc(Oc3ccc(NC(=O)c4cc(-c5ccc(F)cc5)c(=O)n(C(C)C)c4)nc3)c2cc1OC] |
| 24 | 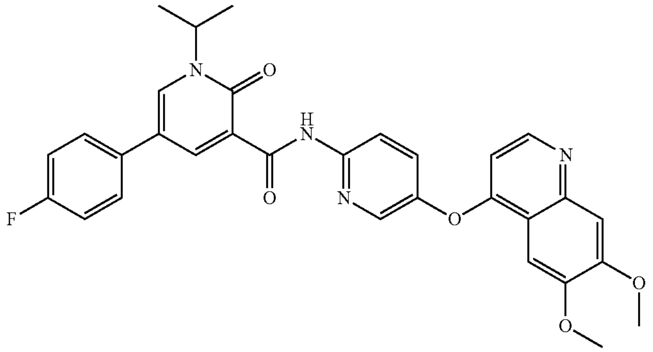 [SMILES: COc1cc2nccc(Oc3ccc(NC(=O)c4cc(-c5ccc(F)cc5)cn(C(C)C)c4=O)nc3)c2cc1OC] |

-continued
| No. | Structure |
|---|---|
| 26 | 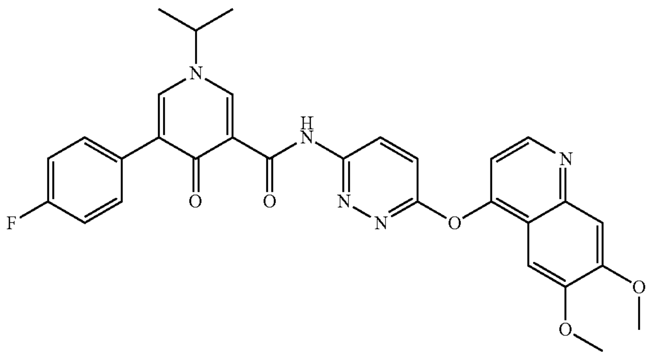 [SMILES: COc1cc2nccc(Oc3ccc(NC(=O)c4cn(C(C)C)cc(-c5ccc(F)cc5)c4=O)nn3)c2cc1OC] |
| 27 | 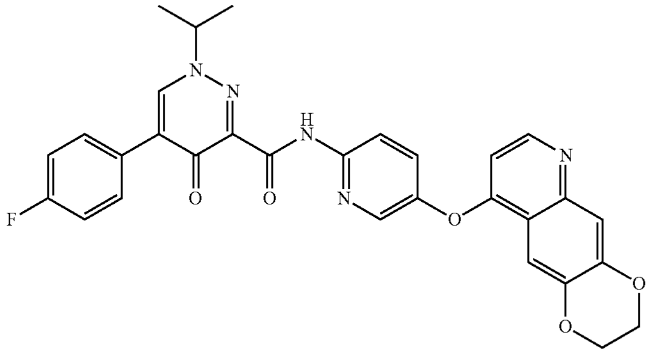 [SMILES: CC(C)n1cc(-c2ccc(F)cc2)c(=O)c(C(=O)Nc2ccc(Oc3ccnc4cc5c(cc34)OCCO5)cn2)n1] |
| 28 | 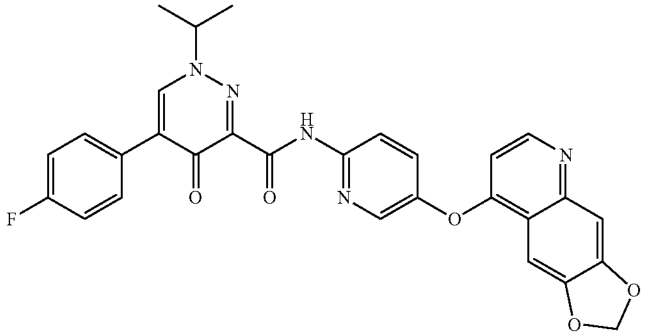 [SMILES: CC(C)n1cc(-c2ccc(F)cc2)c(=O)c(C(=O)Nc2ccc(Oc3ccnc4cc5c(cc34)OCO5)cn2)n1] |
| 29 | 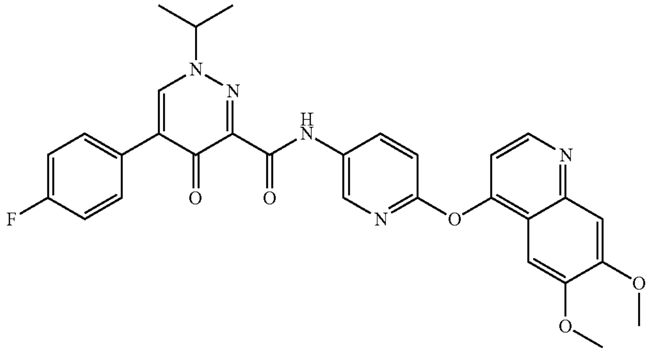 [SMILES: COc1cc2nccc(Oc3ccc(NC(=O)c4nn(C(C)C)cc(-c5ccc(F)cc5)c4=O)cn3)c2cc1OC] |

-continued
| No. | Structure |
|---|---|
| 30 | 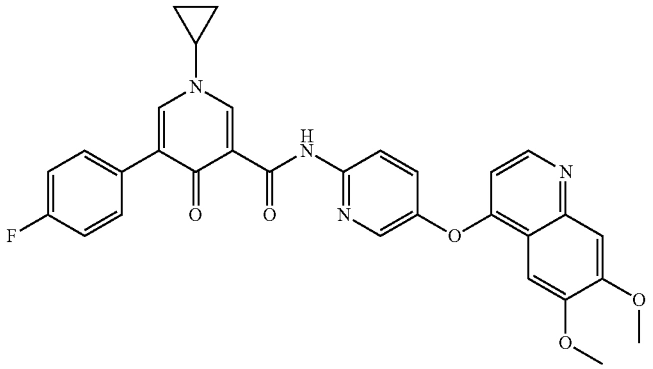 |
| 31 | 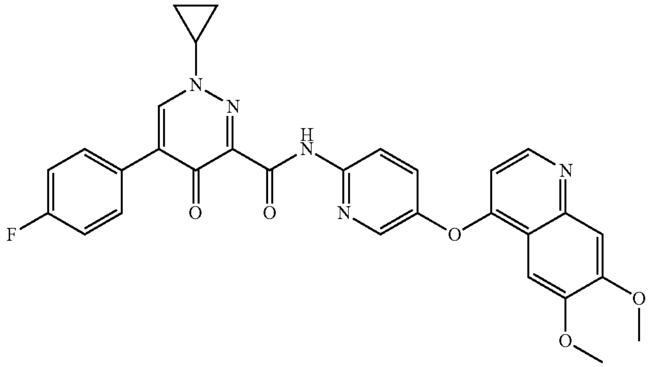 [SMILES: COc1cc2nccc(Oc3ccc(NC(=O)c4nn(C5CC5)cc(-c5ccc(F)cc5)c4=O)nc3)c2cc1OC] |
| 32 | 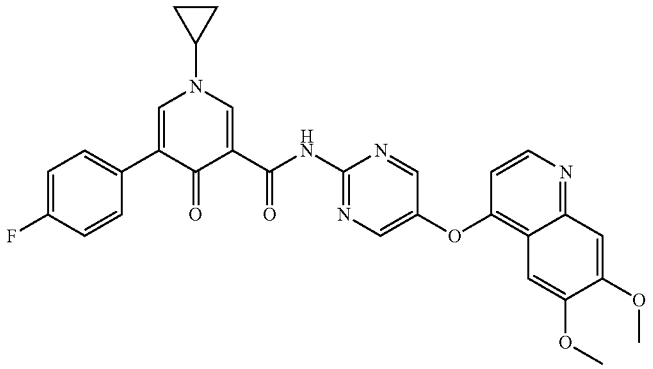 [SMILES: COc1cc2nccc(Oc3cnc(NC(=O)c4cn(C5CC5)cc(-c5ccc(F)cc5)c4=O)nc3)c2cc1OC] |
| 33 | 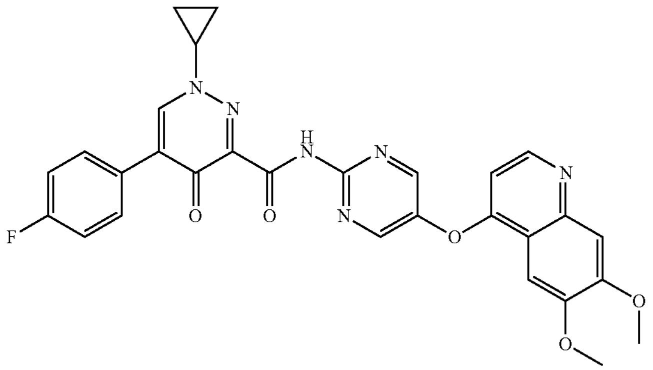 [SMILES: COc1cc2nccc(Oc3cnc(NC(=O)c4nn(C5CC5)cc(-c5ccc(F)cc5)c4=O)nc3)c2cc1OC] |

-continued
| No. | Structure |
|---|---|
| 34 | 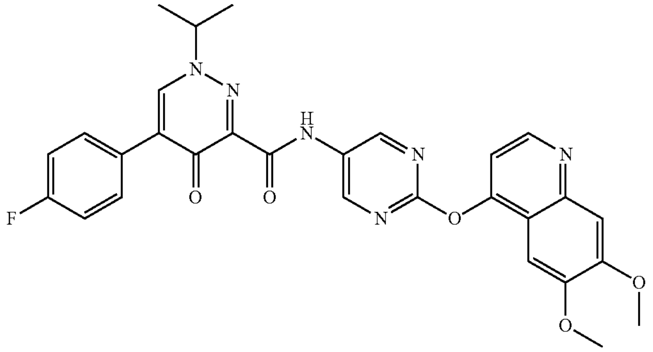 [SMILES: COc1cc2nccc(Oc3ncc(NC(=O)c4nn(C(C)C)cc(-c5ccc(F)cc5)c4=O)cn3)c2cc1OC] |
| 35 | 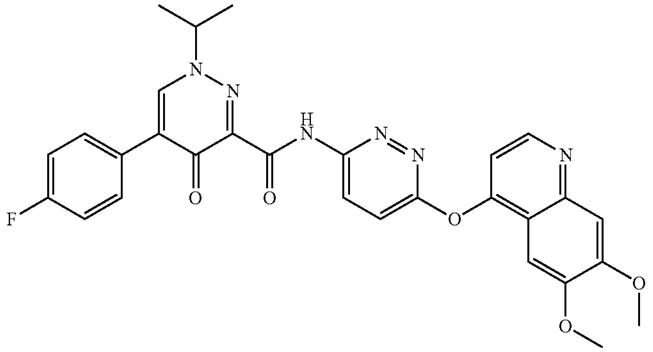 [SMILES: COc1cc2nccc(Oc3ccc(NC(=O)c4nn(C(C)C)cc(-c5ccc(F)cc5)c4=O)nn3)c2cc1OC] |
| 36 | 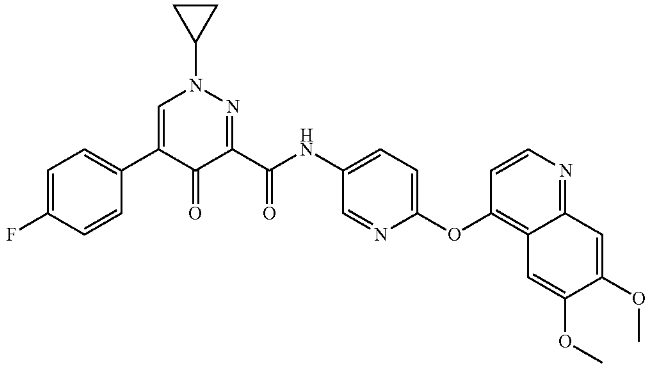 [SMILES: COc1cc2nccc(Oc3ccc(NC(=O)c4nn(C5CC5)cc(-c5ccc(F)cc5)c4=O)cn3)c2cc1OC] |
| 37 | 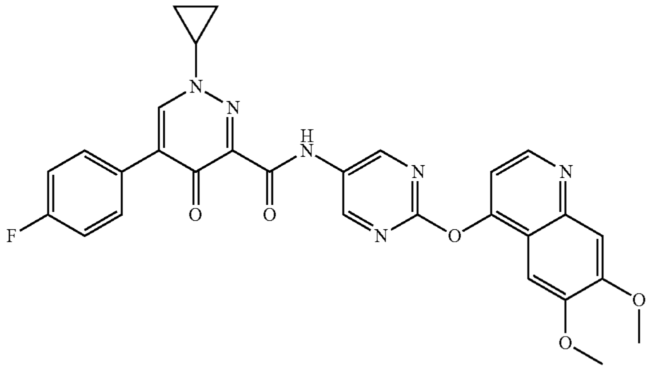 [SMILES: COc1cc2nccc(Oc3ncc(NC(=O)c4nn(C5CC5)cc(-c5ccc(F)cc5)c4=O)cn3)c2cc1OC] |

-continued
| No. | Structure |
|---|---|
| 38 | 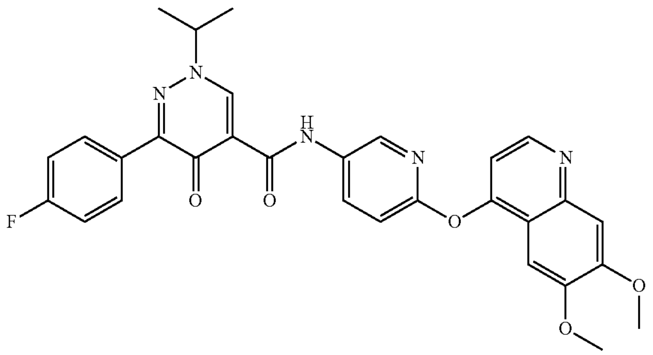 [SMILES: COc1cc2nccc(Oc3ccc(NC(=O)c4cn(C(C)C)nc(-c5ccc(F)cc5)c4=O)cn3)c2cc1OC] |
| 39 | 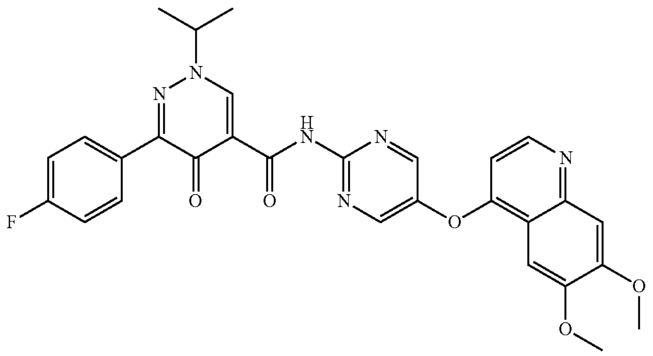 [SMILES: COc1cc2nccc(Oc3cnc(NC(=O)c4cn(C(C)C)nc(-c5ccc(F)cc5)c4=O)nc3)c2cc1OC] |
| 40 | 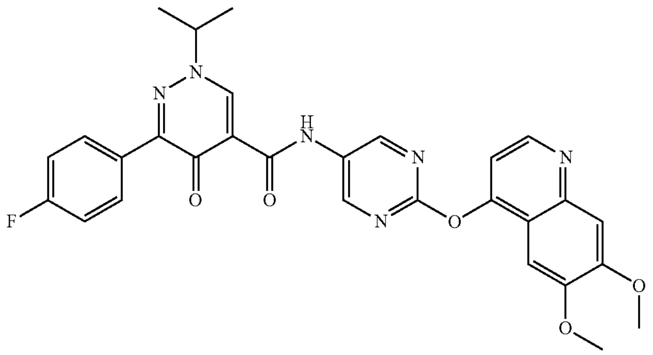 [SMILES: COc1cc2nccc(Oc3ncc(NC(=O)c4cn(C(C)C)nc(-c5ccc(F)cc5)c4=O)cn3)c2cc1OC] |
| 41 | 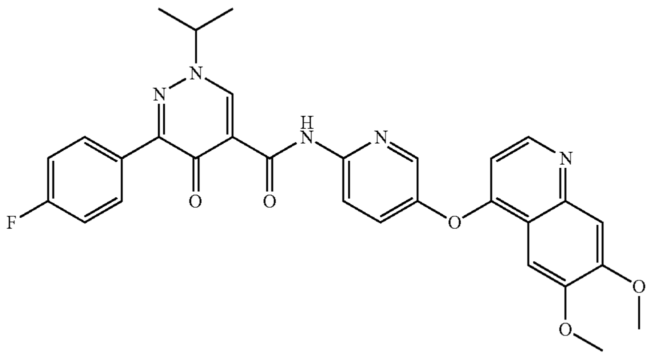 [SMILES: COc1cc2nccc(Oc3ccc(NC(=O)c4cn(C(C)C)nc(-c5ccc(F)cc5)c4=O)nc3)c2cc1OC] |

-continued
| No. | Structure |
|---|---|
| 42 | 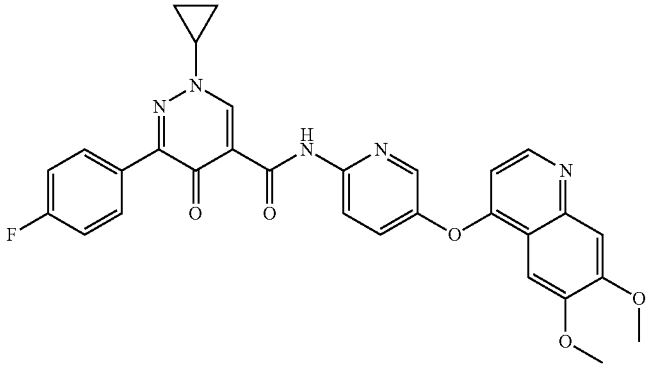 [SMILES: COc1cc2nccc(Oc3ccc(NC(=O)c4cn(C5CC5)nc(-c5ccc(F)cc5)c4=O)nc3)c2cc1OC] |
| 43 | 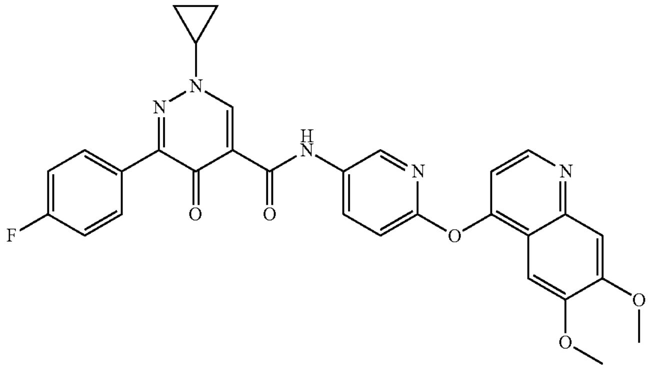 [SMILES: COc1cc2nccc(Oc3ccc(NC(=O)c4cn(C5CC5)nc(-c5ccc(F)cc5)c4=O)cn3)c2cc1OC] |
| 44 | 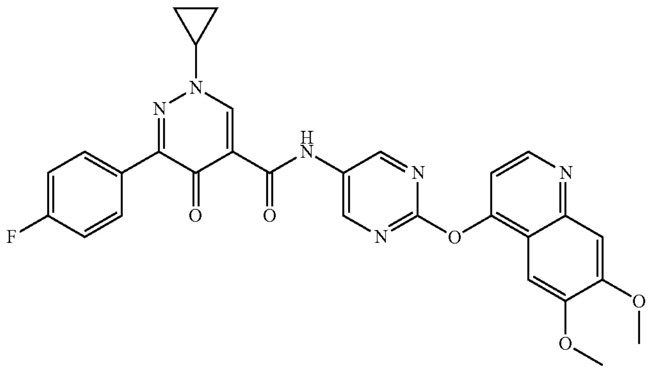 [SMILES: COc1cc2nccc(Oc3ncc(NC(=O)c4cn(C5CC5)nc(-c5ccc(F)cc5)c4=O)cn3)c2cc1OC] |
| 45 | 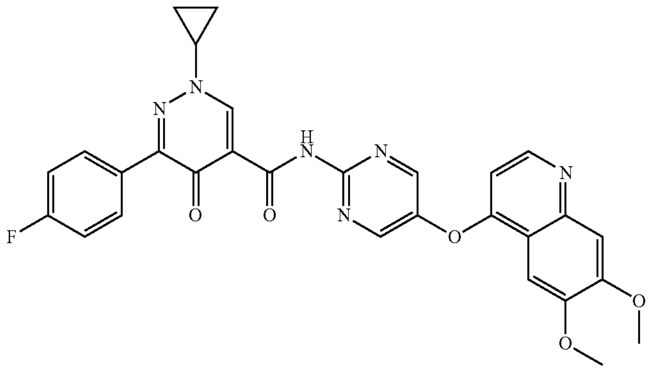 [SMILES: COc1cc2nccc(Oc3cnc(NC(=O)c4cn(C5CC5)nc(-c5ccc(F)cc5)c4=O)nc3)c2cc1OC] |

-continued

| No. | Structure |
| --- | --- |
| 46 | 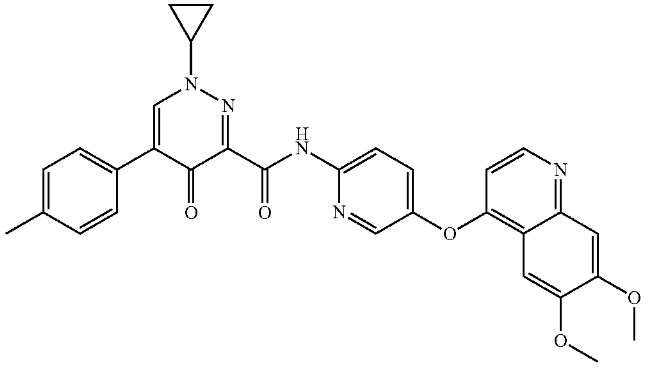 |

The present invention also provides a pharmaceutical composition, which comprises a compound of any of formula (I), formula (II), formula (III) and formula (IV) as above, or a pharmaceutically acceptable salt, an ester, a stereoisomer, or a tautomer thereof.

The present invention also provides a pharmaceutical composition which comprises a compound of any of formula (I), formula (II), formula (III) and formula (IV) as above, or a pharmaceutically acceptable salt, an ester, a stereoisomer, or a tautomer thereof, and which can optionally comprise one or more pharmaceutically acceptable carriers.

The present invention also provides a pharmaceutically acceptable formulation which comprises a compound of any of formula (I), formula (II), formula (III) and formula (IV) as above, or a pharmaceutically acceptable salt, an ester, a stereoisomer, or a tautomer thereof, which optionally comprises one or more pharmaceutically acceptable carriers.

In an embodiment of the present invention, the above-mentioned pharmaceutical composition or formulation can further comprise one or more second therapeutically active agents.

In an embodiment of the present invention, provided is a pharmaceutical composition, which comprises a compound of any of formula (I), formula (II), formula (III) and formula (IV) as above, or a pharmaceutically acceptable salt, an ester, a stereoisomer, or a tautomer thereof, and which can optionally comprise at least one second therapeutically active agent.

In an embodiment of the present invention, the second therapeutically active agent is at least one selected from: antimetabolites, growth factor inhibitors, mitosis inhibitors, antitumor hormones, alkylation agents, platinum group metals, topoisomerase inhibitors, hormones, immunomodulators, tumor suppressor genes, cancer vaccines, immune checkpoints or tumor immunotherapy-related antibodies, small molecular drugs and cell therapy agents.

In an embodiment of the present invention, the pharmaceutical composition or formulation can be administered by any suitable means known in the art, for example, orally, parenterally (including subcutaneously, intramuscularly, intravenously, intraarterially, intradermally, intrathecally and epidurally), transdermally, rectally, nasally, transpulmonarily, topically(including orally and sublingually), vaginally, intraperitoneally, intrapulmonarily and intranasally, to a patient or a subject in need of such prevention and/or treatment.

In an embodiment of the present invention, the pharmaceutical composition or formulation can be made into conventional solid preparations, such as tablets, capsules, pills, and granules; or can also made into oral liquid preparations, such as oral solutions, oral suspensions, and syrups. For making into oral preparations, suitable filler, binder, disintegrant, lubricant and the like can be added. For parenteral administration, the pharmaceutical composition can be made into injections, including sterile powder for injection and concentrated solution for injection. Upon making into injections, the conventional production methods known in the pharmaceutical field can be used, and upon formulating the injection, an additional agent may not be added, or a suitable additional agent can be added according to the drug properties. For rectal administration, the pharmaceutical composition can be made into suppositories and the like. For transpulmonary administration, the pharmaceutical composition can be made into inhalations or aerosols and the like.

In one embodiment of the present invention, provided is use of a compound of any of formula (I), formula (II), formula (III) and formula (IV) as above, or a pharmaceutically acceptable salt, an ester, a stereoisomer, or a tautomer thereof, the above-mentioned pharmaceutical composition, or the above-mentioned formulation in the manufacture of drugs for treating and/or preventing diseases mediated by the abnormal expression of the TAM family kinase receptors and/or ligands thereof, wherein the diseases mediated by the abnormal expression of the TAM family kinase receptors and/or ligands thereof comprise at least one of the following diseases: tumor, tumor immunity, adenomyosis, vascular disease/injury, psoriasis, visual defect/impairment (caused by macular degeneration, diabetes, premature birth and the like), kidney disease, rheumatoid arthritis, osteoporosis, and the like.

In one embodiment of the present invention, a compound of any of formula (I), formula (II), formula (III) and formula (IV) as above, or a pharmaceutically acceptable salt, an ester, a stereoisomer, or a tautomer thereof, the above-mentioned pharmaceutical composition, or the above-mentioned formulation is useful for treating and/or preventing diseases mediated by the abnormal expression of the TAM family kinase receptors and/or ligands thereof, wherein the diseases mediated by the abnormal expression of the TAM family kinase receptors and/or ligands thereof comprise at least one of the following diseases: tumor, tumor immunity, adenomyosis, vascular disease/injury, psoriasis, visual defect/impairment (caused by macular degeneration, diabetes, premature birth and the like), kidney disease, rheumatoid arthritis, osteoporosis, and the like.

In one embodiment of the present invention, provided is use of a compound of any of formula (I), formula (II), formula (III) and formula (IV) as above, or a pharmaceutically acceptable salt, an ester, a stereoisomer, or a tautomer thereof, the above-mentioned pharmaceutical composition, or the above-mentioned formulation in the manufacture of drugs for treating and/or preventing diseases mediated by the abnormal expression of TAM family kinases/ and CSF1R kinase receptors and/or ligands thereof, wherein the diseases mediated by the abnormal expression of TAM family kinases/ and CSF1R kinase receptors and/or ligands thereof comprise at least one of the following diseases: tumor, tumor immunity, adenomyosis, vascular disease/ injury, psoriasis, visual defect/impairment (caused by macular degeneration, diabetes, premature birth and the like), kidney disease, rheumatoid arthritis, osteoporosis, and the like.

In one embodiment of the present invention, provided is a compound of any of formula (I), formula (II), formula (III) and formula (IV) as above, or a pharmaceutically acceptable salt, an ester, a stereoisomer, or a tautomer thereof, the above-mentioned pharmaceutical composition, or the above-mentioned formulation is useful for treating and/or preventing diseases mediated by the abnormal expression of TAM family kinases/ and CSF1R kinase receptors and/or ligands thereof, wherein the diseases mediated by the abnormal expression of TAM family kinases/ and CSF1R kinase receptors and/or ligands thereof comprise at least one of the following diseases: tumor, tumor immunity, adenomyosis, vascular disease/injury, psoriasis, visual defect/impairment (caused by macular degeneration, diabetes, premature birth and the like), kidney disease, rheumatoid arthritis, osteoporosis, and the like.

In one embodiment of the present invention, provided is use of a compound of any of formula (I), formula (II), formula (III) and formula (IV) as above, or a pharmaceutically acceptable salt, an ester, a stereoisomer, or a tautomer thereof, the above-mentioned pharmaceutical composition, or the above-mentioned formulation in the manufacture of drugs for treating and/or preventing related diseases caused by NTRK, in particular, drug-resistant related diseases caused by NTRK mutations, wherein the related diseases caused by NTRK comprise, but are not limited to, non-small cell lung cancer, colorectal cancer, mammary analogue secretory carcinoma, sarcoma, astrocytoma, glioblastoma, Spitz-like melanoma, cholangiocarcinoma, papillary thyroid carcinoma, breast secretory cancer, breast cancer-unknown pathological type and the like.

In one embodiment of the present invention, provided is a compound of any of formula (I), formula (II), formula (III) and formula (IV) as above, or a pharmaceutically acceptable salt, an ester, a stereoisomer, or a tautomer thereof, the above-mentioned pharmaceutical composition, or the above-mentioned formulation is useful for treating and/or preventing related diseases caused by NTRK, in particular drug-resistant related diseases caused by NTRK mutations, wherein the related diseases caused by NTRK comprise, but are not limited to, non-small cell lung cancer, colorectal cancer, mammary analogue secretory carcinoma, sarcoma, astrocytoma, glioblastoma, Spitz-like melanoma, cholangiocarcinoma, papillary thyroid carcinoma, breast secretory cancer, breast cancer-unknown pathological type and the like.

In one embodiment of the present invention, a compound of any of formula (I), formula (II), formula (III) and formula (IV) as above, or a pharmaceutically acceptable salt, an ester, a stereoisomer, or a tautomer thereof, the above-mentioned pharmaceutical composition, or the above-mentioned formulation is useful for treating and/or preventing related diseases caused by NTRK, in particular, drug-resistant related diseases caused by NTRK mutations.

In one embodiment of the present invention, the tumor includes sarcoma, lymphoma and cancer, specifically lung cancer, squamous carcinoma, bladder cancer, gastric cancer, ovarian cancer, peritoneal cancer, breast cancer, breast ductal carcinoma, head and neck cancer, endometrial cancer, corpus uteri carcinoma, rectal cancer, liver cancer, kidney cancer, renal pelvis cancer, esophageal cancer, adenocarcinoma of esophagus, glioma, prostate, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, cancer of pharynx, multiple myeloma, leukemia, non-Hodgkin's lymphoma, villous colon adenoma, melanoma, cell tumor and sarcoma.

Effect of the Invention

The compound of the present invention has an inhibitory effect on the TAM family kinases. In addition, the compound of the present invention can also target the CSF JR kinase, and has an inhibitory effect on the CSF1R kinase. The compound of the present invention may be used for the treatment and/or prevention of diseases mediated by the abnormal expression of the TAM family kinase receptors and/or ligands thereof. In addition, the compound of the present invention may be used for the treatment and/or prevention of diseases mediated by the abnormal expression of TAM family kinases/ and CSF1R kinase receptors and/or ligands thereof The compound of the present invention, by concurrently targeting and inhibiting the TAM family kinases and the CSF1R kinase, reverses the immunosuppression in the tumor microenvironment, inhibits tumor growth, migration, and/or resistant performance, and exerts the tumor immunity effect and the antitumor effect.

In addition, the compound of the present invention has a very good NTRK mutant target activity, has a good application prospect in the acquired resistant patients treated with the first generation of NTRK inhibitors, and can treat and/or prevent related diseases caused by NTRK, in particular, drug-resistant related diseases caused by NTRK mutations.

Furthermore, the compound of the present invention has a long in-vivo half-life, has excellent metabolic stability in vivo, has excellent drug-forming ability, and therefore the compound of the present invention can improve the therapeutic effect of the drug, reduce the patient's burden for administration, and improve the patient compliance.

DETAILED DESCRIPTION OF EMBODIMENTS

The embodiments of the present invention will be described in more detail below with reference to the specific embodiments, but those skilled in the art will understand that the specific embodiments described below are only used to illustrate the invention, and should not be regarded as the limit to the protection scope of the present invention. Rather, the invention is intended to cover all alternatives, modifications and equivalents, which are included in the scope of the invention as defined by the appended claims. Embodiments of the invention may be combined in any manner, unless otherwise stated. Conversions, variations, and modifications of the technical solutions thus obtained are also included in the scope of the present invention and do not depart from the scope of the present invention.

In the context of the present description, unless otherwise explicitly defined, or the meaning is beyond the understanding of those skilled in the art, for hydrocarbons or hydrocarbon derivative groups having 3 or more carbon atoms (such as propyl, propoxy, butyl, butane, butene, butenyl, hexane, and the like), it should be understood that the term without modification by a prefix of "n-" has the same meaning as that with modification by a prefix of "n-". For example, the term propyl is generally understood to represent n-propyl, while butyl is generally understood to represent n-butyl, unless otherwise explicitly defined.

All publications, patent applications, patents and other references mentioned in this description are hereby incorporated by reference. Unless otherwise defined, all technical and scientific terms used in the description have the meaning conventionally understood by those skilled in the art. In case of conflict, the definition of this description shall prevail.

In the context of the present description, unless otherwise explicitly defined, any features or technical means not discussed specifically will be understood with the meanings known in the art without any substantive modification. Moreover, any embodiment described in the description can be associated freely with one or more other embodiments described in the description, and the technical solution or idea formed therefrom is deemed as a part of the original disclosure or original record, but cannot be considered as a new content not disclosed or expected by the description, unless those skilled in the art believe that the combination is obviously unfeasible.

In the present invention, the expression "$C_{a-b}$ group" (a and b represent integers of one or more, a<b) means that the "group" has a-b carbon atoms, for example, $C_{1-4}$alkyl represents an alkyl having 1-4 carbon atoms, $C_{1-4}$alkoxy represents an alkoxy having 1-4 carbon atoms, $C_{3-10}$cycloalkyl represents a cycloalkyl having 3-10 carbon atoms, and $C_{1-4}$alkoxy$C_{1-4}$alkyl represents a group formed by attaching an alkoxy having 1-4 carbon atoms to an alkyl having 1-4 carbon atoms.

In the present invention, "-yl" and "group" mean a monovalent group or a divalent or higher group which conforms to the valence rule as required, for example, "cycloalkyl (also expressed as cycloalkyl group)" includes a monovalent group obtained by removing one hydrogen atom from the corresponding hydrocarbon, or a divalent or higher group obtained by removing two or more hydrogen atoms from the same carbon atom or two or more different carbon atoms of the corresponding hydrocarbon. When "cycloalkyl" is used as a terminal group, it is naturally a monovalent group, and when a cycloalkyl group is used as a linking group in the structure, it is a divalent or higher group. In the present invention, a monovalent or divalent or higher group generally means a monovalent group or a divalent group, but the group may have a higher valence (e.g., trivalent, tetravalent, pentavalent, hexavalent and the like), as needed. Those skilled in the art can unambiguously determine the valence number represented by "-yl" and "group". As used herein, the group "obtained by removing one or more hydrogen atoms" refers to monovalent group obtained by removing one hydrogen atom, bivalent group obtained by removing two hydrogen atoms, trivalent group obtained by removing three hydrogen atoms, tetravalent groups obtained by removing four hydrogen atoms. The number of the hydrogen atom to be removed can be determined according to the valency of the group (e.g. monovalent, bivalent, trivalent, tetravalent, and the like).

As mentioned in the present invention, "halogen atom" refers to a fluorine atom, a chlorine atom, a bromine atom, or an iodine atom, preferably a fluorine atom, a chlorine atom or a bromine atom.

According to the present invention, "halo" refers to such a condition, in which the hydrogen atom(s) on any carbon atom in a substituent group is/are substituted by one or more same or different halogen atoms. "Halogen atom" is as defined above.

As mentioned in the present invention, "$C_{1-6}$alkyl" refers to a linear or branched alkyl obtained derivatively by removing one or more hydrogen atoms from an alkane containing 1-6 carbon atoms, which comprises linear $C_{1-6}$alkyl and branched $C_{1-6}$alkyl. In fact, it is well known by those skilled in the art that, in case that $C_{1-6}$alkyl has a branched chain (branched $C_{1-6}$alkyl), it has at least three carbon atoms. As an example of "$C_{1-6}$alkyl", for example, methyl, ethyl, n-propyl, isopropyl, n-butyl, iso-butyl, see-butyl, tert-butyl, n-pentyl, iso-pentyl, 2-methylbutyl, neo-pentyl, 1-ethylpropyl, n-hexyl, iso-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl and the like can be exemplified. Said "$C_{1-4}$ alkyl" refers to those containing 1-4 carbon atoms in the above-mentioned examples.

As mentioned in the present invention, "hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy$C_{1-6}$alkyl" refer to the groups formed by replacing one or more hydrogen atoms of $C_{1-6}$alkyl respectively and independently with one or more hydroxy, cyano, amino, $C_{1-6}$alkylamino, halogen, and $C_{1-6}$alkoxy groups.

The groups containing "$C_{1-6}$alkyl" such as "$C_{1-6}$alkylamino", "$(C_{1-6}$alkyl$)_2$amino", "$C_{1-6}$alkylaminocarbonyl", "$C_{1-6}$alkylcarbonyl", "$C_{1-6}$alkylcarbonyloxy", "$C_{1-6}$alkylsulfonamido", "$C_{1-6}$alkylsulfonyl", and "$C_{1-6}$alkylthio" refer to the groups formed by attaching $C_{1-6}$alkyl to the corresponding groups such as —NH—, —CO—O—, —NH—CO—, —CO—, —$SO_2$NH—, —$SO_2$—, or —S— respectively. For example, the groups formed by attaching the groups exemplified in the above-mentioned "$C_{1-6}$alkyl" to the corresponding groups such as —NH—, —CO—O—, —NH—CO—, —CO—, —$SO_2$NH—, —$SO_2$—, or —S— respectively can be exemplified.

As mentioned in the present invention, "$C_{2-8}$alkenyl" refers to a linear or branched alkenyl obtained derivatively by removing one or more hydrogen atoms from an alkene containing at least one C—C double bond and 2-8 carbon atoms, for example, ethenyl, 1-propenyl, 2-propenyl, 1-butenyl, 2-butenyl, 1,3-butadiene-1-yl, 1-pentene-3-yl, 2-pentene-1-yl, 3-pentene-1-yl, 3-pentene-2-yl, 1,3-pentadiene-1-yl, 1,4-pentadiene-3-yl, 1-hexene-3-yl, 1,4-hexadiene-1-yl can be exemplified. Preferably, "$C_{2-8}$alkenyl" contains one C—C double bond.

As mentioned in the present invention, "$C_{2-8}$alkynyl" refers to a linear or branched alkynyl obtained derivatively by removing one or more hydrogen atoms from an alkyne containing at least one C—C triple bond and 2-8 carbon atoms, for example, ethynyl, propynyl, 2-butyn-1-yl, 2-pentyn-1-yl, 3-pentyn-1-yl, 4-methyl-2-pentyn-1-yl, 2-hexyn-1-yl, 2-hexyn-2-yl, 3-hexyn-1-yl, 3-hexyn-2-yl and the like can be exemplified. Preferably, "$C_{2-8}$alkynyl" contains one C—C triple bond.

As mentioned in the present invention, "$C_{1-6}$alkoxy" refers to the group obtained from the above-defined "$C_{1-6}$ alkyl" by attaching to the parent group via an oxygen atom, i.e. the group "$C_{1-6}$alkyl-O—", for example, methoxy, ethoxy, n-propoxy, iso-propoxy, n-butoxy, tert-butoxy, n-pentyloxy, neo-pentyloxy and n-hexyloxy, and the like can be exemplified. "$C_{1-4}$alkoxy" refers to those containing 1-4 carbon atoms in the above-mentioned examples, i.e. the group "$C_{1-4}$alkyl-O—".

As mentioned in the present invention, the groups containing "$C_{1-6}$alkoxy" such as "halo$C_{1-6}$alkoxy", "$C_{1-6}$ alkoxy$C_{1-6}$alkoxy", and "$C_{1-6}$alkyl$C_{1-6}$alkoxy" refer to the groups formed by replacing one or more hydrogen atoms of $C_{1-6}$alkoxy respectively and independently with one or more corresponding groups such as halogen, $C_{1-6}$alkoxy, $C_{1-6}$alkyl groups.

As mentioned in the present invention, "polycyclic ring" refers to a polycyclic ring system formed from two or more cyclic structures and in form of fused ring, bridged ring and spiro ring. Said fused ring refers to a polycyclic ring structure formed from two or more cyclic structures, wherein each two cyclic structure shares two adjacent ring atoms (i.e. commonly uses one bond). Said bridged ring refers to a polycyclic ring structure formed from two or more cyclic structures, wherein each two cyclic structure shares two non-adjacent ring atoms. Said spiro ring refers to a polycyclic ring structure formed from two or more cyclic structures, wherein each two cyclic structure shares one ring atom.

As mentioned in the present invention, "cycloalkyl" or "cycloalkyl group" (hereinafter collectively referred to as "cycloalkyl") refers to a monovalent group or a divalent or higher group (as required) formed from a cycloalkane. Said cycloalkane comprises a monocyclic cycloalkane or a polycyclic cycloalkane. It is for example "3-12-membered cycloalkyl", that is to say, it can have 3, 4, 5, 6, 7, 8, 9, 10, 11 or 12 ring-constituting carbon atoms. Unless otherwise specified, X-membered cycloalkyl, comprises all possible monocyclic and polycyclic rings (including fused ring, spiro ring and bridged ring). Cycloalkyl can be a 3-12-membered monovalent group or divalent or higher group (as required), a 3-10-membered monovalent group or divalent or higher group (as required), a 3-8-membered monovalent group or divalent or higher group (as required), a 3-6-membered monovalent group or divalent or higher group (as required), a 4-6-membered monovalent group or divalent or higher group (as required), or a 5-7-membered monovalent group or divalent or higher group (as required).

Specifically, (the monovalent or divalent or higher) monocyclic cycloalkyl can be 3-12-membered cycloalkyl, 3-10-membered cycloalkyl, 3-8-membered cycloalkyl, 3-6-membered cycloalkyl, 4-6-membered cycloalkyl, 5-6-membered cycloalkyl, 5-7-membered cycloalkyl. Its example includes, but is not limited to, cyclopropyl, cyclobutyl, cyclopentyl, cyclohexyl, cycloheptyl, cyclooctyl, cyclopentane-1,3-diyl, cyclohexane-1,4-diyl, cycloheptane-1,4-diyl and the like.

(The monovalent or divalent or higher) polycyclic cycloalkyl comprises fused cycloalkyl, bridged cycloalkyl, spiro cycloalkyl.

(The monovalent or divalent or higher) fused cycloalkyl can be 6-11-membered fused cycloalkyl, or 7-10-membered fused cycloalkyl. Its representative example includes, but is not limited to, a monovalent group or a bivalent or higher group obtained from bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane.

(The monovalent or divalent or higher) bridged ring cycloalkyl can be a monovalent group formed by removing one hydrogen atoms from 6-12-membered bridged ring or 7-11-membered bridged ring, or as required, a divalent or higher group formed by removing two or more hydrogen atoms from the same carbon atom or different carbon atoms. The example of said bridged ring includes, but is not limited to,

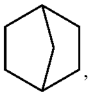, 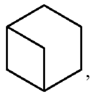, 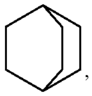, 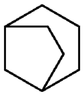, 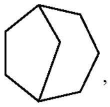, and 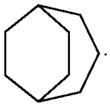.

(The monovalent or divalent or higher) spiro ring cycloalkyl can be a monovalent group formed by removing one hydrogen atoms from 7-12-membered spiro ring or 7-11-membered spiro ring, or as required, a divalent or higher group formed by removing two or more hydrogen atoms from the same carbon atom or different carbon atoms. The example of said spiro ring includes, but is not limited to,

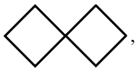, 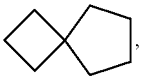, 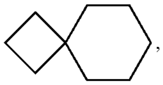, 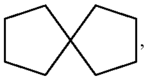, 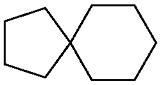, and 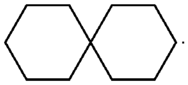.

As mentioned in the present invention, "cycloalkenyl" refers to the group derivable from the above-mentioned cycloalkyl but having at least one double bond. For example, it can be "3-12-membered cycloalkenyl", that is to say, it can have 3, 4, 5, 6, 7, 8, 9, 10, 11 or 12 ring-constituting carbon atoms. Unless otherwise specified, X-membered cycloalkenyl, comprises all possible monocyclic and polycyclic rings (including fused ring, spiro ring and bridged ring). Cycloalkenyl can be 3-12-membered cycloalkenyl, 3-8-membered cycloalkenyl, 4-6-membered cycloalkenyl, 7-11-membered spiro-ring cycloalkenyl, 7-11-membered fused-ring cycloalkenyl, 6-11-membered bridged-ring cycloalkenyl and the like. The example of cycloalkenyl includes, but is not limited to, cyclobutenyl, cyclopentenyl, cyclopentadienyl, cyclohexenyl, 1,4-cyclohexadiene-1-yl, cycloheptenyl, 1,4-cycloheptadiene-1-yl, cyclooctenyl, 1,5-cyclooctadiene-1-yl and the like.

As mentioned in the present invention, "heterocycle" comprises a non-aromatic cyclic hydrocarbon containing at least one heteroatom (for example, 1-5, 1-4, 1-3, 1-2 or 1) selected from O, S, and N as the ring-constituting atom in the ring. It can be a heterocycle having 3, 4, 5, 6, 7, 8, 9, 10, 11, 12, 13 or 14 ring-constituting atoms. Optionally, at least one double bond can be present in the ring. The heterocycle of the present invention can be a monocyclic system, and may also be a polycyclic system (in form of fused ring, spiro ring and bridged ring). As an example of heterocycle, the monocyclic heterocycle such as pyrroline, pyrrolidine, piperidine, piperazine, morpholine, thiomorpholine, tetrahydropyran, dihydropyridine, dihydropyridazine, 1,4-dioxane, oxathiolaneoxathiolane, tetrahydrothiopyrante, tetrahydrofuran, tetrahydropyran, tetrahydrothiazole, and tetrahydroisothiazole; and polycyclic heterocycle such as indoline, isoindoline, benzopyran, benzo-1,4-dioxane, tetrahydroquinoline, benzo[d]oxazole-2(3H)-one, tetrahydrobenzothiophene, can be exemplified. Furthermore, the heterocycle obtained by replacing at least one ring carbon atom of the above-mentioned 7-12-membered spiro ring, 7-11-membered spiro ring, 6-12-membered bridged ring, or 7-11-membered bridged ring with a heteroatom selected from O, S and N, preferably 1-4 heteroatoms, can be exemplified. Furthermore, the following groups according to the present invention can be further exemplified: 6-12-membered fused ring group, 7-10-membered fused ring group, 6-10-membered fused ring group, 6-12-membered saturated fused ring group, 6-12-membered spiro heterocycle, 7-11-membered spiro heterocycle, 6-12-membered saturated spiro heterocycle, 7-11 membered saturated spiro heterocycle, 6-12-membered bridged heterocycle, 7-11-membered bridged heterocycle, 6-12-membered saturated bridged heterocycle, and 7-8-membered saturated bridged heterocycle.

As mentioned in the present invention, "heterocyclyl" or "heterocyclic group" (hereinafter collectively referred to as "heterocyclyl") refers to a monovalent or divalent or higher group obtained derivatively from the above-mentioned "heterocycle". In addition, as mentioned in the present invention, "heterocyclyl" can be also a non-aromatic monovalent or divalent or higher cyclic group obtained derivatively by replacing at least one ring carbon atom of the above-mentioned cycloalkyl or cycloalkenyl with at least one heteroatom selected from O, S and N, preferably 1-4 heteroatoms. In addition, the heterocyclyl also comprises such a situation, in which the carbon atom or the sulfur atom is oxidized or nitridized, for example, the carbon or sulfur atom is replaced with C(=O), S(=O), $S(=O)_2$, or S(=O)(=N).

Specifically, "heterocyclyl" can be a heterocyclic group having 3, 4, 5, 6, 7, 8, 9, 10, 11, 12, 13, or 14 ring-constituting atoms. It can be 3-14-membered heterocyclyl, 3-10-membered heterocyclyl, 4-10-membered heterocyclyl, 3-8-membered heterocyclyl, 4-8-membered heterocyclyl, 4-6-membered heterocyclyl, 3-12-membered heterocyclyl, 4-12-membered heterocyclyl, including monocyclic heterocyclyl or polycyclic heterocyclyl.

In addition, "heterocyclyl" refers to monovalent or (as required) divalent or higher monocyclic heterocyclyl, monovalent or (as required) divalent or higher bicyclic heterocyclic system or monovalent or (as required) divalent or higher polycyclic heterocyclic system (also referred to as polycyclic ring system), including saturated or partially saturated heterocyclyl, but excluding aromatic ring.

Unless otherwise specified, all possible, saturated or partially saturated, monocyclic and polycyclic rings (including fused ring, spiro ring and bridged ring) are included. It can be for example "3-14-membered heterocyclyl".

Monovalent or (as required) divalent or higher monocyclic heterocyclyl can be 3-14-membered heterocyclyl, 3-12-membered heterocyclyl, 3-10-membered heterocyclyl, 4-10-membered heterocyclyl, 3-8-membered heterocyclyl, 3-8-membered saturated heterocyclyl, 4-8-membered heterocyclyl, 3-6-membered heterocyclyl, 4-6-membered heterocyclyl, 4-7-membered heterocyclyl, 5-7-membered heterocyclyl, 5-6-membered heterocyclyl, 5-6-membered oxygen-containing heterocyclyl, 3-8-membered nitrogen-containing heterocyclyl, 5-6-membered nitrogen-containing heterocyclyl, 5-6-membered saturated heterocyclyl and the like. Furthermore, it may also be 3-14-membered oxygen-containing heterocyclyl, 3-14-membered nitrogen-containing heterocyclyl, 3-12-membered oxygen-containing heterocyclyl, 3-12-membered sulfur-containing heterocyclyl, 3-12-membered sulfuryl($S(O)_2$)-containing heterocyclyl, 3-12-membered sulfoxide(S(O))-containing heterocyclyl and the like. The example of "heterocyclyl" includes, but is not limited to, azacyclopropyl, oxacyclopropyl, thiacyclopropyl, azacyclobutyl, oxacyclobutyl, thiacyclobutyl, tetrahydrofuranyl, tetrahydropyrrolyl, tetrahydrothiophenyl, imidazolealkyl, pyrazolealkyl, 1,2-oxazolealkyl, 1,3-oxazolealkyl, 1,2-thiazolealkyl, 1,3-thiazolealkyl, tetrahydro-2H-pyranyl, tetrahydro-2H-thiopyranyl, piperidinyl, piperazinyl, morpholinyl, 1,4-dioxacyclohexyl, 1,4-oxathiacyclohexyl; 4,5-dihydroisoxazolyl, 4,5-dihydrooxazolyl, 2,5-dihydrooxazolyl, 2,3-dihydrooxazolyl, 3,4-dihydro-2H-pyrrolyl, 2,3-dihydro-1H-pyrrolyl, 2,5-dihydro-1H-imidazolyl, 4,5-dihydro-1H-imidazolyl, 4,5-dihydro-1H-pyrazolyl, 4,5-dihydro-3H-pyrazolyl, 4,5-dihydrothiazolyl, 2,5-dihydrothiazolyl, 2H-pyranyl, 4H-pyranyl, 2H-thiopyranyl, 4H-thiopyranyl, 2,3,4,5-tetrahydropyridinyl, 1,2-isoxazinyl, 1,4-isoxazinyl, 6H-1,3-oxazinyl and the like.

Monovalent or (as required) divalent or higher polycyclic heterocycle includes fused heterocyclyl, spiro heterocyclyl, and bridged heterocyclyl, which can be saturated, partially saturated or unsaturated, but not aromatic. Polycyclic heterocyclyl can be a heterocyclyl obtained by fusing the above-mentioned heterocyclyl to 6-14-membered aryl (e.g. benzene ring), 3-12-membered cycloalkyl, 3-12-membered cycloalkenyl, 3-14-membered heterocyclyl or 3-14-membered heteroaryl, 5-6-membered monocyclic cycloalkyl, 5-6-membered monocyclic cycloalkenyl, 5-6-membered monocyclic heterocyclyl or 5-6-membered monocyclic heteroaryl, 5-6-membered monocyclic heterocyclyl.

Said fused heterocyclyl can be 6-12-membered fused ring group, 7-10-membered fused ring group, 6-10-membered fused ring group, or 6-12-membered saturated fused ring group. The representative example includes, but is not limited to, 3-azabicyclo[3.1.0]hexyl, 3,6-diazabicyclo[3.2.0]heptyl, 3,8-diazabicyclo[4.2.0]octyl, 3,7-diazabicyclo[4.2.0]octyl, octahydropyrrolo[3,4-c]pyrrolyl, octahydropyrrolo[3,4-b]pyrrolyl, octahydropyrrolo[3,4-b][1,4]oxazinyl, octahydro-1H-pyrrolo[3,4-c]pyridinyl, 2,3-dihydrobenzofuran-2-yl, 2,3-dihydrobenzofuran-3-yl, indoline-1-yl, indoline-2-yl, indoline-3-yl, 2,3-dihydrobenzothiophene-2-yl, octahydro-1H-indolyl, octahydrobenzofuranyl, octahydrocyclopenta[c]pyrrole, hexabydrocyclopenta[c]furan, 2,2-dioxobexahydrocyclopenta[c]thiophene, 2-imino-2-oxo-octahydrocyclopenta[c]thiophene.

Said spiro heterocyclyl can be a monovalent group obtained by removing one hydrogen atom from 6-12-membered spiro heterocycle, 7-11-membered spiro heterocycle, 6-12-membered saturated spiro heterocycle, or 7-membered saturated spiro heterocycle, or as required, a divalent or higher group obtained by removing hydrogen atoms from the same carbon atom or different carbon atoms of the spiro heterocycle. The example of the spiro heterocycle includes, but is not limited to,

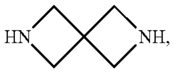, 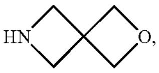, 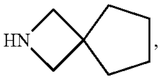,

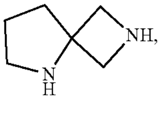, 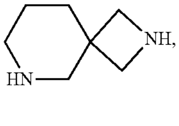, 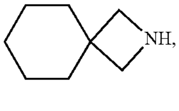,

-continued

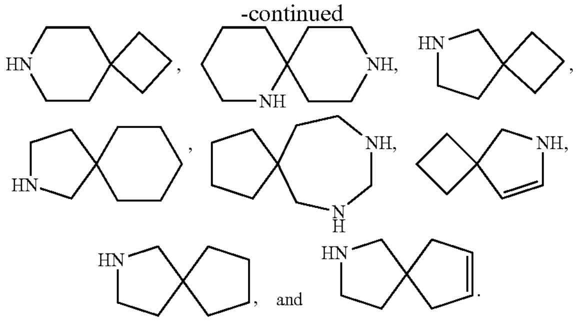

, , , , , and .

Said bridged heterocyclyl can be a monovalent group obtained by removing one hydrogen atom from 6-12-membered bridged heterocycle, 7-11-membered bridged heterocycle, 6-12-membered saturated bridged heterocycle, or 7-8-membered saturated bridged heterocycle, or as required, a divalent or higher group obtained by removing hydrogen atoms from the same carbon atom or different carbon atoms of the bridged heterocycle. The example of the bridged heterocycle includes, but is not limited to,

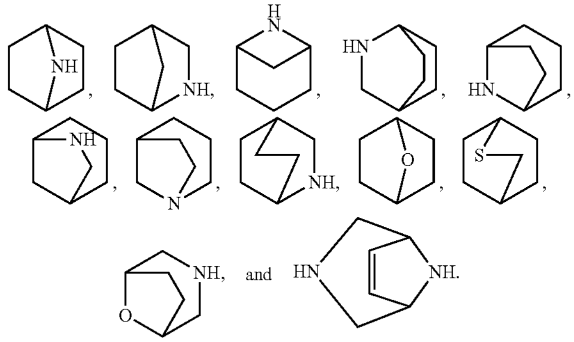

, , , , , , , , , and .

According to the present invention, “aromatic ring” refers to the carboneous cyclic hydrocarbon having the aromatic property. Monovalent or divalent or higher group (as required) is obtained derivatively from the aromatic carboneous cyclic hydrocarbon. Said aromatic carboneous cyclic hydrocarbon includes 6-14-membered aromatic ring, 6-10-membered aromatic ring, 6-8-membered monocyclic aromatic hydrocarbon and 8-14-membered polycyclic aromatic hydrocarbon. 6-8-membered monocyclic aryl is for example phenyl. 8-14-membered polycyclic aryl is for example naphthalenyl, phenanthrenyl, anthracenyl and the like. When it is a divalent group, phenylene, naphthalenediyl and the like can be exemplified.

As mentioned in the present invention, “aryl” or “aromatic group” (hereinafter collectively referred to as “aryl”) refers to monovalent or divalent or higher group (as required) obtained derivatively from aromatic carboneous cyclic hydrocarbon. It comprises 6-14-membered aryl, or 6-10-membered aryl. 6-14-membered aryl is for example phenyl, naphthalenyl, phenanthrenyl, and anthracenyl. 6-10-membered aryl is for example phenyl, and naphthalenyl. When it is a divalent group, phenylene, naphthalenediyl and the like can be exemplified.

As mentioned in the present invention, “heteroaromatic ring” refers to the cyclic hydrocarbon having the aromatic property and having at least one (for example, 1-5, 1-4, 1-3, 1-2 or 1) ring-constituting heteroatoms selected from 0, S, and N. It can be 5, 6, 7, 8, 9, 10, 11, 12, 13 or 14-membered aromatic cyclic group, preferably having 1-3 heteroatoms. In addition, the heteroaromatic ring of the present invention can be a monocyclic system, and may also be a polycyclic system (in form of fused ring, spiro ring and bridged ring). Specifically, monocyclic heteroaromatic ring such as pyrrole, pyrazine, pyrazole, indole, tetrazole, furan, thiophene, pyridine, imidazole, triazole, tetrazole, triazine, pyridazine, pyrimidine, pyrazine, isoxazole, thiazole, isothiazole, thiadiazole, oxazole, oxadiazole can be exemplified; polycyclic heteroaromatic ring such as isoindole, indazole, indolizine, isoindoline, quinoline, isoquinoline, cinnoline, phthalazine, quinazoline, naphthyridine, quinoxaline, purine, pteridine, benzoimidazole, benzoisoxazole, benzooxazole, benzooxadiazole, benzoisothiazole, benzothiazole, benzothiadiazole, benzofuran, isobenzofuran, benzothiophene, benzotriazole, imidazolopyridine, triazolopyridine, imidazolothiazole, pyrazinopyridazine, benzoimidazoline can be further exemplified.

As mentioned in the present invention, “heteroaryl” or “heteroaromatic group” (hereinafter collectively referred to as “heteroaryl”) refers to monovalent or higher group derived from the above-mentioned “heteroaromatic ring”. In addition, as mentioned in the present invention, “heteroaryl” may also be an aromatic cyclic hydrocarbyl containing at least one heteroatom selected from O, S and N and having a ring-constituting atom number of 5, 6, 7, 8, 9, 10, 11, 12, 13 or 14. Namely, it can be 5-14-membered heteroaryl, 5-10-membered heteroaryl, 5-6-membered heteroaryl. Heteroaryl can have 1, 2, 3, 4 or 5 heteroatoms as ring-constituting atom.

In addition, heteroaryl also comprises such a situation, in which the carbon atom or the sulfur atom is oxidized or nitridized, for example, the carbon or sulfur atom is replaced with C(═O), S(═O), $S(═O)_2$, or S(═O)(═N). Heteroaryl comprises monocyclic heteroaryl and polycyclic heteroaryl. Unless otherwise specified, X-membered heteroaryl comprises all possible monocyclic and polycyclic rings, which are completely aromatic or partially aromatic. Monocyclic heteroaryl can be 5-7-membered heteroaryl, or 5-6-membered heteroaryl. Its example includes, but is not limited to, furanyl, imidazolyl, isoxazolyl, thiazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiophenyl, triazolyl and triazinyl. In some embodiments, polycyclic heteroaryl refers to a group obtained by fusing monocyclic heteroaromatic ring to phenyl, cycloalkenyl, heteroaryl, or cycloalkyl, heterocyclyl.

Polycyclic heteroaryl can be 8-12-membered fused heteroaryl, or 9-10-membered fused heteroaryl. Its example includes, but is not limited to, benzoimidazolyl, benzofuranyl, benzothiophenyl, benzooxadiazolyl, benzothiadiazolyl, benzothiazolyl, cinnolinyl, 5,6-dihydroquinoline-2-yl, 5,6-dihydroisoquinoline-l-yl, furopyridinyl, indazolyl, indolyl, isoindolyl, isoquinolinyl, naphthyridinyl, purinyl, quinolinyl, 5,6,7,8-tetrahydroquinoline-2-yl, 5,6,7,8-tetrahydroquinolinyl, 5,6,7,8-tetrahydroquinoline-4-yl, 5,6,7,8-tetrahydroisoquinoline-l-yl, thienopyridinyl, 4,5,6,7-tetrahydrobenzo[c][1,2,5]oxadiazolyl and 6,7-dihydrobenzo[c][1,2,5]oxadiazole-4(5H)-one-yl. Said heteroaryl may also be the divalent group derived from the above-mentioned groups.

As mentioned in the present invention, “5-14-membered cyclic group” refers to a group having 5, 6, 7, 8, 9, 10, 11, 12, 13, or 14 ring-constituting atoms, which can be those having 5-14 ring-constituting atoms as mentioned above for cycloalkyl, cycloalkenyl, heterocyclic group, aromatic cyclic group, or heteroaromatic group of the present invention. It can specifically be 5-10-membered cyclic group, or 5-6-membered cyclic group. In addition, as mentioned in the present invention, "5-6-membered cyclic group" refers to a cyclic structure having 5-6 chemically feasible ring atoms, and the ring atom can optionally be selected from C, N, O, S, C(═O), S(═O), $S(=O)_2$, and S(═O)(═N). The formed cyclic structure can be monocyclic ring or polycyclic ring, which can be saturated, partially saturated or aromatic. Its example includes, but is not limited to, a group obtained derivatively from pyrroline, pyrrolidine, piperidine, piperazine, morpholine, thiomorpholine, tetrahydropyran, dihydropyridine, dihydropyridazine, 1,4-dioxane, oxathiolane, tetrahydrothiopyran, tetrahydrofuran, tetrahydropyran, tetrahydrothiazole, tetrahydroisothiazole, pyrrole, pyrazine, pyrazole, indole, tetrazole, furan, thiophene, pyridine, imidazole, triazole, tetrazole, triazine, pyridazine, pyrimidine, pyrazine, isoxazole, thiazole, isothiazole, thiadiazole, oxazole, oxadiazole, benzene and the like. Preferably, it is 5-6-membered oxygen-containing cyclic group, i.e. cyclic group having at least one oxygen atom and a ring-constituting atom number of 5 or 6.

As mentioned in the present invention, "one or more" means that the number of the substituents can be the number of all of the sites on which group to be substituted can be chemically substituted, preferably 1-6, more preferably 1-5, further preferably 1-3, still preferably 1-2, more further preferably 1.

As mentioned in the present invention, in the term of "optionally substituted by a substituent", the number of the substituent(s) may be 0 (i.e. not substituted), or from 1 to the number of all of the sites on which group to be substituted can be chemically substituted, preferably 1-6, more preferably 1-5, further preferably 1-4, still preferably 1-3, more further preferably 1-2, still further preferably 1.

Specifically, the present invention provides a compound represented by general formula (I), or a pharmaceutically acceptable salt, an ester, a stereoisomer, or a tautomer thereof.

(I)

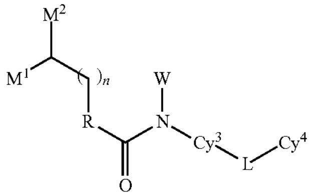

wherein W is selected from hydrogen or $C_{1-6}$alkyl optionally substituted by a substituent;

R represents a group represented by the following general formula (a') (b') or (c')

(a')

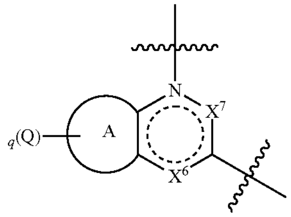

,

-continued (b')

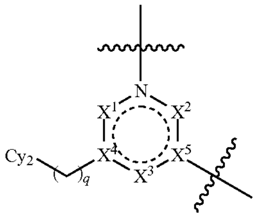

, or (c')

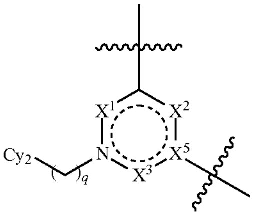

, in formula (a'), ring A represents 6-10-membered aromatic ring, 5-6-membered heteroaromatic ring having 1-3 heteroatoms selected from $NR^b$, O and S, or 5-6-membered heterocyclic ring having 1-4 heteroatoms selected from $NR^b$, O and S;

Q is each independently selected from H, cyano, hydroxy, mercapto, halogen, carboxyl, nitro, —$NR^bR^c$, —C(O)$R^d$, —C(O)$NR^bR^c$, —OC(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R', —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

in formula (a'), the moiety

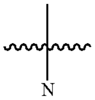

is attached via a linking group to the moiety

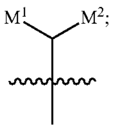

in formula (a'), $X^6$ and $X^7$ are each independently selected from $CR^aR^a$, C═O and $NR^b$, and at least one of $X^6$ and $X^7$ is C═0;

in formula (b'), the moiety

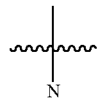 [SMILES: *N]

is attached via a linking group to the moiety

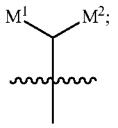

in formula (c), the moiety

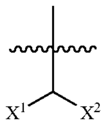

is attached via a linking group to the moiety

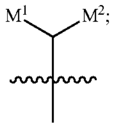

$X^1$, $X^2$, and $X^3$ are each independently selected from $CR^aR^a$, C═O and $NR^b$, and at least one of $X^1$, $X^2$, and $X^3$ is C═O:

$X^4$ and $X^5$ are each independently selected from $CR^a$ or N;

$M^1$ and $M^2$ are each independently selected from H, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, or $M^1$ and $M^2$ together with the atoms to which they are attached may form 3-8-membered cycloalkyl optionally substituted by a substituent, or the

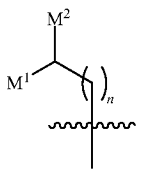

moiety may form a hydrogen atom;

$Cy^2$ is selected from 3-12-membered cycloalkyl optionally substituted by one or more $R^2$, 3-12-membered cycloalkenyl optionally substituted by one or more $R^2$, 3-14-membered heterocyclyl optionally substituted by one or more $R^2$, 6-14-membered aryl optionally substituted by one or more $R^2$, or 5-10-membered heteroaryl optionally substituted by one or more $R^2$, $R^2$ is each independently selected from H, cyano, hydroxy, mercapto, halogen, carboxyl, nitro, —$NR^bR^c$, —C(O)$R^d$, —C(O)$NR^bR^c$, —OC(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R', —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

$Cy^3$ is selected from 3-12-membered cycloalkyl optionally substituted by one or more $R^3$, 3-14-membered heterocyclyl optionally substituted by one or more $R^3$, or 5-10-membered heteroaryl optionally substituted by one or more $R_3$, $R_3$ is each independently selected from H, cyano, hydroxy, mercapto, halogen, carboxyl, nitro, —$NR^bR^c$, —C(O)$R^d$, —C(O)$NR^bR^c$, —OC(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R', —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent; when $X^1$ or $X^2$ represents $NR^b$, $Cy^3$ may also be a 6-14 membered aromatic group optionally substituted by one or more $R^3$;

$Cy^4$ is selected from 3-12-membered cycloalkyl optionally substituted by one or more $R^4$, 3-14-membered heterocyclyl optionally substituted by one or more $R^4$, 5-14-membered heteroaryl optionally substituted by one or more $R^4$, and 6-14-membered aryl optionally substituted by one or more $R^4$, $R^4$ is each independently selected from H, cyano, hydroxy, mercapto, halogen, carboxyl, nitro, —$NR^bR^c$, —C(O)$R^d$, —C(O)$NR^bR^c$, —C(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R', —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent, or two $R^4$ together with the atoms to which they are attached may form a 5-14-membered cyclic group;

L is selected from —$NR^b$—, —O—, —S— and —$(CR^aR^a)_m$—, m is an integer of 1-3;

$R^a$ is absent, or at each occurrence, is each independently selected from H, cyano, hydroxy, mercapto, halogen, carboxyl, nitro, —$NR^bR^c$, —C(O)$R^d$, —C(O)$NR^bR^c$, —OC(O)$NR^bR^c$, —$NR^b$C(O)$R^d$, —$SO_2$—$NR^bR^c$, —$SO_2R^d$, —$NR^bSO_2R^d$, $C_{1-6}$alkyl optionally substituted by a substituent, $C_{1-6}$alkoxy optionally substituted by a substituent, $C_{2-8}$alkenyl optionally substituted by a substituent, $C_{2-8}$alkynyl optionally substituted by a substituent, —$C_{1-6}$alkyl-R' optionally substituted by a substituent, —$C_{1-6}$alkoxy-R' optionally substituted by a substituent, —O—R', —C(O)—R', —$SO_2$—R', —$NR^b$C(O)—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

$R^b$ and $R^c$ are each absent, or at each occurrence, are each independently selected from H, hydroxy, $C_{1-6}$alkyl optionally substituted by a substituent, —$C_{1-6}$alkyl-R' optionally substituted by a substituent, —C(O)—R', —$SO_2$—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

$R^d$ is absent, or at each occurrence, is each independently selected from hydroxy, halogen, amino, -amino($C_{1-6}$ alkyl optionally substituted by a substituent)$_{1-2}$, $C_{1-6}$alkyl optionally substituted by a substituent, $C_{1-6}$alkoxy optionally substituted by a substituent, —$C_{1-6}$alkyl-R' optionally substituted by a substituent, —$C_{1-6}$alkoxy-R' optionally substituted by a substituent, —O—R', 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

R' is each independently selected from 3-12-membered cycloalkyl optionally substituted by a substituent, 3-12-membered cycloalkenyl optionally substituted by a substituent, 3-14-membered heterocyclyl optionally substituted by a substituent, 6-14-membered aryl optionally substituted by a substituent, or 5-10-membered heteroaryl optionally substituted by a substituent;

q is an integer of 0-4;

n is an integer of 0-4;

The substituent in said "optionally substituted by a substituent" is each independently selected from hydroxy, mercapto, amino, carboxyl, cyano, nitro, halogen, $C_{1-6}$alkyl, $C_{1-6}$alkoxy$C_{1-6}$alkyl, $C_{1-6}$alkoxy, $C_{1-6}$alkyl$C_{1-6}$alkoxy, $C_{1-6}$alkoxy$C_{1-6}$alkoxy, $C_{1-6}$alkylamino, $(C_{1-6}alkyl)_2$amino, $C_{1-6}$alkylaminocarbonyl, $(C_{1-6}alkyl)_2$aminocarbonyl, $C_{1-6}$alkylcarbonyl, $C_{1-6}$alkylcarbonyloxy, $C_{1-6}$alkylcarbonylamino, $C_{1-6}$alkylsulfonamido, halo$C_{1-6}$alkyl, halo$C_{1-6}$ alkoxy, $C_{1-6}$alkylsulfonyl, $C_{1-6}$alkylthio, 3-12-membered cycloalkyl, 6-14-membered aryl, 3-12-membered heterocyclyl, 5-10-membered heteroaryl and oxo;

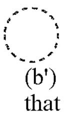 in the groups represented by formula (a'), formula (b') and formula (c') represents a double bond moiety that is optionally present in the cyclic structure;

provided that in the groups represented by formula (a') and formula (c'), the

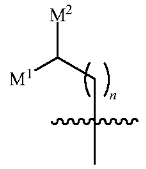

moiety will not form a hydrogen atom;

provided that in the group represented by formula (b'), when $X^1$ and $X^2$ are C═O, and $X^4$ is N, $R^2$ as the substituent of $Cy^2$ does not represent a halogen atom.

In another embodiment of the present invention, the compound represented by formula (I) of the present invention, or a pharmaceutically acceptable salt, an ester, a stereoisomer, or a tautomer thereof is represented by the following formula (II).

(II)

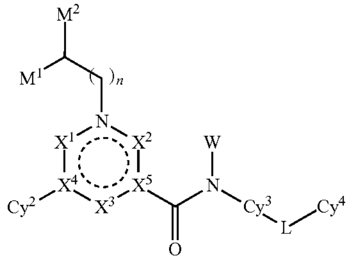

In another embodiment of the present invention, the compound represented by formula (I) of the present invention, or a pharmaceutically acceptable salt, an ester, a stereoisomer, or a tautomer thereof is represented by the following formula (III).

(III)

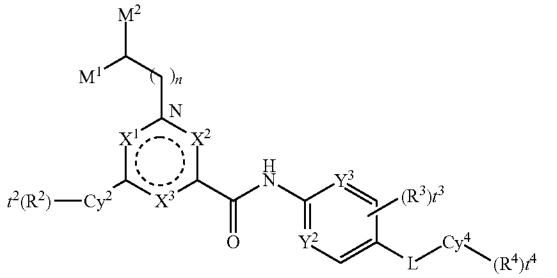

$Y^2$ and $Y^3$ are each independently selected from CH or N, and at least one of $Y^2$ and $Y^3$ is N;

$t^2$, $t^3$, and $t^4$ are each independently selected from an integer of 1-5.

In another embodiment of the present invention, the compound represented by formula (I) of the present invention, or a pharmaceutically acceptable salt, an ester, a stereoisomer, or a tautomer thereof is represented by the following formula (IV).

(III)

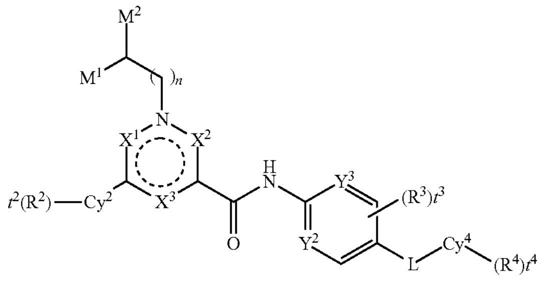

$Y^6$ and $Y^7$ are each independently selected from CH or N, and at least one of $Y^6$ and $Y^7$ is N;

$t^2$, $t^3$ and $t^4$ are each independently selected from an integer of 1-5.

In an embodiment of the present invention, $M^1$ and $M^2$ are each independently selected from H, $C_{1-6}$alkyl optionally substituted by a substituent, and $C_{2-8}$alkenyl optionally substituted by a substituent, or $M^1$ and $M^2$ together with the atoms to which they are attached may form 3-8-membered cycloalkyl optionally substituted by a substituent, or the

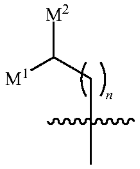

moiety may form a hydrogen atom.

In an embodiment of the present invention, $M^1$ and $M^2$ are each independently $C_{1-6}$alkyl optionally substituted by a substituent, or $M^1$ and $M^2$ together with the atoms to which they are attached may form 3-8-membered cycloalkyl optionally substituted by a substituent, or the

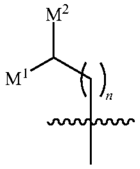

moiety may form a hydrogen atom.

In an embodiment of the present invention, $M^1$ and $M^2$ are each independently $C_{1-6}$alkyl, or $M^1$ and $M^2$ together with the atoms to which they are attached may form cyclopropyl, cyclobutyl, cyclopentyl, cyclohexyl.

In an embodiment of the present invention, $X^1$ is $NR^b$, $X^2$ is $CR^aR^a$, and $X^3$ is C═O.

In an embodiment of the present invention, $X^1$ is $CR^aR^a$, $X^2$ is $NR^b$, and $X^1$ is C═O.

In an embodiment of the present invention, $X^1$ is C═O, $X^2$ is $CR^aR^a$, and $X^1$ is C═O.

In an embodiment of the present invention, $X^1$ is $CR^aR^a$, $X^2$ is C═O, and $X^3$ is C═O.

In an embodiment of the present invention, $X^1$ is $CR^aR^a$, $X^2$ is $CR^aR^a$, and $X^3$ is C═O).

In an embodiment of the present invention, $X^1$ is C═O, $X^2$ is $CR^aR^a$, and $X^3$ is $CR^aR^a$.

In an embodiment of the present invention, $X^1$ is $CR^aR^a$, $X^2$ is C═O, and $X^3$ is $CR^aR^a$.

In an embodiment of the present invention, $X^4$ is N, and $X^5$ is $CR^a$.

In an embodiment of the present invention, $X^4$ is $CR^a$, and $X^5$ is $CR^a$.

In an embodiment of the present invention, $X^4$ is N, and $X^5$ is N.

In an embodiment of the present invention, $X^4$ is $CR^a$, and $X^5$ is N.

In an embodiment of the present invention, $X^6$ is C═O, and $X^7$ is $CR^aR^a$.

In an embodiment of the present invention, $X^6$ is $CR^aR^a$, and $X^7$ is C═O.

In an embodiment of the present invention, $X^6$ is C═O, and $X^7$ is $NR^b$.

In an embodiment of the present invention, $X^6$ is $NR^b$, and $X^7$ is C═O.

In an embodiment of the present invention, in formula (a'), ring A represents 6-10-membered aromatic ring.

In an embodiment of the present invention, in formula (a'), ring A represents benzene ring, naphthalene ring.

In an embodiment of the present invention, in formula (a'), ring A represents benzene ring, naphthalene ring, furan ring, thiophene ring, pyrrole ring, oxazole ring, isoxazole ring, thiazole ring, isothiazole ring, pyrazole ring, thiazole ring, imidazole ring, pyridine ring, pyridazine ring, pyrimidine ring, pyrazine ring, pyran ring, thiopyran ring, pyrrolidine ring, pyrroline ring, tetrahydrofuran ring, tetrahydrothiophene ring, piperidine ring or tetrahydropyran ring.

In an embodiment of the present invention, in formula (a'), Q is each independently selected from H, hydroxy, halogen, carboxyl, nitro, —$NR^bR^c$, $C_{1-6}$alkyl optionally substituted by a substituent and $C_{1-6}$alkoxy optionally substituted by a substituent.

In an embodiment of the present invention, $Cy^2$ is selected from 6-14-membered aryl optionally substituted by one or more $R^2$, or 5-10-membered heteroaryl optionally substituted by one or more $R^2$.

In an embodiment of the present invention, $Cy^2$ is selected from phenyl or naphthalenyl, both of which are optionally substituted by one or more $R^2$.

In an embodiment of the present invention, $Cy^3$ is selected from 3-8-membered cycloalkyl optionally substituted by one or more $R^3$, or 5-10-membered heteroaryl optionally substituted by one or more $R^3$, when $X^1$ or $X^2$ represents $NR^b$, $Cy^3$ may also be 6-10-membered aromatic group optionally substituted by one or more $R^3$.

In an embodiment of the present invention, $Cy^3$ is selected from 3-6-membered cycloalkyl optionally substituted by one or more $R^3$, or 5-6-membered heteroaryl optionally substituted by one or more $R^3$, when $X^1$ or $X^2$ represents $NR^b$, $Cy^3$ may also be selected from phenyl or naphthalenyl, both of which are optionally substituted by one or more $R^3$.

In an embodiment of the present invention, $Cy^3$ is selected from pyrrolyl optionally substituted by one or more $R^3$, pyridinyl optionally substituted by one or more $R^3$, pyrimidinyl optionally substituted by one or more $R^3$, pyridazinyl optionally substituted by one or more $R^3$, or pyrazinyl optionally substituted by one or more $R^3$.

In an embodiment of the present invention, $Cy^3$ represents a group represented by

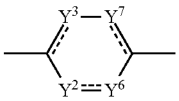

optionally substituted by one or more $R^3$, wherein ⎓ represents a single bond or a double bond, $Y^2$, $Y^3$, $Y^6$ and $Y^7$ are each independently selected from $CR^aR^a$ and $NR^b$, and at least one of $Y^2$, $Y^3$, $Y^6$ and $Y^7$ is $NR^b$.

In an embodiment of the present invention, $Cy^3$ represents a group represented by

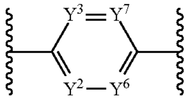

optionally substituted by one or more $R^3$, $Y^2$, $Y^3$, $Y^6$, and $Y^7$ are each independently selected from CH or N, and at least one of $Y^2$, $Y^3$, $Y^6$, and $Y^7$ is N.

In an embodiment of the present invention, $Cy^3$ is selected from the following groups optionally substituted by one or more $R^3$:

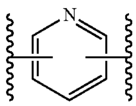, 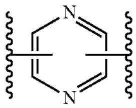, 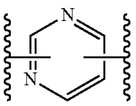, 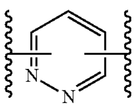, or 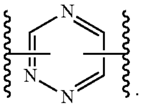.

In an embodiment of the present invention, $Cy^3$ is selected from the following groups optionally substituted by one or more $R^3$:

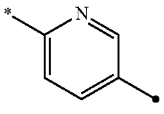, 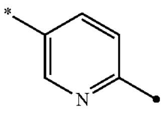, 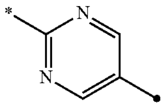, or 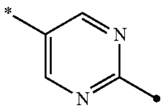, the * end is attached to N, and the • end is attached to L.

In an embodiment of the present invention, $Cy^4$ is selected from 5-10-membered heterocyclyl optionally substituted by one or more $R^4$, 5-10-membered heteroaryl optionally substituted by one or more $R^4$, and 6-10-membered aryl optionally substituted by one or more $R^4$.

In an embodiment of the present invention, $Cy^4$ is selected from 9-10-membered heteroaryl optionally substituted by one or more $R^4$, and phenyl or naphthalenyl, both of which are optionally substituted by one or more $R^4$.

In an embodiment of the present invention, $Cy^4$ represents a group represented by

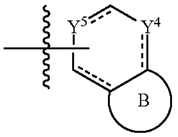

optionally substituted by one or more $R^4$, wherein ⎓ represents a single bond or a double bond, $Y^4$ and $Y^5$ are each independently selected from $CR^aR^a$ and $NR^b$, and at least one of $Y^4$ and $Y^5$ is $NR^b$, ring B is benzene ring, naphthalene ring or 5-6-membered heteroaromatic ring.

In an embodiment of the present invention, $Cy^4$ represents a group represented by

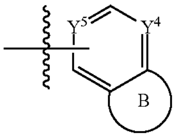

optionally substituted by one or more $R^4$, $Y^4$ and $Y^5$ are each independently selected from CH or N, and at least one of $Y^4$ and $Y^5$ is N.

In an embodiment of the present invention, ring B is benzene ring or 5-6-membered heteroaromatic ring containing 1-3 heteroatoms selected from $NR^b$, O, and S.

In an embodiment of the present invention, $Cy^4$ is selected from the following groups optionally substituted by one or more $R^4$:

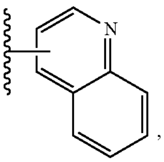, 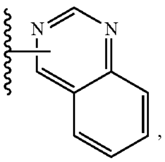, 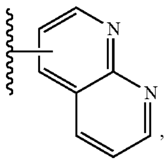, 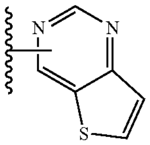, 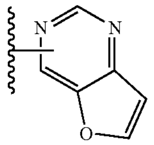, and 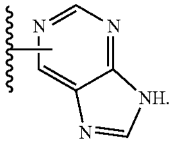

In an embodiment of the present invention, $Cy^4$ is selected from the following group optionally substituted by one or more $R^4$:

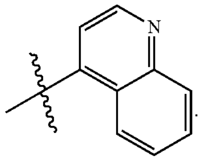 [SMILES: *c1ccnc2ccccc12].

In an embodiment of the present invention, $R^2$ is each independently selected from H, hydroxy, halogen, carboxyl, nitro, —$NR^bR^c$, —C(O)$R^d$, —C(O)$NR^bR^c$, —$NR^b$C(O)O$R^d$, $C_{1-6}$alkyl optionally substituted by a substituent, and $C_{1-6}$alkoxy optionally substituted by a substituent.

In an embodiment of the present invention, $R^2$ is each independently selected from H, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy; preferably, $R^2$ is each independently selected from H, hydroxy, fluoro, chloro, bromo, or $C_{1-4}$alkyl.

In an embodiment of the present invention, $R^3$ is each independently selected from H, hydroxy, halogen, carboxyl, nitro, —$NR^bR^c$, —C(O)$R^d$, —C(O)$NR^bR^c$, —$NR^b$C(O)$R^d$, $C_{1-6}$alkyl optionally substituted by a substituent, and $C_{1-6}$alkoxy optionally substituted by a substituent.

In an embodiment of the present invention, $R^3$ is each independently selected from H, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy; preferably, $R^3$ is each independently selected from H, hydroxy, fluoro, chloro, bromo, or $C_{1-4}$alkyl.

In an embodiment of the present invention, $R^4$ is each independently selected from H, hydroxy, halogen, carboxyl, nitro, —$NR^bR^c$, —C(O)$R^d$, —C(O)$NR^bR^c$, —$NR^b$C(O)$R^d$, $C_{1-6}$alkyl optionally substituted by a substituent, and $C_{1-6}$alkoxy optionally substituted by a substituent, or two $R^4$ together with the atoms to which they are attached may form a 5-6-membered cyclic group.

In an embodiment of the present invention, preferably, $R^4$ is each independently selected from H, hydroxy, halogen, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkyl$C_{1-6}$alkoxy, and $C_{1-6}$alkoxy$C_{1-6}$alkoxy, or two $R^4$ together with the atoms to which they are attached may form a 5-6-membered oxygen-containing cyclic group.

In an embodiment of the present invention, $R^4$ is selected from H, hydroxy, mercapto, halogen, $C_{1-4}$alkyl, halo$C_{1-4}$alkyl, $C_{1-4}$alkoxy, $C_{1-4}$alkoxy$C_{1-4}$alkyl, $C_{1-4}$alkyl$C_{1-4}$alkoxy, $C_{1-4}$alkoxy$C_{1-4}$alkoxy, and halo$C_{1-4}$alkoxy, or two $R^4$ together with the atoms to which they are attached may form a 5-6-membered oxygen-containing cyclic group.

In an embodiment of the present invention, $R^a$ is absent, or at each occurrence, is each independently selected from H, halogen, hydroxy, carboxyl, nitro, —$NR^bR^c$, —C(O)$R^4$, —C(O)$NR^bR^c$, —$NR^b$C(O)$R^d$, $C_{1-6}$alkyl optionally substituted by a substituent, and $C_{1-6}$alkoxy optionally substituted by a substituent.

In an embodiment of the present invention, $R^a$ is absent, or at each occurrence, is each independently selected from H, hydroxy, halogen, carboxyl, nitro, $C_{1-6}$alkyl, $C_{1-6}$alkoxy, or halo$C_{1-6}$alkyl.

In an embodiment of the present invention, $R^a$ is absent, or at each occurrence, is each independently selected from H, $C_{1-6}$alkyl, and $C_{1-6}$alkoxy.

In an embodiment of the present invention, $R^b$ and $R^c$ are each absent, or at each occurrence, are each independently selected from H, or $C_{1-6}$alkyl optionally substituted by a substituent.

In an embodiment of the present invention, $R^b$ and $R^c$ are each absent, or at each occurrence, are each independently selected from H, $C_{1-6}$alkyl, or halo$C_{1-6}$alkyl.

In an embodiment of the present invention, $R^b$ and $R^c$ are each absent, or at each occurrence, are each independently selected from H, or $C_{1-6}$alkyl.

In an embodiment of the present invention, $R^d$ is absent, or at each occurrence, is each independently selected from hydroxy, halogen, amino, -amino($C_{1-6}$alkyl optionally substituted by a substituent)$_{1-2}$, $C_{1-6}$alkyl optionally substituted by a substituent, and $C_{1-6}$alkoxy optionally substituted by a substituent.

In an embodiment of the present invention, $R^d$ is absent, or at each occurrence, is each independently selected from hydroxy, amino, -amino($C_{1-6}$alkyl)$_{1-2}$, $C_{1-6}$alkyl, halo$C_{1-6}$alkyl, $C_{1-6}$alkoxy, or halo$C_{1-6}$alkoxy.

In an embodiment of the present invention, $R^d$ is absent, or at each occurrence, is each independently selected from hydroxy, amino, $C_{1-4}$alkyl, halo$C_{1-4}$alkyl, $C_{1-4}$alkoxy, and halo$C_{1-4}$alkoxy.

In an embodiment of the present invention, R' is selected from 3-8-membered cycloalkyl optionally substituted by a substituent, 3-8-membered cycloalkenyl optionally substituted by a substituent, 3-10-membered heterocyclyl optionally substituted by a substituent, 6-10-membered aryl optionally substituted by a substituent, or 5-6-membered heteroaryl optionally substituted by a substituent.

In an embodiment of the present invention, R' is selected from 3-6-membered cycloalkyl optionally substituted by a substituent, 4-7-membered heterocyclyl optionally substituted by a substituent, 6-10-membered aryl optionally substituted by a substituent, or 5-6-membered heteroaryl optionally substituted by a substituent.

In an embodiment of the present invention, R' is selected from cyclopropyl, cyclobutyl, cyclopentyl, cyclohexyl, phenyl, naphthalenyl, oxacyclopropyl, oxacyclobutyl, oxacyclopentyl, oxacyclohexyl, oxacycloheptyl, pyrrolyl, furanyl, thiophenyl, oxazolyl, isoxazolyl, pyrazolyl, thiazolyl, pyridinyl, pyrimidinyl, and pyridazinyl.

In an embodiment of the present invention, the substituent in said "optionally substituted by a substituent" is each independently selected from hydroxy, mercapto, amino, carboxyl, cyano, nitro, halogen, $C_{1-6}$alkyl, $C_{1-6}$alkoxy$C_{1-6}$alkyl, $C_{1-6}$alkoxy, $C_{1-6}$alkyl$C_{1-6}$alkoxy, $C_{1-6}$alkoxy$C_{1-6}$alkoxy, $C_{1-6}$alkylamino, ($C_{1-6}$alkyl)$_2$amino, $C_{1-6}$alkylaminocarbonyl, ($C_{1-6}$alkyl)$_2$aminocarbonyl, $C_{1-6}$alkylcarbonyl, $C_{1-6}$alkylcarbonyloxy, $C_{1-6}$alkylcarbonylamino, $C_{1-6}$alkylsulfonamido, halo$C_{1-6}$alkyl, halo$C_{1-6}$alkoxy, $C_{1-6}$alkylsulfonyl, $C_{1-6}$alkylthio, 3-8-membered cycloalkyl, 6-10-membered aryl, 3-8-membered heterocyclyl, 5-6-membered heteroaryl and OXO.

In an embodiment of the present invention, the substituent in said "optionally substituted by a substituent" is each independently selected from hydroxy, mercapto, amino, carboxyl, cyano, nitro, halogen, $C_{1-4}$alkyl, $C_{1-4}$alkoxy$C_{1-4}$alkyl, $C_{1-4}$alkoxy, $C_{1-4}$alkyl$C_{1-4}$alkoxy, $C_{1-4}$alkoxy$C_{1-4}$alkoxy, $C_{1-4}$alkylamino, ($C_{1-4}$alkyl)$_2$amino, $C_{1-4}$alkylaminocarbonyl, ($C_{1-4}$alkyl)$_2$aminocarbonyl, $C_{1-4}$alkylcarbonyl, $C_{1-4}$alkylcarbonyloxy, $C_{1-4}$alkylcarbonylamino, $C_{1-4}$alkylsulfonamido, halo$C_{1-4}$alkyl, halo$C_{1-4}$alkoxy, $C_{1-4}$alkylsulfonyl, $C_{1-4}$alkylthio, cyclopropyl, cyclobutyl, cyclopentyl, cyclohexyl, cycloheptyl, phenyl, naphthalenyl, oxacyclopropyl, oxacyclobutyl, oxacyclopentyl, oxacyclohexyl, oxacycloheptyl, pyrrolyl, furanyl, thiophenyl, oxazolyl, isoxazolyl, pyrazolyl, thiazolyl, pyridinyl, pyrimidinyl, pyridazinyl and oxo.

In an embodiment of the present invention, n is 0, 1, 2, 3 or 4.

In an embodiment of the present invention, q is 0, 1, 2, 3 or 4.

In an embodiment of the present invention, L is selected from —$NR^b$—, —O— or —S—.

In an embodiment of the present invention, R represents the group represented by formula (b'), the six-membered ring in the group represented by formula (b') is represented by any of the following, wherein ⩦ represents a single bond or a double bond,

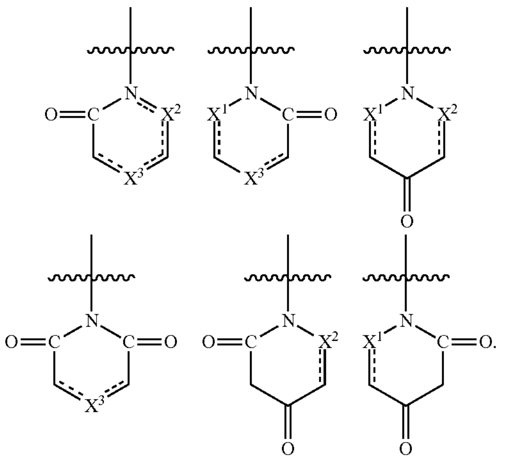

In the present invention,  in the groups represented by formula (a'), formula (b') and formula (c') represents a double bond moiety that is optionally present in the cyclic structure, provided that the valency requirement of each atom is met.

In an embodiment of the present invention, in the compound represented by formula (I) of the present invention, there is not such a situation in which three or more nitrogen atoms as ring-constituting atoms are directly connected.

In an embodiment of the present invention, in the compound represented by formula (I) of the present invention, there is not such a situation in which two or more carbonyl groups (C═O) are directly connected on the ring.

In an embodiment of the present invention, on the ring of formula (a'), only one C═O group is present.

In an embodiment of the present invention, on the ring of formula (b'), only one C═O group is present.

In an embodiment of the present invention, on the ring of formula (c'), only one C═O group is present.

In an embodiment of the present invention, $X^1$ and $X^2$ are each independently selected from $CR^aR^a$ and $NR^b$, $X^3$ represents C═O.

In an embodiment of the present invention, when $X^1$ or $X^2$ is C═O, $X^4$ is not $NR^b$.

In an embodiment of the present invention, $X^4$ is not $NR^b$.

In an embodiment of the present invention, either $X^1$ or $X^2$ is $NR^b$, $X^3$ represents C═O.

As mentioned in the present invention, "ester" refers to a pharmaceutically acceptable ester formed from the compound of the present invention, more specifically, the ester such as formic acid ester, acetic acid ester, propionic acid ester, butyric acid ester, acrylic acid ester and ethyl succinic acid ester of the compound of the present invention, but not limited thereto.

As mentioned in the present invention, "a pharmaceutically acceptable salt" refers to a pharmaceutically acceptable acid and base addition salt or solvate thereof. Such pharmaceutically acceptable salt includes a salt of an acid such as: hydrochloric acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, and alkanoic acid (such as acetic acid, HOOC—$(CH_2)_n$—COOH (wherein n is 0-4)); a salt of a base: sodium salt, potassium salt, calcium salt, ammonium salt and the like. Those skilled in the art know a variety of nontoxic pharmaceutically acceptable addition salts.

Hydrogen atom, fluorine atom, carbon atom, nitrogen atom, oxygen atom, sulfur atom and the like in the present invention also include their respective radioisotopes or stable isotopes.

According to the present invention, "tumor" comprises sarcoma, lymphoma and cancer, and specifically can comprise lung cancer, squamous carcinoma, bladder cancer, gastric cancer, ovarian cancer, peritoneal cancer, breast cancer, breast ductal carcinoma, head and neck cancer, endometrial cancer, corpus uteri carcinoma, rectal cancer, liver cancer, kidney cancer, renal pelvis cancer, esophageal cancer, adenocarcinoma of esophagus, glioma, prostate cancer, thyroid cancer, female reproductive system cancer, carcinoma in situ, lymphoma, neurofibromatosis, bone cancer, skin cancer, brain cancer, colon cancer, testicular cancer, gastrointestinal stromal tumor, oral cancer, cancer of pharynx, multiple myeloma, leukemia, non-Hodgkin's lymphoma, villous colon adenoma, melanoma, cell tumor and sarcoma.

As mentioned in the present invention, "related diseases caused by NTRK" comprise non-small cell lung cancer, colorectal cancer, mammary analogue secretory carcinoma, sarcoma, astrocytoma, glioblastoma, Spitz-like melanoma, cholangiocarcinoma, papillary thyroid carcinoma, breast secretory cancer, breast cancer-unknown pathological type and the like.

According to the present invention, the expression "A/and B" refers to A alone, or both A and B. For example, "the TAM family kinase/and the CSF1R kinase" refers to "the TAM family kinase" alone, or both "the TAM family kinase" and "the CSF1R kinase".

"Stereoisomers" of the compounds of formulae (I), (II), (III) and (IV) of the present invention mean that when an asymmetric atom exists in the compounds of the formulae (I), (II), (III) and (IV), enantiomers can be generated; when a carbon-carbon double bond or cyclic structure is present in the compounds, cis and trans isomers will be generated. All of enantiomers, diastereomers, racemic isomers, cis and trans isomers, geometric isomers, epimers of the compounds of formulae (I), (II), (III) and (IV), and mixtures thereof are included within the scope of the invention. The definition of the compound of the present invention includes all possible stereoisomers and mixtures thereof. In particular, it includes racemic forms and isolated optical isomers having the indicated activities. The racemic form can be resolved by physical methods such as fractional crystallization, separation or crystallization of diastereomeric derivatives or separation by chiral column chromatography. Individual optical isomers can be obtained from the racemate by conventional methods, such as salt formation with an optically active acid followed by crystallization.

"Tautomers" of the compounds of formulae (I), (II), (III) and (IV) of the present invention mean that when a certain atom in the compounds of formulae (I), (II), (III) and (IV) moves rapidly between two positions, functional group isomers will be generated and are referred to as tautomers; when hydrogen on the a position of a functional group containing a carbonyl group is attached to the a carbon, a keto tautomer will be generated, and when hydrogen on the a position of a functional group containing a carbonyl group is attached to the oxygen atom of the carbonyl group, an alcoholic tautomer will be generated.

The pharmaceutical composition of the present invention contains at least one of the compounds represented by formula (I), formula (II), formula (III) and formula (IV), or a pharmaceutically acceptable salt, an ester, a stereoisomer, or a tautomer thereof.

The pharmaceutical composition of the present invention contains the compounds represented by formula (I), formula (II), formula (III) and formula (IV), or a pharmaceutically acceptable salt, an ester, a stereoisomer, or a tautomer thereof and optionally one or more pharmaceutically acceptable carriers.

The pharmaceutical composition of the present invention can be administered by any suitable means known in the art, for example, orally, parenterally (including subcutaneously, intramuscularly, intravenously, intraarterially, intradermally, intrathecally and epidurally), transdermally, rectally, nasally, transpulmonarily, topically (including orally and sublingually), vaginally, intraperitoneally, intrapulmonarily and intranasally, to a patient or a subject in need of such prevention and/or treatment.

The pharmaceutical composition of the present invention can be made into conventional solid preparations, such as tablets, capsules, pills, and granules; or can also be made into oral liquid preparations, such as oral solutions, oral suspensions, and syrups. For making into oral preparations, one or more of excipient, diluent, sweetener, solubilizer, lubricant, binder, tablet disintegrant, stabilizer, preservative or encapsulating material can be suitably added. For parenteral administration, the pharmaceutical composition can be made into injections, including sterile powder for injection and concentrated solution for injection. Upon making into injections, the conventional production methods known in the pharmaceutical field can be used, and upon formulating the injection, an additive may not be added, or a suitable additive can be added according to the drug properties. For rectal administration, the pharmaceutical composition can be made into suppositories and the like. For transpulmonary administration, the pharmaceutical composition can be made into inhalations or aerosols and the like. According to the present invention, suitable solid carriers include, but are not limited to, for example, cellulose, glucose, lactose, mannitol, magnesium stearate, magnesium carbonate, sodium carbonate, sodium saccharin, sucrose, dextrin, talc, starch, pectin, gelatin, tragacanth, acacia, sodium alginate, parabens, methylcellulose, sodium carboxymethylcellulose, low melting wax, cocoa butter and the like. Suitable liquid carriers include but are not limited to water, ethanol, polyol (e.g., glycerol, propylene glycol, liquid polyethylene glycol and the like), vegetable oil, glyceride and mixtures thereof.

Methods for preparing the pharmaceutical composition of the present invention are generally known. The preparation of the pharmaceutical composition of the present invention in a known manner includes conventional methods of mixing, granulating, tableting, coating, dissolving or lyophilizing.

The pharmaceutical formulation is preferably in a unit dosage form. In this form, the formulation is subdivided into unit dosages containing appropriate quantities of the active ingredient. The unit dosage form can be packaged in a package containing discrete quantities of the formulation, such as a packaged tablet, a capsule, or a powder in a vial or ampule.

The dosage of the drug to be administered depends on various factors including the age, weight and condition of the patient and the route of administration. The precise dosages to be administered will be determined based on the judgment of the treating physician. Typical dosages for administration of the active compound would be, for example, from about 0.01 to about 100 mg per day, from about 0.05 to about 75 mg per day, from about 0.1 to about 50 mg per day, or from about 5 to about 10 mg per day. The desired dosage will also depend on the particular compound employed, the severity of the disease, the route of administration, the weight and health condition of the patient, and the judgment of the treating physician.

Method for Preparing the Compound of General Formula (I) of the Present Invention The compounds of the present invention can be prepared by a variety of methods, including standard chemical methods. Unless otherwise stated, any previously defined variables will continue to have the previously defined meaning. Exemplary general synthetic methods are set forth in the schemes below and can be readily modified to prepare other compounds of the present invention. Those skilled in the art can carry out the following reactions according to conventional methods taught in the art (e.g., Organic Synthesis 2nd, Michael B. Smith etc.). Particular compounds of the present invention are specifically prepared in the section of Examples.

The method for preparing the compound represented by general formula (I) comprises the following steps:

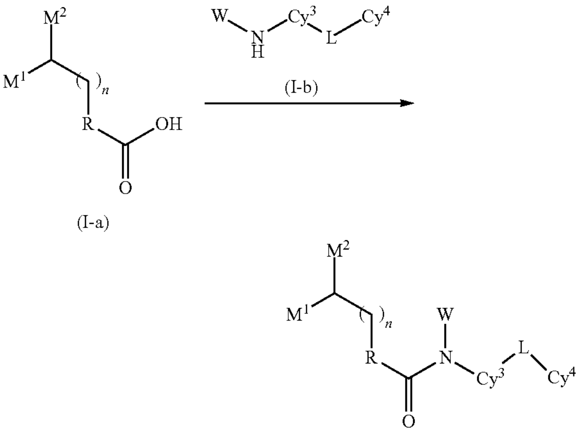

(I-a) (I-b) (I)

- adding formula (I-a) to a solvent, then adding a peptide coupling reagent, a base, and formula (I-b), reacting the resulting mixture completely under stirring, and performing separation to produce formula (I); or,
- adding formula (I-a) and formula (I-b) to a base, then adding dropwise a coupling reagent, reacting the resulting mixture completely under stirring, and performing separation to produce formula (I),
- wherein $M^1$, $M^2$, R, n, W, $Cy^3$, L and $Cy^4$ are as defined above.

The solvent is selected from: N,N-dimethylformamide, N,N-dimethylacetamide, dimethyl sulfoxide, toluene, benzene, xylene, trimethylbenzene, cyclohexane, hexane, dichloromethane, chloroform, 1,2-dichloroethane, tetrahydrofuran, diethyl ether, dioxane, 1,2-dimethoxyethane, methyl acetate, ethyl acetate, acetone, methyl ethyl ketone, acetonitrile, methanol, ethanol, isopropanol, tert-butanol, water, and a mixture thereof;

the base is selected from: methylamine, ethylamine, propylamine, N,N-diisopropylethylamine, trimethylamine, triethylamine, dicyclohexylamine, ethanolamine, diethanolamine, triethanolamine, meglumine, diethanolamine, ethylenediamine, pyridine, picoline, quinoline, and a mixture thereof;

the peptide coupling reagent is selected from: 2-(7-azabenzotriazole-1-yl)-tetramethyluronium hexafluorophosphate (HATUJ), O-benzotriazolyl-N,N,N',N'-tetramethyluronium hexafluorophosphate (HBTU), 2-(1H-benzo[d][1,2,3]triazol-1-yl)-1,1,3,3-tetramethyluronium tetrafluoroborate (TBTU), and a mixture thereof;

the coupling reagent is selected from: phosphorus oxychloride, dicyclohexyl carbodiimide (DCC), N,N'-carbonyldiimidazole, isobutyl chloroformate, 1-n-propyl phosphorus acid anhydride, and a mixture thereof.

Preparation intermediates for the compound of general formula (I) have the structures represented by formula (I-a) or (I-c):

(I-a)

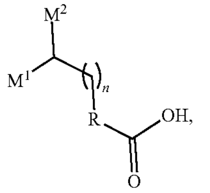

or (I-c)

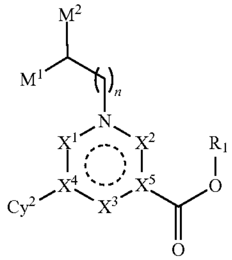

wherein, $R^1$ is $C_{1-6}$alkyl, $X^1$, $X^2$, $X^3$, $X^4$, $X^3$, $M^1$, $M^2$, R, $Cy^2$, n and 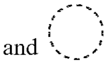 are as defined above.

Reaction Formula

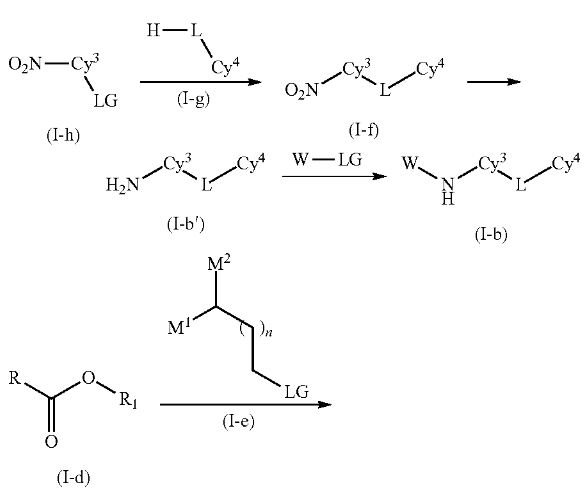

-continued

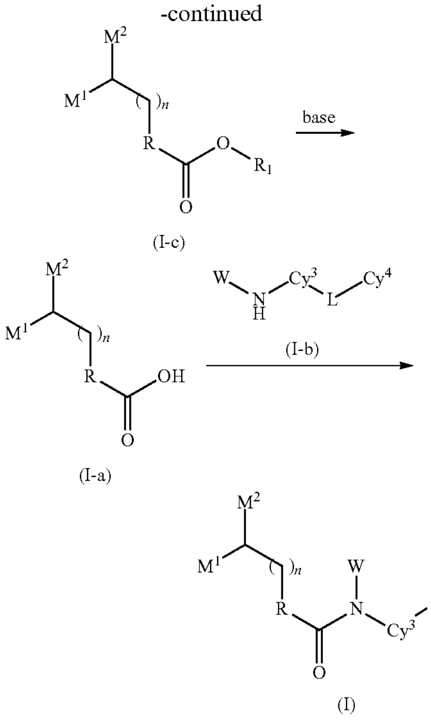

The compound of formula (I) can be prepared by reacting a compound of formula (I-a) with a compound of formula (I-b):

(I-a)

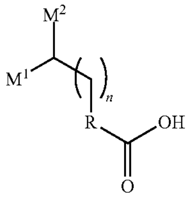

(I-b)

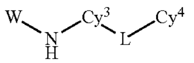

wherein, $M^1$, $M^2$, R, n, W, $Cy^3$, L and $Cy^4$ are as defined above.

Those skilled in the art can prepare the compound of formula (I) from the compound of formula (I-a) and the compound of formula (I-b) according to conventional methods in the art, and the following schematically provides a method for preparing the compound of formula (I) by reacting the compound of formula (I-a) with the compound of formula (I-b):

for example, the compound of formula (I-a) is added to a suitable solvent (e.g., tetrahydrofuran, N,N-dimethylformamide, N,N-dimethylacetamide and the like, preferably N,N-dimethylformamide), to which a suitable peptide coupling reagent (preferably 2-(7-azabenzotriazole-1-yl)-N,N,N',N'-tetramethyluronium hexafluorophosphate) is added, and then a suitable base (e.g., triethylamine, pyridine, N,N-diisopropylethylamine and the like, preferably N,N-diisopropylethylamine) is added. The resulting mixture is cooled to a suitable temperature (e.g., 0° C.), and stirred for a suitable time period (e.g., 10-30 minutes). The compound of formula (I-b) is added, and the resulting mixture is stirred at a suitable temperature (e.g., 0° C. to ambient temperature) for a suitable time period (e.g., 1-16 hours). The reaction liquor is concentrated under reduced pressure. A suitable amount of water is added, and the resulting mixture is extracted with a suitable extractant (e.g., ethyl acetate). The extract is concentrated. The crude product is separated by a conventional purification method (e.g., silica gel column chromatography) to obtain the compound of formula (I).

Again for example, the compound of formula (I-a) and the compound of formula (I-b) are added to a suitable base (e.g., pyridine), and the resulting mixture is cooled to a suitable temperature (e.g., 0° C.). A coupling reagent (e.g., phosphorus oxychloride) is added dropwise. After the completion of the addition, the resulting mixture is stirred for a suitable time period (e.g., 0.5-3 hours) until the reaction is completed. The reaction liquor is concentrated under reduced pressure. A suitable amount of water is added, and the resulting mixture is extracted with a suitable extractant (e.g., ethyl acetate). The extract is concentrated. The crude product is separated by a conventional purification method (e.g., silica gel column chromatography) to obtain the compound of formula (I).

The compound of formula (I-a) can be prepared from the compound of formula (I-c):

(I-c)

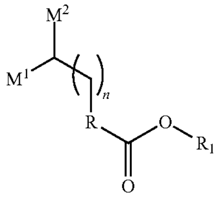

wherein, $R_1$ is $C_{1-6}$alkyl, and $M^1$, $M^2$, R and n are as defined above.

Those skilled in the art can prepare the compound of formula (I-a) from the compound of formula (I-c) according to conventional methods in the art, and the following schematically provides a method for preparing the compound of formula (I-a) from the compound of formula (I-c):

for example, the compound of formula (I-c) is dissolved in a suitable solvent (e.g., methanol, ethanol, tetrahydrofuran, dioxane and the like, preferably methanol), and a suitable base (e.g., lithium hydroxide, sodium hydroxide, potassium hydroxide and the like, preferably lithium hydroxide) is added. The resulting mixture is stirred at a suitable temperature (e.g., room temperature) for a suitable time period (e.g., 0.5-3 hours). After the completion of the reaction, the mixture is concentrated under reduced pressure, adjusted with an aqueous solution of a suitable acid (such as hydrochloric acid and citric acid) to a suitable pH range (e.g., 2-5), and filtered to produce the compound of formula (I-a).

The compound of formula (I-c) can be prepared by reacting the compound of formula (I-d) with the compound of formula (I-e):

(I-d)

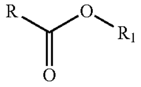

-continued (I-e)

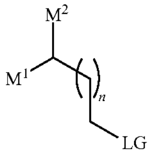

wherein, R and $R_1$ are as defined above; LG is a leaving group such as chlorine, bromine, iodine, mesylate or benzenesulfonate, or boric acid, or borate; $M^1$, $M^2$ and n are as defined above.

Those skilled in the art can prepare the compound of formula (I-c) from the compound of formula (I-d) and the compound of formula (I-e) according to conventional methods in the art, and the following schematically provides a method for preparing the compound of formula (I-c) by reacting the compound of formula (I-d) with the compound of formula (I-e):

for example, the compound of formula (I-d) and the compound of formula (I-e) (LG is a leaving group) are dissolved in a suitable solvent (e.g., acetonitrile, tetrahydrofuran, N,N-dimethylformamide and the like, preferably N,N-dimethylformamide), and a suitable base (e.g., sodium carbonate, potassium carbonate, cesium carbonate and the like, preferably potassium carbonate) is added. The resulting mixture is reacted at a suitable temperature (e.g., 50° C.) under stirring for a suitable time period (e.g., 10-16 hours). After the completion of the reaction, water and a suitable extractant are added. The crude product is separated by a conventional purification means (e.g., silica gel column chromatography) to produce the compound of formula (I-c).

Again for example, the compound of formula (I-d) and the compound of formula (I-e) (LG is boric acid or borate) are dissolved in a suitable solvent (e.g., acetonitrile, dichloromethane, chloroform, pyridine, N,N-dimethylformamide and the like, preferably N,N-dimethylformamide), and a suitable base (e.g., triethylamine, pyridine and the like) and a suitable catalyst (e.g., copper acetate, copper chloride and the like) are added. The resulting mixture is reacted under an air or oxygen condition at a suitable temperature (e.g., room temperature to 50° C.) for a suitable time period (e.g., 14 hours). After the completion of the reaction, the mixture is subjected to the conventional post-treatment (such as extraction and concentration) to provide a crude product. The crude product is subjected to the conventional purification (e.g., silica gel column chromatography) to produce a product.

The compound of formula (f-b) can be prepared by reacting the compound of formula (I-b') with W-LG.

(I-b')

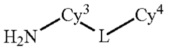

wherein, $Cy^3$, L, $Cy^4$, W and LG are as defined above.

Those skilled in the art can prepare the compound of formula (I-b) from the compound of formula (I-b') according to conventional methods in the art, and the following schematically provides a method for preparing the compound of formula (I-b) from the compound of formula (I-b'):

for example, the compound of formula (I-b') and the compound of formula W-LG are dissolved in a suitable solvent (e.g., acetonitrile, tetrahydrofuran, N,N-dimethylformamide and the like, preferably N,N-dimethylformamide), and a suitable base (e.g., sodium carbonate, potassium carbonate, cesium carbonate and the like, preferably potassium carbonate) is added. The resulting mixture is reacted at a suitable temperature (e.g., 50° C.) under stirring for a suitable time period (e.g., 10-16 hours). After the completion of the reaction, water and a suitable extractant are added. The crude product is separated by a conventional purification means (e.g., silica gel column chromatography) to produce the compound of formula (I-b).

The compound of formula (I-b) can be prepared from the compound of formula (I-f):

(I-f)

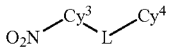

wherein, $Cy^3$, L and $Cy^4$ are as defined above.

Those skilled in the art can prepare the compound of formula (I-b) from the compound of formula (I-f) according to conventional methods in the art, and the following schematically provides a method for preparing the compound of formula (I-b) from the compound of formula (I-f):

for example, the compound of formula (I-f) and a suitable reducing agent (e.g., iron powder, zinc powder, stannous chloride, sodium dithionite and the like, preferably iron powder) are added to a suitable solvent (e.g., ethanol, an aqueous ammonium chloride solution, acetic acid, a mixture of ethanol and an aqueous ammonium chloride solution, and the like). The resulting mixture is reacted at a suitable temperature (e.g., 80° C.) for a suitable time period (e.g., 4 hours). After the completion of the reaction, the mixture is filtered, concentrated under reduced pressure, extracted with a suitable extractant (e.g., dichloromethane), and concentrated under reduced pressure to produce a product.

The compound of formula (I-f) can be prepared by reacting the compound of formula (I-g) with the compound of formula (I-h):

(I-g)

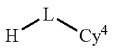

(I-h)

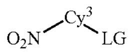

wherein, L, $Cy^4$, $Cy^3$ and LG are as defined above.

Those skilled in the art can prepare the compound of formula (I-f) from the compound of formula (I-g) and the compound of formula (I-h) according to conventional methods in the art, and the following schematically provides a method for preparing the compound of formula (I-f) from the compound of formula (I-g) and the compound of formula (I-h):

for example, the compound of formula (I-g) and the compound of formula (I-h) are added to a suitable solvent (e.g., tetrahydrofuran, acetonitrile, N,N-dimethylformamide, N,N-dimethylacetamide and the like, preferably N,N-dimethylformamide), and a suitable base (e.g., potassium carbonate, sodium carbonate, triethylamine, N,N-diisopropylethylamine and the like, preferably potassium carbonate) is added. The resulting mixture is stirred at a suitable temperature (e.g., room temperature to 80° C.) for a suitable time period (e.g., 14 hours). After the completion of the reaction, the mixture is subjected to the conventional post-treatment (e.g., filtration, extraction, and the like) to provide a crude product. The crude product is separated by a conventional purification means (e.g., silica gel column chromatography) to produce a product.

In some embodiments, the compound of formula (I-b) can be prepared through the following reactions:

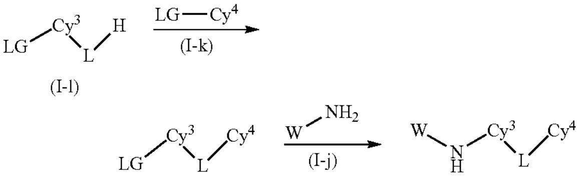

wherein, LG, $Cy^3$, L, $Cy^4$ and W are as defined above.

Those skilled in the art can prepare the compound of formula (I-b) from the compound of formula (I-l) according to conventional methods in the art, and the following schematically provides a method for preparing the compound of formula (I-b) from the compound of formula (I-l):

for example, the compound of formula (I-l) and the compound of formula (I-k) are added to a suitable solvent (e.g., toluene, xylene, trimethylbenzene, N,N-dimethylformamide, N-dimethylacetamide and the like, preferably xylene). The resulting mixture is heated to a suitable temperature (e.g., 140° C.) and stirred for a suitable time period (e.g., 15 hours). After the completion of the reaction, the mixture is subjected to the conventional post-treatment (e.g., filtration, extraction, and the like) to provide the compound of formula (I-i). The compound of formula (I-i) and the compound of formula (I-j) are added to a suitable solvent (e.g., ethanol, water and the like). The resulting mixture is heated to a suitable temperature (e.g., 90° C.). After the completion of the reaction, the mixture is subjected to the conventional post-treatment (e.g., concentration, extraction, filtration and the like) to produce the compound of formula (I-b).

Specifically, when R represents the group represented by general formula (b), the compound of formula (I-c) can be prepared through the following reaction.

(b)

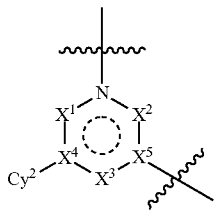

In some embodiments, the compound of formula (I-c) can be prepared through the following reactions:

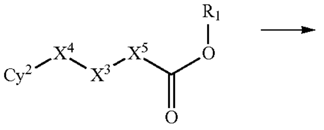

(I-m)

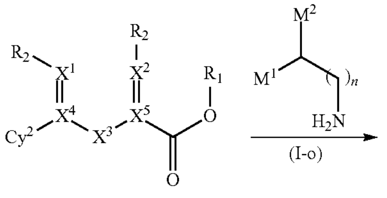

(I-n)

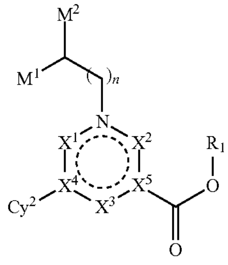

(I-c)

wherein, $X^1$, $X^2$, $X^5$, and $X^4$ are each independently selected from C, CH or $CH_2$; $X^3$ is C═O; $R^2$ is alkoxy or di-substituted amino; $Cy^2$, $R^1$, $M^1$, $M^2$ and n are as defined above.

Those skilled in the art can prepare the compound of formula (I-c) from the compound of formula (I-m) according to conventional methods in the art, and the following schematically provides a method for preparing the compound of formula (I-c) from the compound of formula (I-m):

for example, the compound of formula (I-m) is added to a suitable solvent (e.g., toluene, xylene, trimethylbenzene, N,N-dimethylformamide, N,N-dimethylacetamide and the like, preferably toluene), and a suitable reagent (e.g., N,N-dimethylformamide dimethyl acetal, trimethyl orthoformate, triethyl orthoformate and the like, preferably N,N-dimethylformamide dimethyl acetal) is added. The resulting mixture is heated to a suitable temperature (e.g., 100° C.) and stirred for a suitable time period (e.g., 15 hours). After the completion of the reaction, the mixture is subjected to the conventional post-treatment (e.g., filtration, extraction, concentration and the like) to produce the compound of formula (1-n).

The compound of formula (I-n) and the compound of formula (I-o) are added to a suitable solvent (e.g., ethanol, isopropanol, toluene and the like). The resulting mixture is heated to a suitable temperature (e.g., 100° C.) and reacted for a suitable time period (e.g., 3 h). After the completion of the reaction, the mixture is subjected to the conventional purification (e.g., silica gel column chromatography) to produce the compound of formula (I-c).

In some other embodiments, the compound of formula (I-c) can be prepared through the following reactions:

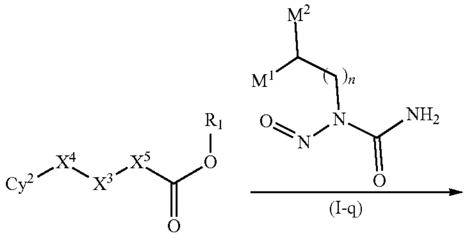

(I-p)

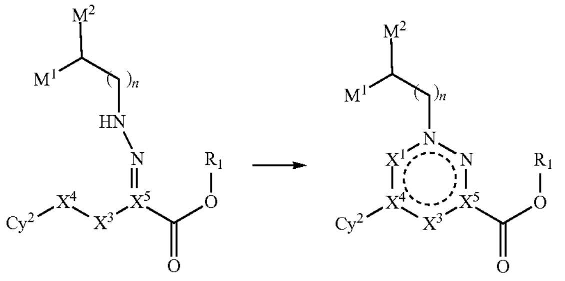

(I-r) (I-c)

wherein, $X^1$, $X^5$, and $X^4$ are each independently selected from C, CH or $CH_2$; $X^3$ is C═O; $Cy^2$, $R^1$, $M^1$, $M^2$ and n are as defined above.

Those skilled in the art can prepare the compound of formula (I-c) from the compound of formula (I-p) according to conventional methods in the art, and the following schematically provides a method for preparing the compound of formula (I-c) from the compound of formula (I-p):

for example, the compound of formula (I-p) and the compound of formula (I-q) are added to a suitable solvent (e.g., dichloromethane, chloroform, 1,2-dichloroethane and the like, preferably dichloromethane), and the resulting mixture is cooled to a suitable temperature (e.g., 0° C.). A suitable base (e.g., potassium carbonate, sodium carbonate, sodium hydroxide and the like, preferably potassium carbonate) is added, and the resulting mixture is slowly warmed to room temperature and reacted for a suitable time period (e.g., 3-15 hours). After the completion of the reaction, the mixture is subjected to the conventional purification (e.g., silica gel column chromatography) to produce the compound of formula (I-r).

The compound of formula (I-r) is added to a suitable solvent (e.g., toluene, xylene, trimethylbenzene, N,N-dimethylformamide, N,N-dimethylacetamide and the like, preferably toluene), and a suitable reagent (e.g., N,N-dimethylformamide dimethyl acetal, trimethyl orthoformate, triethyl orthoformate and the like, preferably N,N-dimethylformamide dimethyl acetal) is added. The resulting mixture is heated to a suitable temperature (e.g., 110° C.) and stirred for a suitable time period (e.g., 15 hours). After the completion of the reaction, the mixture is subjected to the conventional post-treatment (e.g., filtration, extraction, concentration and the like) and the purification (e.g., silica gel column chromatography) to produce the compound of formula (I-c).

In some other embodiments, the compound of formula (I-c) can be prepared according to the following reaction scheme:

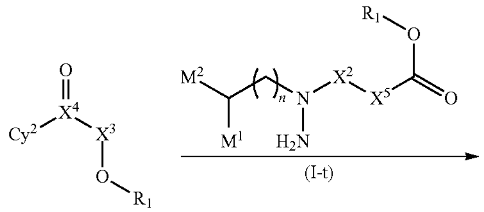

(I-t)

(I-s)

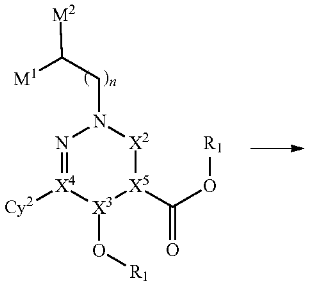

(I-u)

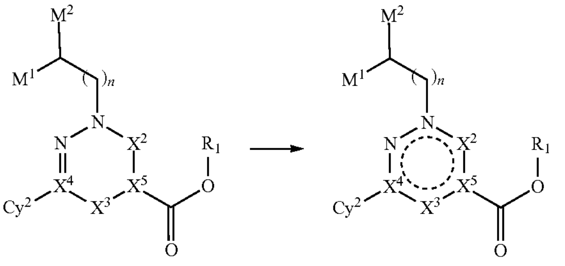

(I-v) (I-c)

wherein, $X^2$, $X^5$, and $X^4$ are each independently selected from C, CH or $CH_2$; $X^3$ is C═O; $Cy^2$, $R^1$, $M^1$, $M^2$ and n are as defined above.

Those skilled in the art can prepare the compound of formula (I-c) from the compound of formula (I-s) according to conventional methods in the art, and the following schematically provides a method for preparing the compound of formula (I-c) from the compound of formula (I-s):

for example, the compound of formula (I-s) and the compound of formula (I-t) are added to a suitable solvent (e.g., methanol, ethanol, isopropanol and the like, preferably ethanol). The resulting mixture is reacted at a suitable temperature (e.g., 80° C.) for a suitable time period (e.g., 15 hours). After the completion of the reaction, the mixture is subjected to the conventional purification (e.g., silica gel column chromatography) to produce the compound of formula (I-u).

The compound of formula (I-u) is added to a suitable solvent (e.g., tetrahydrofuran, 2-methyltetrahydrofuran, N,N-dimethylformamide, N,N-dimethylacetamide, ethanol and the like, preferably 2-methyltetrahydrofuran), and the resulting mixture is cooled to a suitable temperature (e.g., 0° C.). A suitable base (e.g., sodium hydride, sodium tert-butoxide, potassium tert-butoxide, sodium ethoxide and the like, preferably potassium tert-butoxide) is added. After the completion of the addition, the resulting mixture is warmed to a suitable temperature (e.g., room temperature) and stirred for a suitable time period (e.g., 15 hours). After the completion of the reaction, the reaction liquor is adjusted to a suitable pH value (e.g., 5-6). The mixture is subjected to the conventional post-treatment (e.g., filtration, extraction, concentration and the like) and the purification (e.g., silica gel column chromatography) to produce the compound of formula (I-v).

The compound of formula (I-v) is added to a suitable solvent (e.g., acetonitrile), and a suitable oxidant (e.g., copper chloride) is added. The resulting mixture is warmed to a suitable temperature (e.g., 80° C.) and reacted for a suitable time period (e.g., 2-4 hours). After the completion of the reaction, the mixture is subjected to the conventional post-treatment (e.g., filtration, extraction, concentration and the like) and the purification (e.g., silica gel column chromatography) to produce the compound of formula (I-c).

The compound of formula (I-t) can be prepared according to the following reaction scheme:

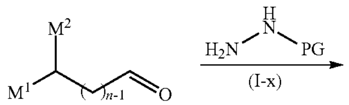

(I-w) (I-x)

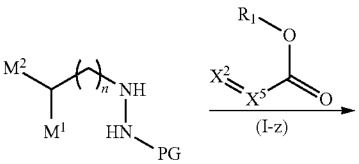

(I-y) (I-z)

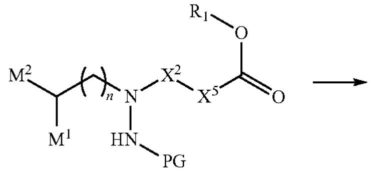

(I-al)

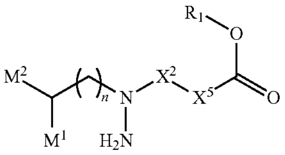

(I-t)

wherein, $X^2$ and $X^5$ are each independently selected from CH or $CH_2$; PG is a protecting group (e.g., tert-butoxycarbonyl, benzyloxycarbonyl, acetyl, p-methoxybenzyl and the like); $R^1$, $M^1$, $M^2$ and n are as defined above, with $n \geq 1$.

Those skilled in the art can prepare the compound of formula (I-t) from the compound of formula (I-w) according to conventional methods in the art, and the following schematically provides a method for preparing the compound of formula (I-t) from the compound of formula (I-w):

for example, the compound of formula (I-w) and the compound of formula (I-x) are added to a suitable solvent (e.g., dichloromethane, methanol, ethanol and the like, preferably dichloromethane), to which a suitable acid (e.g., acetic acid) and a dehydrating agent (e.g., magnesium sulfate) are added, and then a suitable reducing agent (e.g., sodium triacetoxyborohydride, sodium cyanoborohydride and the like) is added. The resulting mixture is reacted at a suitable temperature (e.g., room temperature) for a suitable time period (e.g., 15 hours). After the completion of the reaction, the mixture is subjected to the conventional post-treatment (e.g., filtration, extraction, concentration and the like) to produce the compound of formula (I-y).

The compound of formula (I-y) and the compound of formula (I-z) are added to a suitable solvent (e.g., ethanol). The resulting mixture is reacted at a suitable temperature (e.g., 80° C.) for a suitable time period (e.g., 15 hours). After the completion of the reaction, the mixture is subjected to the conventional post-treatment (e.g., filtration, extraction, concentration and the like) and the purification (e.g., silica gel column chromatography) to produce the compound of formula (I-a1).

The compound of formula (I-a1) is treated by a suitable deprotection process (e.g., acid, base, hydrogenation, oxidation and the like), and then subjected to the conventional post-treatment (e.g., filtration, extraction, concentration and the like) and the purification (e.g., recrystallization, silica gel column chromatography and the like) to produce the compound of formula (I-t).

In some other embodiments, the compound of formula (I-a1) can be prepared according to the following reaction scheme:

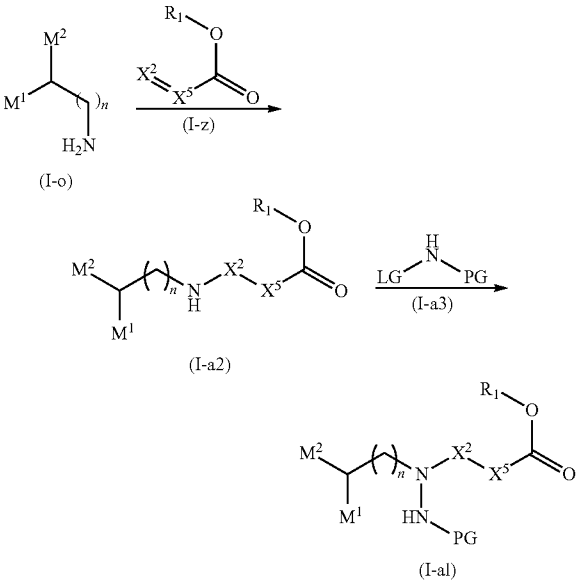

wherein, $X^2$ and $X^5$ are each independently selected from CH or $CH_2$; PG is a protecting group (e.g., tert-butoxycarbonyl, benzyloxycarbonyl, acetyl, p-methoxybenzyl and the like); LG is a leaving group (e.g., benzenesulfonate, mesylate and the like); $R_1$, $M^1$, $M^2$ and n are as defined above.

Those skilled in the art can prepare the compound of formula (I-a1) from the compound of formula (I-o) according to conventional methods in the art, and the following schematically provides a method for preparing the compound of formula (I-a1) from the compound of formula (I-o):

for example, the compound of formula (I-o) is dissolved in a suitable solvent (e.g., ethanol), and the compound of formula (I-z) is added at a suitable temperature (e.g., from 0° C. to room temperature). The resulting mixture is reacted for a suitable time period (2-15 hours). After the completion of the reaction, the mixture is subjected to the conventional post-treatment (e.g., filtration, extraction, concentration and the like) and the purification (e.g., recrystallization, silica gel column chromatography and the like) to produce the compound of formula (I-a2).

The compound of formula (I-a2) is added to a suitable solvent (e.g., dichloromethane, tetrahydrofuran, 2-methyltetrahydrofuran and the like), and a suitable base (e.g., triethylamine, N,N-diisopropylethylamine, N-methylmorpholine and the like) is added. The resulting mixture is cooled to a suitable temperature (e.g. −5° C.). The compound of formula (I-a3) is added, and the resulting mixture is warmed to room temperature and reacted for a suitable time period (e.g., 14 hours).

After the completion of the reaction, the mixture is subjected to the conventional post-treatment (e.g., filtration, extraction, concentration and the like) and the purification (e.g., recrystallization, silica gel column chromatography and the like) to produce the compound of formula (I-a1).

When R represents the group represented by general formula (b), (b)

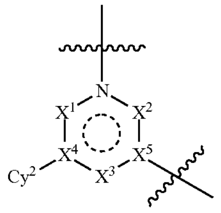

wherein, $X^1$, $X^4$, and $X^5$ are each independently selected from C, CH or $CH_2$; $X^2$ is N; $X^3$ is C═O; and $Cy^2$ is as defined above, the compound of formula (I-d) can be prepared according to the following reaction scheme:

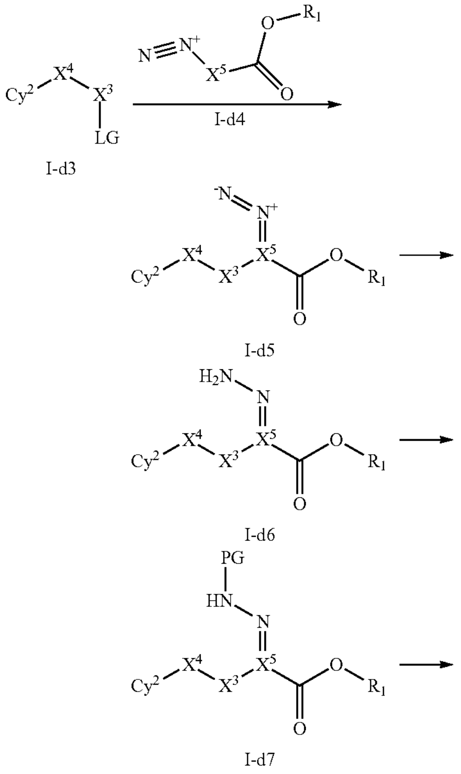

-continued

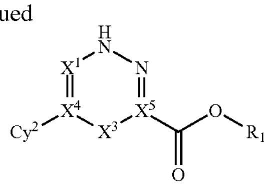

I-d wherein, LG is a leaving group (e.g., chlorine); PG is a protecting group (preferably tert-butoxycarbonyl); and $R^1$ is as defined above.

Those skilled in the art can prepare the compound of formula (I-d) from the compound of formula (I-d3) according to conventional methods in the art, and the following schematically provides a method for preparing the compound of formula (I-d) from the compound of formula (I-d3):

for example, the compound of formula (J-d3) is dissolved in a suitable solvent (e.g., ethyl acetate). The resulting mixture is cooled to a suitable temperature (e.g., 0° C.). The compound of formula (I-d4) is added, and the resulting mixture is warmed to room temperature and reacted for a suitable time period (e.g., 15 hours). After the completion of the reaction, the mixture is quenched by adding a suitable base (e.g., potassium carbonate), and then subjected to the conventional post-treatment (e.g., filtration, extraction, concentration and the like) and the purification (e.g., recrystallization, silica gel column chromatography and the like) to produce the compound of formula (I-d5).

The compound of formula (I-d5) is dissolved in a suitable solvent (e.g., methyl tert-butyl ether), and the resulting mixture is cooled to a suitable temperature (e.g., 0° C.). A suitable reducing agent (e.g., triphenylphosphine, tri-n-butyl phosphine and the like, preferably tri-n-butyl phosphine) is added, and the resulting mixture is warmed to room temperature and reacted for a suitable time period (e.g., 15 hours). After the completion of the reaction, the mixture is subjected to the conventional post-treatment (e.g., filtration, extraction, concentration and the like) and the purification (e.g., recrystallization, silica gel column chromatography and the like) to produce the compound of formula (I-d6).

The compound of formula (I-d6) is dissolved in a suitable solvent (e.g., dichloromethane, tetrahydrofuran and the like), and the resulting mixture is cooled to a suitable temperature (e.g., 0° C.). A suitable base (e.g., triethylamine, N,N-diisopropylethylamine, potassium carbonate, sodium carbonate and the like, preferably triethylamine) and a suitable protecting group agent (e.g., di-tert-butyl dicarbonate) are added. The resulting mixture is warmed to room temperature and reacted for a suitable time period (e.g., 15 hours). After the completion of the reaction, the mixture is subjected to the conventional post-treatment (e.g., filtration, extraction, concentration and the like) and the purification (e.g., recrystallization, silica gel column chromatography and the like) to produce the compound of formula (I-d7).

The compound of formula (I-d7) is added to a suitable solvent (e.g., toluene, xylene, trimethylbenzene, N,N-dimethylformamide, N,N-dimethylacetamide and the like, preferably toluene), and a suitable reagent (e.g., N,N-dimethylformamide dimethyl acetal, trimethyl orthoformate, triethyl orthoformate and the like, preferably N,N-dimethylformamide dimethyl acetal) is added. The resulting mixture is heated to a suitable temperature (e.g., 60° C.) and stirred for a suitable time period (e.g., 15 hours). After the completion of the reaction, the mixture is subjected to the conventional post-treatment (e.g., filtration, extraction, concentration and the like) and the purification (e.g., recrystallization, silica gel column chromatography and the like) to produce the compound of formula (I-d).

In the synthesis of the compound of the present invention, a solvent commonly used in the art may be used as the reaction solvent, including but not limited to ethers, alkanes, halogenated alkanes, aromatic hydrocarbons, alcohols and the like. Specifically, the following solvents can be exemplified such as N,N-dimethylformamide, N,N-dimethylacetamide, dimethyl sulfoxide, aromatic hydrocarbons (e.g., toluene, benzene, xylene, trimethylbenzene and the like), saturated hydrocarbons (e.g., cyclohexane, hexane and the like), halogenated hydrocarbons (e.g., dichloromethane, chloroform, 1,2-dichloroethane and the like), ethers (e.g., tetrahydrofuran, diethyl ether, dioxane, 1,2-dimethoxyethane and the like), esters (e.g., methyl acetate, ethyl acetate and the like), ketones (e.g., acetone, methyl ethyl ketone and the like), nitriles (e.g., acetonitrile and the like), alcohols (e.g., methanol, ethanol, isopropanol, tert-butanol and the like), water and mixed solvents thereof.

In the synthesis of the compound of the present invention, the base to be used may be a base commonly used in the art, including an organic base and an inorganic base. As the organic base, methylamine, ethylamine, propylamine, N,N-diisopropylethylamine, trimethylamine, triethylamine, dicyclohexylamine, ethanolamine, diethanolamine, triethanolamine, meglumine, diethanolamine, ethylenediamine, pyridine, picoline, quinoline and the like can be exemplified; as the inorganic base, hydroxide, carbonate and bicarbonate of alkali metal (e.g., lithium, sodium, potassium, and cesium); hydroxide, carbonate and bicarbonate of alkaline earth metal (magnesium, calcium, strontium, and barium); sodium tert-butoxide, potassium tert-butoxide, sodium ethoxide and the like can be exemplified.

In the synthesis of the compound of the present invention, the acid to be used may be an acid commonly used in the art, including an organic acid and an inorganic acid. As the organic acid, formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methylsulfonic acid and ethylsulfonic acid can be exemplified; as the inorganic acid, hydrochloric acid, sulfuric acid, nitric acid, carbonic acid, hydrobromic acid, phosphoric acid, hydroiodic acid and the like can be exemplified.

In the synthesis of the compound of the present invention, the reducing agent to be used may be a reducing agent commonly used in the art, including but not limited to, triphenylphosphine, tri-n-butylphosphine, sodium triacetoxyborohydride, sodium cyanoborohydride, sodium borohydride, iron powder, zinc powder, stannous chloride, sodium dithionite, hydrogen, and the like.

In the synthesis of the compound of the present invention, the oxidizing agent to be used may be an oxidizing agent commonly used in the art, including but not limited to, copper chloride, manganese dioxide, permanganate, dichromate, peracetic acid, peroxybenzoic acid, and the like.

In the synthesis of the compound of the present invention, the catalyst to be used may be a catalyst commonly used in the art, including but not limited to, for example, copper acetate, copper chloride, palladium on carbon, iron chloride, palladium acetate, [1,1'-bis(diphenylphosphino)ferrocene] palladium dichloride and the like.

EXAMPLES

The present invention can be better understood from the following examples and assays. It will be readily understood by those skilled in the art that the contents in these examples and assays are only for the illustration of the present invention, and the invention as claimed in the appended claims cannot and should not be limited by these examples and assays.

In case that the specific reaction conditions are not indicated in the examples, these examples are carried out according to conventional conditions or the conditions recommended by the manufacturer. In case that the manufacturers of the reagents or instruments used are not indicated, these reagents or instruments are conventional products which are commercially available.

In the present invention, unless otherwise stated, (i) the temperature is expressed in degrees Celsius (° C.), and unless otherwise stated, the operation is carried out at room temperature; (ii) the reaction is traced by thin-layer chromatography (TLC) or LC-MS; (iii) the final products have clear proton nuclear magnetic resonance spectroscopy ($^1$H-NMR) data and mass spectrometry (MS) data. The abbreviations and English expressions used in the present invention have the following meanings.

DAST: diethylaminosulfur trifluoride
DCM: dichloromethane
-Boc: tert-butoxycarbonyl
TEA: triethylarnine
TBSCl: tert-butyldimethylchlorosilane
TBS-: tert-butyldimethylsilyl
DMSO: dimethyl sulfoxide
NaHMDS: sodium hexamethyldisilazide
TBAF: tetrabutylammonium fluoride
MsCl: methanesulfonyl chloride
TFA: trifluoroacetic acid
DMF: N,N-dimethylformamide
$Pd_2(dba)_3$: tris(dibenzylideneacetone)dipalladium
conc.HCl: concentrated hydrochloric acid
NBS: N-bromosuccinimide
AIBN: azodiisobutyronitrile
THF: tetrahydrofuran
TMSCN: trimethylsilyl cyanide
CPBA: m-chloroperoxybenzoic acid
TMSI: trimethylsilyl imidazole
BHT: dibutylhydroxytoluene
$Pd(PPh_3)_2Cl_2$: bis(triphenylphosphine)dichloropalladium
EA: ethyl acetate
EtOH: ethanol
MTBE: methyltert-butyl ether
PE: petroleum ether
HATU: 2-(7-azabenzotriazole-1-yl)-tetramethyluronium hexafluorophosphate
reflux: reflux
pyridine: pyridine
toluene: toluene
PBu3: tributylphosphine
1,4-dioxane: 1,4-dioxane
DMF-DMA: N,N-dimethylformamide dimethyl acetal
DIPEA/DIEA: N,N-diisopropylethylamine
DEC: dichloroethane
$Pd(dppf)Cl_2 \cdot CH_2Cl_2$: [1,1-bis(diphenylphosphino)ferrocene]palladium
dichloride dichloromethane complex
DMAP: 4-dimethylaminopyridine
rt: room temperature

Example 1: Synthesis of N-(5-((6,7-dimethoxyquinolin-4-yl)oxy)pyridin-2-yl)-5-(4-fluorophenyl)-1-isopropyl-4-oxo-1,4-dihydropyridin-3-carboxamide (Compound 14)

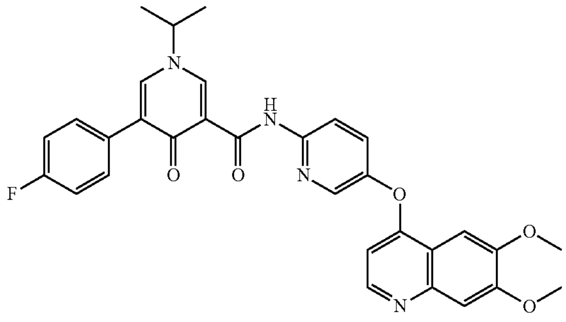

Scheme

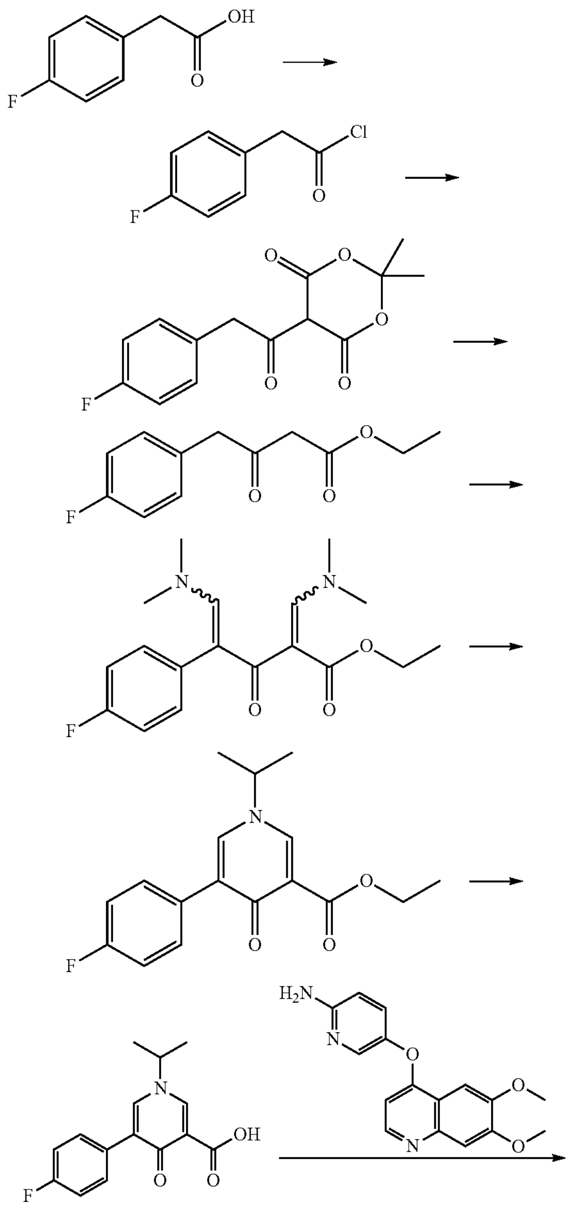

-continued

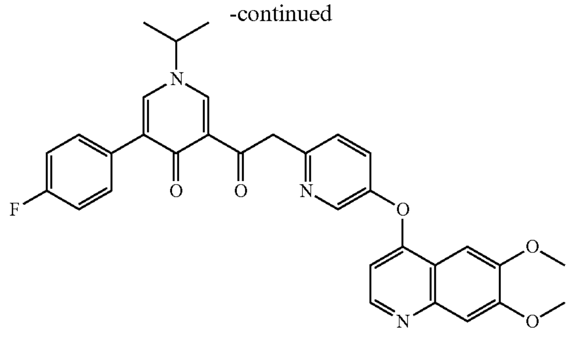

Step: 1 Synthesis of 2-(4-fluorophenyl)acetyl chloride

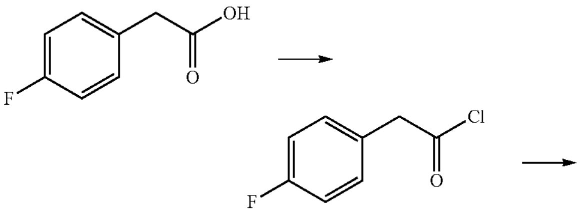

2-(4-fluorophenyl)acetic acid (50.0 g, 324.380 mmol, 1.0 eq) and thionyl chloride (77.18 g, 648.761 mmol, 2.0 eq) were dissolved in dichloromethane (250.0 mL). The mixture was warmed to 60° C. under the nitrogen protection, and reacted under reflux for 3 hours. TLC showed the completion of the reaction. The reaction liquor was concentrated under reduced pressure, to which an appropriate amount of dichloromethane was added, and the resulting mixture was concentrated. The above process was repeated twice to produce a yellow oily product.

Step 2: Synthesis of 5-(2-(4-fluorophenyl)acetyl)-2,2-dimethyl-1,3-dioxane-4,6-dione

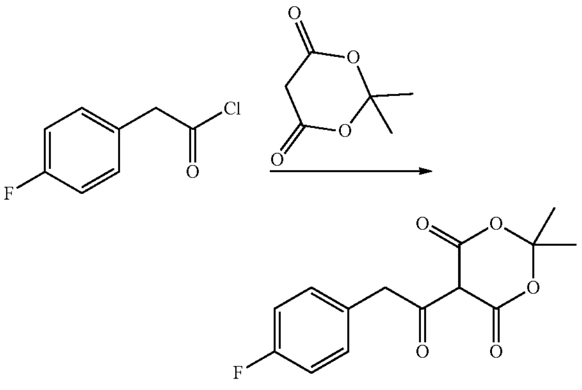

2,2-dimethyl-1,3-dioxane-4,6-dione (56.10 g, 389.3 mmol, 1.2 eq) and triethylamine (78.78 g, 7798.5 mmol, 2.4 eq) were dissolved in dichloromethane (250.0 mL). The mixture was cooled to 0° C. under the nitrogen protection. The crude product 2-(4-fluorophenyl) acetyl chloride obtained in the above step was diluted with dichloromethane (100.0 mL), and slowly dropwise added to the reaction liquor. After the completion of the dropwise addition, the resulting mixture was warmed to room temperature. After 3 hours, TLC detection showed the completion of the reaction. The reaction liquor was washed three times with 1 mol/L HCl, and the pH of the aqueous phase was 3-4. The reaction liquor was washed again twice with a saturated aqueous NaCl solution, dried, and concentrated under reduced pressure to produce a yellow oily product.

Step 3: Synthesis of ethyl 4-(4-fluorophenyl)-3-oxobutanoate

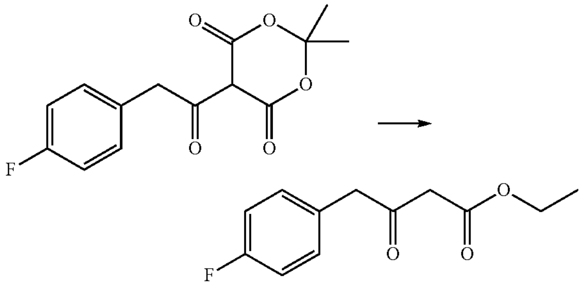

5-(2-(4-fluorophenyl) acetyl)-2,2-dimethyl-1,3-dioxane-4,6-dione was dissolved in ethanol (250.0 mL). The mixture was warmed to 100° C., and reacted under reflux for 3 hours. TLC showed the incompletion of the reaction. Concentrated HCl (10.0 mL) was added. After 2 hours, TLC showed the completion of the reaction. The reaction liquor was concentrated under reduced pressure, and the crude product was purified by silica gel column chromatography (PE:EA=75:1-10:1) to produce a yellow oily product (35.0 g, yield in three steps: 48.1%).

Step 4: Synthesis of ethyl 5-(dimethylamino)-2-((dimethylamino)methylene)-4-(4-fluorophenyl)-3-oxopent-4-enoate

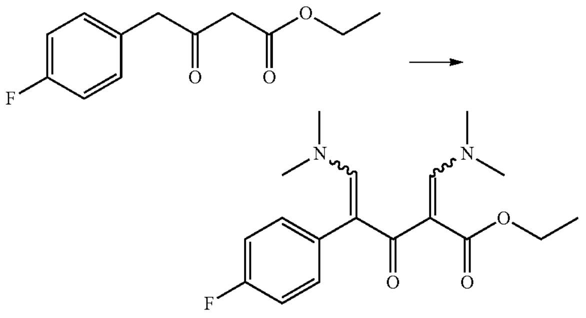

Ethyl 4-(4-fluorophenyl)-3-oxobutanoate (2.0 g, 8.92 mmol, 1.0 eq) was dissolved in toluene (20.0 mL), and DMF-DMA (3.188 g, 26.76 mmol, 3.0 eq) was added. The mixture was warmed to 100° C. and reacted overnight. TLC showed the completion of the reaction. The reaction liquor was concentrated under reduced pressure to produce a product (2.5 g, crude product).

Step 5: Synthesis of ethyl 5-(4-fluorophenyl)-1-isopropyl-4-oxo-1,4-dihydropyridin-3-carboxylate

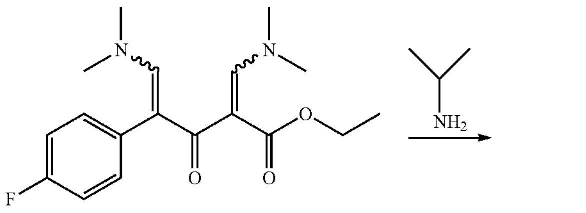

-continued

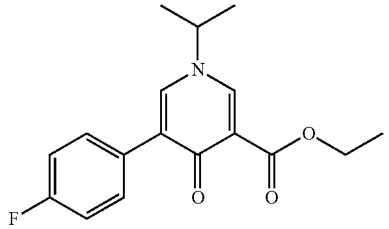

5-(dimethylamino)-2-((dimethylamino)methylene)-4-(4-fluorophenyl)-3-oxopent-4-enoate (3.5 g, crude product) was dissolved in ethanol (20.0 mL), and isopropylamine (791.0 mg, 13.38 mmol, 1.5 eq) was added. The mixture was warmed to 100° C. and reacted for 3 hours. TLC showed the completion of the reaction. The reaction liquor was concentrated under reduced pressure, and the crude product was purified by silica gel column chromatography (PE:EA=50:1-2:1) to produce a product (1.0 g, yield in two steps: 50%).

Step 6: Synthesis of 5-(4-fluorophenyl)-1-isopropyl-4-oxo-1,4-dihydropyridin-3-carboxylic acid

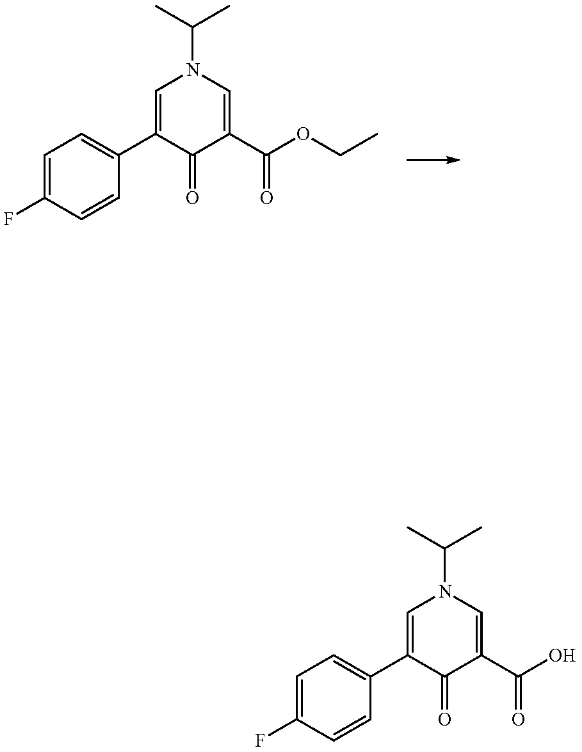

Ethyl 5-(4-fluorophenyl)-1-isopropyl-4-oxo-1,4-dihydropyridin-3-carboxylate (1.0 g, 3.297 mmol, 1.0 eq) was dissolved in tetrahydrofuran (10.0 mL), and 1 mol/L of an aqueous LiOH solution (5.0 mL) was added. The mixture was stirred at room temperature for 0.5 hour. TLC showed the completion of the reaction. The mixture was concentrated under reduced pressure, and adjusted to a pH value of 4-5. A large amount of solid was precipitated, and the mixture was filtered by suction. The filter cake was dried to produce a white solid product (700.0 mg, yield: 70%).

Step 7: Synthesis of N-(5-((6,7-dimethoxyquinolin-4-yl)oxy)pyridin-2-yl)-5-(4-fluorophenyl)-1-isopropyl-4-oxo-1,4-dihydropyridin-3-carboxamide

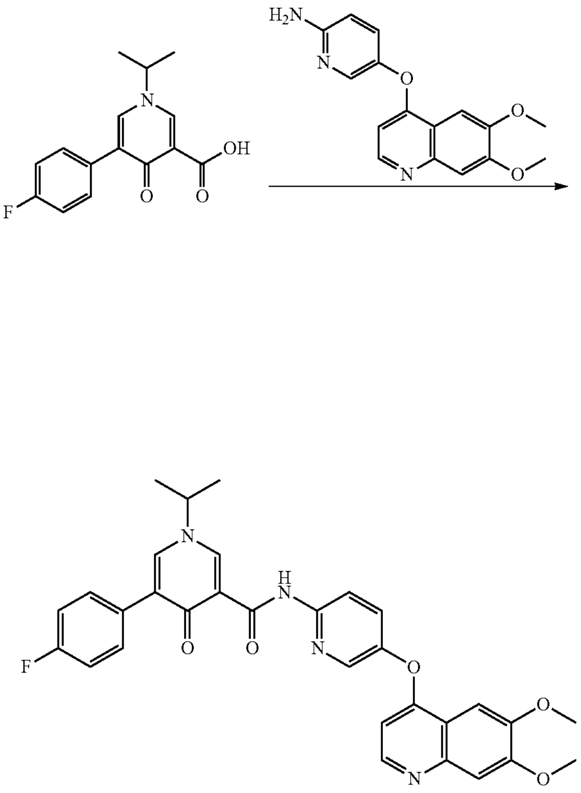

5-(4-fluorophenyl)-1-isopropyl-4-oxo-1,4-dihydropyridin-3-carboxylic acid (250.0 mg, 0.91 mmol, 1.0 eq) and N,N-diisopropylethylamine (352.0 mg, 2.72 mmol, 3.0 eq) were dissolved in N,N-dimethylformamide (2.5 mL), and the mixture was cooled to 0° C. HATU (518.0 mg, 1.362 mmol, 1.5 eq) was added under the nitrogen protection, and the mixture was stirred for 0.5 hour. 5-((6,7-dimethoxyquinolin-4-yl)oxy)pyridin-2-amine (270.0 mg, 0.908 mmol, 1.0 eq) was added, and the mixture was slowly warmed to room temperature. After 1 hour, TLC showed the completion of the reaction. The reaction liquor was concentrated under reduced pressure. Ethyl acetate was added, and the mixture was washed twice with a saturated aqueous $NaHCO_3$ solution, washed with water for four times, dried, and concentrated under reduced pressure to produce a crude product, which was treated with silica gel column chromatography (DCM:MeOH=150:1-30:1). The obtained solid was dissolved in tetrahydrofuran, and 1 mol/L HCl was added to adjust the pH value to 7-8. The mixture was stirred for 0.5 hour, and filtered by suction. The filter cake was washed with water and dried to produce a product (313.0 mg, yield: 62.0%).

1H NMR (400 MHz, DMSO-d6) δ (ppm): 13.47 (s, 1H), 8.80 (s, 1H), 8.69-8.68 (d, 1H), 8.48-8.44 (m, 2H), 8.28 (s, 1H), 7.94-7.92 (m, 1H), 7.75 (s, 2H), 7.67 (s, 1H), 7.52 (s, 1H), 7.31-7.27 (m, 2H), 6.84 (s, 1H), 4.66 (m, 1H), 4.01 (s, 6H), 1.54-1.52 (d, 6H).

Molecular formula: $C_{31}H_{27}FN_4O_5$, molecular weight: 554.58 LC-MS (Pos, m/z)=555.35 $[M+H]^+$.

Example 2: Synthesis of N-(5-((6,7-dimethoxyquinolin-4-yl)oxy)pyridin-2-yl)-1-isopropyl-4-oxo-5-p-tolyl-1,4-dihydropyridin-3-carboxamide (Compound 1)

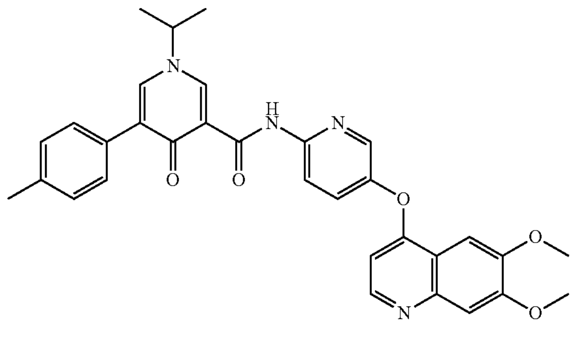

Step 1: Synthesis of ethyl 1-isopropyl-4-oxo-5-p-tolyl-1,4-dihydropyridin-3-carboxylate

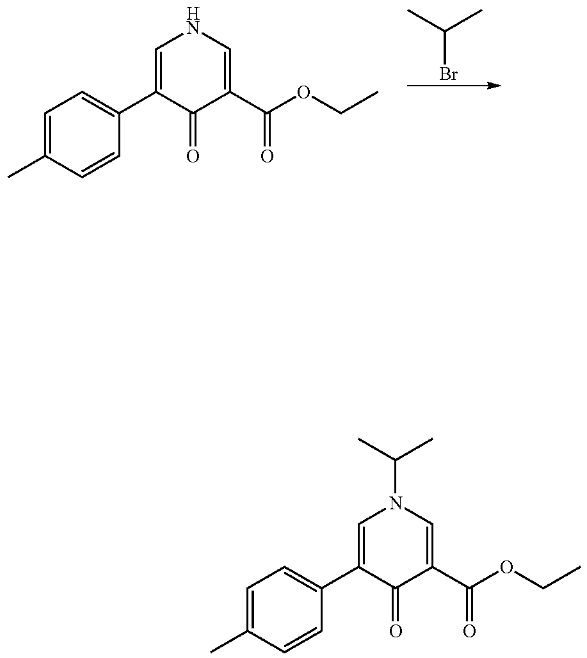

Ethyl 4-oxo-5-p-tolyl-1,4-dihydropyridin-3-carboxylate (2.00 g, 7.77 mmol, 1.0 eq), isopropyl bromide (1.15 g, 9.33 mmol, 1.2 eq) and potassium carbonate (3.22 g, 23.32 mmol, 3.0 eq) were added to DMF (20 mL). The mixture was reacted at 50° C. under stirring overnight. TLC detection showed the completion of the reaction. The mixture was filtered, and the filter cake was eluted with ethyl acetate. The filtrate was concentrated under reduced pressure. The crude product was dissolved in ethyl acetate (20 mL). The mixture was successively washed with distilled water (10 mL×4) and saturated brine (10 mL), dried over anhydrous sodium sulfate, and filtered by suction. The filtrate was concentrated under reduced pressure. The crude product was purified by silica gel column chromatography (PE:EA=4:1-1:4) to produce a product (1.60 g, yield: 68.8%).

Step 2: Synthesis of 1-isopropyl-4-oxo-5-p-tolyl-1,4-dihydropyridin-3-carboxylic acid

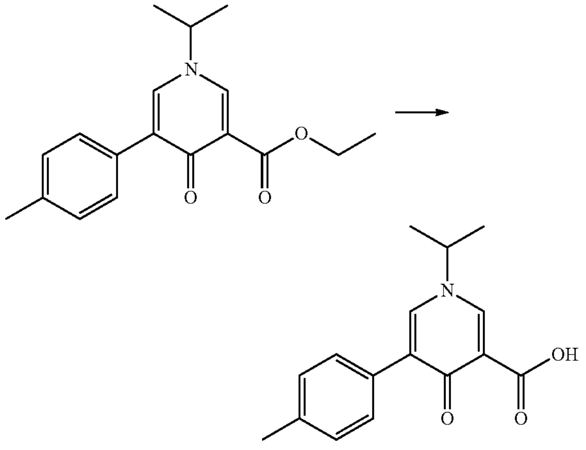

Ethyl 1-isopropyl-4-oxo-5-p-tolyl-1,4-dihydropyridin-3-carboxylate (1.60 g, 5.34 mmol, 1.0 eq) was dissolved in methanol (20 mL), and an aqueous solution (10 mL) of lithium hydroxide monohydrate (1.01 g, 24.05 mmol, 4.5 eq) was added. The mixture was reacted at room temperature under stirring for 1 hour. TLC detection showed the completion of the reaction. The mixture was concentrated under reduced pressure. A solid was precipitated. Water was added, and the mixture was stirred until the solid dissolved. The mixture was adjusted with concentrated HCl to a pH value of 3-4 under an ice bath, and stirred for 30 minutes. The mixture was filtered, and the filter cake was dissolved in dichloromethane. The mixture was dried over anhydrous sodium sulfate, and filtered by suction. The filtrate was concentrated under reduced pressure to produce a product (1.00 g, yield: 69.0%).

Step 3: Synthesis of N-(5-((6,7-dimethoxyquinolin-4-yl)oxy)pyridin-2-yl)-1-isopropyl-4-oxo-5-p-tolyl-1,4-dihydropyridin-3-carboxamide

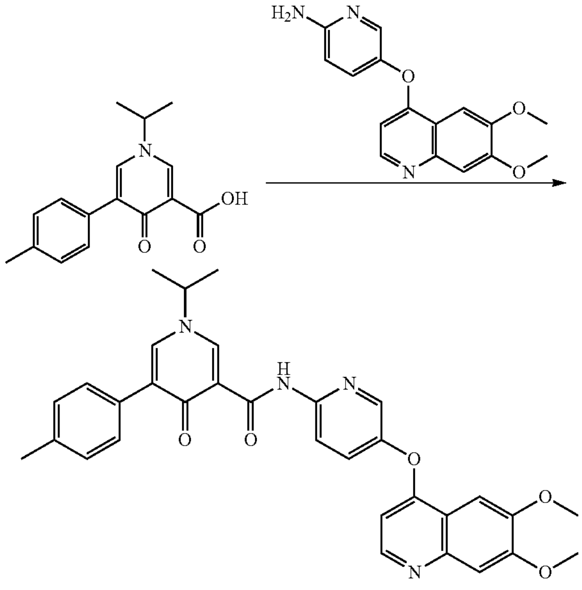

1-isopropyl-4-oxo-5-p-tolyl-1,4-dihydropyridin-3-carboxylic acid (200.0 mg, 0.74 mmol, 1.2 eq.) was dissolved in DMF (2 mL). HATU (350.4 mg, 0.62 mmol, 1.5 eq) and DIPEA (238.2 mg, 1.84 mmol, 3.0 eq) were added. The mixture was stirred for 10 minutes and then 5-((6,7-dimethoxyquinolin-4-yl)oxy)pyridin-2-amine (182.6 mg, 0.62 mmol, 1.0 eq) was added. The mixture was reacted at room temperature under stirring for 1 hour. TLC detection showed the completion of the reaction. The mixture was concentrated under reduced pressure. The crude product was dissolved in ethyl acetate (10 mL). The mixture was successively washed with a saturated aqueous $NaHCO_3$ solution (5 mL), a saturated aqueous $NH_4Cl$ solution (5 mL), water (5 mL×4) and saturated brine (5 mL), dried over anhydrous sodium sulfate, and filtered by suction. The filtrate was concentrated under reduced pressure. The crude product was purified by preparative thin-layer chromatography (developing agent: ethyl acetate) to produce a product (216 mg, yield: 53.2%).

$^1$HNMR (400 MHz, DMSO-$d_6$) δ (ppm): 13.47 (s, 1H), 8.78-8.77 (d, 1H), 8.51-8.50 (d, 1H), 8.45-8.43 (d, 1H), 8.38-8.37 (d, 1H), 8.22-8.21 (d, 1H), 7.87-7.84 (m, 1H), 7.61-7.59 (d, 2H), 7.55 (s, 1H), 7.42 (s, 1H), 7.27-7.25 (d, 2H), 6.58-6.56 (d, 1H), 4.68-4.62 (m, 1H), 3.96-3.95 (d, 6H), 2.35 (s, 3H), 1.53-1.52 (d, 6H).

Molecular formula: $C_{32}H_{30}N_4O_5$, molecular weight: 550.61 LC-MS (Pos, m/z)=551.38 $[M+H]^+$.

Example 3: Synthesis of N-(5-((6,7-dimethoxyquinolin-4-yl)oxy)pyridin-2-yl)-5-(4-fluorophenyl)-1-isopropyl-4-oxo-1,4-dihydropyridazine-3-carboxamide (Compound 15)

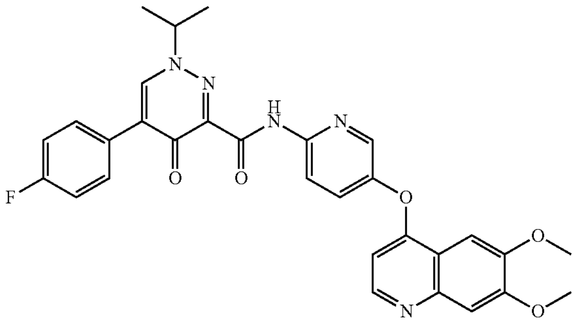 [SMILES: COc1cc2nccc(Oc3ccc(NC(=O)c4nn(C(C)C)cc(-c5ccc(F)cc5)c4=O)nc3)c2cc1OC]

Step 1: Synthesis of 6,7-dimethoxy-4-((6-nitropyridin-3-yl)oxy)quinoline

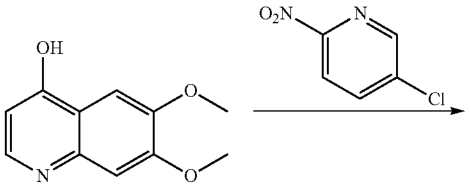

-continued

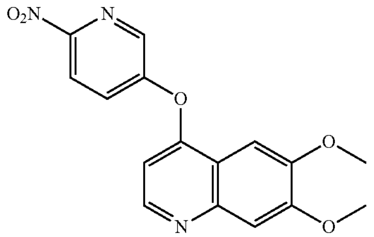

6,7-dimethoxyquinolin-4-ol (15.00 g, 73.10 mmol, 1.0 eq), 5-chloro-2-nitropyridine (11.60 g, 73.10 mmol, 1.0 eq) and potassium carbonate (20.20 g, 146.11 mmol, 2.0 eq) were added to DMF (120 mL). The mixture was reacted at 80° C. overnight under stirring under the nitrogen protection. TLC detection showed the completion of the reaction. The mixture was filtered, and the filter cake was eluted with dichloromethane. The filtrate was concentrated under reduced pressure, and dissolved in dichloromethane (50 mL). The mixture was successively washed with distilled water (20×4 mL) and saturated brine (20 mL), dried over anhydrous sodium sulfate, and filtered by suction. The filtrate was concentrated under reduced pressure. The crude product was purified by silica gel column chromatography (PE:EA=1:9-EA) to produce a product (4.70 g, yield: 19.6%).

Step 2: Synthesis of 5-((6,7-dimethoxyquinolin-4-yl)oxy)pyridin-2-amine

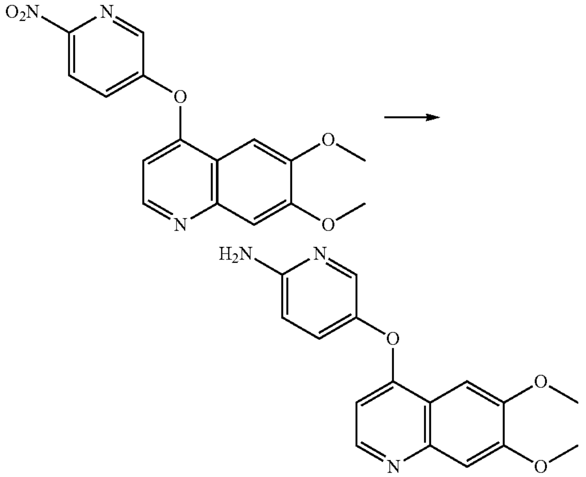

6,7-dimethoxy-4-((6-nitropyridin-3-yl)oxy) quinoline (4.70 g, 14.36 mmol, 1.0 eq), reduced iron powder (4.81 g, 86.16 mmol, 6.0 eq) and $NH_4Cl$ (9.22 g, 172.32 mmol, 12.0 eq) were added to a mixed solvent of ethanol (100 mL) and water (40 mL). The mixture was reacted at 80° C. under stirring for 4 hours. TLC detection showed the completion of the reaction. The mixture was filtered hot, and the filter cake was eluted with dichloromethane. The filtrate was concentrated under reduced pressure. The aqueous phase was extracted with dichloromethane (20 mL×3). The organic phases were combined, washed with saturated brine (20 mL), dried over anhydrous sodium sulfate, and filtered by suction. The filtrate was concentrated under reduced pressure to produce a product (4.07 g, yield: 95.3%).

Step 3: Synthesis of N-(5-((6,7-dimethoxyquinolin-4-yl)oxy)pyridin-2-yl)-5-(4-fluorophenyl)-1-isopropyl-4-oxo-1,4-dihydropyridazine-3-carboxamide

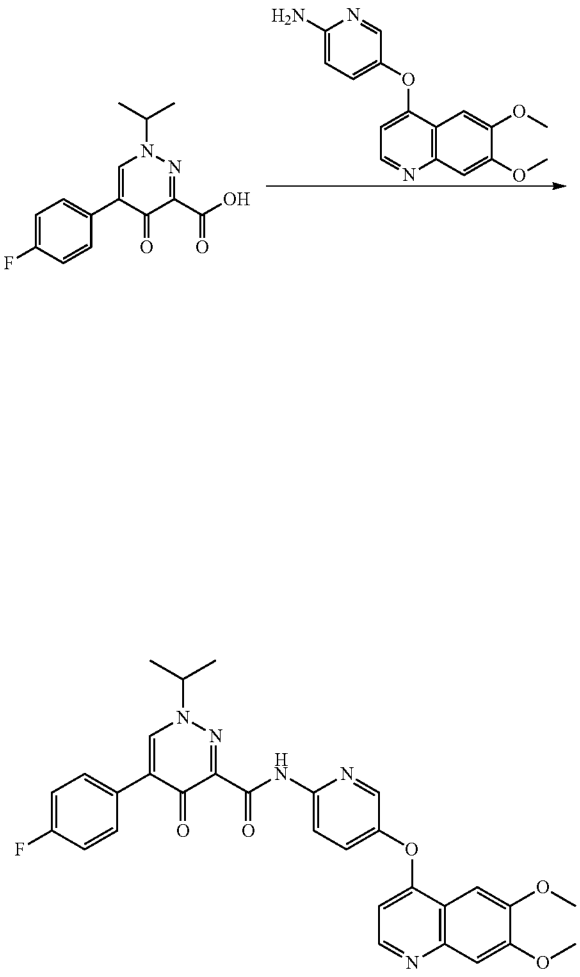

1-isopropyl-4-oxo-5-(4-fluorophenyl)-1,4-dihydro-pyridazine-3-carboxylic acid (149.0 mg, 0.54 mmol, 1.0 eq) and 5-((6,7-dimethoxyquinolin-4-yl)oxy)pyridin-2-amine (192.4 mg, 0.65 mmol, 1.2 eq) were dissolved in anhydrous pyridine (2 mL), and the mixture was stirred for 10 minutes. $POCl_3$ was slowly dropwise added until the solid dissolved. TLC detection showed the completion of the reaction. The mixture was concentrated under reduced pressure. Ethyl acetate (10 mL) was added to dissolve the solid, and the mixture was successively washed with 1 mol/L HCl (5 mL), a saturated aqueous $NaHCO_3$ solution (5 mL), water (5 mL×2) and saturated brine (5 mL), dried over anhydrous sodium sulfate, and filtered by suction. The filtrate was concentrated under reduced pressure. The crude product was purified by silica gel column chromatography (PE:EA=1:1) to produce a product (151 mg, yield: 50.4%).

$^1$H NMR (400 MHz, DMSO-$d_6$) δ (ppm): 13.08 (s, 1H), 8.94 (s, 1H), 8.52-8.50 (d, 1H), 8.44-8.42 (t, 2H), 7.98-7.95 (m, 2H), 7.91-7.88 (q, 1H), 7.55 (s, 1H), 7.42 (s, 1H), 7.37-7.33 (t, 2H), 6.60-6.58 (d, 1H), 4.80-4.74 (m, 1H), 3.96-3.95 (d, 6H), 1.54-1.53 (d, 6H).

Molecular formula: $C_{30}H_{26}FN_5O_5$, molecular weight: 555.57 LC-MS (Pos, m/z)=556.33 $[M+H]^+$.

Example 4: Synthesis of N-(5-((6,7-dimethoxyquinolin-4-yl)oxy)pyrimidine-2-yl)-5-(4-fluorophenyl)-1-isopropyl-4-oxo-1,4-dihydropyridazine-3-carboxamide (Compound 16)

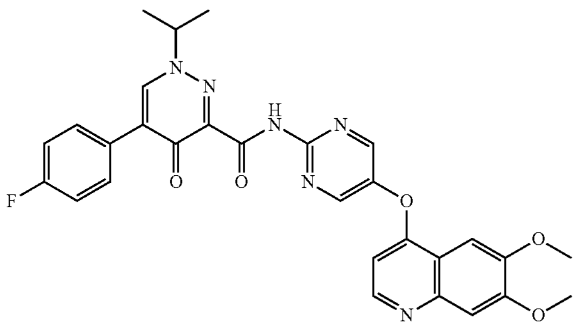 [SMILES: COc1cc2nccc(Oc3cnc(NC(=O)c4nn(C(C)C)cc(-c5ccc(F)cc5)c4=O)nc3)c2cc1OC]

Step 1: Synthesis of 2-(4-fluorophenyl)acetyl chloride

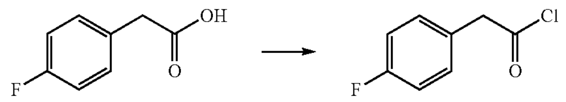

2-(4-fluorophenyl) acetic acid (100.0 g, 0.649 mol, 1.0 eq) was dissolved in dichloromethane (200 mL), and thionyl chloride (193.0 g, 1.62 mol, 2.5 eq) was added. The mixture was reacted at 50° C. under stirring for 2 hours. TLC detection showed the completion of the reaction. The mixture was concentrated under reduced pressure to produce a product (116.0 g, crude product).

Step 2: Synthesis of ethyl 2-diazo-4-(4-fluorophenyl)-3-oxobutanoate

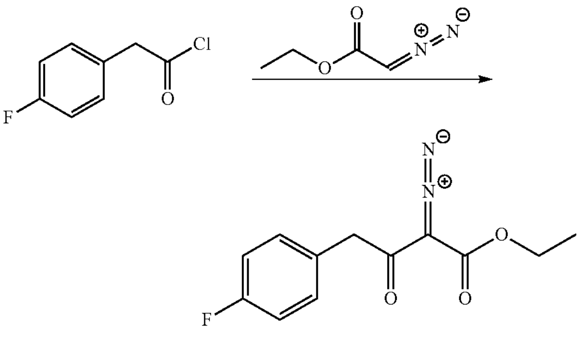

2-(4-fluorophenyl) acetyl chloride (116.0 g, crude product) was dissolved in ethyl acetate (50 mL), and ethyl 2-diazoacetate (153.3 g, 1344 mmol, 2.0 eq) was added under an ice bath. The mixture was gradually warmed to room temperature, and stirred overnight. TLC detection showed the completion of the reaction. A saturated aqueous potassium carbonate solution (100 mL) was dropwise added under an ice bath. The mixture was stirred for 20 minutes, and subjected to the liquid separation. The organic phase was dried over anhydrous sodium sulfate, filtered, and concentrated. The crude product was purified by silica gel column chromatography (petroleum ether:ethyl acetate=100:1-60:1) to produce a product (60.3 g, yield in two steps: 37.1%).

Step 3: Synthesis of ethyl 4-(4-fluorophenyl)-2-hydrazono-3-oxobutanoate

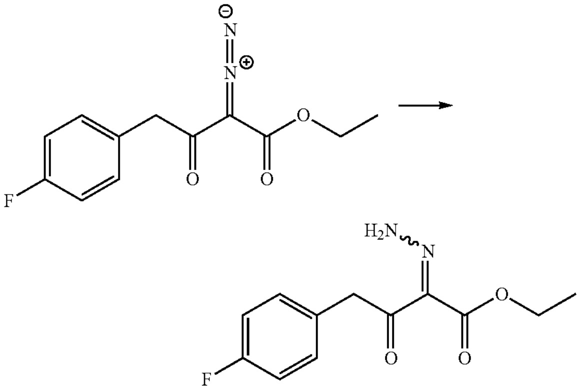

Ethyl 2-diazo-4-(4-fluorophenyl)-3-oxobutanoate (57.1 g, 228 mmol, 1.0 eq) was dissolved in methyl tert-butyl ether (270.0 mL), and tributylphosphine (55.4 g, 273 mmol, 1.2 eq) was added under an ice bath. The mixture was gradually warmed to room temperature, and stirred overnight. TLC detection showed the completion of the reaction. Ethyl acetate (150 mL) and water (200 mL) were added, and the mixture was subjected to the liquid separation. The organic phase was washed with saturated brine (100 mL), dried over anhydrous sodium sulfate, and filtered by suction. The filtrate was concentrated under reduced pressure to produce a product (125.3 g, crude product).

Step 4: Synthesis of tert-butyl 2-(1-ethoxy-4-(4-fluorophenyl)-1,3-dioxobutane-2-ylidene)hydrazine-1-carboxylate

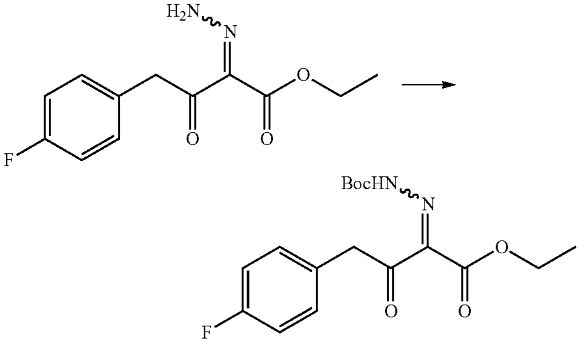

Ethyl 4-(4-fluorophenyl)-2-hydrazono-3-oxobutanoate (93.0 g, crude product) was dissolved in tetrahydrofuran (150 mL). The mixture was cooled in an ice bath to 0° C. Triethylamine (37.2 g, 368 mmol) and di-tert-butyl dicarbonate (96.5 g, 442.0 mmol) were added, and DMAP (13.4 g, 110.0 mmol) was added in batch. The mixture was gradually warmed to room temperature, and stirred overnight. TLC detection showed the completion of the reaction. The mixture was concentrated under reduced pressure. Ethyl acetate (300 mL) and water (500 mL) were added, and the mixture was subjected to the liquid separation. The organic phase was dried over anhydrous sodium sulfate, and filtered by suction. The filtrate was concentrated under reduced pressure to produce a product (52.0 g, crude product).

Step 5: Synthesis of ethyl 5-(4-fluorophenyl)-4-oxo-1,4-dihydropyridazine-3-carboxylate

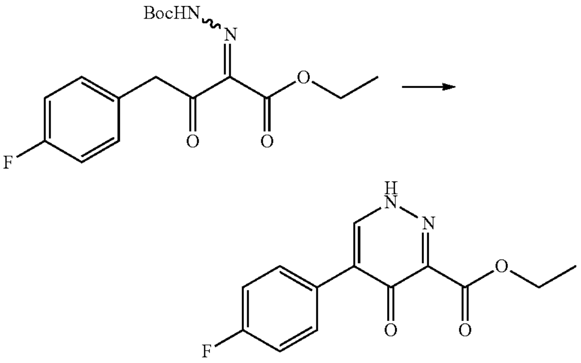

Tert-butyl 2-(1-ethoxy-4-(4-fluorophenyl)-1,3-dioxobutane-2-ylidene) hydrazine-1-carboxylate (52.0 g, crude product) was dissolved in toluene (100 mL). N,N-dimethylformamide dimethyl acetal (35.1 g, 338 mmol, 2.0 eq) was added. The mixture was stirred at 60° C. overnight. LC-MS detection showed the completion of the reaction. The system was cooled to room temperature. The mixture was filtered by suction. The filter cake was dried to produce a product (22.1 g, yield in three steps: 49.8%).

Step 6: Synthesis of ethyl 5-(4-fluorophenyl)-1-isopropyl-4-oxo-1,4-dihydropyridazine-3-carboxylate

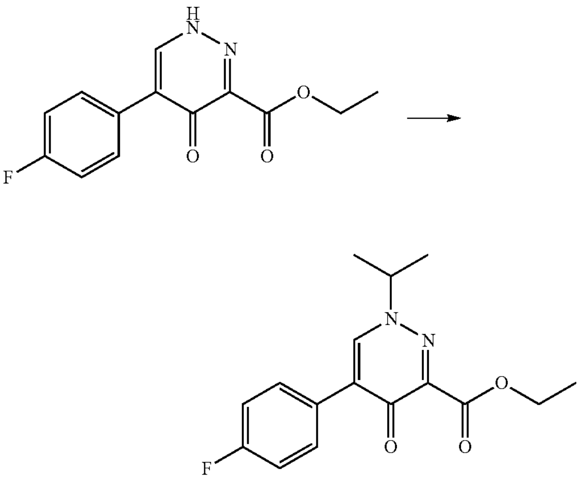

Ethyl 5-(4-fluorophenyl)-4-oxo-1,4-dihydropyridazine-3-carboxylate (8.80 g, 33.5 mmol, 1.0 eq) was dissolved in DMF (30 mL). Potassium carbonate (9.26 g, 67.0 mmol, 2.0 eq) and bromoisopropane (6.18 g, 50.3 mmol, 1.5 eq) were added. The mixture was stirred at 50° C. under the nitrogen protection overnight, TLC detection showed the completion of the reaction. The mixture was concentrated under reduced pressure. Ethyl acetate (150 mL) and water (200 mL) were added, and the mixture was subjected to the liquid separation. The organic phase was dried over anhydrous sodium sulfate, filtered, and concentrated. The crude product was purified by silica gel column chromatography (petroleum ether:ethyl acetate=10:1-3:1) to produce a product (8.49 g, yield: 84.0%).

Step 7: Synthesis of 5-(4-fluorophenyl)-1-isopropyl-4-oxo-1,4-dihydropyridazine-3-carboxylic acid

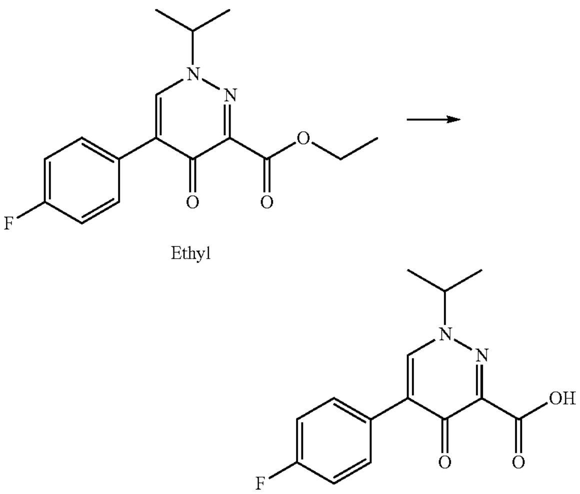

5-(4-fluorophenyl)-1-isopropyl-4-oxo-1,4-dihydro-pyridazine-3-carboxylate (7.47 g, 24.0 mmol, 1.0 eq) was dissolved in methanol (30.0 mL). An aqueous solution (15.0 mL) of lithium hydroxide monohydrate (3.08 g, 73.0 mmol, 3.0 eq) was added. The mixture was reacted at room temperature under stirring for 0.5 hour. TLC detection showed the completion of the reaction. The mixture was concentrated under reduced pressure, adjusted with HCl (1 mol/L, 4.0 mL) to a pH value of about 4, stirred for 20 minutes, and filtered by suction. The filter cake was dried to produce a product (6.29 g, yield: 94.8%).

Step 8: Synthesis of N-(5-((6,7-dimethoxyquinolin-4-yl)oxy)pyrimidine-2-yl)-5-(4-fluorophenyl)-1-isopropyl-4-oxo-1,4-dihydropyridazine-3-carboxamide

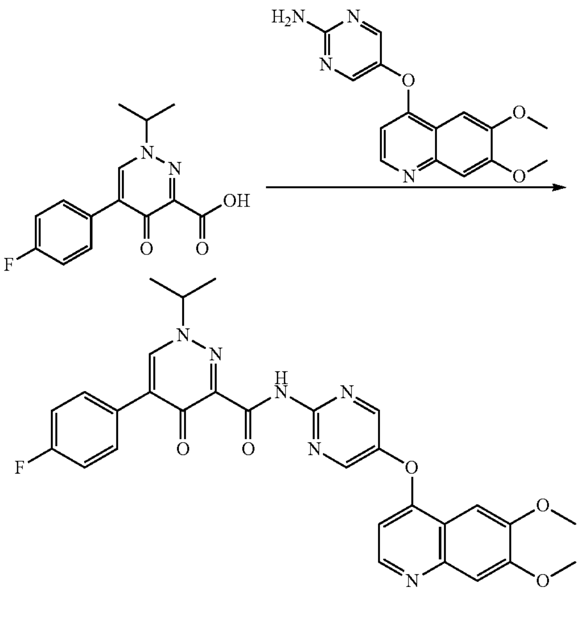

5-(4-fluorophenyl)-1-isopropyl-4-oxo-1,4-dihydro-pyridazine-3-carboxylic acid (2.0 g, 7.23 mmol, 1.0 eq) and 5-((6,7-dimethoxyquinolin-4-yl)oxy)pyrimidine-2-amine (2.15 g, 7.23 mmol, 1.0 eq) were added to pyridine (8 mL), and phosphorus oxychloride (0.5 mL) was dropwise added. The mixture was stirred for 30 minutes. TLC detection showed the completion of the reaction. The mixture was concentrated under reduced pressure. Water (50 mL) was added. The mixture was extracted with ethyl acetate (100 mL×2). The organic phase was dried over anhydrous sodium sulfate, filtered, and concentrated. The crude product was purified by silica gel column chromatography (dichloromethane:methanol=80:1-60:1) to produce a product (2.1 g, yield: 51.2%).

$^1$H NMR (400 MHz, DMSO-$d_6$) δ (ppm): 12.89 (s, 1H), 8.89 (s, 1H), 8.80 (s, 2H), 8.50-8.51 (m, 1H), 7.93-7.97 (m, 2H), 7.55 (s, 1H), 7.43 (s, 1H), 7.31-7.35 (m, 2H), 6.68-6.69 (d, 1H), 4.72-4.75 (m, 1H), 3.95-3.96 (m, 6H), 1.50-1.52 (m, 6H).

Molecular formula: $C_{29}H_{25}FN_6O_5$, molecular weight: 556.55 LC-MS (Pos, m/z)=557.38 $[M+H]^+$.

Example 5: Synthesis of N-(5-((6,7-dimethoxyquinolin-4-yl)oxy)pyrimidine-2-yl)-5-(4-fluorophenyl)-1-isopropyl-4-oxo-1,4-dihydropyridin-3-carboxamide (Compound 20)

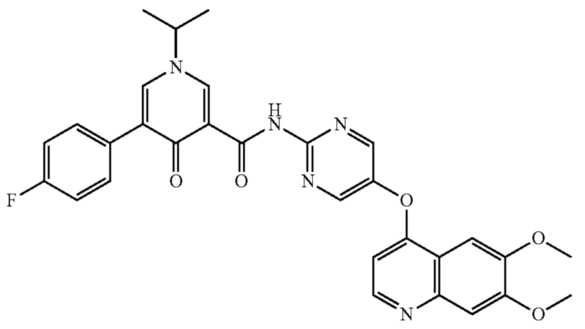 [SMILES: COc1cc2nccc(Oc3cnc(NC(=O)c4cn(C(C)C)cc(-c5ccc(F)cc5)c4=O)nc3)c2cc1OC]

Step 1: Synthesis of N-(5-((6,7-dimethoxyquinolin-4-yl)oxy)pyrimidine-2-yl)-5-(4-fluorophenyl)-1-isopropyl-4-oxo-1,4-dihydropyridin-3-carboxamide

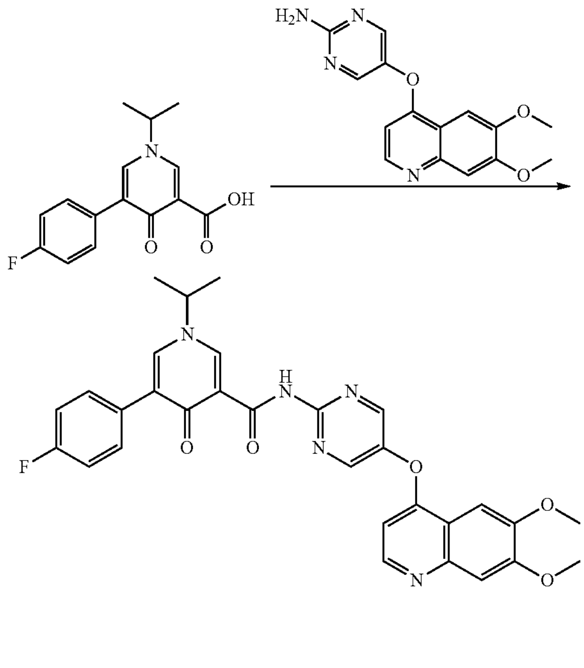

5-(4-fluorophenyl)-1-isopropyl-4-oxo-1,4-dihydropyridin-3-carboxylic acid (450.0 mg, 1.63 mmol, 1.0 eq) and 5-((6,7-dimethoxyquinolin-4-yl)oxy)pyrimidine-2-amine (487.31 mg, 1.63 mmol, 1.0 eq) were added to pyridine (18 mL), and phosphorus oxychloride (0.2 mL) was slowly dropwise added under an ice bath. The mixture was slowly warmed to room temperature and reacted for 3 hours. TLC detection showed the completion of the reaction. Ethyl acetate (10 mL) and water (20 mL) were added, and the mixture was subjected to the liquid separation. The organic phase was dried over anhydrous sodium sulfate, and filtered by suction. The filtrate was concentrated under reduced pressure. The crude product was purified by silica gel column chromatography (dichloromethane:methanol=100:1-10:1) to produce a product (200.0 mg, yield: 22.1%).

$^1$HNMR (400 MHz, DMSO-$d_6$) δ (ppm): 13.67 (s, 1H), 8.80 (s, 2H), 8.77-8.76 (d, 1H), 8.52-8.51 (d, 1H), 8.28 (s, 1H), 7.77-7.73 (m, 2H), 7.56 (s, 1H), 7.43 (s, 1H), 7.31-7.27 (m, 2H), 6.71-6.70 (d, 1H), 4.68-4.65 (t, 1H), 3.97-3.96 (d, 6H), 1.53-1.52 (d, 6H).

Molecular formula: $C_3CH_{26}FN_5O_5$, molecular weight: 555.57 LC-MS (Pos, m/z)=556.3 [M+H]$^+$.

Example 6: Synthesis of N-(6-((6,7-dimethoxyquinolin-4-yl)oxy)pyridin-3-yl)-1-isopropyl-4-oxo-5-para-fluorophenyl-1,4-dihydropyridazine-3-carboxamide (Compound 29)

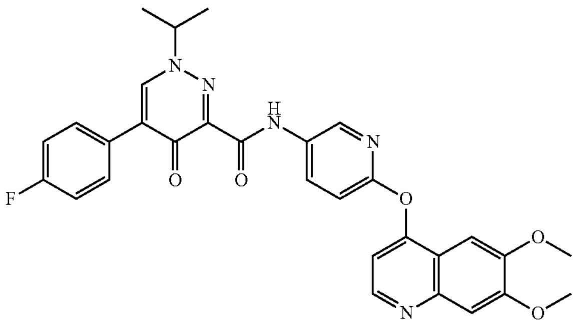 [SMILES: COc1cc2nccc(Oc3ccc(NC(=O)c4nn(C(C)C)cc(-c5ccc(F)cc5)c4=O)cn3)c2cc1OC]

Step 1: Synthesis of 6,7-dimethoxy-4-((5-nitropyridin-2-yl)oxy)quinoline

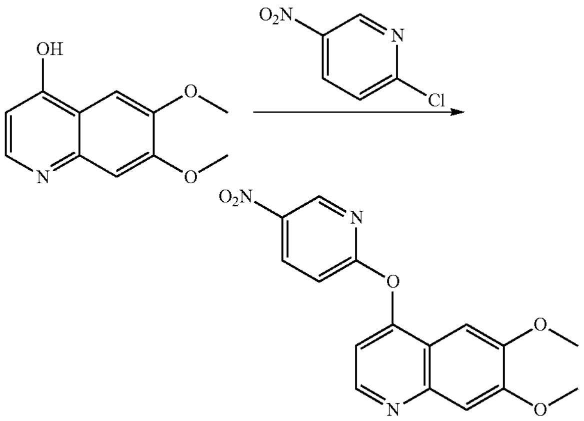

6,7-dimethoxyquinolin-4-ol (5.00 g, 24.36 mmol, 1.0 eq), 2-chloro-5-nitropyridine (3.86 g, 24.36 mmol, 1.0 eq) and potassium carbonate (6.73 g, 48.73 mmol, 2.0 eq) were added to DMF (50 mL). The mixture was reacted at 40° C. under stirring under the nitrogen protection overnight. TLC detection showed the completion of the reaction. The mixture was filtered, and the filter cake was eluted with dichloromethane. The filtrate was concentrated under reduced pressure. Dichloromethane (20 mL) and methanol (20 mL) were added to dissolve the crude product. The mixture was dried over anhydrous sodium sulfate, and filtered by suction. The filtrate was concentrated under reduced pressure. The residue was purified by silica gel column chromatography (DCM:MeOH=80:1-30:1) to produce a product (0.60 g, yield: 7.52%).

Step 2: Synthesis of 6-((6,7-dimethoxyquinolin-4-yl)oxy)pyridin-3-amine

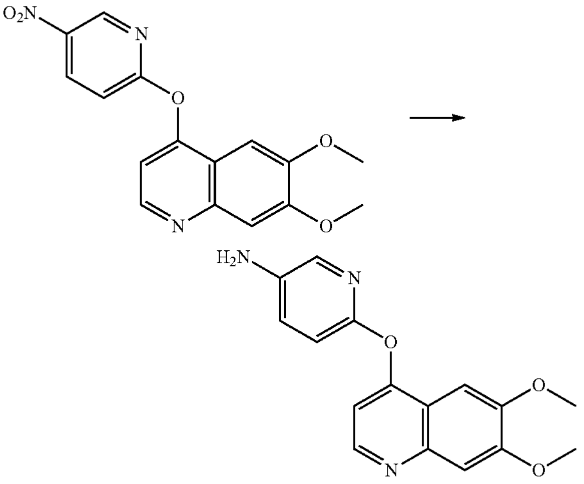

6,7-dimethoxy-4-((6-nitropyridin-3-yl)oxy) quinoline (366.0 mg, 1.12 mmol, 1.0 eq), reduced iron powder (374.7 mg, 6.71 mmol, 6.0 eq) and $NH_4Cl$ (717.8 mg, 13.42 mmol, 12.0 eq) were added to a mixed solvent of ethanol (10 mL) and water (5 mL). The mixture was reacted at 80° C. under stirring for 4 hours. TLC detection showed the completion of the reaction. Celite was added into the solution, and the mixture was filtered hot, and the filter cake was eluted with EtOH. The filtrate was concentrated under reduced pressure, and extracted with dichloromethane (5 mL×3). The organic phases were combined, dried over anhydrous sodium sulfate, and filtered by suction. The filtrate was concentrated under reduced pressure to produce a product (188.0 mg, yield: 56.6%).

Step 3: Synthesis of N-(6-((6,7-dimethyquinolin-4-yl)oxy)pyridin-3-yl)-1-isopropyl-4-oxo-5-para-fluorophenyl-1,4-dihydropyridazine-3-carboxamide

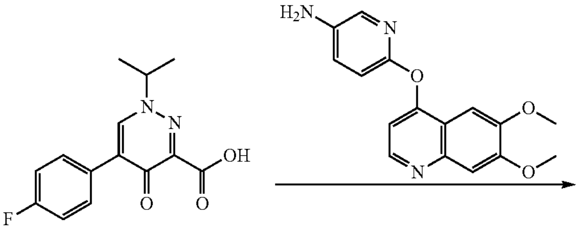

-continued

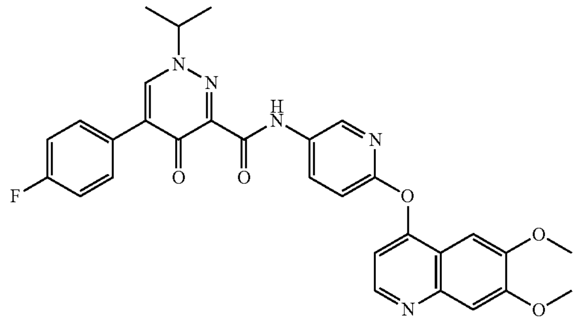

1-isopropyl-4-oxo-5-para-fluorophenyl-1,4-dihydro-pyridazine-3-carboxylic acid (184.6 mg, 0.66 mmol, 1.1 eq) was dissolved in DMF (2 mL). HATU (346.4 mg, 0.91 mmol, 1.5 eq) and DIPEA (235.4 mg, 1.82 mmol, 3.0 eq) were added. The mixture was stirred for 10 minutes. 6-((6,7-dimethoxyquinolin-4-yl)oxy)pyridin-3-amine (180.6 mg, 0.61 mmol, 1.0 eq) was added. The mixture was reacted at room temperature under stirring for 1 hour. TLC detection showed the completion of the reaction. The mixture was concentrated under reduced pressure. The crude product was dissolved in ethyl acetate (10 mL). The mixture was successively washed with a saturated aqueous $NaHCO_3$ solution (5 mL), a saturated aqueous $NH_4Cl$ solution (5 mL), water (5 mL×4) and saturated brine (5 mL), dried over anhydrous sodium sulfate, and filtered by suction. The filtrate was concentrated under reduced pressure. The crude product was purified by preparative thin-layer chromatography (DCM:MeOH=15:1) to produce a product (230 mg, yield: 67.9%).

$^1$H NMR (400 MHz, DMSO-$d_6$) δ (ppm): 12.38 (s, 1H), 8.92 (s, 1H), 8.63-8.62 (d, 1H), 8.59-8.58 (d, 1H), 8.40-8.37 (t, 1H), 7.97-7.94 (m, 2H), 7.43 (s, 1H), 7.39-7.32 (m, 4H), 6.91-6.90 (d, 1H), 4.78-4.71 (m, 1H), 3.96 (s, 3H), 3.89 (s, 3H), 1.53-1.51 (d, 6H).

Molecular formula: $C_3CH_{26}FN_5O_5$, molecular weight: 555.57 LC-MS (Pos, m/z)=556.28 $[M+H]^+$.

Example 7: Synthesis of N-(5-((6,7-dimethoxyquinolin-4-yl)oxy)pyridin-2-yl)-1-cyclopropyl-4-oxo-5-para-fluorophenyl-1,4-dihydropyridin-3-carboxamide (Compound 30)

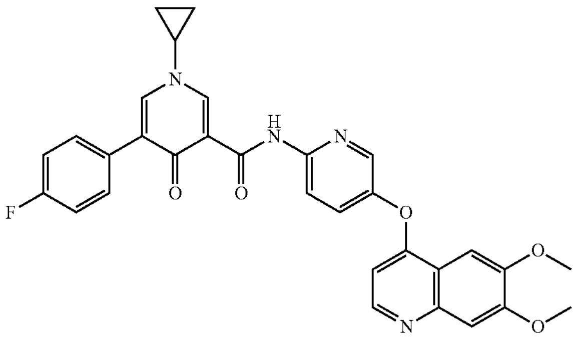

Step 1: Synthesis of ethyl 5-(dimethylamino)-2-((dimethylamino)methylene)-4-para-fluorophenyl-3-oxopentan-4-enoate

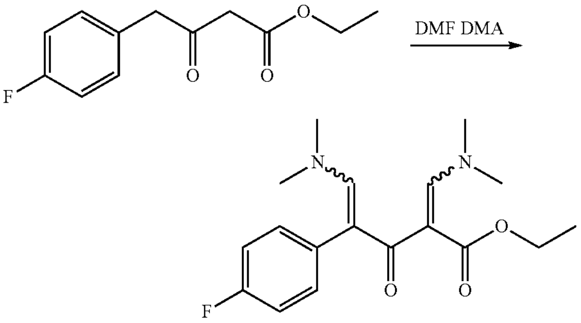

Ethyl 4-para-fluorophenyl-3-oxobutanoate (5.00 g, 22.30 mmol, 1.0 eq) and DMF-DMA (15.94 g, 133.79 mmol, 6 eq) were added to toluene (50 mL). The mixture was reacted at 100° C. under stirring overnight. TLC detection showed the completion of the reaction. The mixture was concentrated under reduced pressure to produce a crude product, which was directly used in the next step without purification.

Step 2: Synthesis of ethyl 1-cyclopropyl-4-oxo-5-para-fluorophenyl-1,4-dihydropyridin-3-carboxylate

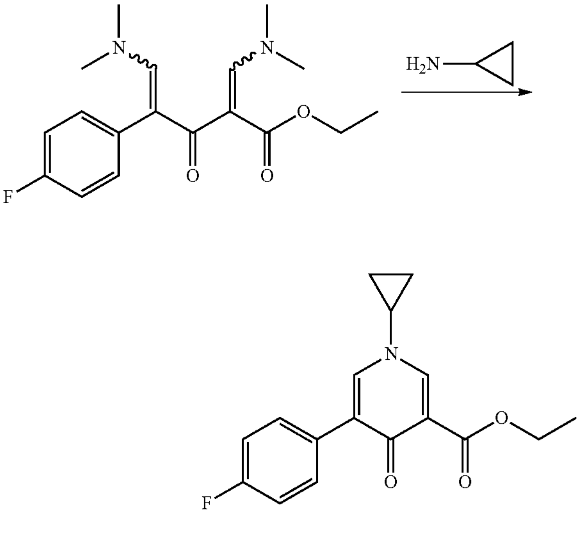

The crude product obtained in the previous step, ethyl 5-(dimethylamino)-2-((dimethylamino)methylene)-4-para-fluorophenyl-3-oxopenta n-4-enoate and cyclopropyl amine (1.91 g, 33.45 mmol, 1.5 eq) were added to EtOH (30 mL). The mixture was reacted at 80° C. under stirring overnight. TLC detection showed the completion of the reaction. The mixture was concentrated under reduced pressure. The crude product was dissolved in ethyl acetate (20 mL). The mixture was washed with saturated brine (10 mL), dried over anhydrous sodium sulfate, and filtered by suction. The filtrate was concentrated under reduced pressure. The crude product was purified by silica gel column chromatography (DCM: MeOH=20:1) to produce a product (2.67 g, yield in two steps: 39.7%).

Step 3: Synthesis of 1-cyclopropyl-4-oxo-5-para-fluorophenyl-1,4-dihydropyridin-3-carboxylic acid

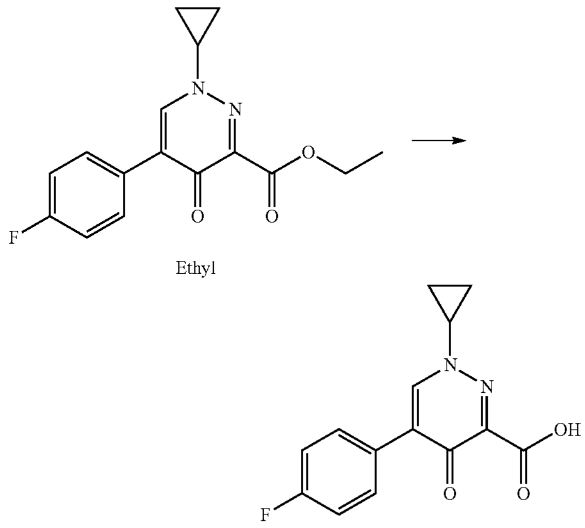

1-cyclopropyl-4-oxo-5-para-fluorophenyl-1,4-dihydro-pyridin-3-carboxylate (2.67 g, 8.86 mmol, 1.0 eq) was dissolved in methanol (40 mL). An aqueous solution (20 mL) of lithium hydroxide monohydrate (1.67 g, 39.87 mmol, 4.5 eq) was added. The mixture was reacted at room temperature under stirring for 1 hour. TLC detection showed the completion of the reaction. The mixture was concentrated under reduced pressure. Water was added under stirring until the solid completely dissolved. The mixture was adjusted with concentrated HCl to a pH value of 3-4 under an ice bath, and stirred for 30 minutes. The solid was filtered off, and dissolved in dichloromethane. The mixture was dried over anhydrous sodium sulfate, and filtered by suction. The filtrate was concentrated under reduced pressure to produce a product (1.25 g, yield: 51.6%).

Step 4: Synthesis of N-(5-((6,7-dimethoxyquinoin-4-yl)oxo)pyridin-2-yl)-1-cyclopropyl-oxo-5-para-fluorophenyl-1,4-dihydropyridin-3-carboximide

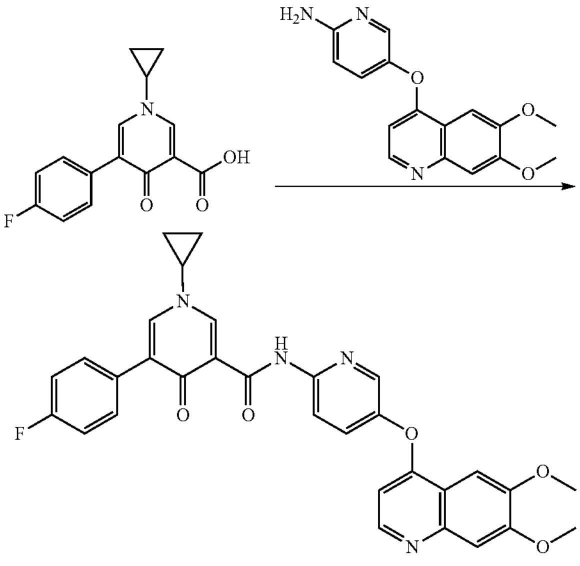

1-cyclopropyl-4-oxo-5-para-fluorophenyl-1,4-dihydro-pyridin-3-carboxylic acid (150.0 mg, 0.55 mmol, 1.1 eq) was dissolved in DMF (1.5 mL). HATU (285.0 mg, 0.75 mmol, 1.5 eq) and DIPEA (193.0 mg, 1.50 mmol, 3.0 eq) were added. The mixture was stirred for 10 minutes. 5-((6,7-dimethoxyquinolin-4-yl)oxy)pyridin-2-amine (148.0 mg, 0.50 mmol, 1.0 eq) was added. The mixture was reacted at room temperature under stirring for 1 hour. TLC detection showed the completion of the reaction. The mixture was concentrated under reduced pressure. The crude product was dissolved in ethyl acetate (10 mL). The mixture was successively washed with a saturated sodium bicarbonate solution (5 mL), a saturated ammonium chloride solution (5 mL), water (5 mL×4) and saturated brine (5 mL), dried over anhydrous sodium sulfate, and filtered by suction. The filtrate was concentrated under reduced pressure. The crude product was purified by preparative thin-layer chromatography (DCM:MeOH=15:1) to produce a product (140.0 mg, yield: 50.7%).

$^1$H NMR (400 MHz, DMSO-$d_6$) δ (ppm): 13.29 (s, 1H), 8.66 (s, 1H), 8.50-8.49 (d, 1H), 8.43-8.37 (m, 2H), 8.14 (s, 1H), 7.86-7.84 (d, 1H), 7.75 (s 2H), 7.54 (s, 1H), 7.42 (s, 1H), 7.30-7.28 (d, 2H), 6.57-6.56 (d, 1H), 3.95 (d, 7H), 1.26 (s, 2H), 1.11 (s, 2H).

Molecular formula: $C_{31}H_{25}FN_4O_5$, molecular weight: 552.56 LC-MS (Pos, m/z)=553.25 $[M+H]^+$.

Example 8: Synthesis of 1-cyclopropyl-N-(5-((6,7-dimethoxyquinolin-4-yl)oxy)pyrimidine-2-yl)-5-(4-fluoro phenyl)-4-oxo-1,4-dihydropyridin-3-carboxamide (Compound 32)

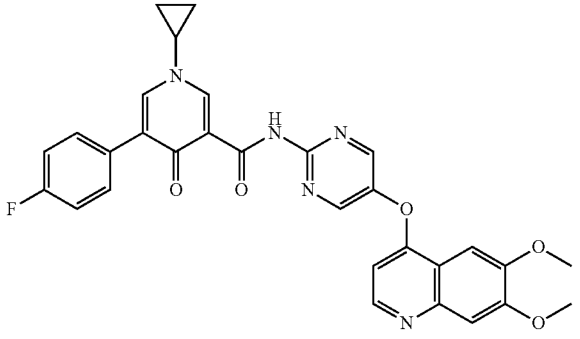

Step 1: Synthesis of 1-cyclopropyl-N-(5-((6,7-dimethoxyquinolin-4-yl)oxy)pyrimidine-2-yl)-5-(4-fluorophenyl)-4-oxo-1,4-dihydropyridin-3-carboxamide

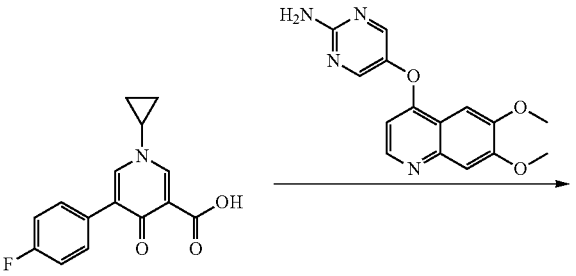

-continued

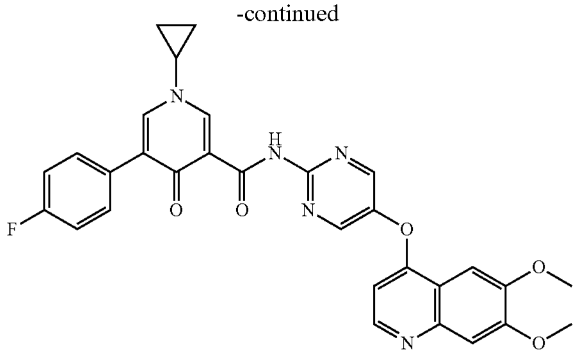

1-cyclopropyl-5-(4-fluorophenyl)-4-oxo-1,4-dihydropyridin-3-carboxylic acid (227.0 mg, 1.0 eq) and 0.83 mmol, 5-((6,7-dimethoxyquinolin-4-yl)oxy)pyrimidine-2-amine (247.8 mg, 0.83 mmol, 1.0 eq) were added to pyridine (4 mL), and phosphorus oxychloride (0.3 ml) was dropwise added. The mixture was stirred for 30 minutes. TLC detection showed the completion of the reaction. The mixture was concentrated under reduced pressure. Ethyl acetate (20 mL) and water (15 mL) were added, and the mixture was subjected to the liquid separation. The organic phase was dried over anhydrous sodium sulfate, filtered, and concentrated. The crude product was purified by preparative thin-layer chromatography (dichloromethane:methanol=15:1) to produce a product (110.0 mg, yield: 23.9%).

$^1H$ NMR (400 MHz, DMSO-$d_6$) δ (ppm): 13.53 (s, 1H), 8.80 (s, 2H), 8.63 (m, 1H), 8.51-8.52 (m, 1H), 8.13-8.14 (m, 1H), 7.73-7.76 (m, 2H), 7.55 (s, 1H), 7.43 (s, 1H), 7.26-7.30 (m, 2H), 6.69-6.71 (m, 1H), 3.95-3.96 (s, 6H), 3.88-3.91 (m, 1H). 1.23-1.25 (m, 2H), 1.08-1.09 (m, 2H).

Molecular formula: $C_{30}H_{24}FN_5O_5$, molecular weight: 553.55 LC-MS (Pos,m/z)=554.26 $[M+H]^+$.

Example 9: Synthesis of 1-cyclopropyl-N-(5-((6,7-dimethylquinolin-4-yl)oxy)pyridin-2-yl)-5-(4-fluorophenyl)-4-oxo-1,4-dihydropyridazine-3-carboxamide (Compound 31)

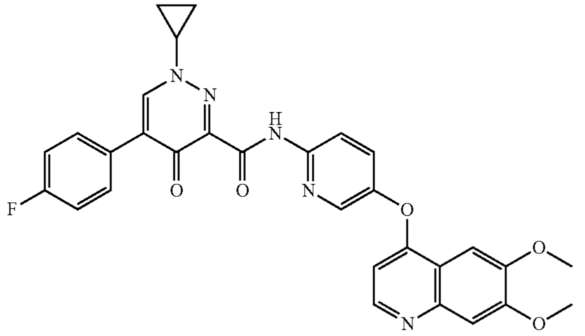 [SMILES: COc1cc2nccc(Oc3ccc(NC(=O)c4nn(C5CC5)cc(-c5ccc(F)cc5)c4=O)nc3)c2cc1OC]

Step 1: Synthesis of ethyl 1-cyclopropyl-5-(4-fluorophenyl)-4-oxo-1,4-dihydropyridazine-3-carboxylate

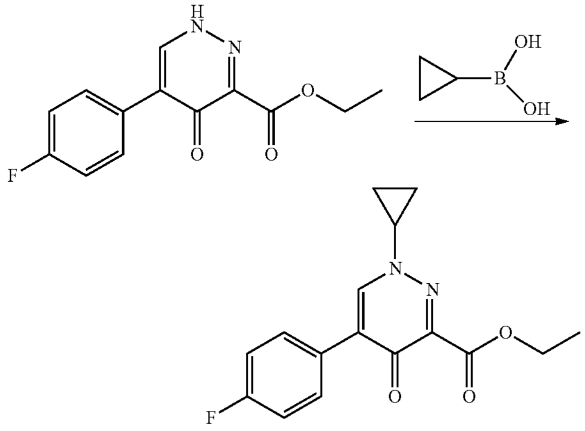

Ethyl 5-(4-fluorophenyl)-4-oxo-1,4-dihydropyridazine-3-carboxylate (2.0 g, 7.627 mmol, 1.0 eq), cyclopropylboronic acid (1.965 g, 22.880 mmol, 3.0 eq), triethylamine (3.858 g, 38.133 mmol, 5.0 eq), pyridine (4.826 g, 61.013 mmol, 8.0 eq) and copper acetate (1.385 g, 7.627 mmol, 1.0 eq) were dissolved in DMF (20.0 mL), and the mixture was reacted at 50° C. overnight under an oxygen condition. TLC showed the completion of the reaction. The mixture was concentrated under reduced pressure. Water was added. The mixture was extracted with ethyl acetate. The organic phase was dried over anhydrous sodium sulfate, and concentrated. The crude product was purified by preparative thin-layer chromatography (DCM:MeOH=40:1) to produce a product (38.0 mg, yield: 1.65%).

Step 2: Synthesis of 1-cyclopropyl-5-(4-fluorophenyl)-4-oxo-1,4-dihydropyridazine-3-carboxylic acid

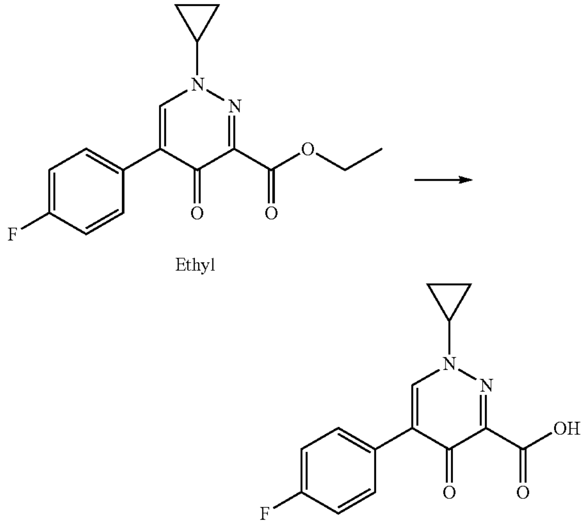

1-cyclopropyl-5-(4-fluorophenyl)-4-oxo-1,4-dihydropyridazine-3-carboxylate (38.0 mg, 0.126 mmol, 1.0 eq) was dissolved in tetrahydrofuran (1.0 mL). An aqueous LiOH solution (1 mol/L) was added. The mixture was reacted at room temperature for 1 hour. TLC showed the completion of the reaction. The reaction liquor was concentrated under reduced pressure. Water (15.0 mL) was added. The mixture was extracted with ethyl acetate (6.0 mL×2). The organic phases were combined, dried over anhydrous sodium sulfate, and filtered. The filtrate was concentrated under reduced pressure to produce a product (59.0 mg, crude product).

Step 3: Synthesis of 1-cyclopropyl-N-(5-((6,7-dimethoxyquinolin-4-yl)oxy)pyridin-2-yl)-5-(4-fluorophenyl)-4-oxo-1,4-dihydropyridazine-3-carboxamide

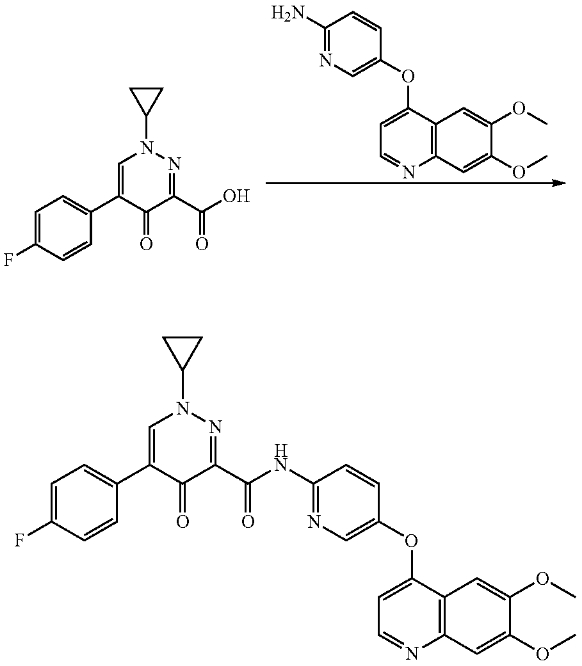

1-cyclopropyl-5-(4-fluorophenyl)-4-oxo-1,4-dihydropyridazine-3-carboxylic acid (59.0 mg, crude product) and N,N-diisopropylethylamine (48.7 mg, 0.377 mmol, 3.0 eq) were dissolved in DMF (1.0 mL). The mixture was cooled to 0° C. HATU (71.7 mg, 0.188 mmol, 1.5 eq) was added under the nitrogen protection. The mixture was stirred at 0° C. for 0.5 hour. 5-((6,7-dimethoxyquinolin-4-yloxy)pyridin-2-amine (37.0 mg, 0.126 mmol, 1.0 eq) was added. The mixture was reacted at room temperature for 3 hours. TLC showed the completion of the reaction. The reaction liquor was poured into water (20.0 mL). The mixture was extracted with ethyl acetate (10.0 mL×2). The organic phase was successively washed with a saturated aqueous sodium carbonate solution (3.0 mL), a saturated aqueous $NH_4Cl$ solution (3.0 mL) and a saturated aqueous sodium chloride solution (3.0 mL), dried over anhydrous sodium sulfate, filtered, and concentrated under reduced pressure. The crude product was purified by preparative thin-layer chromatography plate (DCM:MeOH=20:1) to produce a product (40.0 mg, yield in two steps: 57.5%).

$^1$H NMR (400 MHz, DMSO-$d_6$) δ (ppm): 12.98 (s, 1H), 8.94 (s, 1H), 8.52-8.50 (m, 1H), 8.43-8.40 (m, 2H), 7.97-7.93 (m, 2H), 7.91-7.87 (m, 1H), 7.55 (s, 1H), 7.42 (s, 1H), 7.37-7.32 (m, 2H), 6.60-6.57 (m, 1H), 4.17-4.11 (m, 1H), 3.97-3.95 (d, 6H), 1.35-1.23 (m, 2H), 1.15-1.14 (m, 2H).

Molecular formula: $C_{30}H_{24}FN_5O_5$, molecular weight: 553.55 LC-MS (Pos, m/z)=554.32 $[M+H]^+$.

Example 10: Synthesis of 1-cyclopropyl-N-(5-((6,7-dimethoxyquinolin-4-yl)oxy)pyrimidine-2-yl)-5-(4-fluoro phenyl)-4-oxo-1,4-dihydropyridazine-3-carboxamide (Compound 33)

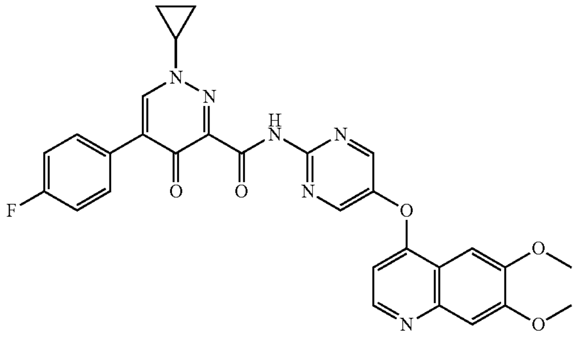 [SMILES: COc1cc2nccc(Oc3cnc(NC(=O)c4nn(C5CC5)cc(-c5ccc(F)cc5)c4=O)nc3)c2cc1OC]

Step 1: Synthesis of 1-cyclopropyl-N-(5-((6,7-dimethoxyquinolin-4-yl)oxo)pyrimidine-2-yl)-5-(4-fluorophenyl)-4-oxo-1,dihydropyridazine-3-carboximide

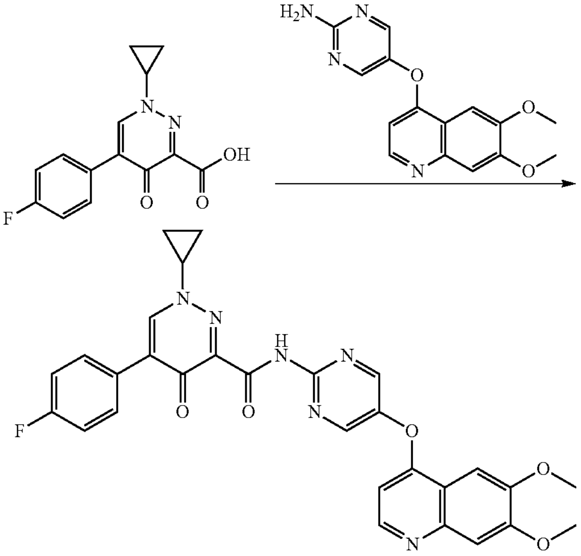

1-cyclopropyl-5-(4-fluorophenyl)-4-oxo-1,4-dihydropyridazine-3-carboxylic acid (200.0 mg, 0.729 mmol, 1.0 eq) and 5-((6,7-dimethoxyquinolin-4-yloxy)pyrimidine-2-amine (217.5 mg, 0.729 mmol, 1.0 eq) were dissolved in pyridine (4.0 mL). The mixture was cooled to 0° C. Phosphorus oxychloride (0.2 mL) was dropwise added under the nitrogen protection. The mixture was reacted at room temperature for 0.5 hour. TLC showed the completion of the reaction. The reaction liquor was poured into water (20.0 mL), and adjusted to a pH value of 6-7. The mixture was extracted with ethyl acetate (10.0 mL×2). The organic phase was washed with 2 mol/L of HCl solution (2.0 mL×2), dried over anhydrous sodium sulfate, and concentrated under reduced pressure. The crude product was purified by silica gel column chromatography (DCM:MeOH=100:1-20:1) to produce a product (200.0 mg, yield: 49.5%).

$^1$H NMR (400 MHz, DMSO-$d_6$) δ (ppm): 12.82 (s, 1H), 8.90 (s, 1H), 8.86-8.80 (m, 2H), 8.52-8.50 (m, 1H), 7.95-

7.93 (m, 2H), 7.55 (s, 1H), 7.44 (s, 1H), 7.36-7.31 (m, 2H), 6.70-6.69 (m, 1H), 4.11-4.10 (m, 1H), 3.97-3.95 (d, 6H), 1.31-1.24 (m, 2H), 1.13-1.11 (m, 2H).

Molecular formula: $C_{29}H_{23}FN_6O_5$, molecular weight: 554.54 LC-MS (Pos, m/z)=554.66 $[M+H]^+$.

Example 11: Synthesis of N-(2-((6,7-dimethoxyquinolin-4-yl)oxy)pyrimidine-5-yl)-5-para-fluorophenyl-1-iso propyl-4-oxo-1,4-dihydropyridazine-3-carboxamide (Compound 34)

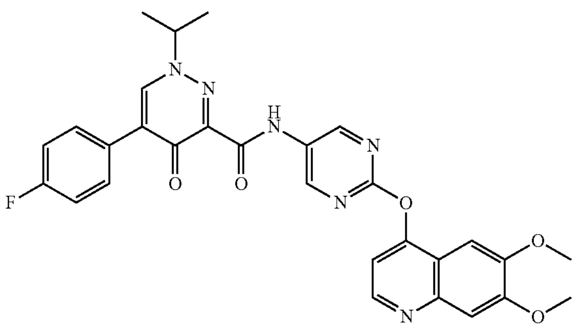 [SMILES: COc1cc2nccc(Oc3ncc(NC(=O)c4nn(C(C)C)cc(-c5ccc(F)cc5)c4=O)cn3)c2cc1OC]

Step 1: Synthesis 6,7-dimethoxy-4-((5-nitropyrimidine-2-yl)oxy)quinoline

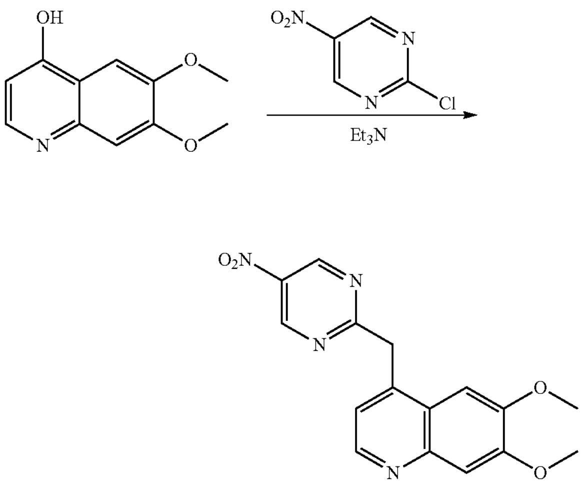

6,7-dimethoxyquinolin-4-ol (3.86 g, 18.81 mmol, 1.0 eq.), 2-chloro-5-nitropyrimidine (3.00 g, 18.81 mmol, 1.0 eq) and triethylamine (2.28 g, 22.57 mmol, 1.2 eq.) were added to DMF (60 mL). The mixture was reacted at room temperature under stirring under the nitrogen protection overnight. TLC detection showed the completion of the reaction. A saturated aqueous $NH_4Cl$ solution (30 mL) was added. The mixture was concentrated under reduced pressure. Saturated brine (30 mL) was added. The mixture was extracted with dichloromethane (20 mL×3). The organic phases were combined, dried over anhydrous sodium sulfate, and filtered by suction. The filtrate was concentrated under reduced pressure. The crude product was purified by 200-300 mesh silica gel column chromatography (DCM: MeOH=150:1-120:1) to produce a product (1.70 g, yield: 27.5%).

Step 2: Synthesis of 6-((6,7-dimethoxyquinolin-4-yl)oxy)pyrimidine-5-amine

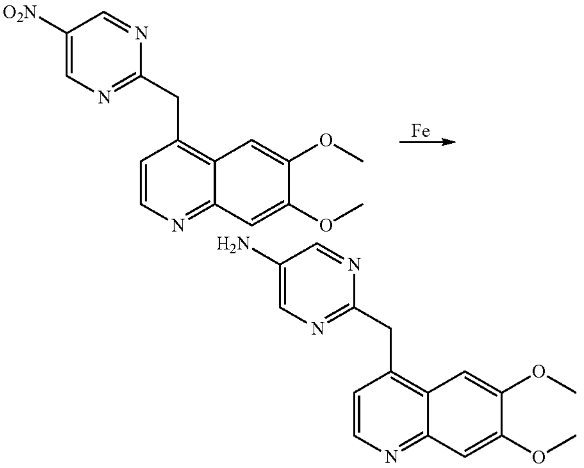

6,7-dimethoxy-4-((5-nitropyrimidine-2-yl)oxy) quinoline (1.70 g, 5.18 mmol, 1.0 eq.), reduced iron powder (1.74 g, 31.07 mmol, 6.0 eq.) and $NH_4Cl$ (3.32 g, 62.14 mmol, 12.0 eq.) were added to a mixed solvent of ethanol (30 mL) and water (15 mL). The mixture was reacted at 80° C. under stirring for 2 hours. TLC detection showed the completion of the reaction. The mixture was filtered hot, and the filter cake was eluted with dichloromethane. The mixture was concentrated under reduced pressure, and extracted with dichloromethane (10 mL×3). The organic phases were combined, washed with saturated brine (10 mL), dried over anhydrous sodium sulfate, and filtered by suction. The filtrate was concentrated under reduced pressure to produce a product (0.93 g, yield: 60.2%).

Step 3: Synthesis of N-(2-((6,7-dimethoxyquinolin-4-yl)oxy)pyrimidine-5-yl)-5-para-fluorophenyl-1-isopropyl-4-oxo-1,4-dihydropyridazine-3-carboxamide

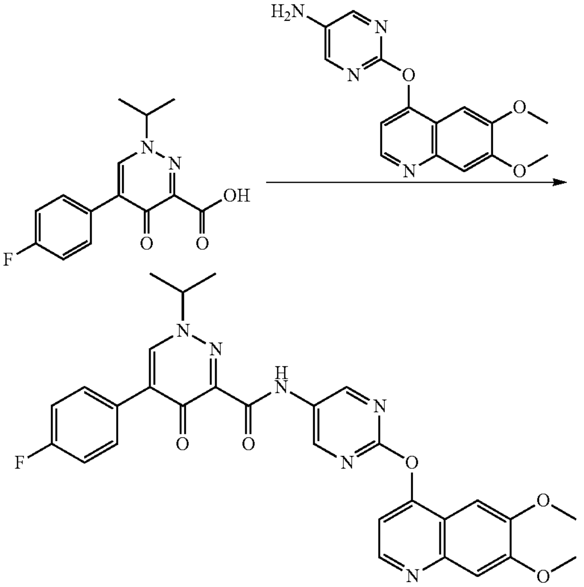

5-para-fluorophenyl-1-isopropyl-4-oxo-1,4-dihydropyridazine-3-carboxylic acid (947.4 mg, 3.43 mmol, 1.1 eq.)

was dissolved in DMF (12 mL). DIPEA (1208.8 mg, 9.35 mmol, 3.0 eq.) and HATU (1778.2 mg, 4.68 mmol, 1.5 eq.) were successively added with cooling in an ice bath. The mixture was stirred for 10 minutes and then 6-((6,7-dimethoxyquinolin-4-yl)oxy)pyrimidine-5-amine (930.0 mg, 3.12 mmol, 1.0 eq.) was added. The mixture was warmed to room temperature and reacted under stirring overnight. TLC detection showed the completion of the reaction. The solvent was removed by evaporation under reduced pressure. Ethyl acetate (20 mL) was added to dissolve the solid. The mixture was successively washed with a saturated aqueous $NaHCO_3$ solution (10 mL), a saturated aqueous $NH_4Cl$ solution (10 mL), distilled water (10 mL×4) and saturated brine (10 mL), dried over anhydrous sodium sulfate, and filtered by suction. The filtrate was concentrated under reduced pressure. The crude product was purified by preparative thin-layer chromatography (the developing agent is DCM:MeOH=15:1) to produce a product (1410.0 mg, yield: 81.3%).

$^1$HNMR (400 MHz, DMSO-$d_6$) δ (ppm): 12.50 (s, 1H), 9.08 (s, 2H), 8.93 (s, 1H), 8.68-8.67 (d, 1H), 7.97-7.93 (m, 2H) 7.46 (s, 1H), 7.36-7.32 (t, 2H), 7.23-7.20 (t, 2H), 4.78-4.72 (m, 1H), 3.96 (s, 3H), 3.85 (s, 3H), 1.52-1.51 (d, 6H).

Molecular formula: $C_{29}H_{25}FN_6O_5$, molecular weight: 556.55 LC-MS (Pos, m/z)=557.31 [M+H]+.

Example 12: Synthesis of ethyl 1-cyclopropyl-5-(4-fluorophenyl)-4-oxo-1,4-dihydropyridazine-3-carboxylate as an Intermediate

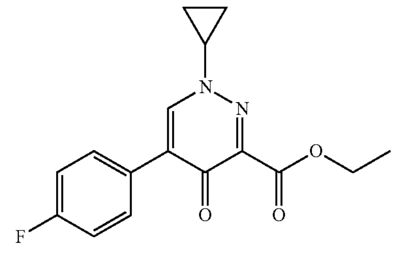 [SMILES: CCOC(=O)c1nn(C2CC2)cc(-c2ccc(F)cc2)c1=O]

Step 1: Synthesis of 1-cyclopropylurea

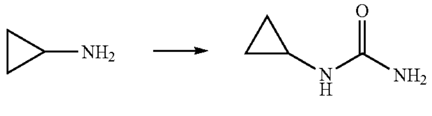

Cyclopropylamine (10.0 g, 0.175 mol) and potassium cyanate (16.8 g, 0.21 mol) were added to water (60 mL). The mixture was reacted at 100° C. under reflux for 30 minutes. The mixture was concentrated under reduced pressure. Isopropyl alcohol was added. The mixture was heated to 85° C. and stirred for 30 minutes. The mixture was filtered, and the filter cake was washed with isopropyl alcohol. The filtrate was concentrated under reduced pressure to produce a product (6.0 g, yield: 34.3%).

Step 2: Synthesis of 1-cyclopropyl-1-nitrosourea

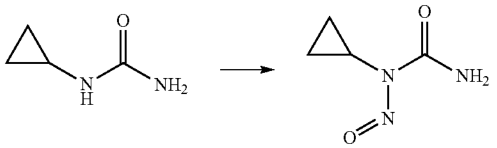

1-cyclopropylurea (6.0 g, 60 mmol) and sodium nitrite (8.7 g, 126 mmol) were added to water (42 mL). The mixture was cooled in an ice bath to 0° C., and concentrated HCl (13.44 mL) was slowly dropwise added. The mixture was reacted at 0° C. for 1 hour. TLC detection showed the completion of the reaction. The mixture was filtered to produce a product (3.5 g, yield: 45.2%).

Step 3: Synthesis of ethyl 2-(2-cyclopropylhydrazino)-4-(4-fluorophenyl)-3-oxobutanoate

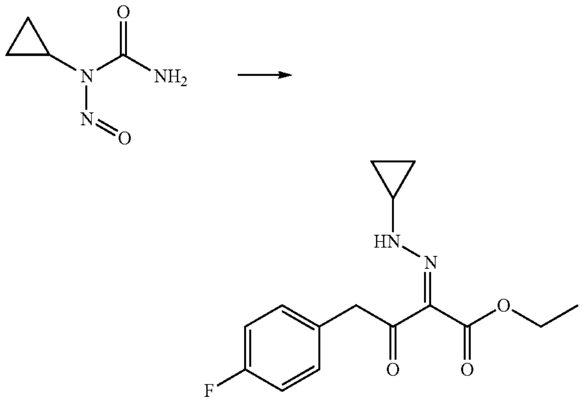

1-cyclopropyl-1-nitrosourea (3.33 g, 25.8 mmol) and ethyl (4.82 g, 21.5 mmol) were added to 4-(4-fluorophenyl)-3-oxobutanoate dichloromethane (33.3 mL). The mixture was cooled in an ice bath to 0° C., and potassium carbonate (8.92 g, 77.3 mmol) was added. The mixture was slowly warmed to room temperature and reacted for 3 hours. TLC showed the completion of the reaction. The mixture was filtered, and the filtrate was concentrated under reduced pressure. The crude product was purified by silica gel column chromatography (PE:EA=15:1-10:1) to produce a product (1.5 g, yield: 19.92%).

Step 4: Synthesis of ethyl 2-(2-cyclopropylhydrazono)-5-(dimethylamino)-4-(4-fluorophenyl)-3-oxopent-4-enoate

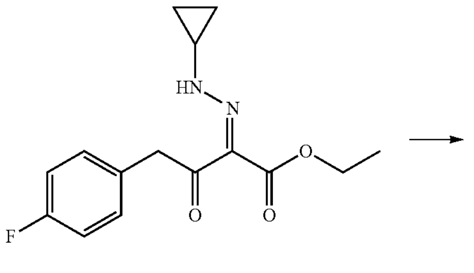

-continued

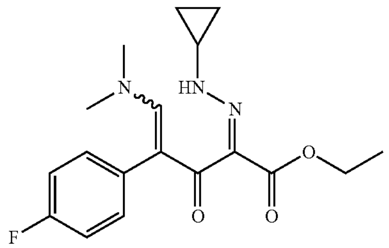

Ethyl 2-(2-cyclopropylhydrazino)-4-(4-fluorophenyl)-3-oxobutanoate (1.5 g, 5.13 mmol) and DMF-DMA (917.8 mg, 7.7 mmol) were added to toluene (10 mL). The mixture was heated to 110° C. and reacted under reflux overnight. TLC showed the completion of the reaction. The mixture was concentrated under reduced pressure to produce a product (1.8 g, crude product).

Step 5: Synthesis of ethyl 1-cyclopropyl-5-(4-fluorophenyl)-4-oxo-1,4-dihydropyridazine-3-carboxylate

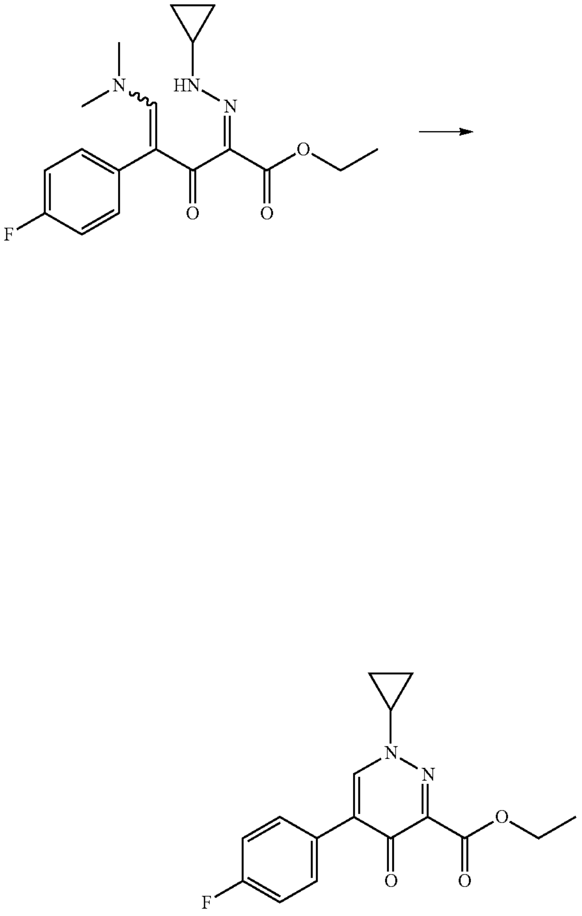

2-(2-cyclopropylhydrazono)-5-(dimethylamino)-4-(4-fluorophenyl)-3-oxopent-4-enoate (1.8 g, crude product) was added to ethanol (15 mL). The mixture was heated to 80° C. and reacted overnight. TLC showed the completion of the reaction. The mixture was concentrated under reduced pressure to produce a product (1.56 g, crude product).

Example 13: Synthesis of 1-cyclopropyl-N-(6-((6,7-dimethylquinolin-4-yl)oxy)pyridin-3-yl)-5-(4-fluorophenyl)-4-oxo-1,4-dihydropyridazine-3-carboxamide (Compound 36)

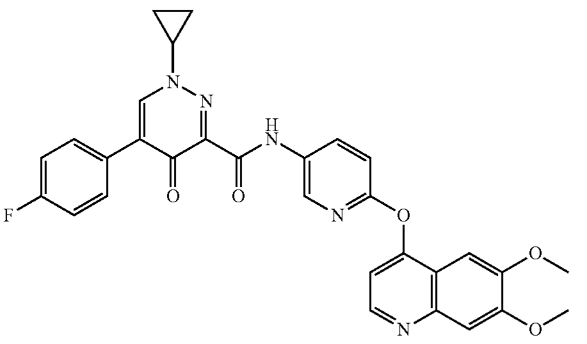 [SMILES: COc1cc2nccc(Oc3ccc(NC(=O)c4nn(C5CC5)cc(-c5ccc(F)cc5)c4=O)cn3)c2cc1OC]

Step 1: Synthesis of 1-cyclopropyl-5-(4-fluorophenyl)-4-oxo-1,4-dihydropyridazine-3-carboxylic acid

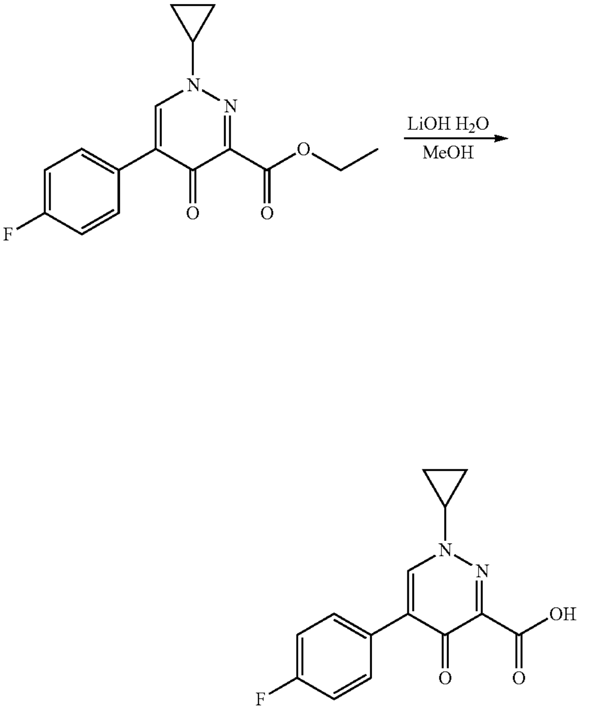

1-cyclopropyl-5-(4-fluorophenyl)-4-oxo-1,4-dihydropyridazine-3-carboxylate (1.17 g, 3.87 mmol, 1.0 eq.) was added to methanol (10 mL). After the mixture was stirred to dissolve the solid, an aqueous solution (4 mL) of lithium hydroxide monohydrate (487.0 mg, 11.6 mmol, 3.0 eq) was added. The mixture was stirred at room temperature for 2 hours. TLC detection showed the completion of the reaction, and then the mixture was concentrated under reduced pressure, adjusted with 2 mol/L HCl (5 mL) to a pH value of 3-4, and extracted with DCM (100 mL). The organic phase was dried over anhydrous sodium sulfate, and concentrated under reduced pressure to produce a product (903.5 mg, yield: 85%).

Step 2: Synthesis of 1-cyclopropyl-N-(6-((6,7-dimethylquinolin-4-yl)oxy)pyridin-3-yl)-5-(4-fluorophenyl)-4-oxo-1,4-dihydropyridazine-3-carboxamide

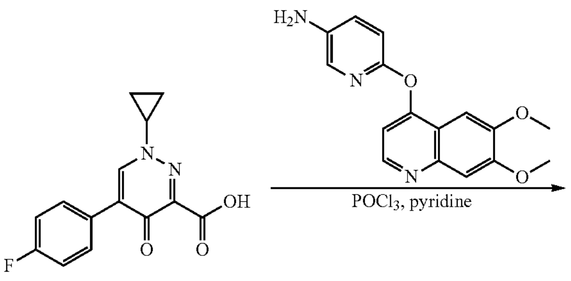

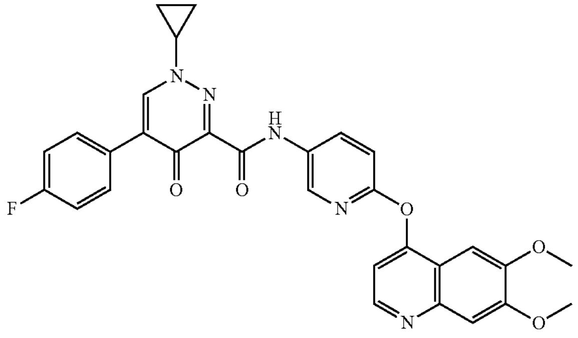

1-cyclopropyl-5-(4-fluorophenyl)-4-oxo-1,4-dihydropyridazine-3-carboxylic acid mg, (230.0 mg, 0.84 mmol, 1.0 eq.) and 6-((6,7-dimethoxyquinolin-4-yl)oxy)pyridin-3-amine (274.2 mg, 0.92 mmol, 1.1 eq.) were added to pyridine (4 mL), and phosphorus oxychloride (0.1 mL) was dropwise added. The mixture was stirred for 5 minutes. TLC detection showed the completion of the reaction. The mixture was concentrated under reduced pressure. Ethyl acetate (50 mL) and water (70 mL) were added, and the mixture was subjected to the liquid separation. The organic phase was washed with a saturated aqueous sodium chloride solution (50 mL), dried over anhydrous sodium sulfate, and concentrated. The crude product was purified by preparative thin-layer chromatography (dichloromethane:methanol=20:1) to produce a product (122.0 mg, yield in two steps: 26.5%).

$^1$H NMR (400 MHz, DMSO-$d_6$) δ (ppm): 12.27 (s, 1H), 8.92 (s, 1H), 8.57-8.60 (m, 2H), 8.36-8.39 (m, 1H), 7.92-7.96 (m, 2H), 7.42 (s, 1H), 7.31-7.42 (m, 4H), 6.89-6.90 (m, 1H), 4.08-4.12 (m, 1H), 3.95 (s, 3H), 3.89-3.91 (s, 3H), 1.30-1.31 (m, 2H), 1.10-1.12 (m, 2H).

Molecular formula: $C_3CH_{24}FN_5O_5$, molecular weight: 553.55 LC-MS (Pos, m/z)=553.80 $[M+H]^+$.

Example 14: Synthesis of 1-cyclopropyl-N-(2-((6,7-dimethoxyquinolin-4-yl)oxy)pyrimidine-5-yl)-5-para-fluorophenyl-4-oxo-1,4-dihydropyridazine-3-carboxamide (Compound 37)

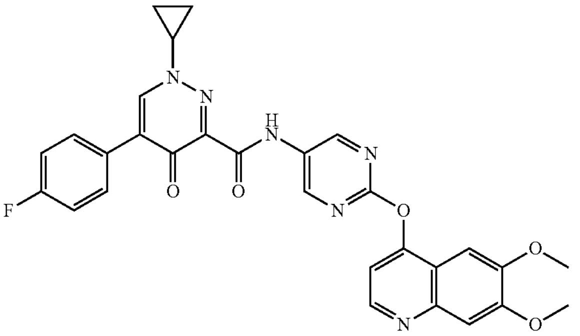 [SMILES: COc1cc2nccc(Oc3ncc(NC(=O)c4nn(C5CC5)cc(-c5ccc(F)cc5)c4=O)cn3)c2cc1OC]

Step 1: Synthesis of 1-cyclopropyl-N-(2-((6,7-dimethoxyquinolin-4-yl)oxy)pyrimidine-5-yl)-5-para-fluorophenyl)-4-oxo-1,4-dihydropyridazine-3-carboxamide

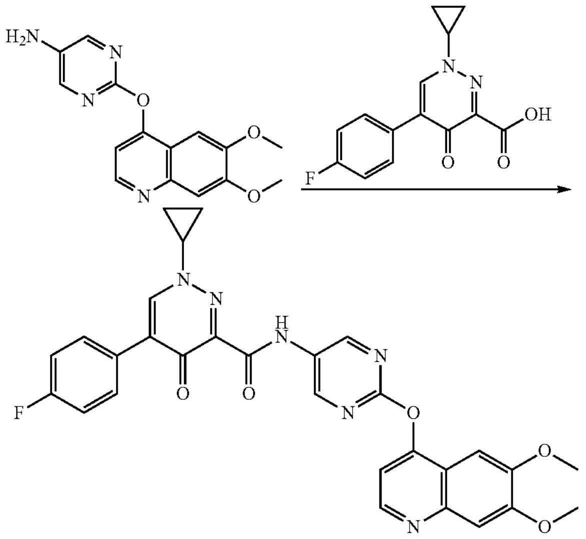

1-cyclopropyl-5-para-fluorophenyl-4-oxo-1,4-dihydropyridazine-3-carboxylic acid (190.0 mg, 0.69 mmol, 1.0 eq.) was dissolved in DMF (3 mL). DIPEA (211.5 mg, 2.08 mmol, 3.0 eq.) and HATU (395.1 mg, 1.04 mmol, 1.5 eq.) were successively added with cooling in an ice bath. The mixture was stirred for 10 minutes and then 6-((6,7-dimethoxyquinolin-4-yl)oxy)pyrimidine-5-amine (207.0 mg, 0.69 mmol, 1.0 eq.) was added. The mixture was warmed to room temperature and reacted under stirring overnight. TLC detection showed the completion of the reaction. The solvent was removed by evaporation under reduced pressure. Ethyl acetate (10 mL) was added to dissolve the solid. The mixture was successively washed with a saturated aqueous $NaHCO_3$ solution (5 mL), a saturated aqueous $NH_4Cl$ solution (5 mL), distilled water (5 mL×4) and saturated brine (5 mL), dried over anhydrous sodium sulfate, and filtered by suction. The filtrate was concentrated under reduced pressure. The crude product was purified by preparative thin-layer chromatography (the developing agent is DCM:MeOH=15:1) to produce a product (90.0 mg, yield: 23.4%).

$^1$HNMR (400 MHz, DMSO-$d_6$) δ (ppm): 12.41 (s, 1H), 9.08 (s, 2H), 8.93 (s, 1H), 8.68-8.67 (d, 1H), 7.94 (s, 2H) 7.46 (s, 1H), 7.36-7.32 (t, 2H), 7.23-7.21 (t, 2H), 4.12 (s, 1H), 3.96 (s, 3H), 3.85 (s, 3H), 1.31-1.24 (d, 2H), 1.12-1.10 (d, 2H).

Molecular formula: $C_{29}H_{23}FN_6O_5$, molecular weight: 554.54 LC-MS (Pos, m/z)=554.79 $[M+H]^+$.

Example 15 Synthesis of N-(6-((6,7-dimethoxyquinolin-4-yl)oxy)pyridin-3-yl)-6-para-fluorophenyl-2-isopropyl-5-oxo-2,5-dihydropyridazine-4-carboxamide (Compound 38)

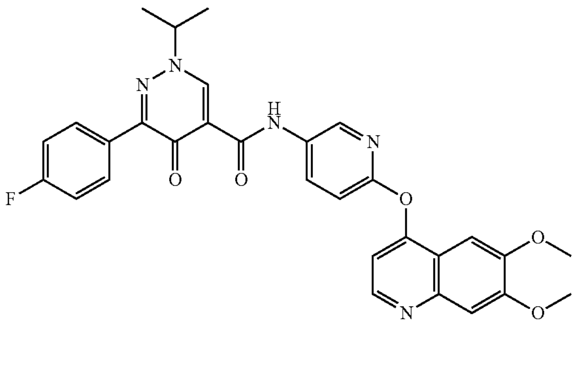 [SMILES: COc1cc2nccc(Oc3ccc(NC(=O)c4cn(C(C)C)nc(-c5ccc(F)cc5)c4=O)cn3)c2cc1OC]

Step 1: Synthesis of N-(6-((6,7-dimethoxyquinolin-4-yl)oxy)pyridin-3-yl)-6-para-fluorophenyl-2-isopropyl-5-oxo-2,5-dihydropyridazine-4-carboxamide

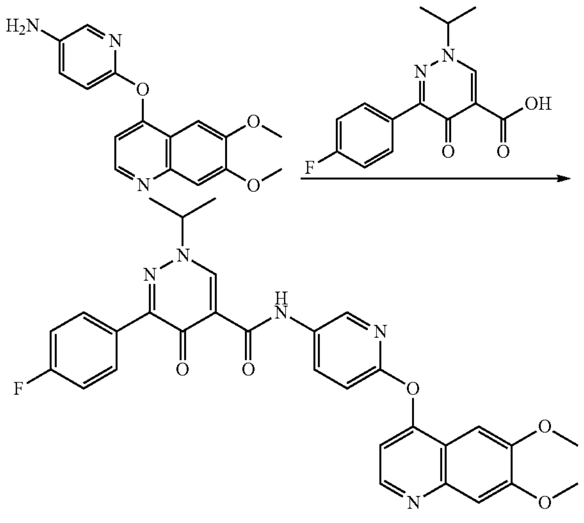

6-para-fluorophenyl-2-isopropyl-5-oxo-2,5-dihydropyridazine-4-carboxylic acid (150.0 mg, 0.54 mmol, 1.0 eq) was dissolved in DMF (3 mL). DIPEA (164.8 mg, 1.63 mmol, 3.0 eq) and HATU (309.7 mg, 0.81 mmol, 1.5 eq) were successively added with cooling in an ice bath. The mixture was stirred for 10 minutes and then 6-((6,7-dimethoxyquinolin-4-yl)oxy)pyridin-3-amine (177.6 mg, 0.59 mmol, 1.1 eq) was added. The mixture was warmed to room temperature and reacted under stirring overnight. TLC detection showed the completion of the reaction. The solvent was removed by evaporation under reduced pressure. Ethyl acetate (10 mL) was added to dissolve the solid. The mixture was successively washed with a saturated aqueous $NaHCO_3$ solution (5 mL), a saturated aqueous $NH_4Cl$ solution (5 mL), distilled water (5 mL×4) and saturated brine (5 mL), dried over anhydrous sodium sulfate, and filtered by suction. The filtrate was concentrated under reduced pressure. The crude product was purified by preparative thin-layer chromatography (DCM:MeOH=15:1) to produce a product (205.0 mg, yield: 68.0%).

$^1$HNMR (400 MHz, DMSO-$d_6$) δ (ppm): 12.34 (s, 1H), 9.23 (s, 1H), 8.64-8.63 (d, 1H), 8.60-8.59 (d, 1H), 8.42-8.40 (dd, 1H), 8.21-8.18 (q, 2H), 7.43 (s, 1H), 7.40-7.35 (m, 4H), 6.92-6.91 (d, 1H), 4.91-4.85 (m, 1H), 3.96 (s, 3H), 3.89 (s, 3H), 1.51-1.50 (d, 6H).

Molecular formula: $C_3CH_{26}FN_5O_5$, molecular weight: 555.57 LC-MS (Pos, m/z)=556.26 $[M+H]^+$.

Example 16: Synthesis of N-(5-((6,7-dimethoxyquinolin-4-yl)oxy)pyrimidine-2-yl)-6-(4-fluorophenyl)-2-isopropyl-5-oxo-2,5-dihydropyridazine-4-carboxamide (Compound 39)

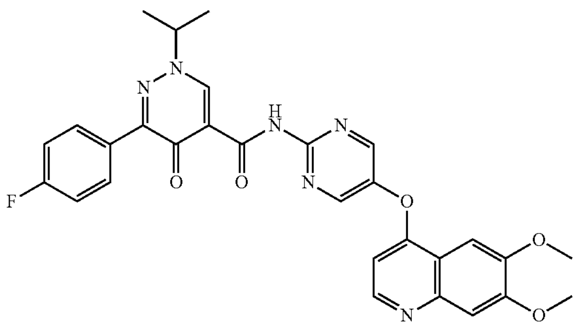 [SMILES: COc1cc2nccc(Oc3cnc(NC(=O)c4cn(C(C)C)nc(-c5ccc(F)cc5)c4=O)nc3)c2cc1OC]

Step 1: Synthesis of N-(5-((6,7-dimethoxyquinolin-4-yl)oxy)pyrimidine-2-yl)-6-(4-fluorophenyl)-2-isopropyl-5-oxo-2,5-dihydropyridazine-4-carboxamide

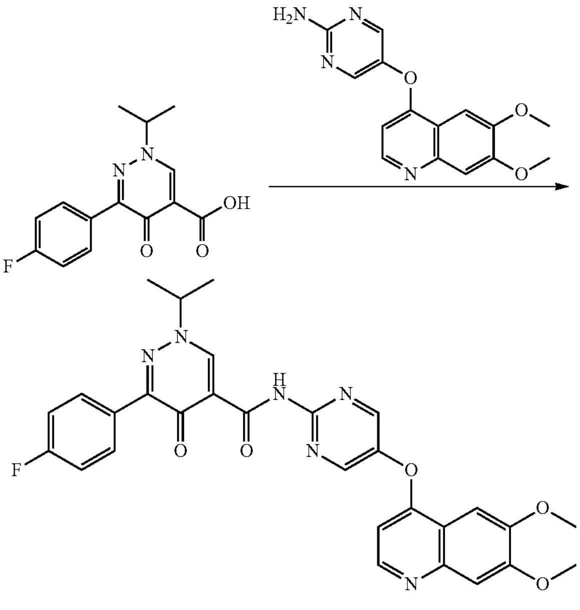

6-(4-fluorophenyl)-2-isopropyl-5-oxo-2,5-dihydropyridazine-4-carboxylic acid (100.0 mg, 0.36 mmol, 1.0 eq) was added to pyridine (3 mL). The mixture was stirred to dissolve the solid, and then 5-((6,7-dimethoxyquinolin-4-yl)oxy)pyrimidine-2-amine (118.7 mg, 0.39 mmol, 1.1 eq) and phosphorus oxychloride (0.2 mL) were added. The mixture was stirred at room temperature for 10 minutes. After TLC detection showed the completion of the reaction, water (40 mL) and ethyl acetate (60 mL) were added to the system, and the system was subjected to the liquid separation. The organic phase was dried over anhydrous sodium sulfate, and filtered by suction. The filtrate was concentrated under reduced pressure. The crude product was purified by preparative thin-layer chromatography (DCM:MeOH=15:1) to produce a product (123.0 mg, yield: 61.1%).

$^1$HNMR (400 MHz, DMSO-$d_6$) δ (ppm): 12.95 (s, 1H), 9.21 (s, 1H), 8.84 (s, 2H), 8.51-8.53 (m, 1H), 8.18-8.22 (m, 2H), 7.56 (s, 1H), 7.43 (s, 1H), 7.34-7.38 (m, 2H), 6.71-6.73 (m, 1H), 4.89-4.92 (m, 1H), 3.96 (s, 6H), 1.50-1.52 (m, 6H).

Molecular formula: $C_{29}H_{25}FN_6O_5$, molecular weight: 556.55 LC-MS (Pos,m/z)=557.24 $[M+H]^+$.

Example 17: Synthesis of N-(2-((6,7-dimethoxyquinolin-4-yl)oxy)pyrimidine-5-yl)-6-(4-fluorophenyl)-2-isopropyl-5-oxo-2,5-dihydropyridazine-4-carboxamide (Compound 40)

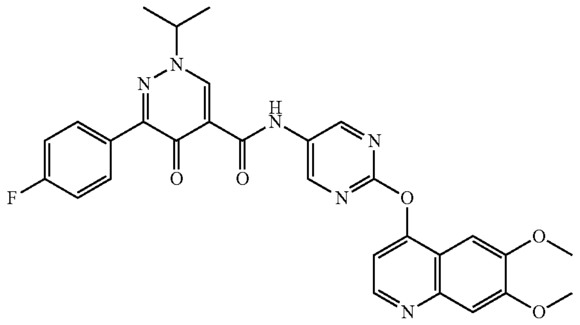 [SMILES: COc1cc2nccc(Oc3ncc(NC(=O)c4cn(C(C)C)nc(-c5ccc(F)cc5)c4=O)cn3)c2cc1OC]

Step 1: Synthesis of N-(2-((6,7-dimethoxyquinolin-4-yl)oxy)pyrimidine-5-yl)-6-(4-fluorophenyl)-2-isopropyl-5-oxo-2,5-dihydropyridazine-4-carboxamide

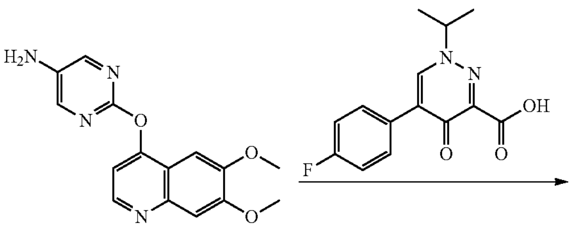

-continued

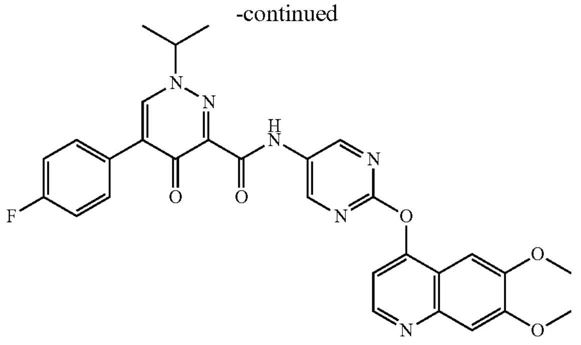

6-(4-fluorophenyl)-2-isopropyl-5-oxo-2,5-dihydropyridazine-4-carboxylic acid (101.9 mg, 0.37 mmol, 1.1 eq) was dissolved in DMF (3 mL). DIPEA (101.8 mg, 1.01 mmol, 3.0 eq) and HATU (191.3 mg, 0.50 mmol, 1.5 eq) were successively added with cooling in an ice bath. The mixture was stirred for 10 minutes and then 6-((6,7-dimethoxyquinolin-4-yl)oxy)pyrimidine-5-amine (100.0 mg, 0.34 mmol, 1.0 eq) was added. The mixture was warmed to room temperature and reacted under stirring overnight. TLC detection showed the completion of the reaction. The solvent was removed by evaporation under reduced pressure. Ethyl acetate (10 mL) was added to dissolve the solid. The mixture was successively washed with a saturated aqueous $NaHCO_3$ solution (5 mL), a saturated aqueous $NH_4Cl$ solution (5 mL), distilled water (5 mL×4) and saturated brine (5 mL), dried over anhydrous sodium sulfate, and filtered by suction. The filtrate was concentrated under reduced pressure. The crude product was purified by preparative thin-layer chromatography (DCM:MeOH=15:1) to produce a product (90.0 mg, yield: 48.2%).

$^1$HNMR (400 MHz, DMSO-$d_6$) δ (ppm): 12.29 (s, 1H), 9.23 (s, 1H), 9.10 (s, 2H), 8.68-8.67 (d, 1H), 8.22-8.18 (q, 2H), 7.46 (s, 1H), 7.39-7.34 (t, 2H), 7.22-7.20 (d, 2H), 4.90-4.84 (m, 1H), 3.96 (s, 3H), 3.85 (s, 3H), 1.51-1.50 (d, 6H).

Molecular formula: $C_{29}H_{25}FN_6O_5$, molecular weight: 556.55 LC-MS (Pos, m/z)=557.23 $[M+H]^+$.

Example 18 Synthesis of 6-(4-fluorophenyl)-2-isopropyl-5-oxo-2,5-dihydropyridazine-4-carboxylic Acid as an Intermediate

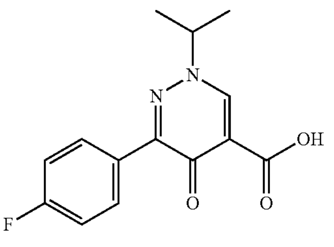 [SMILES: CC(C)n1cc(C(=O)O)c(=O)c(-c2ccc(F)cc2)n1]

Step 1: Synthesis of tert-butyl 2-isopropylhydrazine-1-carboxylate

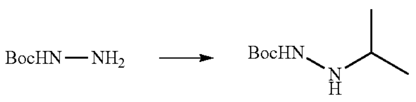

Tert-butyl hydrazine carboxylate (20.0 g, 0.151 mol), acetone (9.26 g 0.16 mol), acetic acid (2 mL), magnesium sulfate (10.0 g) and sodium triacetoxyborohydride (96.64 g, 0.456 mol) were added to dichloromethane (100 mL). The mixture was reacted at room temperature overnight. TLC detection showed the completion of the reaction. The mixture was filtered. The filtrate was concentrated under reduced pressure to produce a product (25 g, yield: 95.6%).

Step 2: Synthesis of tert-butyl 2-(3-ethpxy-3-oxopropyl)-2-isopropylhydrazine-1-carboxylate

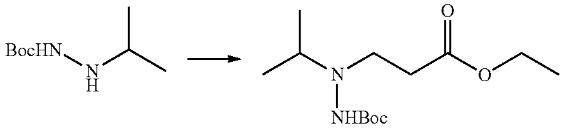

Tert-butyl 2-isopropylhydrazine-1-carboxylate (19.0 g, 0.109 mmol) and ethyl acrylate (12.01 g, 0.12 mol) were added to ethanol (60 mL). The mixture was heated to 80° C. and reacted overnight. TLC detection showed the completion of the reaction. The mixture was concentrated under reduced pressure. Water was added.

The mixture was extracted with ethyl acetate. The organic phases were combined, and dried over anhydrous sodium sulfate. The crude product was purified by silica gel column chromatography (DCM:MeOH=200:1-80:1) to produce a product (24.2 g, yield: 81.0%).

Step 3: Synthesis of ethyl-3-(1-isopropylhydrazinyl)propionate

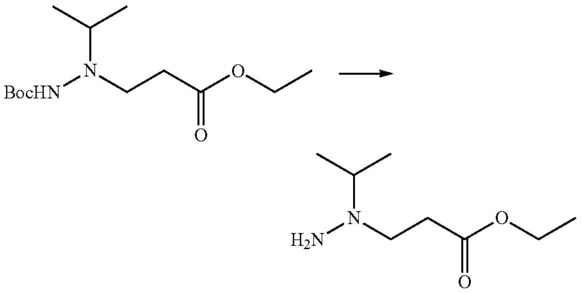

Tert-butyl 2-(3-ethoxy-3-oxopropyl)-2-isopropylhydrazine-1-carboxylate (24.1 g, 0.088 mol) was added to dichloromethane (75 mL). The mixture was cooled in an ice bath to 0° C. Trifluoroacetic acid (35 mL) was added. The mixture was slowly warmed to room temperature overnight. TLC showed the completion of the reaction.

The mixture was concentrated under reduced pressure to produce a product (18.9 g, crude product).

Step 4: Synthesis of ethyl 2-(4-fluorophenyl)-2-oxoacetate

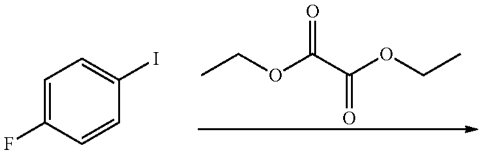

-continued

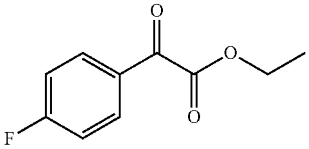

Para-fluoro-iodobenzene (10.0 g. 0.0451 mol) was added to 2-methyltetrahydrofuran (10 mL). The mixture was cooled in an ice bath to 0° C. Isopropyl magnesium chloride (2 mol/L, 24.78 mL, 0.049 mol) was added. The mixture was reacted at 0° C. under stirring for 30 minutes. The above reaction liquor was dropwise added to a solution of diethyl oxalate (7.25 g, 0.0496 mol) in 2-methyltetrahydrofuran (50 mL). The mixture was slowly warmed to room temperature overnight. TLC showed the completion of the reaction. The reaction liquor was added to an aqueous citric acid solution. The mixture was kept at a pH value of 5-6. The aqueous phase was extracted with ethyl acetate. The organic phases were combined, washed with water, washed with brine, dried over anhydrous sodium sulfate, and filtered. The filtrate was concentrated under reduced pressure. The crude product was purified by silica gel column chromatography (PE:EA=120:1-40:1) to produce a product (8 g, yield: 90.5%).

Step 4: Synthesis of ethyl 3-(2-(2-ethyl-1-(4-fluorophenyl)-2-oxoethylidene)-1-isopropylhydrazinyl)propionate

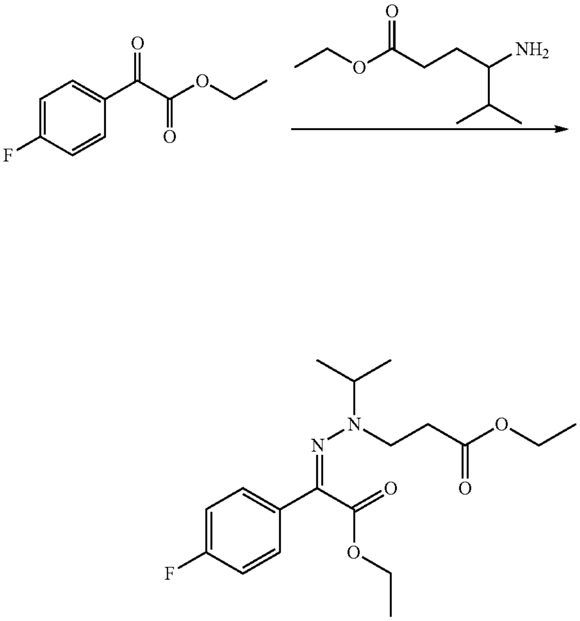

Ethyl 2-(4-fluorophenyl)-2-oxoacetate (4.43 g, 22.6 mmol) and ethyl 3-(1-isopropylhydrazinyl)propionate (11.81 g, crude product) were added to ethanol (10 mL). The mixture was heated to 80° C. and reacted overnight. TLC showed the completion of the reaction. The mixture was filtered by suction. Water was added to the filtrate. The mixture was extracted with ethyl acetate. The organic phases were combined, dried over anhydrous sodium sulfate, and filtered. The filtrate was concentrated under reduced pressure. The crude product was purified by silica gel column chromatography (PE:EA=60:1-10:1) to produce a product (2.3 g, yield: 28.9%).

Step 6: Synthesis of ethyl 6-(4-fluorophenyl)-2-isopropyl-5-oxo-2,3,4,5-tetrahydropyridazine-4-carboxylate

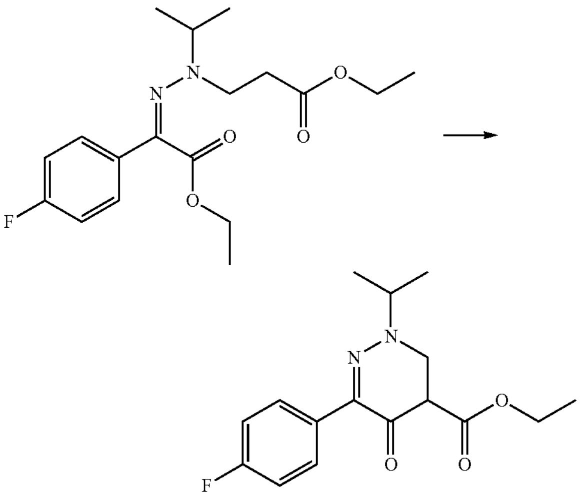

Ethyl 3-(2-(2-ethoxy-1-(4-fluorophenyl)-2-oxoethylidene)-1-isopropylhydrazinyl)propionate (2.27 g, 6.45 mmol) was added to 2-methyltetrahydrofuran (10 mL). The mixture was cooled in an ice bath to 0° C. Potassium tert-butoxide (1.81 g, 16.11 mmol) was added. The mixture was slowly warmed to room temperature overnight. TLC showed the completion of the reaction. The reaction liquor was added to an aqueous citric acid solution. The mixture was kept at a pH value of 5-6. The mixture was extracted with ethyl acetate. The organic phases were combined, dried over anhydrous sodium sulfate, and filtered. The filtrate was concentrated under reduced pressure to produce a product (1.27 g, yield: 64.5%).

Step 7: Synthesis of ethyl 6-(4-fluorophenyl)-2-isopropyl-5-oxo-2,5-dihydropyridazine-4-carboxylate

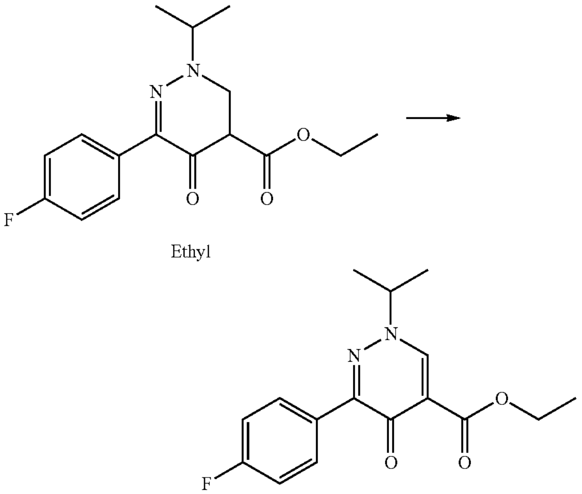

Ethyl 6-(4-fluorophenyl)-2-isopropyl-5-oxo-2,3,4,5-tetrahydropyridazine-4-carboxylate (1.2 g, 3.92 mmol) and copper chloride dihydrate (2.67 g, 15.68 mmol) were added to acetonitrile (10 mL). The mixture was reacted at 80° C. for 4 hours. TLC showed the completion of the reaction, Water was added to the reaction liquor. The mixture was extracted with ethyl acetate. The organic phases were combined, washed with water, washed with saturated brine, dried over anhydrous sodium sulfate, and filtered. The filtrate was concentrated under reduced pressure. The crude product was purified by silica gel column chromatography (PE:EA=100:1-40:1) to produce a product (730.0 mg, yield: 61.2%).

Step 8: Synthesis of 6-(4-fluorophenyl)-2-isopropyl-5-oxo-2,5-dihydropyridazine-4-carboxylic acid

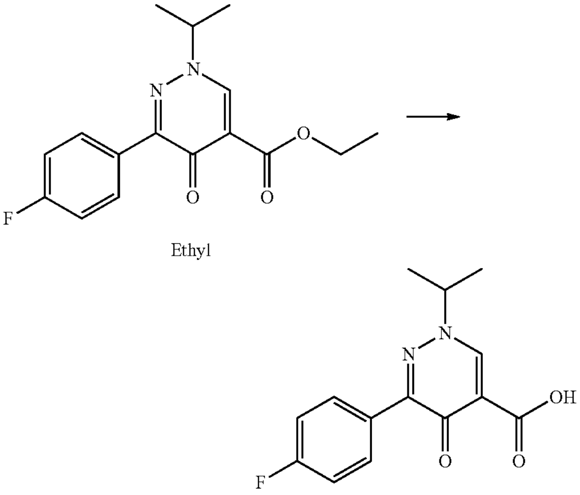

Ethyl 6-(4-fluorophenyl)-2-isopropyl-5-oxo-2,5-dihydropyridazine-4-carboxylate (700.0 mg, 2.3 mmol) was added to a mixed solvent of methanol (6 mL) and water (5 mL), and lithium hydroxide monohydrate (284.4 mg, 6.91 mmol) was added. The mixture was stirred at room temperature for 1 hour. TLC showed the completion of the reaction. The mixture was adjusted with citric acid to a pH value of 2-3. A solid was precipitated. The mixture was filtered by suction. Dichloromethane was added to dissolve the filter cake. The mixture was dried over anhydrous sodium sulfate, and filtered. The filtrate was concentrated under reduced pressure to produce a product (600.0 mg, yield: 94.5%).

Example 19: Synthesis of N-(5-((6,7-dimethoxyquinolin-4-yl)oxy)pyridin-2-yl)-6-(4-fluorophenyl)-2-isopropyl-5-oxo-2,5-dihydropyridazine-4-carboxamide (Compound 41)

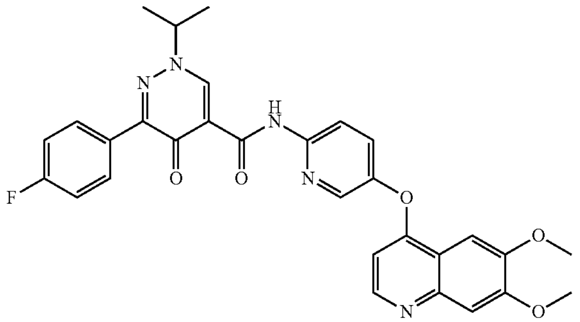 [SMILES: COc1cc2nccc(Oc3ccc(NC(=O)c4cn(C(C)C)nc(-c5ccc(F)cc5)c4=O)nc3)c2cc1OC]

Step 1: Synthesis of *N*-(5-((6,7-dimethoxyquinolin-4-yl)oxy)pyridin-2-yl-6-(4-fluorophenyl)-2-isopropyl-5-oxo-2,5-dihydropyridazine-4-carboxamide

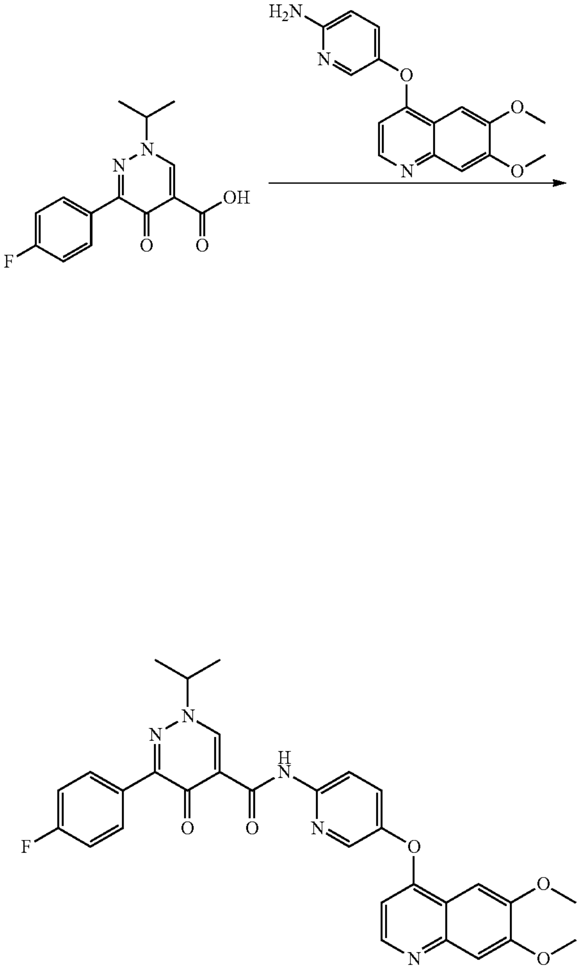

6-(4-fluorophenyl)-2-isopropyl-5-oxo-2,5-dihydropyridazine-4-carboxylic acid (50.0 mg, 0.181 mmol, 1.0 eq) and DIPEA (70.0 mg, 0.543 mmol, 3.0 eq) were dissolved in DMF (1.0 mL). HATU (103.0 mg, 0.272 mmol, 1.5 eq) was added at 0° C. under the nitrogen protection. The mixture was stirred for 0.5 hour. 5-((6,7-dimethoxyquinolin-4-yl)oxy)pyridin-2-amine (54.0 mg, 0.181 mmol, 1.0 eq) was added. The mixture was slowly warmed to room temperature overnight. TLC showed the completion of the reaction. Ethyl acetate (30.0 ml) was added to the reaction liquor, and the mixture was successively washed with a saturated aqueous sodium carbonate solution (2.0 mL), a saturated aqueous $NH_4Cl$ solution (2.0 mL) and a saturated aqueous sodium chloride solution (2.0 mL). The organic phase was dried and concentrated under reduced pressure. The crude product was purified by silica gel column chromatography (DCM:MeOH=100:1-30:1) to produce a product (75.0 mg, yield: 74.6%).

$^1$HNMR (400 MHz, DMSO-$d_6$) δ(ppm): 12.75 (s, 1H), 9.25 (s, 1H), 8.51-8.49 (d, 1H), 8.45-8.42 (m, 2H), 8.23-8.19 (m, 2H), 7.92-7.88 (m, 1H), 7.55 (s, 1H), 7.43-7.34 (M, 3H), 6.59-6.57 (d, 1H), 4.93-4.86 (m, 1H), 3.96-3.95 (d, 6H), 1.53-1.50 (d, 6H).

Molecular formula: $C_{30}H_{26}FN_5O_5$, molecular weight: 555.57 LC-MS (Pos, m z)=556.28 $[M+H]^+$.

Example 20: Synthesis of 2-cyclopropyl-N-(5-((6,7-dimethoxyquinolin-4-yl)oxy)pyridin-2-yl)-6-(4-fluorophenyl)-5-oxo-2,5-dihydropyridazine-4-carboxamide (Compound 42)

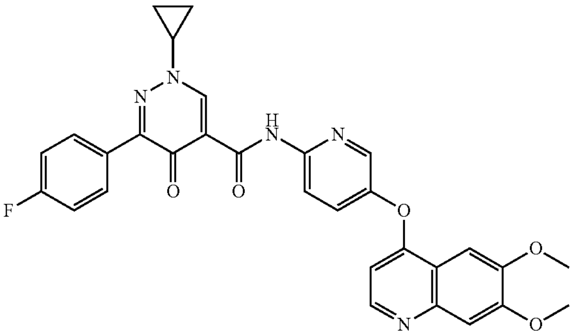 [SMILES: COc1cc2nccc(Oc3ccc(NC(=O)c4cn(C5CC5)nc(-c5ccc(F)cc5)c4=O)nc3)c2cc1OC]

Step 1: Synthesis of tert-butyl tosyloxycarbamate

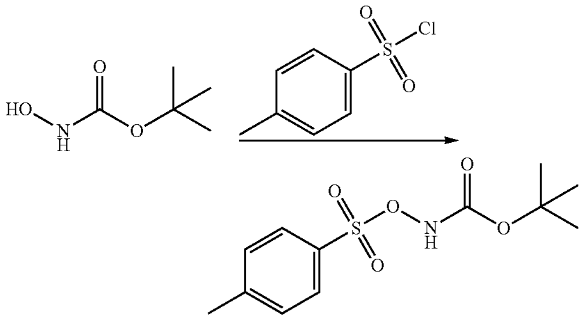

Tert-butyl hydroxycarbamate (230.0 g, 1.72 mol, 1.0 eq.) was dissolved in methyl tert-butyl ether (1.15 L). 4-methylbenzene-1-sulfonyl chloride (329.3 g, 1.72 mol, 1.0 eq.) was added. Triethylamine (182.7 g, 1.80 mol, 1.05 eq) was dropwise added under stirring under an ice bath. The mixture was gradually warmed to room temperature and stirred for 14 hours. TLC detection showed the completion of the reaction. The mixture was filtered, and the filtrate was concentrated under reduced pressure. The crude product was slurried with n-hexane (200 mi), and filtered. The filter cake was dried to produce a product (411.0 g, yield: 83.1%).

Step 2: Synthesis of tert-butyl 2-cyclopropyl-2-(3-ethoxy-3-oxopropyl)hydrazine-1-carboxylate

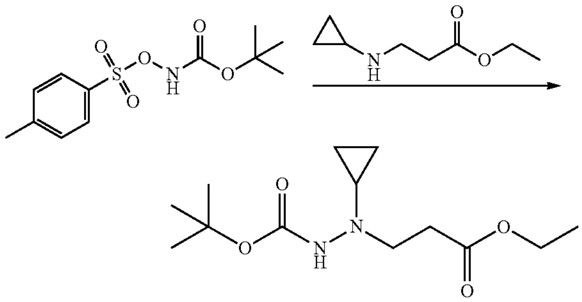

Ethyl 3-(cyclopropylamino)propionate (156.5 g, 0.99 mol, 1.2 eq.) was dissolved in DCM (700 mL). The mixture was cooled to −5° C. in an ice-salt bath. N-methylmorpholine (100.7 g, 0.99 mol, 1.2 eq.) was added, and tert-butyl tosyloxycarbamate (240 g, 0.83 mol, 1.0 eq.) was added in batch. The mixture was gradually warmed to room temperature and stirred for 14 hours. TLC detection showed the completion of the reaction. Water (500 mL) was added, and the mixture was subjected to the liquid separation. The organic phase was dried over anhydrous sodium sulfate, and filtered. The filtrate was concentrated under reduced pressure. The crude product was purified by silica gel column chromatography (petroleum ether:ethyl acetate=20:1-15:1) to produce a product (71.30 g, yield: 31.5%).

Step 3: Synthesis of ethyl 3-(1-cyclopropylhydrazine)propionate

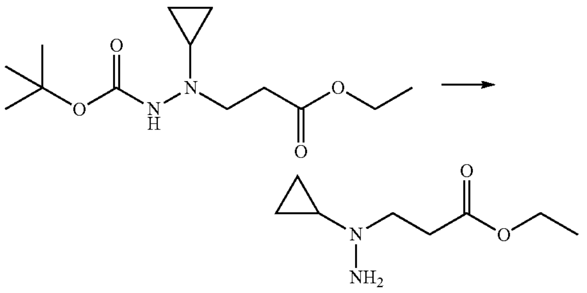

Tert-butyl 2-cyclopropyl-2-(3-ethoxy-3-oxopropyl)hydrazine-1-carboxylate (71.30 g, 0.26 mol, 1.0 eq.) was dissolved in DCM(136.0 mL). Trifluoroacetic acid (91.0 mL) was dropwise added with cooling in an ice bath. After the completion of the dropwise addition, the mixture was gradually warmed to room temperature and stirred for 14 hours. TLC detection showed the completion of the reaction. The system was concentrated under reduced pressure to produce a product (88.1 g, crude product).

Step 4: Synthesis of ethyl 2-4-fluorophenyl)-2-oxoacetate

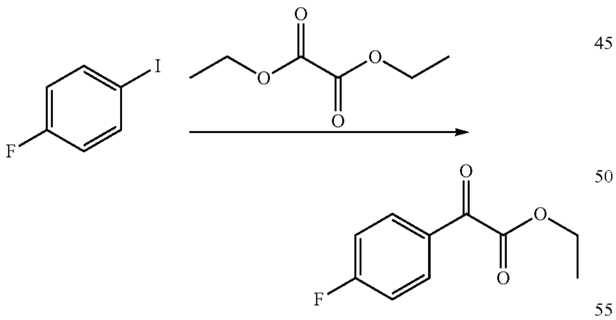

Para-fluoro-iodobenzene (400.0 g, 1.8 mol, 1.0 eq) was added to 2-methyltetrahydrofuran (2 L), and isopropyl magnesium chloride (2 mol/L, 990.0 mL) was dropwise added under an ice-salt bath. The mixture was stirred for 30 minutes. The above reaction liquor was dropwise added to a solution of diethyl oxalate (289.7 g, 1.98 mol, 1.1 eq) in 2-methyltetrahydrofuran (2.0 L). The mixture was gradually warmed to room temperature and stirred for 15 hours. TLC detection showed the completion of the reaction. The reaction liquor was added to a saturated aqueous citric acid solution and controlled to a pH value of 5-6. Ethyl acetate (2.0 L) was added, and the mixture was subjected to the liquid separation. The organic phase was washed with saturated brine, dried over anhydrous sodium sulfate, and filtered. The filtrate was concentrated under reduced pressure. The crude product was purified by silica gel column chromatography (petroleum ether:ethyl acetate=120:1-40:1) to produce a product (282.4 g, yield: 80%).

Step 5: Synthesis of ethyl 3-(1-cyclopropyl-2-(2-ethoxy-1-(4-fluorophenyl)-2-oxoethylidene)hydrazinyl)propionate

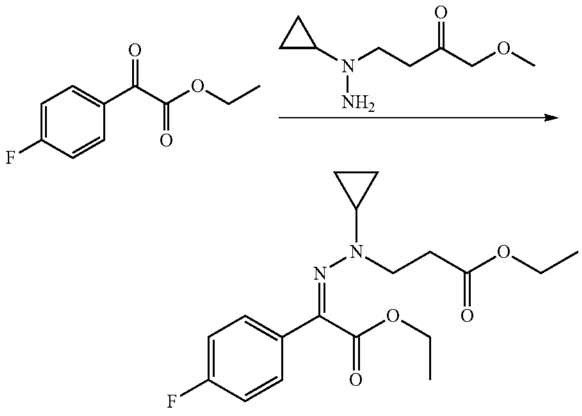

Ethyl 3-(1-cyclopropylhydrazine)propionate (88.1 g, 0.26 nmol, 1.0 eq) and ethyl 2-(4-fluorophenyl)-2-oxoacetate (61.4 g, 0.31 mol, 1.19 eq) were added to ethanol (105.0 mL). The mixture was reacted at 80° C. for 15 hours. TLC detection showed the completion of the reaction. The mixture was cooled to room temperature, and concentrated under reduced pressure. The crude product was purified by silica gel column chromatography (petroleum ether:ethyl acetate=40:1-15:1) to produce a product (5.76 g, yield in two steps: 6.3%).

Step 6: Synthesis of ethyl 2-cyclopropyl-6-(4-fluorophenyl)-5-oxo-2,3,4,5-tetrahydropyridazine-4-carboxylate

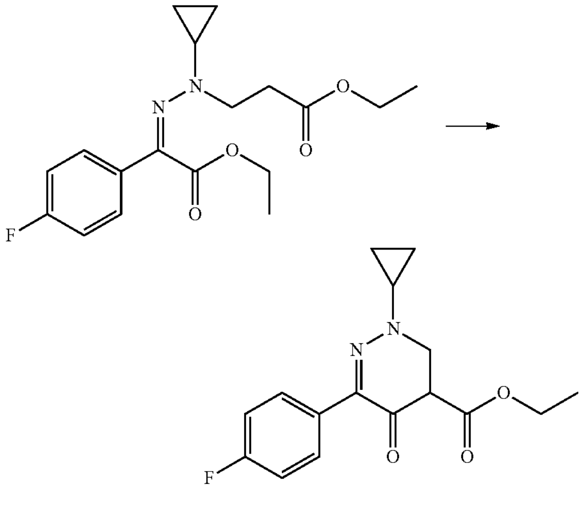

Ethyl 3-(1-cyclopropyl-2-(2-ethoxy-1-(4-fluorophenyl)-2-oxoethylidene)hydrazinyl)propionate (5.76 g. 0.01 mol, 1.0 eq) was added to 2-methyltetrahydrofuran (33.0 mL).

Potassium tert-butoxide (4.6 g, 0.04 mol, 2.5 eq) was added in batch under an ice bath. The mixture was gradually warmed to room temperature and stirred for 15 hours. TLC detection showed the completion of the reaction. The reaction liquor was added to an aqueous citric acid solution (10%), and controlled to a pH value of 5-6. Ethyl acetate (70 mL) was added, and the mixture was subjected to the liquid separation. The organic phase was dried over anhydrous sodium sulfate, and filtered.

The filtrate was concentrated under reduced pressure. The crude product was purified by silica gel column chromatography (petroleum ether:ethyl acetate=40:1-10:1) to produce a product (2.81 g, yield: 56.2%).

Step 8: Synthesis of 2-cyclopropyl-6-(4-fluorophenyl)-5-oxo-2,5-dihydropyridazine-4-carboxylate

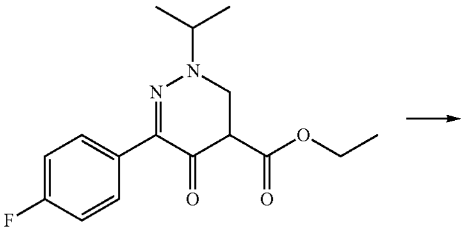

Ethyl

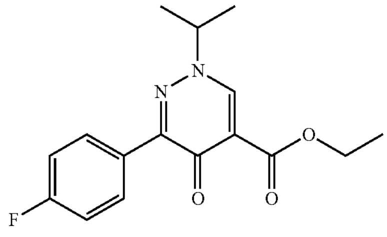

Ethyl 2-cyclopropyl-6-(4-fluorophenyl)-5-oxo-2,3,4,5-tetrahydropyridazine-4-carboxylate (2.81 g, 9.23 mmol, 1.0 eq) and copper chloride monohydrate (6.28 g, 36.9 mmol, 4.0 eq) were added to acetonitrile (18 mL). The mixture was reacted at 80° C. for 2 hours. TLC detection showed the completion of the reaction. The mixture was cooled to room temperature, and concentrated under reduced pressure. The crude product was purified by silica gel column chromatography (DCM:MeOH=60:1-30:1) to produce a product (1.5 g, yield: 53.7%).

Step 8: Synthesis of 2-cyclopropyl-6-(4-fluorophenyl)-5-oxo-2,5-dihydropyridazine-4-carboxylic acid

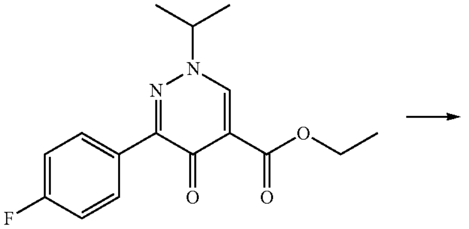

Ethyl

-continued

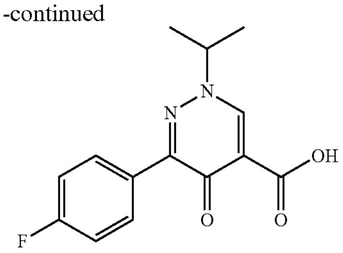

Ethyl 2-cyclopropyl-6-(4-fluorophenyl)-5-oxo-2,5-dihydropyridazine-4-carboxylate (1.5 g, 4.96 mmol, 1.0 eq) was added to methanol (22 mL) and water (12 mL), and lithium hydroxide monohydrate (624.3 mg, 14.8 mmol, 3.0 eq) was added. The mixture was reacted at room temperature for 2 hours. TLC detection showed the completion of the reaction. The mixture was concentrated under reduced pressure. The aqueous phase was adjusted with 2 mol/L, HCl to a pH value of 4. A white solid was precipitated. The mixture was stirred for 0.5 hour and filtered by suction. The filter cake was dried to produce a product (1.3 g, yield: 95.5%).

Step 9: Synthesis of 2-cyclopropyl-*N*-(5-((6,7-dimethoxyquinolin-4-yl)oxy)pyridin-2-yl-6-(4-fluorophenyl)-5-oxo-2,5-dihydropyridazine-4-carboxamide

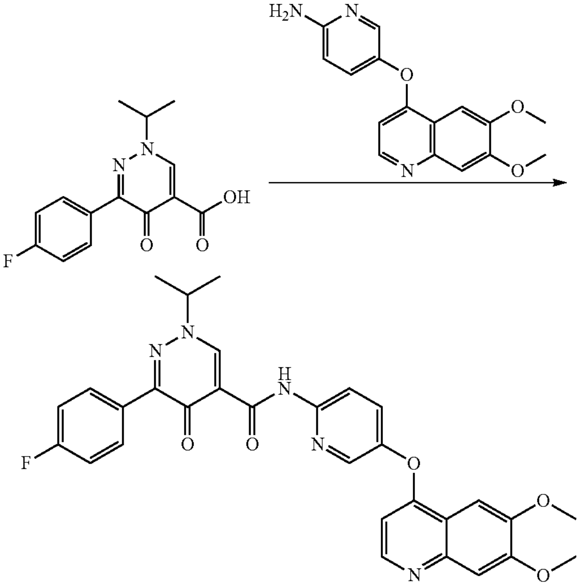

2-cyclopropyl-6-para-fluorophenyl-5-oxo-2,5-dihydropyridazine-4-carboxylic acid (250.0 mg, 0.91 mmol, 1.0 eq.) was dissolved in DMF (5 ml), and DIPEA (353.2 mg, 2.73 mmol, 3.0 eq.) and HATU (519.5 mg, 1.36 mmol, 1.5 eq.) were added at 0° C. The mixture was stirred at 0° C. for 2 hours. 5-((6,7-dimethoxyquinolin-4-yl)oxy)pyridin-2-amine (298.1 mg, 1.0 mmol, 1.1 eq.) was added. The mixture was reacted at room temperature under stirring for 13 hours. TLC detection showed the completion of the reaction. The mixture was concentrated under reduced pressure. The crude product was purified by silica gel column chromatography (DCM:MeOH=60:1-30:1) to produce a product (220.0 mg, yield: 43.6%).

$^1$HNMR (400 MHz, $CDCl_3$) δ (ppm): 12.68 (s, 1H), 9.02 (s, 1H), 8.53-8.55 (m, 1H), 8.45-8.47 (m, 1H), 8.35 (m, 1H), 8.22-8.25 (m, 2H), 7.57-7.61 (m, 2H), 7.46 (s, 1H), 7.15-7.20 (s, 2H), 6.49-6.50 (m, 1H), 4.08 (m, 6H), 3.84-3.88 (m, 114), 1.37-1.39 (n, 2H), 1.27 (m, 2H).

Molecular formula: $C_{30}H_{24}FN_5O_5$, molecular weight: 553.55 LC-MS (Pos, m/z)=554.45[M+H]$^+$.

Example 21: Synthesis of 2-cyclopropyl-N-(6-((6,7-dimethoxyquinolin-4-yl)oxy)pyridin-3-yl)-6-para-fluorophenyl-5-oxo-2,5-dihydropyridazine-4-carboxamide (Compound 43)

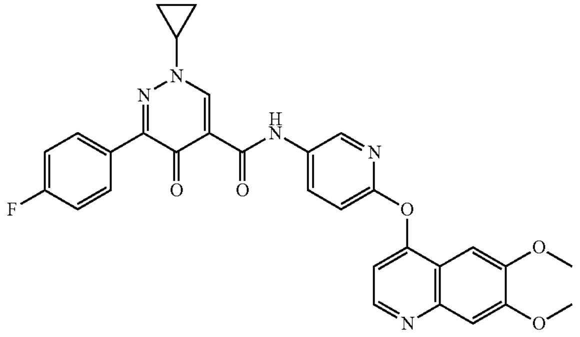 [SMILES: COc1cc2nccc(Oc3ccc(NC(=O)c4cn(C5CC5)nc(-c5ccc(F)cc5)c4=O)cn3)c2cc1OC]

Step 1: Synthesis of 6,7-dimethoxy-4-((5-nitropyridin-2-yl)oxy)quinoline

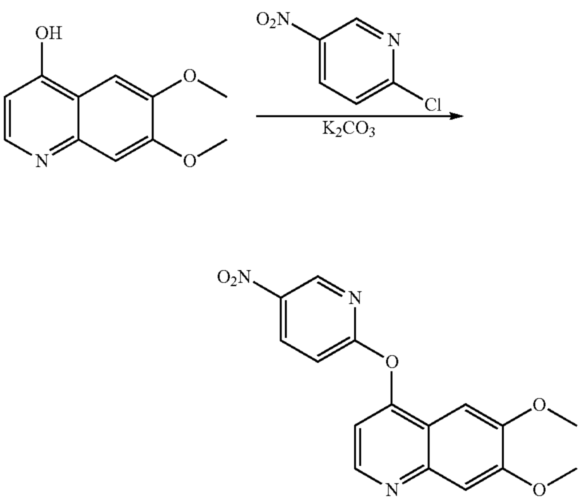

6,7-dimethoxyquinolin-4-ol (5.00 g, 24.36 mmol, 1.0 eq.), 2-chloro-5-nitropyridine (3.86 g, 24.36 mmol, 1.0 eq) and potassium carbonate (6.73 g, 48.73 mmol, 2.0 eq.) were added to DMF (50 mL). The mixture was reacted at 40° C. under stirring under the nitrogen protection overnight. TLC detection showed the completion of the reaction. The mixture was filtered, and the filter cake was eluted with dichloromethane and methanol. The filtrate was concentrated under reduced pressure. Dichloromethane (20 mL) and methanol (20 mL) were added to dissolve the solid. The mixture was dried over anhydrous sodium sulfate, filtered by suction, and concentrated under reduced pressure. The crude product was purified by silica gel column chromatography (DCM:MeOH=80:1-30:1) to produce a product (0.60 g, yield: 7.52%).

Step 2: Synthesis of 6-((6,7-dimethoxyquinolin-4-yl)oxy)pyridin-3-amine

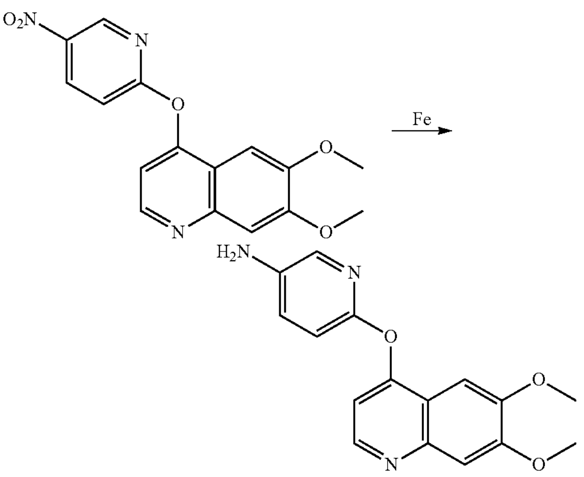

6,7-dimethoxy-4-((6-nitropyridin-3-yl)oxy) quinoline (366.0 mg, 1.12 mmol, 1.0 eq.), reduced iron powder (374.7 mg, 6.71 mmol, 6.0 eq.) and $NH_4Cl$ (717.8 mg, 13.42 mmol, 12.0 eq.) were added to a mixed solvent of ethanol (10 mL) and water (5 mL). The mixture was reacted at 80° C. under stirring for 4 hours. TLC detection showed the completion of the reaction. Celite was added to the solution, and the mixture was filtered hot, and the filter cake was eluted with EtOH. The filtrate was concentrated under reduced pressure. The residual aqueous phase was extracted with dichloromethane (5 mL×3). The organic phases were combined, dried over anhydrous sodium sulfate, and filtered by suction. The filtrate was concentrated under reduced pressure to produce a product (188.0 mg, yield: 56.6%).

Step 3: Synthesis of 2-cyclopropyl-*N*-(6-((6,7-dimethoxyquinolin-4-yl)oxy)pyridin-3-yl)-6-para-fluorophenyl)-5-oxo-2,5-dihydropyridazine-4-carboxamide

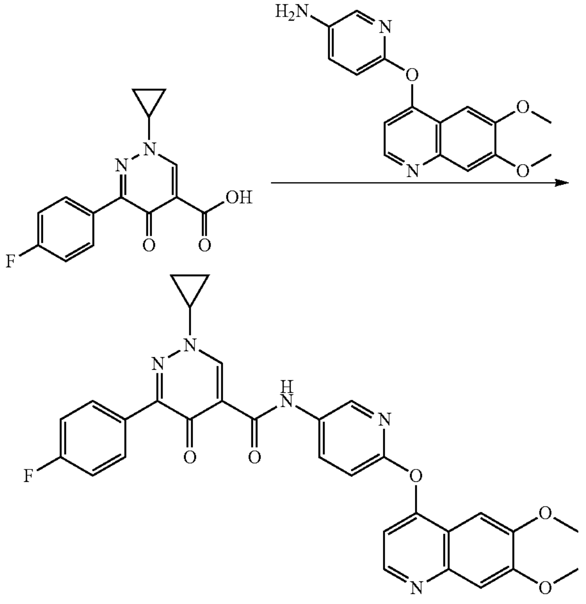

2-cyclopropyl-6-para-fluorophenyl-5-oxo-2,5-dihydropyridazine-4-carboxylic acid (250 mg, 0.91 mmol, 1.0 eq.)

was dissolved in DMF (2 mL). DIPEA (353.4 mg, 2.73 mmol, 3.0 eq.) and HATU (519.9 mg, 1.37 mmol, 1.5 eq.) were added, and the mixture was stirred for 10 minutes. 6-((6,7-dimethoxyquinolin-4-yl)oxy)pyridin-3-amine (271.0 mg, 0.91 mmol, 1.0 eq.) was added. The mixture was reacted at room temperature under stirring for 1 hour. After TLC detection showed the completion of the reaction, the solvent was removed by evaporation under reduced pressure. Dichloromethane (10 mL) was added to dissolve the solid. The mixture was successively washed with a saturated aqueous $NaHCO_3$ solution (5 mL), a saturated aqueous $NH_4Cl$ solution (5 mL) and saturated brine (5 mL×3). The organic phase was dried over anhydrous sodium sulfate. The mixture was filtered by suction. The filtrate was added to methanol (5 mL), and the mixture was concentrated under reduced pressure until a solid just began to precipitate out. The mixture was kept by standing at room temperature for 1 hour. The solid was filtered off, washed with methyl tert-butyl ether, and dried to produce a product (292.7 mg, yield: 58.0%).

$^1$HNMR (400 MHZ, $CDCl_3$) δ (ppm): 12.29 (s, 1H), 9.04 (s, 1H), 8.66-8.63 (m, 2H), 8.39-8.36 (m, 1H), 8.16-8.12 (m, 2H), 7.48-7.46 (d, 2H), 7.23-7.16 (m, 3H), 6.85-6.83 (d, 1H), 4.07 (s, 3H), 4.03 (s, 3H), 3.89-3.86 (m, 1H), 1.40-1.37 (m, 2H), 1.27-1.21 (m, 2H).

Molecular formula: $C_{30}H_{24}FN_5O_5$, molecular weight: 553.55 LC-MS (Pos, m/z)=553.84 $[M+H]^+$.

Example 22: Synthesis of 2-cyclopropyl-N-(2-((6,7-dimethoxyquinolin-4-yl)oxy)pyrimidine-5-yl)-6-para-fluorophenyl-5-oxo-2,5-dihydropyridazine-4-carboxamide (Compound 44)

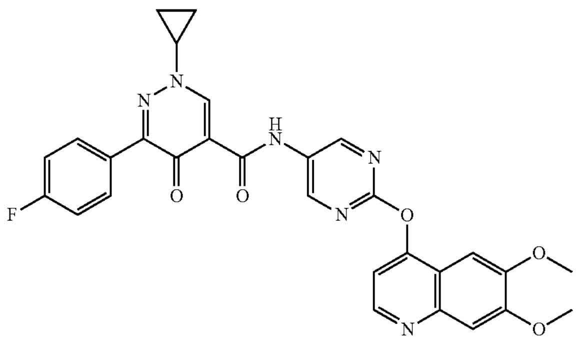 [SMILES: COc1cc2nccc(Oc3ncc(NC(=O)c4cn(C5CC5)nc(-c5ccc(F)cc5)c4=O)cn3)c2cc1OC]

Step 1: Synthesis of 6,7-dimethoxy-4-((5-nitropyrimidine-2-yl)oxy)quinoline

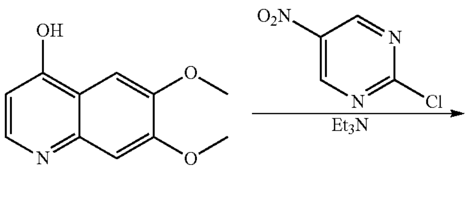

-continued

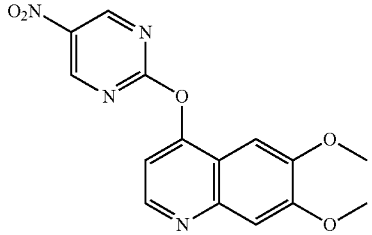

6,7-dimethoxyquinolin-4-ol (3.86 g, 18.81 mmol, 1.0 eq.), 2-chloro-5-nitropyrimidine (3.00 g, 18.81 mmol, 1.0 eq) and triethylamine (2.28 g, 22.57 mmol, 1.2 eq.) were added to DMF (60 mL). The mixture was reacted at room temperature under stirring under the nitrogen protection overnight. TLC detection showed the completion of the reaction. A saturated aqueous $NH_4Cl$ solution (30 mL) was added. The solvent was removed by evaporation under reduced pressure. Saturated brine (30 mL) was added. The mixture was extracted with dichloromethane (20 mL×3). The organic phases were combined, dried over anhydrous sodium sulfate, and filtered by suction. The filtrate was concentrated under reduced pressure. The crude product was purified by silica gel column chromatography (DCM: MeOH=150:1-120:1) to produce a product (1.70 g, yield: 27.5%).

Step 2: Synthesis of 6-((6,7-dimethoxyquinolin-4-yl)oxy)pyrimidine-5-amine

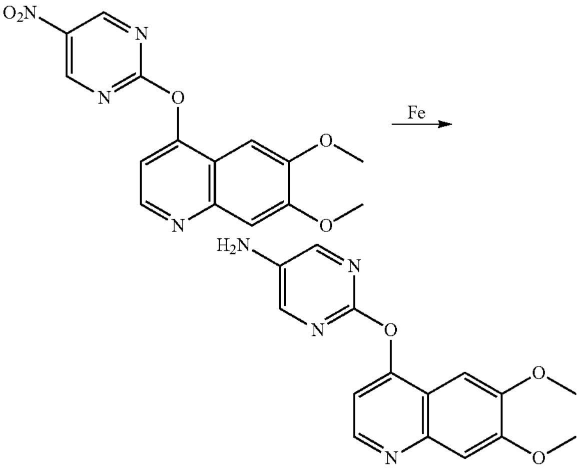

6,7-dimethoxy-4-((5-nitropyrimidine-2-yl)oxy) quinoline (1.70 g, 5.18 mmol, 1.0 eq.), reduced iron powder (1.74 g, 31.07 mmol, 6.0 eq.) and $NH_4Cl$ (3.32 g, 62.14 mmol, 12.0 eq.) were added to a mixed solvent of ethanol (30 mL) and water (15 mL). The mixture was reacted at 80° C. under stirring for 2 hours. TLC detection showed the completion of the reaction. The mixture was filtered hot, and the filter cake was eluted with dichloromethane. The filtrate was concentrated under reduced pressure. The residual aqueous phase was extracted with dichloromethane (10 mL×3). The organic phases were combined, washed with saturated brine (10 mL), dried over anhydrous sodium sulfate, and filtered by suction. The filtrate was concentrated under reduced pressure to produce a product (0.93 g, yield: 60.2%).

Step 3: Synthesis of 2-cyclopropyl-*N*-(2-((6,7-dimethoxyquinolin-4-yl)oxy)pyrimidine-5-yl)-6-para-fluorophenyl-5-oxo-2,5-dihydropyridazine-4-carboxamide

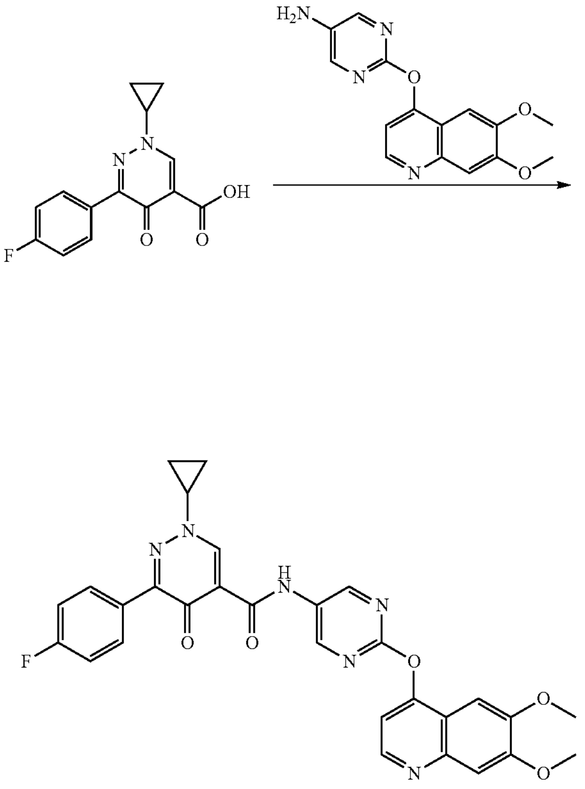

2-cyclopropyl-6-para-fluorophenyl-5-oxo-2,5-dihydropyridazine-4-carboxylic acid (250 mg, 0.91 mmol, 1.0 eq.) was dissolved in DMF (2 mL). DIPEA (353.4 mg, 2.73 mmol, 3.0 eq.) and HATU (519.9 mg, 1.37 mmol, 1.5 eq.) were added, and the mixture was stirred for 10 minutes. 2-((6,7-dimethoxyquinolin-4-yl)oxy)pyrimidine-5-amine (271.9 mg, 0.91 mmol, 1.0 eq.) was added. The mixture was reacted at room temperature under stirring for 1 hour. TLC detection showed the completion of the reaction. The solvent was removed by evaporation under reduced pressure. Dichloromethane (10 mL) was added to dissolve the residue. The mixture was successively washed with a saturated aqueous $NaHCO_3$ solution (5 mL), a saturated aqueous $NH_4Cl$ solution (5 mL) and saturated brine (5 mL×3). The organic phase was dried over anhydrous sodium sulfate. The mixture was filtered by suction. The filtrate was added to methanol (5 mL), and the mixture was concentrated under reduced pressure until a solid just began to precipitate out. The mixture was kept by standing at room temperature for 1 hour. The solid was filtered off, washed with methyl tert-butyl ether, and dried to produce a product (372.9 mg, yield: 73.8%).

$^1$HNMR (400 MHZ, $CDCl_3$) δ (ppm): 12.36 (s, 1H), 9.07 (s, 2H), 9.03 (s, 1H), 8.75-8.74 (d, 1H), 8.15-8.12 (m, 2H), 7.49 (s, 1H), 7.38 (s, 1H), 7.23-7.18 (m, 2H), 7.15-7.13 (d, 1H), 4.07 (s, 3H), 3.99 (s, 3H), 3.89-3.85 (m, 1H), 1.41-1.37 (m, 2H), 1.28-1.21 (m, 2H).

Molecular formula: $C_{29}H_{23}FN_6O_5$, molecular weight: 554.54 LC-MS (Pos, m/z)=554.65 $[M+H]^+$.

Example 23: Synthesis of 2-cyclopropyl-N-(5-((6,7-dimethoxyquinolin-4-yl)oxy)pyrimidine-2-yl)-6-(4-fluorophenyl)-5-oxo-2,5-dihydropyridazine-4-carboxamide (Compound 45)

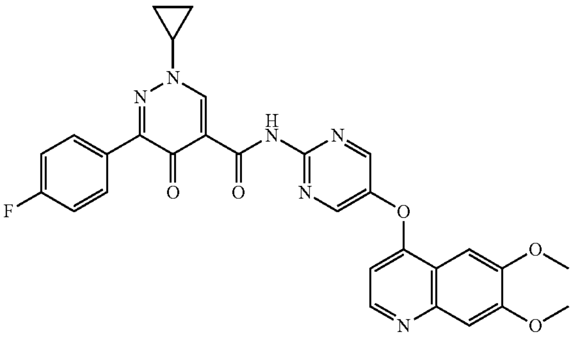 [SMILES: COc1cc2nccc(Oc3cnc(NC(=O)c4cn(C5CC5)nc(-c5ccc(F)cc5)c4=O)nc3)c2cc1OC]

Step 1: Synthesis of 4-((2-chloropyrimidine-5-yl)oxy)-6,7-dimethoxyquinoline

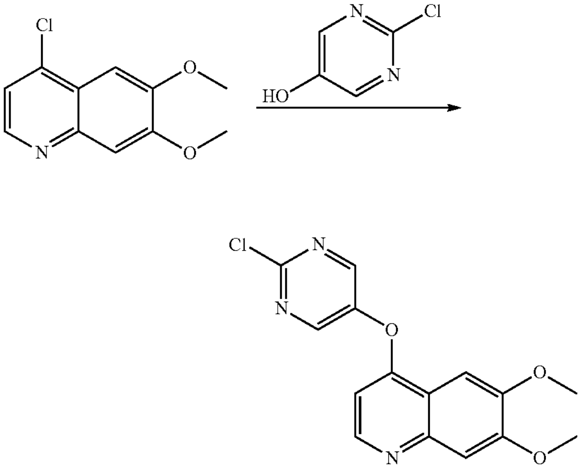

2-chloropyrimidine-5-ol (50.0 g, 0.38 mol, 1.0 eq) was added to xylene (300 mL), and 4-chloro-6,7-dimethoxyquinoline (85.6 g, 0.38 mol, 1.0 eq) was added. The mixture was stirred at 140° C. under reflux for 15 hours. TLC detection showed the completion of the reaction. The mixture was cooled to room temperature and filtered. The filter cake was dried to produce a product (24.6 g, crude product).

Step 2: Synthesis of 5-((6,7-dimethoxyquinolin-4-yl)oxy)pyrimidine-2-amine

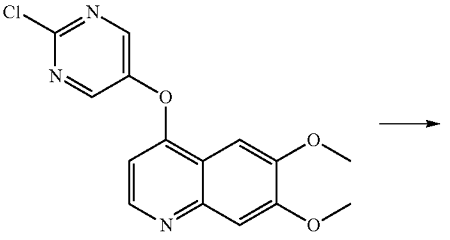

-continued

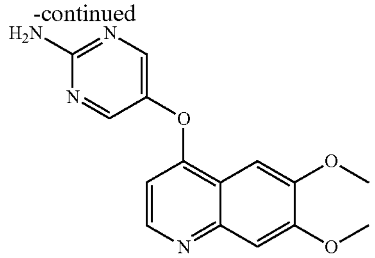

4-((2-chloropyrimidine-5-yl)oxy)-6,7-dimethoxyquinoline (24.6 g, crude product) was added to aqueous ammonia (200 mL), and the mixture was reacted at 90° C. in a sealed tube for 15 hours. TLC detection showed the completion of the reaction. The mixture was cooled to room temperature, and concentrated under reduced pressure to produce a product (18.3 g, yield in two steps: 16.1%).

Step 3: Synthesis of 2-cyclopropyl-*N*-(5-((6,7-dimethoxyquinolin-4-yl)oxy)pyrimidine-2-yl)-6-(4-fluorophenyl)-5-oxo-2,5-dihydropyridazine-4-carboxamide

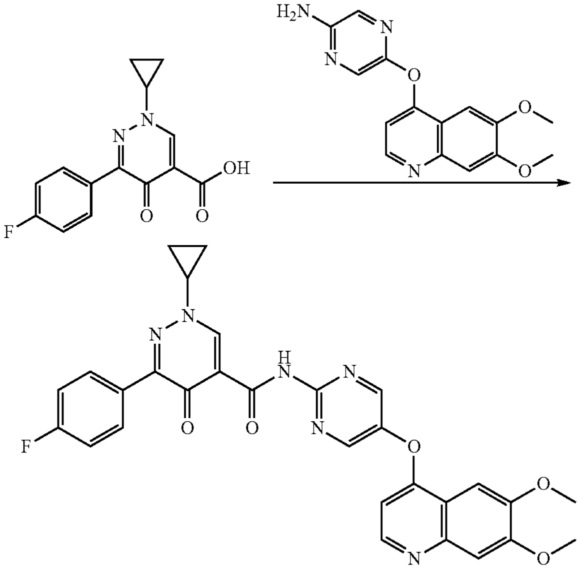

2-cyclopropyl-6-para-fluorophenyl-5-oxo-2,5-dihydropyridazine-4-carboxylic acid (250.0 mg, 0.91 mmol, 1.0 eq.) was dissolved in pyridine (7 mL). 5-((6,7-dimethoxyquinolin-4-yl)oxy)pyrimidine-2-amine (272.0 mg, 0.91 mmol, 1.0 eq.) was added, and phosphorus oxychloride (0.5 mL) was dropwise added. The mixture was stirred at room temperature for 30 minutes. TLC detection showed the completion of the reaction. The solvent was removed by evaporation under reduced pressure. DCM (50 mL) and water (100 mL) were added, and the mixture was subjected to the liquid separation. The organic phase was washed with saturated brine, dried over anhydrous sodium sulfate, and filtered. The filtrate was concentrated under reduced pressure. The crude product was purified by silica gel column chromatography (DCM:MeOH=60:1-30:1) to produce a product (155.0 mg, yield: 30.6%).

$^1$HNMR (400 MHz, $CDCl_3$) δ (ppm): 13.00 (s, 1H), 9.06 (s, 1H), 8.66 (s, 2H), 8.56-8.58 (d, 1H), 8.20-8.24 (m, 2H), 7.54 (s, 1H), 7.47 (s, 1H), 7.16-7.20 (t, 2H), 6.49-6.51 (d, 1H), 4.08-4.09 (m, 6H), 3.88 (m, 1H), 1.39-1.41 (m, 2H), 1.24-1.27 (m, 2H).

Molecular formula: $C_{29}H_{23}FN_6O_5$, molecular weight: 554.54 LC-MS (Pos, m/z)=554.79 $[M+H]^+$.

Example 24: Synthesis of 1-cyclopropyl-N-(5-((6,7-dimethoxyquinolin-4-yl)oxy)pyridin-2-yl)-4-oxo-5-p-tolyl-1,4-dihydropyridazine-3-carboxamide (Compound 46)

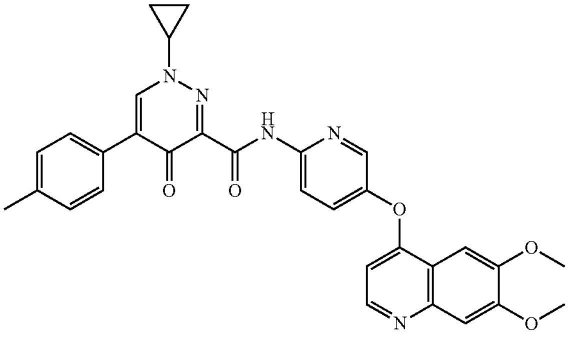

Step 1: Synthesis of para-methylbenzeneacetyl chloride

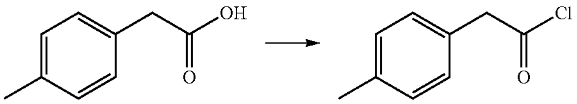

Para-methylbenzeneacetic acid (50.0 g, 0.33 mol) and thionyl chloride (78.52 g, 0.66 mol) were added to dichloromethane (100 mL). The mixture was heated to 45° C. and reacted under reflux for 6 hours. TLC detection showed the completion of the reaction. The mixture was concentrated under reduced pressure to produce a product (55.6 g, crude product).

Step 2: Synthesis of 2,2-dimethyl-5-(2-(p-tolyl)acetyl)-1,3-dioxane-4,6-dione

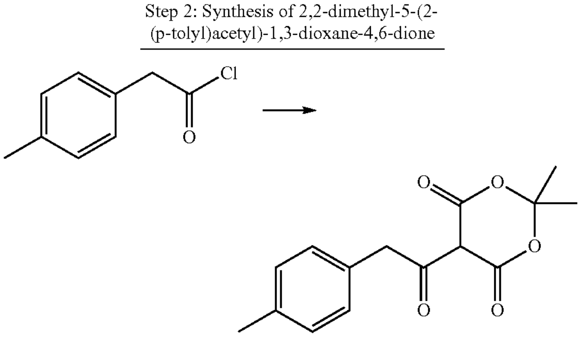

A solution of para-methylbenzeneacetyl chloride (55.4 g, crude product) in dichloromethane (100 mL) was dropwise added to a solution of 2,2-dimethyl-1,3-dioxane-4,6-dione (47.6 g, 0.33 mol) and triethylamine (66.8 g, 0.66 mol) in dichloromethane (100 mL). During the dropwise addition, the reaction system was kept in an ice bath at a temperature of 0-5° C. The mixture was slowly warmed to room temperature overnight. TLC detection showed the completion of the reaction. The reaction system was successively washed with a saturated aqueous $NH_4Cl$ solution, water, and saturated brine, dried over anhydrous sodium sulfate, and concentrated under reduced pressure to produce a product (101.0 g, crude product).

Step 3: Synthesis of ethyl 3-oxo-4-(para-tolyl)butanoate

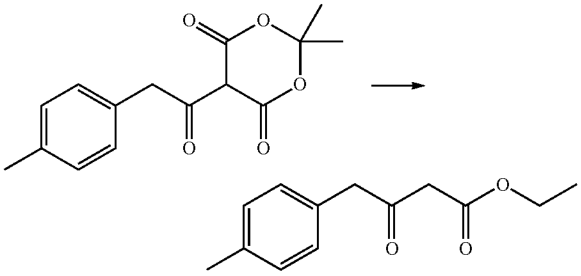

2,2-dimethyl-5-(2-(p-tolyl) acetyl)-1,3-dioxane-4,6-dione (101.0 g, crude product) was added to ethanol (200 mL). The mixture was heated under reflux overnight. TLC detection showed the completion of the reaction. The mixture was concentrated under reduced pressure. The crude product was purified by silica gel column chromatography (PE:EA=40:1-20:1) to produce a product (11.5 g, yield in three steps: 15.8%).

Step 4: Synthesis of ethyl 2-(2-cyclopropylhydrazono)-3-oxo-4-(p-tolyl)butanoate

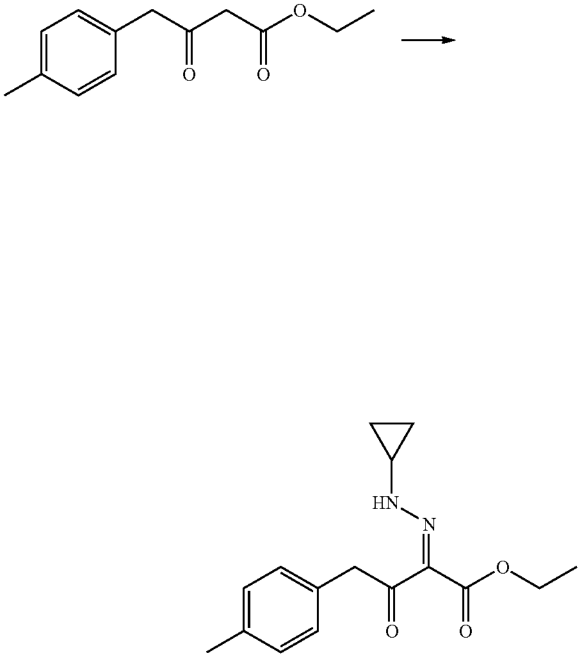

1-cyclopropyl-1-nitrosourea (3.36 g, 26.0 mmol), and ethyl 3-oxo-4-(para-tolyl) butanoate (4.8 g, 22.0 mmol) were added to dichloromethane (30 mL), and the mixture was cooled to 0° C. under an ice bath. Potassium carbonate (9.12 g, 66.0 mmol) was added, and the mixture was slowly warmed from 0° C. to room temperature and reacted overnight. TLC detection showed the completion of the reaction. The mixture was filtered, and the filtrate was concentrated under reduced pressure. The crude product was purified by silica gel column chromatography (PE:EA=40-10:1) to produce a product (460.0 mg, yield: 7.3%).

Step 5: Synthesis of ethyl 2-(2-cyclopropylhydrazono)-5-(dimethylamino)-3-oxo-4-(p-tolyl)pent-4-enoate

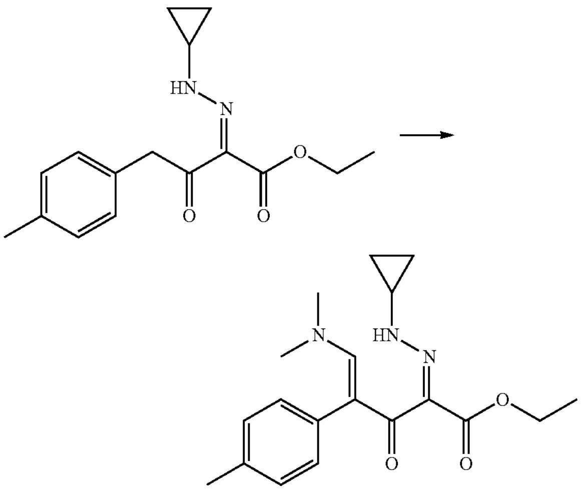

Ethyl 2-(2-cyclopropylhydrazono)-3-oxo-4-(p-tolyl) butanoate (460.0 mg, 1.6 mmol) and DMF-DMA (285.9 mg, 2.4 mmol) were added to toluene (3 mL). The mixture was heated to 110° C. and reacted under reflux overnight. TLC showed the completion of the reaction. The mixture was concentrated under reduced pressure to produce a product (549.5 mg, crude product).

Step 6: Synthesis of ethyl 1-cyclopropyl-4-oxo-5-p-tolyl-1,4-dihydropyridazine-3-carboxylate

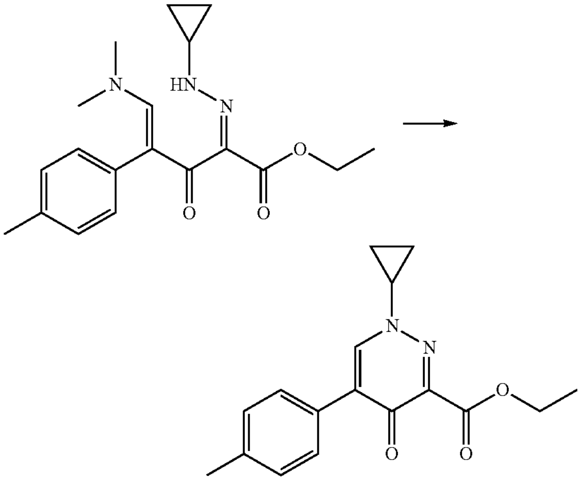

Ethyl 2-(2-cyclopropylhydrazono)-5-(dimethylamino)-3-oxo-4-(p-tolyl) pent-4-enoate (549.1 mg, 1.6 mmol) was added to ethanol (6 mL). The mixture was heated under reflux overnight. TLC detection showed the completion of the reaction. The mixture was concentrated under reduced pressure. Water and ethyl acetate were added, and the mixture was subjected to the liquid separation. The organic phase was washed with water, washed with saturated brine, dried over anhydrous sodium sulfate, and concentrated under reduced pressure to produce a product (450.0 mg, yield in two steps: 94.3%).

Step 7: Synthesis of 1-cyclopropyl-4-oxo-5-p tolyl-1,4-dihydropyridazine-3-carboxylic acid

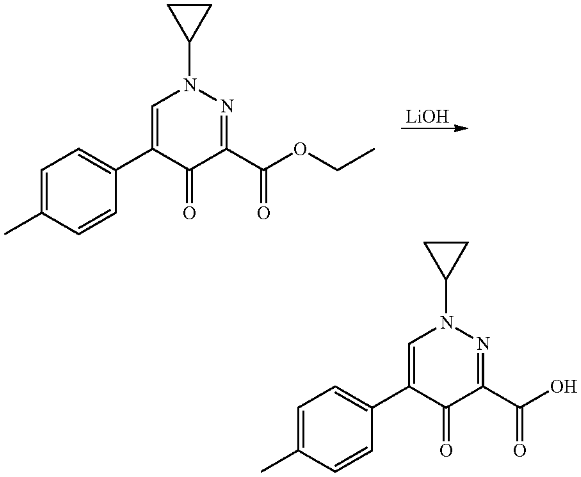

Ethyl 1-cyclopropyl-4-oxo-5-p-tolyl-1,4-dihydropyridazine-3-carboxylate (450.0 mg, 1.51 mmol, 1.0 eq.) was dissolved in methanol (6 mL). A solution of lithium hydroxide monohydrate (284.8 mg, 6.79 mmol, 4.5 eq.) in water (3 mL) was added. The mixture was reacted at room temperature under stirring for 1 hour. TLC detection showed the completion of the reaction. The mixture was concentrated under reduced pressure, and extracted with ethyl acetate (3 mL). The aqueous phase was stirred and adjusted with concentrated HCl to a pH value of 3-4. A white solid was precipitated. The solid-liquid mixture was extracted with dichloromethane (3 mL×2). The organic phases were combined, dried over anhydrous sodium sulfate, filtered by suction, and concentrated under reduced pressure to produce a product (300.0 mg, yield: 73.6%).

Step 8: Synthesis of 1-cyclopropyl-*N*-(5-((6,7-dimethoxyquinolin-4-yl)oxy)pyridin-2-yl)-4-oxo-5-p-tolyl-1,4-dihydropyridazine-3-carboxamide

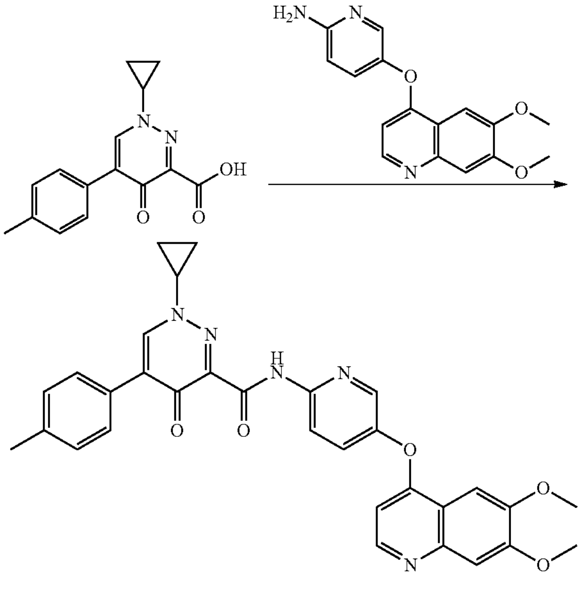

Ethyl 1-cyclopropyl-4-oxo-5-p-tolyl-1,4-dihydropyridazine-3-carboxylic acid (300 mg, 1.11 mmol, 1.0 eq.) was dissolved in DMF (4 mL). The mixture was cooled in an ice bath to 0° C. DIPEA (430.3 mg, 3.33 mmol, 3.0 eq.) and HATU (633.1 mg, 1.66 mmol, 1.5 eq.) were successively added. The mixture was stirred for 10 minutes. 5-((6,7-dimethoxyquinolin-4-yl)oxy)pyridin-2-amine (363.0 mg, 1.22 mmol, 1.1 eq.) was added. The mixture was warmed to room temperature and reacted under stirring overnight. TLC detection showed the completion of the reaction. The solvent was removed by evaporation under reduced pressure. Ethyl acetate (10 mL) was added to dissolve the solid. The mixture was successively washed with a saturated aqueous $NaHCO_3$ solution (5 mL), a saturated aqueous $NH_4Cl$ solution (5 mL), distilled water (5 mL×4) and saturated brine (5 mL), dried over anhydrous sodium sulfate, filtered by suction, and concentrated under reduced pressure. The crude product was purified by preparative thin-layer chromatography (DCM:MeOH=15:1) to produce a product (334.9 mg, yield: 54.9%).

$^1$HNMR (400 MHZ, $CDCl_3$) δ (ppm): 13.22 (s, 1H), 8.58-8.54 (t, 2H), 8.34 (s, 1H), 8.25 (s, 1H), 7.70-7.68 (d, 2H), 7.61-7.58 (d, 2H), 7.49 (s, 1H), 7.32-7.28 (t, 2H), 6.52-6.51 (d, 1H), 4.08 (s, 6H), 3.92 (s, 1H), 2.43 (s, 3H), 1.45 (s, 2H), 1.28-1.26 (d, 2H).

Molecular formula: $C_{31}H_{27}N_5O_5$, molecular weight: 549.59 LC-MS (Pos, m/z)=549.90 $[M+H]^+$.

Assay 1: Stability Assessment of the Compounds of the Present Invention in Liver Microsome of Mice and Dogs Test substances: the compounds of the present invention, wherein the structures and preparations thereof were as described above.

The Composition of the Incubation System:

| Substance to be added | Initial concentration | Proportion (%) | Final concentration |
|---|---|---|---|
| Phosphate buffer | 100 mM | 50 | 50 mM |
| $MgCl_2$ | 20 mM | 5 | 1 mM |
| Liver microsome | 20 mg protein/mL | 2.5 | 0.5 mg protein/mL |
| Water to be supplemented | — | 22.5 | — |
| Compound | 10 μM | 10 | 1 μM |
| β-NADPH | 10 mM | 10 | 1 mM |

Preparation of Test Substances:

An appropriate amount of the compound was accurately weighed and dissolved in DMSO to prepare a 5.0 mM stock solution. The 5.0 mM stock solution was diluted to 1.0 mM with DMSO, and finally diluted with water to a 10 μM test substance working solution for use (the DMSO content in the reaction system was 0.1%).

Assay Steps:

(1) The liver microsome (20 mg protein/mL) was taken out from the −80° C. refrigerator, pre-incubated at 37° C. with a water-bathing constant temperature vibrator for 3 minutes, and melted for use.

(2) A mixed solution of the incubation system (excluding compounds and β-NADPH) according to the above "composition of the incubation system" for the assay was prepared, and pre-incubated at 37° C. with a water-bathing constant temperature vibrator for 2 minutes.

(3) Control group (excluding β-NADPH): 30 μL of water and 30 μL of compound working solution (10 μM) were added to 240 μL of the mixed solution of the incubation system of step (2), and vortexed for 30 seconds to mix well. The total reaction volume was 300 μL. A duplicate sample was prepared. The sample was incubated at 37° C. with a water-bathing constant temperature vibrator. The timekeeping began and the sampling time points were set at 0 minute and 60 minutes.

(4) Sample group: 70 μL of β-NADPH solution (10 mM) and 70 μL of compound working solution (10 μM) were added to 560 μL of the mixed solution of step (2). The total reaction volume was 700 μL. The resulting mixture was vortexed for 30 seconds to mix well. A duplicate sample was prepared. The sample was incubated at 37° C. with a water-bathing constant temperature vibrator. The timekeeping began and the sampling time points were set at 0 minute, 5 minutes, 10 minutes, 20 minutes, 30 minutes, and 60 minutes after timekeeping.

(5) After vortexing for 3 minutes, the sample was centrifuged at 4000 rpm for 10 minutes.

(6) 50 μL of the supernatant was taken and 150 μL of water was added. The resulting mixture was vortexed to mix well, and analyzed by LC/MS/MS.

Data Analysis:

The half-life ($t_{1/2}$) and clearance rate (Cl) were calculated using the following first-order kinetic formula:

$$C_t=C_0*e^{-kt}$$

$$t_{1/2}=\ln 2/k=0.693/k$$

$$Cl_{int}=V_d*k$$

$$V_d=1/\text{protein content in liver microsome}$$

Note: k was the slope of the logarithm of the remaining amount of the compound versus time, and Va was the apparent distribution volume.

The test results were shown in Table 1 below:

TABLE 1

Stability test of the compounds of the present invention in liver microsome of mice and dogs

| | Mouse | | Dog | |
|---|---|---|---|---|
| Compound No. | $CL_{int}$ (mL/min/mg) | $t_{1/2}$ (min) | $CL_{int}$ (mL/min/mg) | $t_{1/2}$ (min) |
| Compound 1 | 0.0182 | 76.2 | 0.1102 | 12.6 |
| Compound 14 | 0.0074 | 187 | 0.0090 | 154 |
| Compound 15 | 0.0036 | 385 | 0.0062 | 224 |
| Compound 16 | 0.0142 | 97.6 | 0.0028 | 495 |
| Compound 20 | 0.0042 | 330 | 0.0038 | 365 |
| Compound 29 | 0.0072 | 193 | 0.0106 | 131 |
| Compound 30 | 0.0260 | 53.3 | 0.0246 | 56.3 |
| Compound 31 | 0.0016 | 866 | →0 | →∞ |
| Compound 32 | 0.0056 | 248 | 0.0066 | 210 |
| Compound 33 | 0.0084 | 165 | →0 | →∞ |
| Compound 34 | 0.0050 | 277 | 0.0028 | 495 |
| Compound 36 | 0.0046 | 301 | 0.0120 | 116 |
| Compound 37 | 0.0026 | 533 | 0.0082 | 169 |
| Compound 39 | 0.004 | 3465 | →0 | →∞ |
| Compound 40 | 0.0026 | 533 | →0 | →∞ |
| Compound 42 | →0 | →∞ | →0 | →∞ |
| Compound 43 | 0.0022 | 630 | 0.0096 | 144 |
| Compound 44 | 0.0108 | 128 | 0.0062 | 224 |
| Compound 45 | 0.0070 | 198 | 0.0024 | 578 |
| Compound 46 | →0 | →∞ | 0.1112 | 12.5 |

Test conclusion: It can be seen from the test results of Table 1 that the compounds of the present invention have lower clearance rate and higher half-life, and have good stability in liver microsome, which indicates that the compounds of the present invention have excellent metabolic stability.

Assay 2: Rat PK Evaluation for the Compounds of the Present Invention Animal administration and sample collection:

The test compounds 14, 15, 16, 20, 29, 30, 31, 32, 33, 34, 36, 37, 47 and 48 were dissolved in 5% DMSO+20% (30% solutol)+75% saline to prepare the compound solutions. Each of the compound solutions was intragastrically administered to SD rats at a dose of 5.0 mg/kg. The time points of blood collection were: 15 minutes, 30 minutes, 1 hour, 2 hours, 4 hours, 6 hours, 8 hours, 24 hours, 30 hours, and 48 hours.

The test compounds 38, 39, 40 and 41 were dissolved in 5% NMP+5% Tween-80+90% saline to prepare the compound solutions. Each of the compound solutions was intragastrically administered to SD rats at a dose of 5.0 mg/kg. The time points of blood collection were: 15 minutes, 30 minutes, 1 hour, 2 hours, 4 hours, 6 hours, 8 hours, 24 hours, 30 hours, and 48 hours.

The test compounds 14, 15, 16, 20, 29, 30, 31, 32, 33, 34, 36, 37, 47 and 48 were dissolved in 5% DMSO+20% (30% solutol)+75% saline to prepare the compound solutions. Each of the compound solutions was administered by intravenous bolus injection to SD rats at a dose of 1 mg/kg. The time points of blood collection were: 5 minutes, 15 minutes, 30 minutes, 1 hour, 2 hours, 4 hours, 6 hours, 8 hours, 24 hours, and 48 hours.

The test compounds 38, 39, 40 and 41 were dissolved in 5% NMP+5% Tween-80+90% saline to prepare the compound solutions. Each of the compound solutions was administered by intravenous bolus injection to SD rats at a dose of 1 mg/kg. The time points of blood collection were: 5 minutes, 15 minutes, 30 minutes, 1 hour, 2 hours, 4 hours, 6 hours, 8 hours, 24 hours, and 48 hours.

The animal was fixed. The tail was heated in a water bath pot 10 minutes before each time point. About 100 μL of blood was collected through the tail vein. The blood was collected and placed in an anti-coagulation tube containing EDTA-K2. The blood sample was centrifuged at 8000 rpm for 6 minutes at 4° C. to obtain a plasma sample. The plasma was prepared within 30 minutes after the blood collection. The plasma was stored in a −80° C. refrigerator before testing.

Sample Analysis Method:

The sample to be tested was taken out from the −80° C. refrigerator, naturally melted at room temperature and vortexed for 5 minutes. 20 μL of plasma sample was accurately pipetted into a 1.5 mL centrifuge tube. 200 μL of an internal standard working solution (a solution of tolbutamide in methanol) having a concentration of 100 ng/mL was added and mixed well. The mixture was vortexed for 5 minutes, and centrifuged at 12000 rpm for 5 minutes. 50 μL of the supernatant was accurately pipetted into a 96-well plate pre-filled with 150 μL/well of water. The plate was vortexed for 5 minutes and mixed well, and then the LC-MS/MS determination and analysis were performed.

Data Processing Method:

The concentration of the test substance was output using Analyst 1.6.3 from AB Company. Parameters such as mean, standard deviation, and coefficient of variation were calculated with Microsoft Excel (direct outputs from Analyst 1.6.3 were not calculated), and the PK parameters were calculated using Pharsight Phoenix 6.1 software NCA ($T_{max}$ was the median).

The results were shown in Table 2 below:

TABLE 2

PK parameters of the compounds in SD rats (IV: 1 mg/kg, PO: 5 mg/kg, n = 3)

| Compound | $t_{z1/2}$ iv/po (h) | $V_{z_obs}$IV (L/kg) | $Cl_{\_obs}$ iv (L/h/kg) | $T_{max}$ PO (h) | $AUC_{last}$ iv/po (h*ng/mL) | F % |
|---|---|---|---|---|---|---|
| Compound 14 | 6.30/12.1 | 0.25 | 0.027 | 2.00 | 34938/110489 | 63.2 |
| Compound 15 | 18.5/20.5 | 1.23 | 0.047 | 8.00 | 18138/67446 | 78.9 |
| Compound 16 | 4.13/5.67 | 0.12 | 0.021 | 1.00 | 48583/86432 | 35.6 |
| Compound 20 | 3.10/5.40 | 0.18 | 0.040 | 6.00 | 29133/77887 | 53.3 |
| Compound 29 | 13.7/12.2 | 0.42 | 0.036 | 4.00 | 78615/245712 | 59.1 |
| Compound 30 | 8.68/13.4 | 0.30 | 0.024 | 6.00 | 41396/151916 | 78.7 |
| Compound 31 | 32.6/19.2 | 0.14 | 0.0030 | 4.00 | 223649/310000 | 27.7 |
| Compound 32 | 3.74/5.04 | 0.23 | 0.045 | 4.00 | 23934/90462 | 75.4 |
| Compound 33 | 5.47/4.73 | 0.146 | 0.018 | 2.00 | 55725/88756 | 31.7 |
| Compound 34 | 7.46/8.31 | 0.15 | 0.013 | 4.00 | 80953/320929 | 80.4 |
| Compound 36 | 11.6/12.7 | 0.095 | 0.0058 | 4.00 | 167027/462555 | 57.5 |
| Compound 37 | 5.98/7.73 | 0.12 | 0.014 | 4.00 | 69744/272532 | 78.7 |
| Compound 38 | 15.2/12.1 | 3.32 | 0.15 | 4.00 | 5995/25534 | 81.6 |
| Compound 39 | 5.89/5.67 | 1.21 | 0.15 | 2.00 | 6915/32420 | 90.2 |
| Compound 40 | 9.18/8.68 | 1.84 | 0.14 | 4.00 | 7274/22966 | 63.4 |
| Compound 41 | 14.1/13.7 | 6.81 | 0.35 | 4.00 | 2753/14406 | 103 |

Note:
$t_{z1/2}$: terminal elimination half-life,
$Cl_{obs}$: clearance rate,
$V_{z_obs}$: apparent distribution volume,
$T_{max}$: time to peak plasma concentration,
$AUC_{last}$: area under the drug-time curve from 0 to 48 hours, F%: absolute bioavailability.

It can be seen from the test results of Table 2 that the compounds of the present invention have good pharmacokinetic properties and good drug-forming ability.

Assay 3: Enzymatic Activity Test of the Compounds of the Present Invention

Test substances: the compounds of the present invention, wherein the structures and preparations thereof were as described above.

Test Method:

(1) Preparation of the Compound Stock Solution

The compound was dissolved in 100% DMSO to prepare a stock solution with a maximum concentration of 500 μM.

(2) Preparation of the Compound Working Solution

The compound stock solution was diluted to final concentrations of 500, 150, 50, 15, 5, 1.5, 0.5, 0.15 and 0.05 M to become the compound working solutions (50×).

(3) Preparation of Different Enzyme Reaction Solutions a) Axl (h)

The Axl (h) enzyme was dissolved in 8 mM MOPS (pH 7.0), 0.2 mM EDTA, and 250 μM KKSRGDYMTMQIG (SEQ ID NO: 2) to prepare an enzyme solution having a final concentration of 1.7 nM. The enzymatic reaction was activated by using 10 mM magnesium acetate and 10 μM [γ-$^{33}$P]-ATP to form an Mg/ATP mixed solution.

b) Mer (h)

The Mer (h) enzyme was dissolved in 8 mM MOPS (pH 7.0), 0.2 mM EDTA, 30 mM NaCl, and 250 μM GGMEDIYFEFMGGKKK (SEQ ID NO: 3) to prepare an enzyme solution having a final concentration of 3.1 nM. The enzymatic reaction was activated by using 10 mM magnesium acetate and 10 μM [γ-$^{33}$P]-ATP to form an Mg/ATP mixed solution.

c) Tyro-3 (h)

The Tyro3 (h) enzyme was dissolved in 8 mM MOPS (pH 7.0), 0.2 mM EDTA, 1 mM $MnCl_2$, and 250 μM KVEKIGEGTYGVVYK (SEQ ID NO: 4) to prepare an enzyme solution having a final concentration of 38 nM. The enzymatic reaction was activated by using 10 mM magnesium acetate and 10 μM [γ-$^{33}$P]-ATP to form an Mg/ATP mixed solution.

d) CSF1R (h)

The CSF1R (h) enzyme was dissolved in 8 mM MOPS (pH 7.0), 0.2 mM EDTA, and 250 μM KKSRGDYMTMQIG (SEQ ID NO: 2) to prepare an enzyme solution having a final concentration of 64 nM. The enzymatic reaction was activated by using 10 mM magnesium acetate and 10 μM [γ-$^{33}$P]-ATP to form an Mg/ATP mixed solution.

(4) Enzymatic Reaction

In a 384-well plate, the compound working solution was added to final concentrations of 10000, 3000, 1000, 300, 100, 30, 10, 3, and 1 nM. Then different enzyme reaction solutions prepared according to the above conditions were added. The incubation was carried out for 40 minutes at room temperature. The test was terminated by the addition of a 0.5% phosphoric acid solution. 10 μL of the reaction solution was taken and dropped to the P30 filter paper. The filter paper was washed 4 times with 0.425% phosphoric acid solution and once with methanol, and then placed on a scintillation counter. The grayscale analysis of the results was performed using Image J software and the $IC_{50}$ values were calculated using GraphPad 5.0 software.

The test results were shown in Table 3 below:

TABLE 3

Inhibitory activities of the compounds of the present invention on different kinases - $IC_{50}$ (nM)

| Compound | Axl(h) | Mer(h) | Tyro-3(h) | CSF1R(h) |
|---|---|---|---|---|
| 1 | 17 | 2 | 29 | 200 |
| 14 | 8 | 2 | 21 | 55 |
| 15 | 11 | <1 | 13 | 38 |
| 16 | 13 | 2 | 12 | 61 |
| 20 | 17 | 3 | 21 | 78 |
| 29 | 5 | 1 | 12 | 51 |
| 30 | 7 | <1 | 16 | 61 |
| 31 | 4 | <1 | 7 | 20 |
| 32 | 5 | 2 | 11 | 93 |
| 33 | 2 | <1 | 8 | 37 |

TABLE 3-continued

| Inhibitory activities of the compounds of the present invention on different kinases - $IC_{50}$ (nM) | | | | |
|---|---|---|---|---|
| Compound | Axl(h) | Mer(h) | Tyro-3(h) | CSF1R(h) |
| 34 | 5 | 2 | 7 | 161 |
| 36 | 3 | <1 | 7 | 68 |
| 37 | 2 | <1 | 12 | — |
| 38 | 3 | 3 | 93 | 57 |
| 39 | 4 | 3 | 36 | 34 |
| 40 | 4 | 12 | 143 | 259 |
| 41 | 12 | 2 | 65 | 84 |

— indicates no determination.

As can be seen from the test results in Table 3, the compounds of the present invention have good inhibitory activities against Axl (h), Mer (h), Tyro3 (h) and CSF1R (h), and thus the compounds of the present invention are useful for preventing and/or treating diseases mediated by the Axl (h), Mer (h), Tyro-3 (h) and CSF1R (h).

Assay 4: Enzymatic Activity Test of the Compound of the Present Invention

Test substances: the compounds of the present invention, wherein the structures and preparations thereof were as described above.

Test Method:

Preparation of the Compound Stock Solution

The compound was dissolved in 100% DMSO to prepare a stock solution with a maximum concentration of 500 μM.

Preparation of the Compound Working Solution

The compound stock solution was diluted to final concentrations of 500, 150, 50, 15, 5, 1.5, 0.5, 0.15 and 0.05 μM to become the compound working solutions (50×).

Preparation of Different Enzyme Reaction Solutions

TrkA (h)

The TrkA (h) enzyme was dissolved in 8 mM MOPS (pH 7.0), 0.2 mM EDTA, and 250 μM KKKSPGEYVNIEFG (SEQ ID NO: 5) to prepare an enzyme solution having a final concentration of 1.7 nM. The enzymatic reaction was activated by using 10 mM magnesium acetate and 10 μM [γ-$^{33}$P]-ATP to form an Mg/ATP mixed solution.

TrkB (h)

The TrkB (h) enzyme was dissolved in 8 mM MOPS (pH 7.0), 0.2 mM EDTA, and 0.1 mg/mL poly(Glu, Tyr) 4:1 to prepare an enzyme solution having a final concentration of 3.1 nM. The enzymatic reaction was activated by using 10 mM magnesium acetate and 10 μM [γ-$^{33}$P]-ATP to form an Mg/ATP mixed solution.

TrkC (h)

The TrkC (h) enzyme was dissolved in 8 mM MOPS (pH 7.0), 0.2 mM EDTA, and 500 μM GEEPLYWSFPAKKK (SEQ ID NO: 6) to prepare an enzyme solution having a final concentration of 38 nM. The enzymatic reaction was activated by using 10 mM magnesium acetate and 10 μM [γ-$^{33}$P]-ATP to form an Mg/ATP mixed solution.

Enzymatic Reaction

In a 384-well plate, the compound working solution was added to final concentrations of 10000, 3000, 1000, 300, 100, 30, 10, 3, and 1 nM. Then different enzyme reaction solutions prepared according to the above conditions were added. The incubation was carried out for 40 minutes at room temperature. The test was terminated by the addition of a 0.5% phosphoric acid solution. 10 μL of the reaction solution was taken and dropped to the P30 filter paper. The filter paper was washed 4 times with 0.425% phosphoric acid solution and once with methanol, and then placed on a scintillation counter. The grayscale analysis of the results was performed using Image J software and the $IC_{50}$ values were calculated using GraphPad 5.0 software.

The test results were shown in Table 4 below:

TABLE 4

| Inhibitory activities of the compounds of the present invention on different kinases - $IC_{50}$ (nM) | | | |
|---|---|---|---|
| Test substances | TrkA(h) | TrkB(h) | TrkC(h) |
| Compound 15 | 6 | 3 | 6 |
| Compound 31 | 3 | 3 | 3 |
| Compound 33 | 13 | 8 | 5 |
| Compound 34 | 5 | 3 | 6 |
| Compound 36 | 2 | 4 | 3 |
| Compound 37 | 7 | 6 | 4 |
| Compound 38 | 11 | 11 | 8 |
| Compound 39 | 18 | 17 | 10 |
| Compound 40 | 7 | 6 | 14 |
| Compound 41 | 5 | — | — |

— indicates no determination.

As can be seen from the test results in Table 4, the compounds of the present invention have good inhibitory activities against TrkA (h), TrkB (h) and TrkC (h), and thus the compounds of the present invention are useful for preventing and/or treating diseases mediated by the TrkA (h), TrkB (h) and TrkC (h).

Assay 5: Test for Inhibitory Activities of the Compounds of the Present Invention on the Cell pAxl H1299 is a non-small cell lung cancer cell.

Test substances: the compounds of the present invention, wherein the structures thereof were as described above.

Test equipment: protein electrophoresis apparatus (manufactured by Bio Rad), transfer unit (manufactured by Bio Rad), exposure unit (manufactured by Tanon), $CO_2$ cell incubator (manufactured by Thermo).

Test Method:

The H1299 cells were inoculated in a 6-well plate (containing 10% FBS 1640 medium, $5\times10^5$ cells per well), and adherent cells were cultivated at 37° C. in a 5% $CO_2$ condition for 18 hours. The cells were starved overnight. Different concentrations of compounds were added. The final compound concentrations were 1.1, 3.3, 10, and 30 nM, and the final DMSO content was 1% %. The negative control wells contained the medium containing 1% % DMSO. After incubating at 37° C. in a 5% $CO_2$ condition for 60 minutes, hGAS6 (R&D, final concentration 200 ng/ml) was added to each well. After further incubating for 60 minutes, the cell total protein was extracted for Western Blot and the $IC_{50}$ values were calculated using GraphPad 5.0 software. The inhibitory activity of the compound on the cell pAxl was examined.

The test results were shown in Table 5 below:

TABLE 5

| Inhibitory activities of the compounds of the present invention on the cell pAxl | |
|---|---|
| Compound | $IC_{50}$ (nM) |
| 1 | <1.1 |
| 14 | <1.1 |
| 15 | <1.1 |
| 16 | <1.1 |
| 20 | <1.1 |
| 29 | <1.1 |
| 30 | <1.1 |
| 31 | <1.1 |
| 32 | <1.1 |

TABLE 5-continued

| Inhibitory activities of the compounds of the present invention on the cell pAxl | |
|---|---|
| Compound | $IC_{50}$ (nM) |
| 33 | <1.1 |
| 34 | <1.1 |
| 36 | <1.1 |
| 37 | <1.1 |
| 38 | 3.3 |
| 39 | 3.3 |
| 40 | 10 |
| 41 | <10 |
| 42 | 1.1-3.3 |
| 43 | 3.3 |
| 44 | 3.3-10 |
| 45 | 1.1 |
| 46 | <1.1 |

As can be seen from the test results of Table 5, the compounds of the present invention have significant inhibitory effect on H1299 cell pAxl, indicating that the compounds of the present invention can effectively inhibit Axl activity at the cellular level and are an excellent Axl inhibitor.

Assay 6: Test for Inhibitory Activities of the Compounds of the Present Invention on the Cell pMer H1299 is a non-small cell lung cancer cell.

Test substances: the compounds of the present invention, wherein the structures thereof were as described above.

Test equipment: protein electrophoresis apparatus (manufactured by Bio Rad), transfer unit (manufactured by Bio Rad), exposure unit (manufactured by Tanon), $CO_2$ cell incubator (manufactured by Thermo).

Test Method:

The H1299 cells were inoculated in a 6-well plate (containing 10% FBS 1640 medium, $5\times10^5$ cells per well), and adherent cells were cultivated at 37° C. in a 5% $CO_2$ condition for 18 hours. The cells were starved overnight. Different concentrations of compounds were added. The final compound concentrations were 0.35, 1.1, 3.3 and 10 nM, and the final DMSO content was 1% %. The negative control wells contained the medium containing 1% % DMSO. After incubating at 37° C. in a 5% $CO_2$ condition for 60 minutes, Human MerMab (R&D, final concentration 200 ng/mL) was added to each well. After further incubating for 60 minutes, the cell total protein was extracted for Western Blot and the $IC_{50}$ values were calculated using GraphPad 5.0 software. The inhibitory activity of the compound on the cell pMer was examined.

The test results were shown in Table 6 below:

TABLE 6

| Inhibitory activities of the compounds of the present invention on the cell pMer | |
|---|---|
| Compound | $IC_{50}$ (nM) |
| 1 | 1.1-3.3 |
| 14 | 0.35 |
| 15 | <0.35 |
| 16 | <1.1 |
| 20 | 1.1 |
| 29 | <1.1 |
| 30 | 1.1-3.3 |
| 31 | <0.35 |
| 32 | <1.1 |
| 33 | <1.1 |
| 34 | <1.1 |

TABLE 6-continued

| Inhibitory activities of the compounds of the present invention on the cell pMer | |
|---|---|
| Compound | $IC_{50}$ (nM) |
| 36 | <0.35 |
| 37 | 1.1-3.3 |
| 38 | 10 |
| 39 | 1.1 |
| 40 | 10 |
| 41 | <3.3 |
| 42 | <1.1 |
| 43 | <1.1 |
| 44 | 10 |
| 45 | <1.1 |
| 46 | <0.37 |

As can be seen from the test results of Table 6, the compounds of the present invention have significant inhibitory effect on H1299 cell pMer, indicating that the compounds of the present invention can effectively inhibit Mer activity at the cellular level and are an excellent Mer inhibitor.

Assay 7: Test for Inhibitory Activities of the Compounds of the Present Invention on the Cell pCSF1R HEK293T is a human renal epithelial cell.

CSF1R plasmid.

Test substances: the compounds of the present invention, wherein the structures thereof were as described above.

Test equipment: protein electrophoresis apparatus (manufactured by Bio Rad), transfer unit (manufactured by Bio Rad), exposure unit (manufactured by Tanon), $CO_2$ cell incubator (manufactured by Thermo).

Test Method:

The HEK293T cells were inoculated in a 6-well plate (containing 10% FBS DMEM medium, $4\times10^5$ cells per well), and adherent cells were cultivated at 37° C. in a 5% $CO_2$ condition for 6 hours. Each well was transfected with 2 μg CSFIR plasmid, and the cells were cultivated at 37° C. in a 5% $CO_2$ condition overnight. At 24 hours after transfection, different concentrations of compounds were added to the administration group. The final compound concentrations were 30, 100, 300, and 1000 nM, and the final DMSO content was 1% %. The negative control wells contained the medium containing 1% % DMSO. After incubating at 37° C. in a 5% $CO_2$ condition for 120 minutes, the cell total protein was extracted for Western Blot, the grayscale analysis of the results was performed using Image J software and the $IC_{50}$ values were calculated using GraphPad 5.0 software. The inhibitory activity of the compound on the cell pCSF1R was examined.

Test results: inhibitory activities of the compounds of the present invention on the cell pCSF1R were determined, and the $IC_{50}$ values thereof were more than 0 and less than or equal to 300 nM.

TABLE 7

| Inhibitory activities of the compounds of the present invention on the cell pCSF1R | |
|---|---|
| Compound | $IC_{50}$ (nM) |
| 15 | 100-300 |
| 31 | 30-100 |

The results show that the compounds of the present invention have significant inhibitory effect on pCSF1R-transfected HEK293T cells, and the inhibitory effect increases with increasing doses. It is indicated that the compounds of the present invention can effectively inhibit CSFIR activity at the cellular level and are an excellent CSFIR inhibitor.

Assay 8: Cell Viability Test of the Compounds of the Present Invention

Ba/F3 LMNA-NTRK1 is an NTRK1 wild type cell;

Ba/F3 ETV6-NTRK2 is an NTRK2 wild type cell;

Ba/F3 LMNA-NTRK1 G667C and Ba/F3 LMNA-NTRK1-V573M are NTRK1 gene mutant cells.

Test substances: the compounds of the present invention, wherein the structures thereof were as described above.

Test instrument: SpectraMax multi-label microplate reader.

Test Method:

Each cell was inoculated in a 96-well plate and adherent cells were cultivated overnight. Different concentrations of the compounds (9 dose groups, 3.16 times DMSO serial dilution) were added to give the final concentration of 0.1-1000 nM, and the final DMSO content was 1% %. The negative control wells contained the medium containing 1% % DMSO. The cells were incubated at 37° C. in a condition of 5% $CO_2$ and 95% humidity for 72 hours for use. An equal volume of CTG reagent was added to each well, and the cells were lysed by shaking for 5 minutes on an orbital shaker, and incubated for 20 minutes at room temperature to stabilize the cold light signal. The cold light signal was read with a microplate reader. Data were analyzed using GraphPad Prism 5.0 software, and data were fitted using nonlinear S-curve regression to derive a dose-response curve and thereby calculate $IC_{50}$ values.

The test results were shown in Table 8:

TABLE 8

Inhibitory activities of the compounds of the present invention on cells ($IC_{50}$) (nM)

| Compound | Ba/F3 LMNA-NTRK1 | Ba/F3 ETV6-NTRK2 | Ba/F3 LMNA-NTRK1 G667C | Ba/F3 LMNA-NTRK1-V573M |
|---|---|---|---|---|
| Compound 15 | 3.28 | 16.45 | 0.09 | 0.51 |
| Compound 31 | 17.3 | — | 1.4 | 1.4 |
| Compound 34 | 14.34 | 109.47 | 0.68 | 2.7 |
| Compound 39 | 42.4 | — | 8.1 | 5 |

TABLE 8-continued

Inhibitory activities of the compounds of the present invention on cells ($IC_{50}$) (nM)

| Compound | Ba/F3 LMNA-NTRK1 | Ba/F3 ETV6-NTRK2 | Ba/F3 LMNA-NTRK1 G667C | Ba/F3 LMNA-NTRK1-V573M |
|---|---|---|---|---|
| Compound 33 | 73 | — | 3 | 6 |
| Compound 38 | 55.1 | — | 5.7 | 7.5 |
| Compound 40 | 52.1 | — | 9.1 | 9.1 |

— indicates no determination.

It can be seen from the test results in Table 8 that the compounds of the present invention have good inhibitory activities against NTRK wild-type cells such as Ba/F3 LMNA-NTRK1 and Ba/F3 ETV6-NTRK2 and even higher inhibitory activities against NTRK gene mutant cells such as Ba/F3 LMNA-NTRK1 G667C and Ba/F3 LMNA-NTRK1-V573M, indicating that the compounds of the present invention can be used to treat NTRK fusion tumors and drug-resistant tumors caused by NTRK mutations, and have very good clinical value.

INDUSTRIAL APPLICABILITY

The prevent invention provides a novel TAM family kinase inhibitor compound. Said compound has good kinase inhibitory activities and can be used to prevent and/or treat diseases mediated by the abnormal expression of TAM family kinase receptors and/or ligands thereof. Moreover, the compound of the present invention can also target the CSFIR kinase, and can be used to prevent and/or treat diseases mediated by the abnormal expression of TAM family kinases/and CSFIR kinase receptors and/or ligands thereof. Furthermore, the compound of the present invention can inhibit the growth, migration, and/or drug resistance of tumors caused by the TAM family kinase/and CSFIR kinase. In addition, the compound of the present invention can treat and/or prevent related diseases caused by NTRK, in particular, related drug resistant diseases caused by NTRK mutations. Furthermore, the compound of the present invention has a long in-vivo half-life, has an excellent metabolic stability in vivo, and therefore the compound of the present invention can improve the therapeutic effect of the drug, reduce the patient's burden for administration, and improve the patient compliance.

The invention claimed is:

1. A compound represented by general formula (II), or a pharmaceutically acceptable salt, a stereoisomer or a tautomer thereof:

(II)

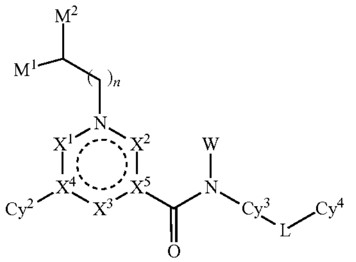

wherein W is selected from hydrogen or $C_{1-6}$alkyl;

$X^1$, and $X^2$ are each independently selected from $CR^a$, or N, and $X^3$ is C═O;

$X^4$ and $X^5$ are each C;

$M^1$ and $M^2$ are each independently selected from hydrogen, $C_{1-6}$alkyl, or $M^1$ and $M^2$ together with the atoms to which they are attached may form a 3-8-membered cycloalkyl;

$Cy^2$ is 6-14-membered aryl, which is optionally substituted by one or more $R^2$, $R^2$ is each independently selected from hydrogen, cyano, hydroxy, halogen, carboxyl, nitro, —$NR^bR^c$, —C(O)$R_d$, —C(O)$NR^bR^c$, —OC(O)$NR^bR^c$, —$NR^b$C(O)$OR^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R' 3-12-membered cycloalkyl, 3-12-membered cycloalkenyl, 3-14-membered heterocyclyl, 6-14-membered aryl, or 5-10-membered heteroaryl;

$Cy^3$ is 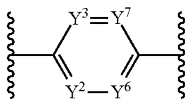

optionally substituted by one or more $R^3$; $Y^2$, $Y^3$, $Y^6$, and $Y^7$ are each independently selected from CH or N, and at least one of $Y^2$, $Y^3$, $Y^6$, and $Y^7$ is N, $R^3$ is each independently selected from hydrogen, cyano, hydroxy, halogen, carboxyl, nitro, —$NR^bR^c$, —C(O)$R^d$, —C(O)$NR^bR^c$, —OC(O) $NR^bR^c$, —$NR^b$C(O)$OR^d$, —$NR^b$C(O)$R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$ alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^b$C(O)—R', 3-12-membered cycloalkyl, 3-12-membered cycloalkenyl, 3-14-membered heterocyclyl, 6-14-membered aryl, or 5-10-membered heteroaryl; when $X^1$ or $X^2$ represents N, $Cy^3$ may also be a 6-14 membered aromatic group optionally substituted by one or more $R^3$;

$Cy^4$ is

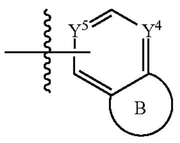

optionally substituted by one or more $R^4$, $Y^4$ and $Y^5$ are independently selected from CH or N, and at least one of $Y^4$ and $Y^5$ is N, ring B is phenyl or 5-6-membered heteroaryl, $R^4$ is each independently selected from hydrogen, cyano, hydroxy, halogen, carboxyl, nitro, —$NR^bR^c$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', $SO_2$—R', 3-12-membered cycloalkyl, 3-12-membered cycloalkenyl, 3-14-membered heterocyclyl, 6-14-membered aryl, or 5-10-membered heteroaryl, or two $R^4$ together with the atoms to which they are attached may form a 5-6-membered cyclic group;

L is selected from —$NR^b$—, —O—, —S—, or —($CR^aR^a$)$_m$—, m is an integer of 1-3;

$R^a$ is absent, or at each occurrence, is each independently selected from hydrogen, cyano, hydroxy, halogen, carboxyl, nitro, —$NR^eR^f$, —$SO_2$—$NR^eR^f$, —$SO_2$R—, —$NR^eSO_2R^g$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —$SO_2$—R', 3-12-membered cycloalkyl, 3-12-membered cycloalkenyl, 3-14-membered heterocyclyl, 6-14-membered aryl, or 5-10-membered heteroaryl;

$R^b$ and $R^c$ are absent, or at each occurrence, are each independently selected from hydrogen, hydroxy, —C(O)$R^g$, —C(O)$NR^eR^f$, —$SO_2$—$NR^eR^f$, —$SO_2R^g$, $C_{1-6}$alkyl, hydroxy$C_{1-6}$alkyl, cyano$C_{1-6}$alkyl, amino$C_{1-6}$ alkyl, $C_{1-6}$alkylamino$C_{1-6}$alkyl, halo$C_{1-6}$alkyl, $C_{1-6}$alkoxy$C_{1-6}$alkyl, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

$R^d$ is absent, or at each occurrence, is each independently selected from hydrogen, —$NR^eR^f$, —$NR^e$C(O)$OR^g$, —$NR^e$C(O)$R^g$, —$NR^eSO_2R^f$, $C_{1-6}$alkyl, hydroxy$C_{1-6}$ alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy $C_{1-6}$alkoxy$C_{1-6}$alkyl, $C_{1-6}$alkoxy$C_{1-6}$alkoxy, —$C_{1-6}$alkyl-R', —$C_{1-6}$alkoxy-R', —O—R', —$NR^e$C(O)—$R^g$, 3-12-membered cycloalkyl, 3-12-membered cycloalkenyl, 3-14-membered heterocyclyl, 6-14-membered aryl, or 5-10-membered heteroaryl;

$R^e$ and $R^f$ are absent, or at each occurrence, are each independently selected from hydrogen, hydroxy, carboxyl, cyano, nitro, halogen, $C_{1-6}$alkyl, hydroxy$C_{1-6}$ alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy$C_{1-6}$alkyl, —$C_{1-6}$ alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

$R^g$ is absent, or at each occurrence, is each independently selected from hydrogen, $C_{1-6}$alkyl, hydroxy$C_{1-6}$alkyl, cyano$C_{1-6}$alkyl, amino$C_{1-6}$alkyl, $C_{1-6}$alkylamino$C_{1-}$ 6alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

R' is selected from 3-12-membered cycloalkyl, 3-12-membered cycloalkenyl, 3-14-membered heterocyclyl, 6-14-membered aryl, or 5-10-membered heteroaryl;

n is an integer of 0-4;

 represents two double bonds that are present between $X^1$ and $X^4$, $X^2$ and $X^5$.

2. The compound according to claim 1, or a pharmaceutically acceptable salt, a stereoisomer or a tautomer thereof, having a structure represented by the following general formula (II),

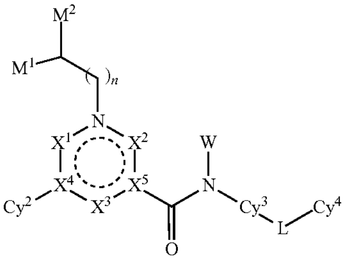

(II)

wherein W is selected from hydrogen or $C_{1-6}$alkyl;

$X^1$, and $X^2$ are each independently selected from $CR^a$, or N, and $X^3$ is C═O;

$X^4$ and $X^5$ are each C;

$M^1$ and $M^2$ are each independently selected from hydrogen, $C_{1-6}$alkyl, or $M^1$ and $M^2$ together with the atoms to which they are attached may form a 3-8-membered cycloalkyl;

$Cy^2$ is 6-14-membered aryl, which is optionally substituted by one or more $R^3$, $R^2$ is each independently selected from hydrogen, cyano, hydroxy, halogen, carboxyl, nitro, —$NR^bR^c$, —$C(O)R^d$, —$C(O)NR^bR^c$, —$OC(O)NR^bR^c$, —$NR^bC(O)OR^d$, —$NR^bC(O)R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$ alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^bC(O)$—R', 3-8-membered cycloalkyl, 3-8-membered cycloalkenyl, 3-14-membered heterocyclyl, 6-14-membered aryl, or 5-10-membered heteroaryl;

$Cy^3$ is 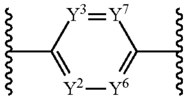

optionally substituted by one or more $R^3$; $Y^2$, $Y^3$, $Y^6$, and $Y^7$ are each independently selected from CH or N, and at least one of $Y^2$, $Y^3$, $Y^6$ and $Y^7$ is N, $R^3$ is each independently selected from hydrogen, cyano, hydroxy, halogen, carboxyl, nitro, —$NR^bR^c$, —$C(O)R^d$, —$C(O)NR^bR^c$, —$OC(O)NR^bR^c$, —$NR^bC(O)OR^d$, —$NR^bC(O)R^d$, —$SO_2$—$NR^bR^c$, —$SO_2R^d$, —$NR^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$ alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —C(O)—R', —$SO_2$—R', —$NR^bC(O)$—R', 3-8-membered cycloalkyl, 3-8-membered cycloalkenyl, 3-14-membered heterocyclyl 6-14-membered aryl, or 5-10-membered heteroaryl; when $X^1$ or $X^2$ represents N, $Cy^3$ may also be a 6-14 membered aromatic group optionally substituted by one or more $R^3$;

$Cy^4$ is 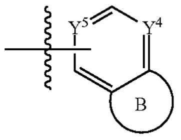

optionally substituted by one or more $R^4$; $Y^4$ and $Y^5$ are independently selected from CH or N, and at least one of $Y^4$ and $Y^5$ is N, ring B is phenyl or 5-6-membered heteroaryl, $R^4$ is each independently selected from hydrogen, cyano, hydroxy, halogen, carboxyl, nitro, —$NR^bR^c$, —$SO_2$—$NR^bR^c$, —$SO_2R^d$, —$R^bSO_2R^d$, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$ alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', —$SO_2$—R', 3-8-membered cycloalkyl, 3-8-membered cycloalkenyl, 3-14-membered heterocyclyl, 6-14-membered aryl, or 5-10-membered heteroaryl, or two $R^4$ together with the atoms to which they are attached may form a 5-6-membered cyclic group;

L is selected from —$NR^b$—, —O—, or —S—;

$R^a$ is absent, or at each occurrence, is each independently selected from hydrogen, cyano, hydroxy, halogen, carboxyl, nitro, —$NR^eR^f$, —$SO_2$—$NR^eR^f$, —$SO_2R^g$, —$NR^eSO_2R^g$, $C_{1-6}$alkyl, hydroxy$C_{1-6}$alkyl, cyano$C_{1-6}$ alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, $C_{2-8}$alkenyl, $C_{2-8}$alkynyl, —$C_{1-6}$alkyl-R', —$C_{1-6}$alkoxy-R', —O—R', 3-8-membered cycloalkyl, 3-8-membered cycloalkenyl, 3-14-membered heterocyclyl, 6-14-membered aryl, or 5-10-membered heteroaryl;

$R^b$ and $R^c$ are absent, or at each occurrence, are each independently selected from hydrogen, hydroxy, —$C(O)R^g$, —$C(O)NR^eR^f$, —$SO_2$—$NR^eR^f$, —$SO_2R^g$, $C_{1-6}$alkyl, hydroxy$C_{1-6}$alkyl, cyano$C_{1-6}$alkyl, amino$C_{1-6}$ alkyl, $C_{1-6}$alkylamino$C_{1-6}$alkyl, halo$C_{1-6}$alkyl, $C_{1-6}$alkoxy$C_{1-6}$alkyl, —$C_{1-6}$alkyl-R', —C(O)—R', —$SO_2$—R', 3-8-membered cycloalkyl, 3-8-membered cycloalkenyl, 3-14-membered heterocyclyl, 6-14-membered aryl, or 5-10-membered heteroaryl;

$R^d$ is absent, or at each occurrence, is each independently selected from hydrogen, —$NR^eR^f$, —$NR^eC(O)OR^g$, —$NR^eC(O)R^g$, —$NR^eSO_2R^g$, $C_{1-6}$alkyl, hydroxy$C_{1-6}$ alkyl, cyano$C_{1-6}$alkyl, amino$C_{1-6}$alkyl, $C_{1-6}$alkylamino$C_{1-6}$alkyl, halo$C_{1-6}$alkyl, $C_{1-6}$alkoxy, halo$C_{1-6}$ alkoxy, $C_{1-6}$alkoxy$C_{1-6}$alkyl, $C_{1-6}$alkoxy$C_{1-6}$alkoxy, —$C_{1-6}$alkyl-R', —$C_{1-6}$alkoxy-R', —O—R', —$NR^eC$ (O)—R', 3-8-membered cycloalkyl, 3-8-membered cycloalkenyl, 3-14-membered heterocyclyl, 6-14-membered aryl, or 5-10-membered heteroaryl;

$R^e$ and $R^f$ are absent, or at each occurrence, are independently selected from hydrogen, hydroxy, carboxyl, cyano, nitro, halogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy$C_{1-6}$alkyl, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

$R^g$ is absent, or at each occurrence, is independently selected from hydrogen, $C_{1-6}$alkyl, hydroxy$C_{1-6}$alkyl, cyano$C_{1-6}$alkyl, amino$C_{1-6}$alkyl, $C_{1-6}$alkylamino$C_{1-6}$ alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, —$C_{1-6}$alkyl-R', —C(O)—R', —$SO_2$—R', 3-12-membered cycloalkyl, 3-12-membered cycloalkenyl, 3-14-membered heterocyclyl, 6-14-membered aryl, or 5-10-membered heteroaryl;

R' is selected from 3-8-membered cycloalkyl, 3-8-membered cycloalkenyl, 3-14-membered heterocyclyl, 6-14-membered aryl, or 5-10-membered heteroaryl;

n is an integer of 0-3

 represents two double bonds that are present between $X^1$ and $X^4$, $X^2$ and $X^5$.

3. The compound according to claim 2, or a pharmaceutically acceptable salt, a stereoisomer or a tautomer thereof, wherein $X^1$, and $X^2$ are each independently selected from $CR^a$, or N, and is C═O;

$X^4$ is C, $X^5$ is C;

$M^1$ and $M^2$ are each independently selected from hydrogen, or $C_{1-6}$alkyl, or $M^1$ and $M^2$ together with the atoms to which they are attached may form a 3-8-membered cycloalkyl;

$Cy^2$ is phenyl, which is optionally substituted by one or more $R^2$, $R^2$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$Cy^3$ is

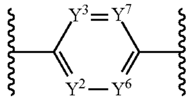

optionally substituted by one or more $R^3$; $Y^2$, $Y^3$, $Y^6$, and $Y^7$ are each independently selected from CH or N, and at least one of $Y^2$, $Y^3$, $Y^6$, and $Y^7$ is N, $R^3$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$Cy^4$ is

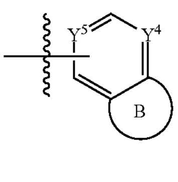

optionally substituted by one or more $R^4$; $Y^4$ and $Y^5$ are independently selected from CH or N, and at least one of $Y^4$ and $Y^5$ is N, ring B is phenyl or 5-6-membered heteroaryl, $R^4$ is each independently selected from hydrogen, hydroxy, halogen, nitro, —$NR^bR^c$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2.

4. The compound according to claim 3, or a pharmaceutically acceptable salt, an ester, a stereoisomer or a tautomer thereof, $X^1$, and $X^2$ are each independently selected from $CR^a$, or N, and $X^3$ is C═O;

$X^4$ is C, $X^5$ is C;

$Cy^2$ is phenyl, which is optionally substituted by one or more $R^2$;

$Cy^3$ represents

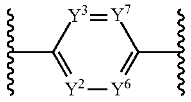

optionally substituted by one or more $R^3$;

$Y^2$, $Y^3$, $Y^6$ and $Y^7$ are each independently selected from CH or N, and at least one of $Y^2$, $Y^3$, $Y^6$ and $Y^7$ is N;

$Cy^4$ is

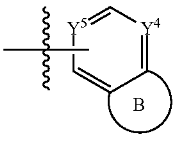

optionally substituted by one or more $R^4$; $Y^4$ and $Y^5$ are independently selected from CH or N, and at least one of $Y^4$ and $Y^5$ is N, ring B is phenyl or 5-6-membered heteroaryl;

$M^1$ and $M^2$ are each independently selected from hydrogen, or $C_{1-6}$alkyl, or $M^1$ and $M^2$ together with the atoms to which they are attached may form a 3-6-membered cycloalkyl;

$R^2$ is each independently selected from hydrogen, hydroxy, halogen, carboxyl, nitro, —$NR^bR^c$, —C(O) $R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^3$ is each independently selected from hydrogen, hydroxy, halogen, carboxyl, nitro, —$NR^bR^c$, —C(O) $R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, nitro, —$NR^bR^c$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2.

5. The compound according to claim 4, or a pharmaceutically acceptable salt, a stereoisomer or a tautomer thereof, having a structure represented by general formula (III), (III)

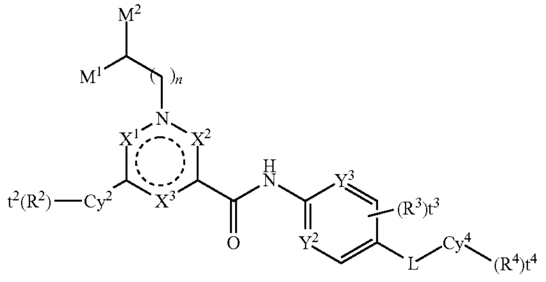

wherein $X^1$, and $X^2$ are each independently selected from $CR^a$, or N; $X^3$ is C═O;

$Cy^2$ is phenyl;

$Y^2$ and $Y^3$ are each independently selected from CH or N, and at least one of $Y^2$ and $Y^3$ is N;

$Cy^4$ is

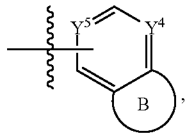

, $Y^4$ and Y are independently selected from CH or N, and at least one of $Y^4$ and $Y^5$ is N, ring B is phenyl or 5-6-membered heteroaryl;

$M^1$ and $M^2$ are each independently selected from hydrogen, or $C_{1-6}$alkyl, or $M^1$ and $M^2$ together with the atoms to which they are attached may form a 3-6-membered cycloalkyl;

$R^2$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, nitro, —$NR^bR^c$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2;

$t^2$, $t^3$ and $t^4$ are each independently selected from an integer of 1-5.

6. The compound according to claim 5, or a pharmaceutically acceptable salt, a stereoisomer or a tautomer thereof, wherein $M^1$ and $M^2$ together with the atoms to which they are attached may form cyclopropyl, and/or $R^2$ is each independently selected from fluoro.

7. The compound according to claim 4, or a pharmaceutically acceptable salt, a stereoisomer or a tautomer thereof, having a structure represented by general formula (IV), (IV)

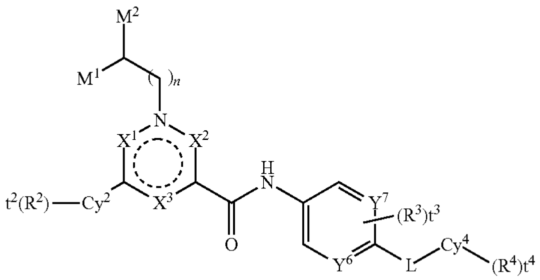

wherein $X^1$, and $X^2$ are each independently selected from $CR^a$, or N; $X^3$ is C═O;

$Cy^2$ is phenyl;

$Y^6$ and $Y^7$ are each independently selected from CH or N, and at least one of $Y^6$ and $Y^7$ is N;

$Cy^4$ is

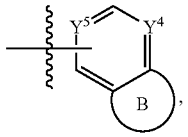

, $Y^4$ and Y are independently selected from CH or N, and at least one of $Y^4$ and $Y^5$ is N, ring B is phenyl or 5-6-membered heteroaryl;

$M^1$ and $M^2$ are each independently selected from hydrogen, or $C_{1-6}$alkyl, or $M^1$ and $M^2$ together with the atoms to which they are attached may form a 3-6-membered cycloalkyl;

$R^2$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^3$ is each independently selected from hydrogen, hydroxy, halogen, carboxyl, nitro, —$NR^bR^c$, —C(O)$R^d$, —C(O)$NR^bR^c$, —$NR^b$C(O)$R^d$, $C_{1-6}$alkyl, hydroxy$C_{1-6}$alkyl, amino$C_{1-6}$alkyl, halo$C_{1-6}$alkyl, $C_{1-6}$alkoxy, or halo$C_{1-6}$alkoxy;

$R^4$ is each independently selected from hydrogen, hydroxy, halogen, nitro, —$NR^bR^c$, $C_{1-6}$alkyl, hydroxy$C_{1-6}$alkyl, amino$C_{1-6}$alkyl, halo$C_{1-6}$alkyl, $C_{1-6}$alkoxy, halo$C_{1-6}$alkoxy, $C_{1-6}$alkoxy$C_{1-6}$alkyl, $C_{1-6}$alkoxy$C_{1-6}$alkoxy, or 3-14-membered heterocyclyl, or two $R^4$ together with the atoms to which they are attached may form a 5-6-membered oxygen-containing cyclic group;

L is selected from —$NR^b$—, —O—, or —S—;

$R^a$ is absent, or at each occurrence, is each independently selected from hydrogen, $C_{1-6}$alkyl, or halo$C_{1-6}$alkyl;

$R^b$ and $R^c$ are absent, or at each occurrence, are each independently selected from hydrogen, or $C_{1-6}$alkyl;

$R^d$ is absent, or at each occurrence, is each independently selected from hydrogen, or $C_{1-6}$alkyl;

n is an integer of 0-2;

$t^2$, $t^3$ and $t^4$ are each independently selected from an integer of 1-5.

8. The compound according to claim 7, or a pharmaceutically acceptable salt, a stereoisomer or a tautomer thereof, wherein $M^1$ and $M^2$ together with the atoms to which they are attached may form cyclopropyl, and/or $R^2$ is each independently selected from fluoro.

9. The compound according to claim 1, or a pharmaceutically acceptable salt, a stereoisomer or a tautomer thereof, wherein W is hydrogen;

$X^1$ and $X^2$ are each independently selected from $CR^a$ or N, $X^3$ is C═O;

$X^4$ is C;

$M^1$ and $M^2$ are each independently selected from: hydrogen, or $C_{1-4}$alkyl, or $M^1$ and $M^2$ together with the atoms to which they are attached may form a 3-6-membered cycloalkyl;

$Cy^2$ is

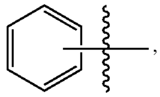, which is optionally substituted by one or more $R^2$, $R^2$ is each independently selected from hydrogen, hydroxy, fluoro, chloro, bromo, or $C_{1-4}$alkyl;

$Cy^3$ is selected from

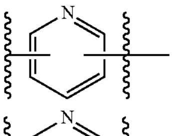, 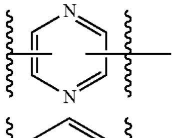, 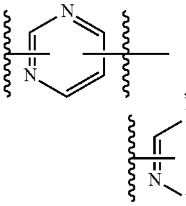, 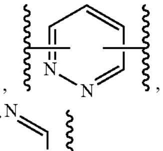, or 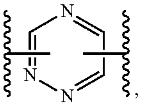, all of which are optionally substituted by one or more $R^3$, $R^3$ is each independently selected from hydrogen, hydroxy, fluoro, chloro, bromo, or $C_{1-4}$alkyl;

$Cy^4$ is selected from the following groups optionally substituted by one or more $R^4$:

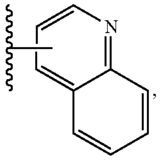, 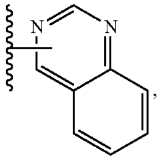, 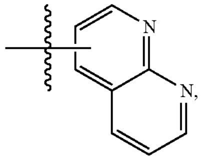

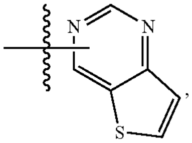, 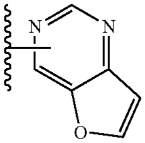, or

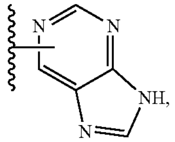

$R^4$ is each independently selected from hydrogen, hydroxy, halogen, $C_{1-4}$alkyl, halo$C_{1-4}$alkyl, $C_{1-4}$alkoxy, halo$C_{1-4}$alkoxy, or 3-14-membered heterocyclyl, or two $R^4$ together with the atoms to which they are attached may form a 5-6-membered oxygen-containing cyclic group;

L is —O—;

$R^a$ is absent, or at each occurrence, is each independently selected from hydrogen, $C_{1-6}$alkyl, or halo$C_{1-6}$alkyl;

$R^b$ is absent, or at each occurrence, is each independently selected from hydrogen, or $C_{1-6}$alkyl;

n is an integer of 0-1.

10. The compound according to claim 9, or a pharmaceutically acceptable salt, a stereoisomer or a tautomer thereof, wherein W is hydrogen;

$X^1$ and $X^2$ are selected from $CR^a$ or N, $X^3$ is C═O;

$X^4$ is C;

$M^1$ and $M^2$ are each independently selected from hydrogen, or $C_{1-4}$alkyl, or $M^1$ and $M^2$ together with the atoms to which they are attached may form a 3-6-membered cycloalkyl;

$Cy^2$ is

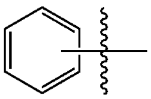

optionally substituted by one or more $R^2$, $R^2$ is each independently selected from hydrogen, fluoro, chloro, or $C_{1-4}$alkyl;

$Cy^3$ is selected from

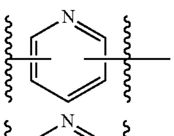, 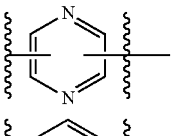,

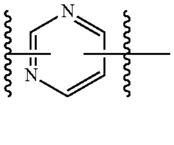, 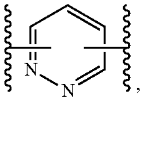, or

-continued

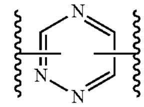

, all of which are optionally substituted by one or more $R^3$, $R^3$ is each independently selected from hydrogen, fluoro, chloro, or $C_{1-4}$alkyl;

$Cy^4$ is

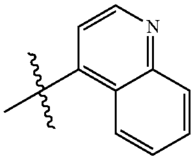 [SMILES: *c1ccnc2ccccc12]

optionally substituted by one or more $R^4$, $R^4$ is each independently selected from hydrogen, halogen, $C_{1-4}$alkyl, or $C_{1-4}$alkoxy, or two $R^4$ together with the atoms to which they are attached may form a 5-6-membered oxygen-containing cyclic group;

L is —O—;

$R^a$ is absent, or at each occurrence, is each independently selected from hydrogen, $C_{1-4}$alkyl, or halo$C_{1-6}$alkyl;

$R^b$ is absent, or at each occurrence, is each independently selected from hydrogen, or $C_{1-4}$alkyl;

n is an integer of 0-1.

11. The compound according to claim 1, or a pharmaceutically acceptable salt, a stereoisomer or a tautomer thereof, wherein $X^1$ is N, $X^2$ is $CR^a$, and $X^3$ is C═O; or $X^1$ is $CR^a$, $X^2$ is N, and $X^3$ is C═O; or X is $CR^a$, $X^2$ is $CR^a$, and $X^3$ is C═O.

12. A compound or a pharmaceutically acceptable salt, a stereoisomer, or a tautomer thereof, wherein the compound is selected from the compounds having the following structures:

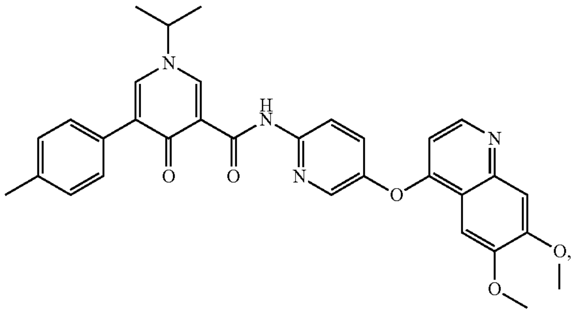

,

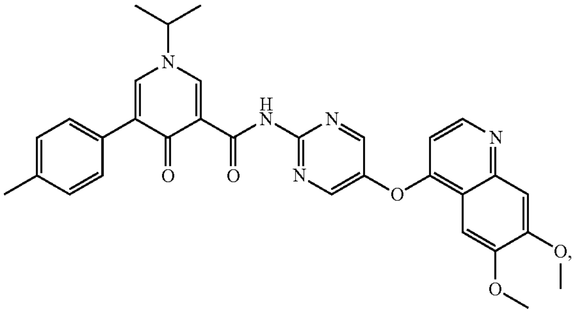

,

-continued

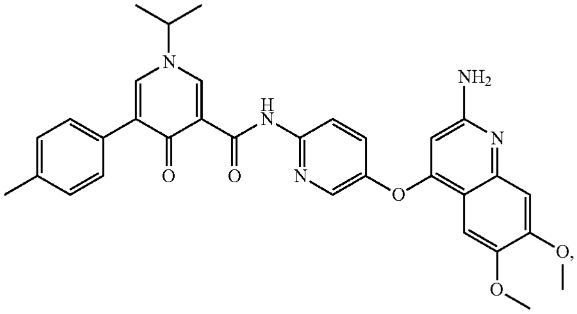

,

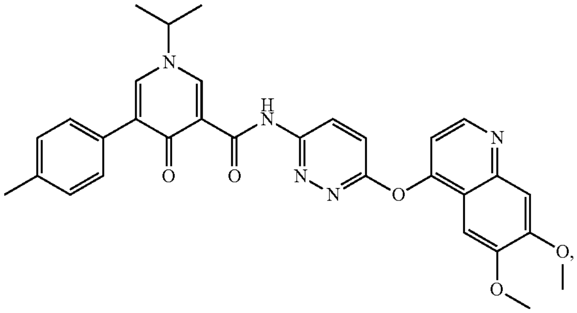

,

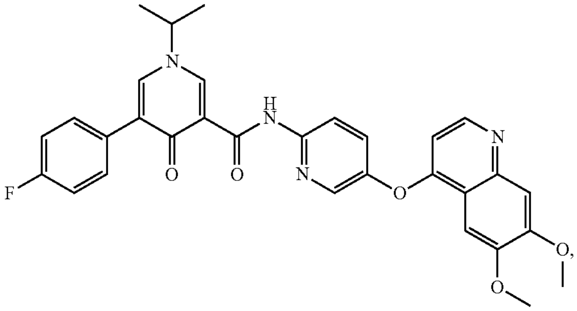

,

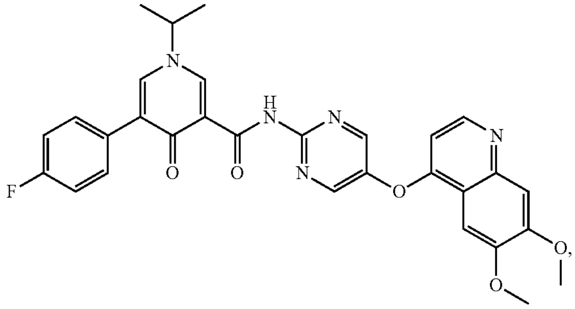

,

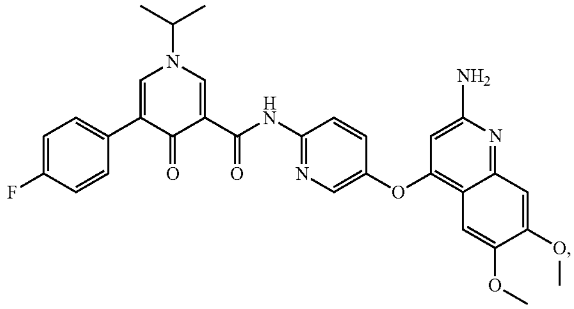

,

-continued
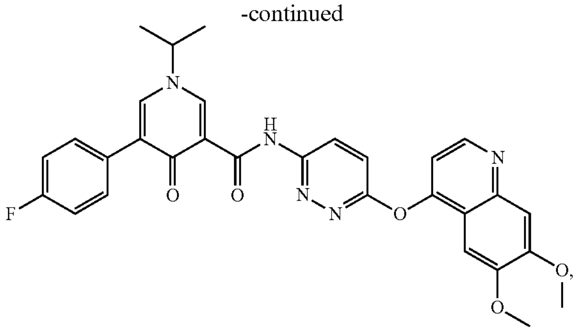
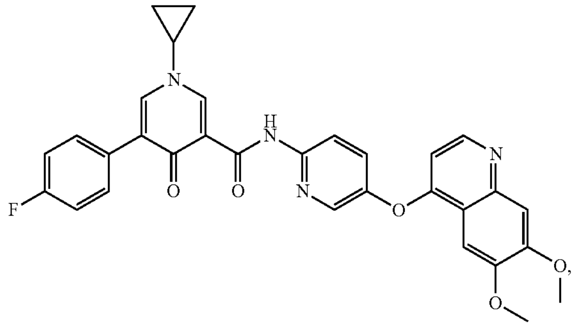
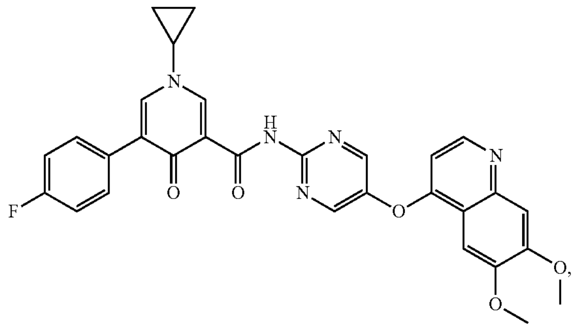
13. A compound or a pharmaceutically acceptable salt, a stereoisomer, or a tautomer thereof, wherein the compound is selected from the compounds having the following structures:
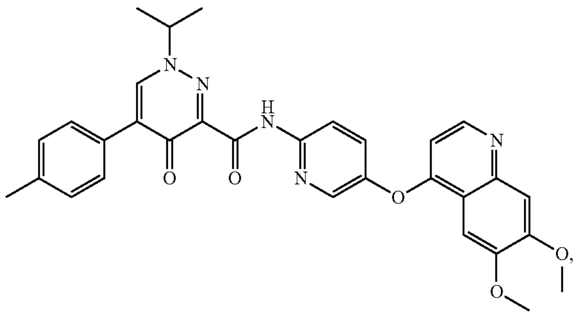
-continued
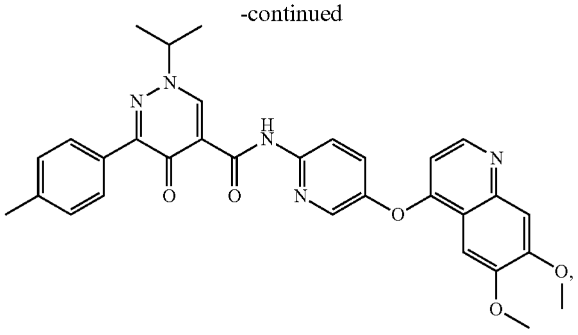
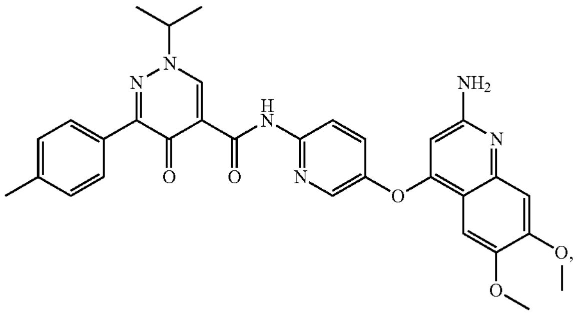
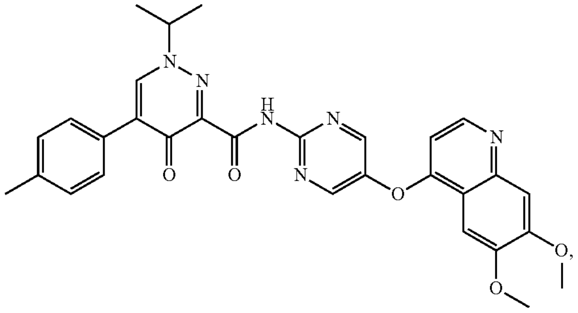
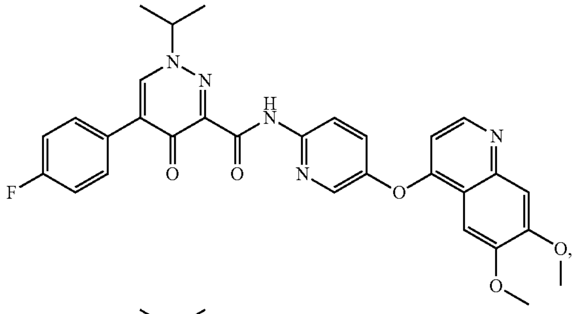
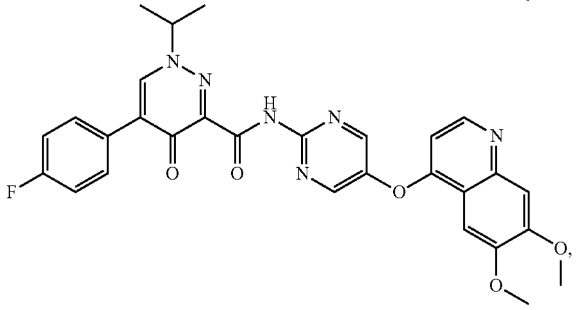

-continued
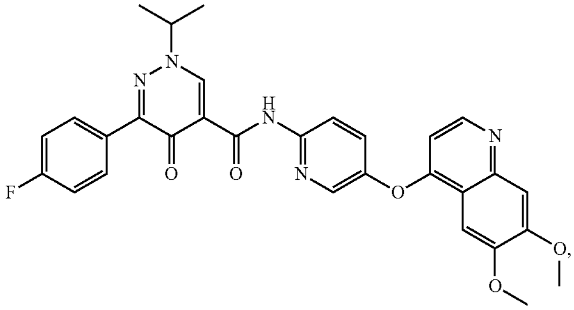
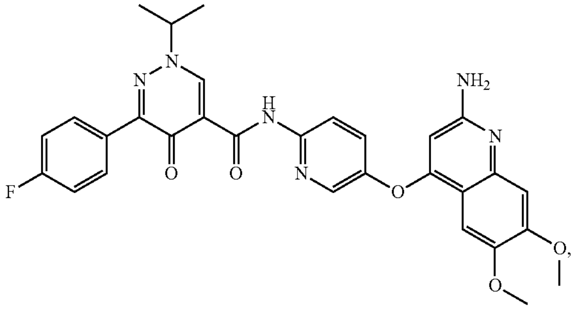
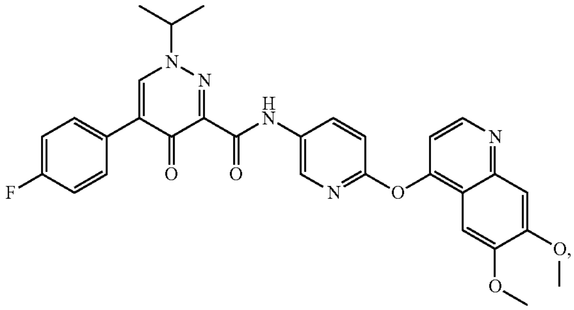
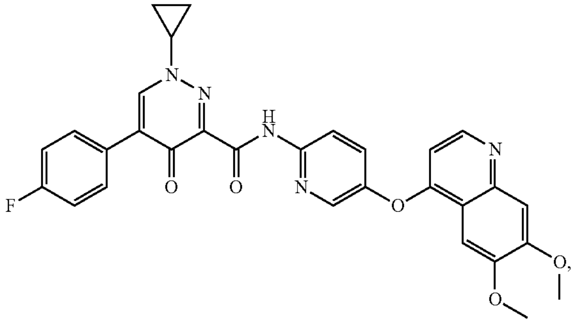
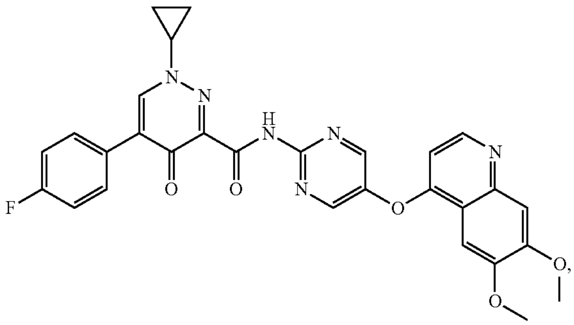
-continued
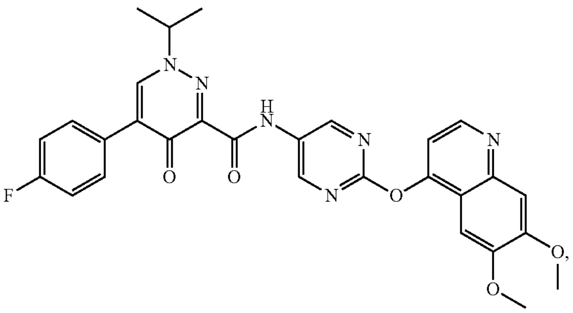
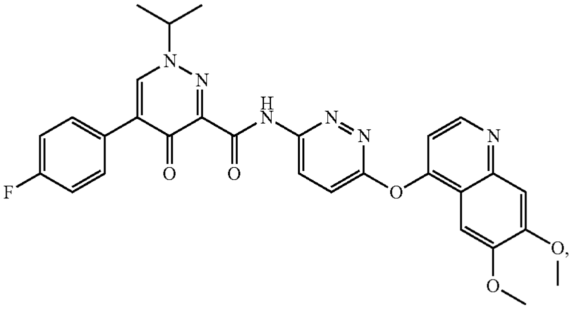
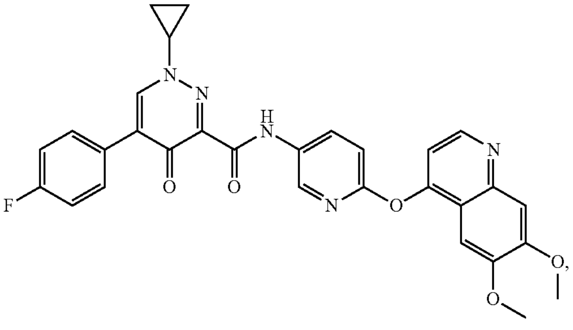
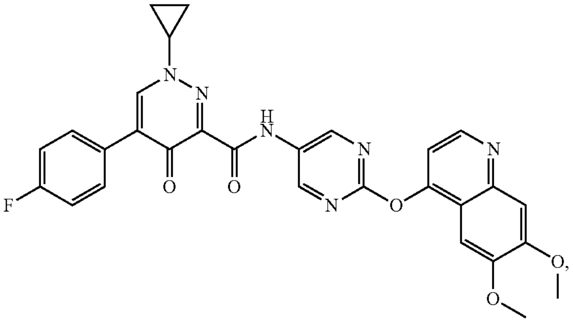
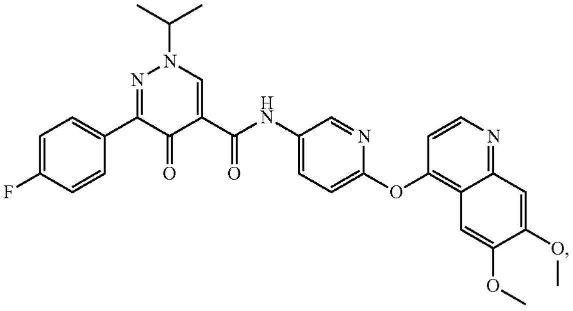

-continued

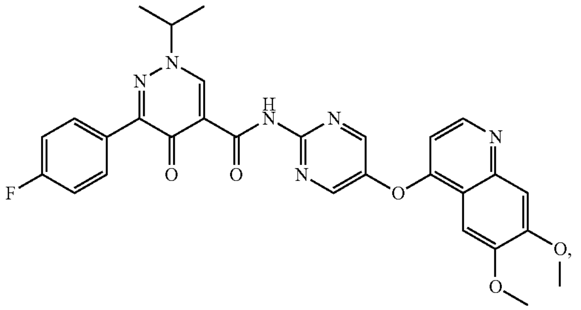

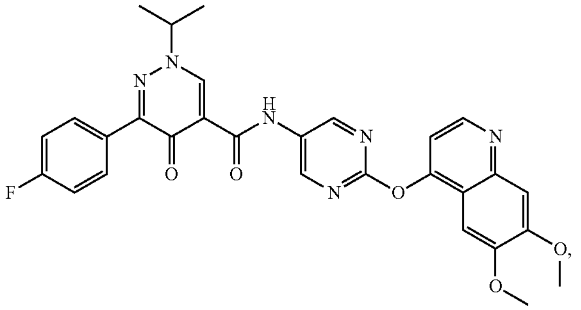

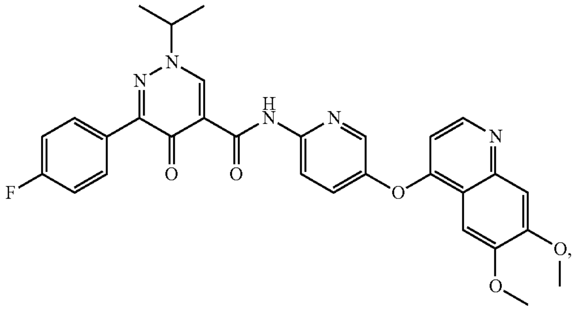

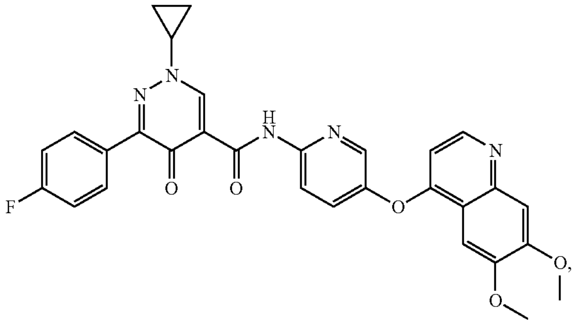

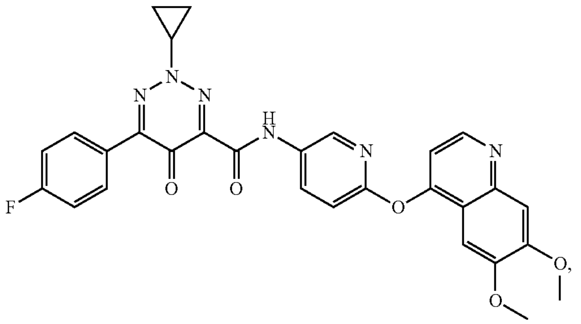

-continued

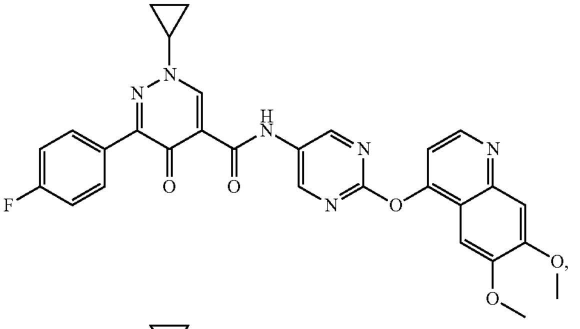

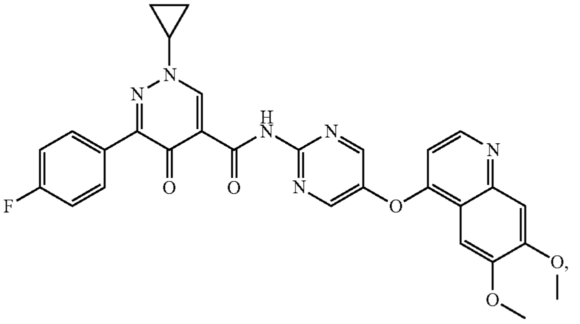

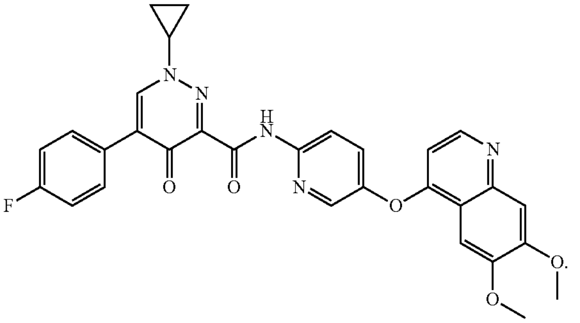

14. A method of treating related diseases caused by abnormal signaling pathways due to the abnormal expression of the TAM family receptors and/or ligands thereof, wherein the compound according to claim 1, or a pharmaceutically acceptable salt, a stereoisomer or a tautomer thereof, is administered to a subject suffering from said disease and said related diseases caused by abnormal signaling pathways due to the abnormal expression of the TAM family receptors and/or ligands thereof is at least one selected from the group consisting of adenomyosis, vascular disease/injury, psoriasis, visual defect/impairment, kidney disease, rheumatoid arthritis, osteoporosis, or a tumor selected from the group consisting of lung cancer, squamous carcinoma, bladder cancer, gastric cancer, ovarian cancer, peritoneal cancer, breast cancer, breast ductal carcinoma, head and neck cancer, endometrial cancer, corpus uteri carcinoma, rectal cancel; liver cancel; kidney cancer, renal pelvis cancer, esophageal cancel; adenocarcinoma of esophagus, glioma, prostate, thyroid cancer, female reproductive system cancer, lymphoma, neurofibromatosis, bone cancer, skin cancer, brain cancer, colon cancel; testicular cancer, gastrointestinal stromal tumor, oral cancer, cancer of pharynx, multiple myeloma, leukemia, non-Hodgkin's lymphoma, villous colon adenoma and melanoma.

15. A method of treating related diseases caused by abnormal signaling pathways due to the abnormal expression of TAM family kinases, or TAM family kinases and CSF1R kinase receptors and/or ligands thereof, wherein the compound according to claim 1, or a pharmaceutically acceptable salt, a stereoisomer or a tautomer thereof, is administered to a subject suffering from said disease, and said related diseases caused by abnormal signaling pathways due to the abnormal expression of TAM family kinases, or TAM family kinases and CSF1R kinase receptors and/or ligands thereof is at least one selected from the group consisting of adenomyosis, vascular disease/injury, psoriasis, visual defect/impairment, kidney disease, rheumatoid arthritis, osteoporosis, or a tumor selected from the group consisting of lung cancer, squamous carcinoma, bladder cancer, gastric cancer, ovarian cancer, peritoneal cancer, breast cancer, breast ductal carcinoma, head and neck cancer, endometrial cancer, corpus uteri carcinoma, rectal cancer, liver cancer, kidney cancer, renal pelvis cancer, esophageal cancer, adenocarcinoma of esophagus, glioma, prostate, thyroid cancer, female reproductive system cancer, lymphoma, neurofibromatosis, bone cancer, skin cancer, brain cancer, colon cancer, testicular cancer, gastrointestinal stromal tumor, oral cancer, cancer of pharynx, multiple myeloma, leukemia, non-Hodgkin's lymphoma, villous colon adenoma and melanoma.

16. A method of treating related diseases caused by NTRK, wherein the compound according to claim 1, or a pharmaceutically acceptable salt, a stereoisomer or a tautomer thereof, is administered to a subject suffering from said disease, and said disease caused by NTRK is at least one selected from the group consisting of non-small cell lung cancer, colorectal cancer, mammary analogue secretory carcinoma, sarcoma, astrocytoma, glioblastoma, Spitz-like melanoma, cholangiocarcinoma, papillary thyroid carcinoma, breast secretory cancer and breast cancer.

17. A method of treating drug-resistant related diseases caused by NTRK mutations, wherein the compound according to claim 1, or a pharmaceutically acceptable salt, a stereoisomer or a tautomer thereof, is administered to a subject suffering from said disease, and said disease caused by NTRK mutations is at least one selected from the group consisting of non-small cell lung cancer, colorectal cancer, mammary analogue secretory carcinoma, sarcoma, astrocytoma, glioblastoma, Spitz-like melanoma, cholangiocarcinoma, papillary thyroid carcinoma, breast secretory cancer and breast cancer.

* * * * *